US009049878B2

(12) United States Patent
Tachdjian et al.

(10) Patent No.: US 9,049,878 B2
(45) Date of Patent: *Jun. 9, 2015

(54) SWEET FLAVOR MODIFIER

(71) Applicant: SENOMYX, INC., San Diego, CA (US)

(72) Inventors: Catherine Tachdjian, San Diego, CA (US); Xiao Qing Tang, San Diego, CA (US); Donald S. Karanewsky, Escondido, CA (US); Guy Servant, San Diego, CA (US); Xiaodong Li, San Diego, CA (US); Feng Zhang, San Diego, CA (US); Qing Chen, San Diego, CA (US); Hong Zhang, San Diego, CA (US); Timothy Davis, Santee, CA (US); Vincent Darmohusodo, Enchitas, CA (US); Melissa Wong, San Diego, CA (US); Victor Selchau, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/061,013

(22) Filed: Oct. 23, 2013

(65) Prior Publication Data

US 2014/0128481 A1 May 8, 2014

Related U.S. Application Data

(63) Continuation of application No. 13/076,632, filed on Mar. 31, 2011, now Pat. No. 8,592,592.

(60) Provisional application No. 61/320,528, filed on Apr. 2, 2010, provisional application No. 61/422,341, filed on Dec. 13, 2010.

(51) Int. Cl.
| | |
|---|---|
| *A23L 1/236* | (2006.01) |
| *A23L 1/22* | (2006.01) |
| *A23L 1/226* | (2006.01) |
| *C07D 215/54* | (2006.01) |
| *C07D 215/60* | (2006.01) |
| *C07D 401/12* | (2006.01) |
| *C07D 405/12* | (2006.01) |
| *C07D 471/04* | (2006.01) |
| *C07D 491/048* | (2006.01) |
| *C07D 495/04* | (2006.01) |
| *A61K 47/22* | (2006.01) |

(52) U.S. Cl.
CPC ......... *A23L 1/22091* (2013.01); *A23L 1/22678* (2013.01); *C07D 215/54* (2013.01); *C07D 215/60* (2013.01); *C07D 401/12* (2013.01); *C07D 405/12* (2013.01); *C07D 471/04* (2013.01); *C07D 491/048* (2013.01); *C07D 495/04* (2013.01); *A61K 47/22* (2013.01)

(58) Field of Classification Search
CPC .. A23L 1/22678; A23L 1/235; A23L 1/22091
See application file for complete search history.

(56) References Cited

U.S. PATENT DOCUMENTS

| | | | |
|---|---|---|---|
| 5,240,934 | A | 8/1993 | Hasegawa |
| 5,593,997 | A | 1/1997 | Dow et al. |
| 6,194,493 | B1 | 2/2001 | Stahrfeldt et al. |
| 6,339,077 | B1 | 1/2002 | Hofmeister et al. |
| 6,410,529 | B1 | 6/2002 | Chan et al. |
| 7,928,111 | B2 | 4/2011 | Tachdjian et al. |
| 8,592,592 | B2 | 11/2013 | Tachdjian et al. |
| 2005/0009815 | A1 | 1/2005 | Devita et al. |
| 2005/0032158 | A1 | 2/2005 | Adler et al. |
| 2005/0084506 | A1 | 4/2005 | Tachdjian et al. |
| 2006/0045953 | A1 | 3/2006 | Tachdjian et al. |
| 2006/0135552 | A1 | 6/2006 | Malherbe et al. |
| 2007/0104709 | A1 | 5/2007 | Li et al. |
| 2008/0306093 | A1 | 12/2008 | Servant et al. |

FOREIGN PATENT DOCUMENTS

| | | |
|---|---|---|
| CL | 20152004 | 8/2004 |
| CL | 14702006 | 6/2006 |
| CL | 16652008 | 6/2008 |
| CL | 24733008 | 8/2008 |
| JP | 59-51283 A | 3/1964 |
| JP | 51-48440 A | 4/1976 |
| JP | 57-159784 A | 10/1982 |
| JP | 62-190185 A | 8/1987 |
| JP | 63-22074 | 1/1988 |
| JP | 6-199855 A | 7/1994 |
| JP | 7-501313 A | 2/1995 |

(Continued)

OTHER PUBLICATIONS

Putz A. et al. "Depth-related alkaloid variation in mediterranean *Aplysina* sponges", Zeitschrift fuer Naturforschung, C: Journal of Biosciences, 2009, 64(3/4), 279-287.
Atechain, S. et al. "New vistas in quinoline synthesis", Tetrahedron, 2007, 63(13), 2811-2823.
Fang, V. et al. "Hypoglycemic activity and chemical structure of the salicylates", Journal of Pharmaceutical Sciences, 1968, 578(12), 2111-16.
O'Donnell, F. et al. "A Study of the analytical behavior of selected synthetic and naturally occuring quinolines using electrospray ionisation ion trap mass spectrometry, liquid chromatography and gas chromatography and the construction of an appropriate database for quinoline characterisation", Analytica Chimica Acta, 2006, 572(1) 63-76.
Li, Min et al., "Synthesis of new fluroquinolone NM394", Zhongguo Xinyao Zazhi, 2005, 14(1), 67-69.

(Continued)

*Primary Examiner* — David K O Dell
(74) *Attorney, Agent, or Firm* — Knobbe Martens Olson & Bear LLP

(57) ABSTRACT

The present invention includes compounds having structural formula (I), or pharmaceutically acceptable salts, solvate, and/or ester thereof. These compounds are useful as sweet flavor modifiers. The present invention also includes compositions comprising the present compounds and methods of enhancing the sweet taste of ingestible compositions. Furthermore, the present invention provides methods for preparing the compounds.

27 Claims, No Drawings

(56) References Cited

FOREIGN PATENT DOCUMENTS

| JP | 8-3046 | A | 1/1996 |
|---|---|---|---|
| JP | 2005-518365 | A | 6/2005 |
| JP | 2009-531443 | A | 9/2009 |
| JP | 2012-544816 | A | 4/2013 |
| WO | 03037259 | | 5/2003 |
| WO | 2005015158 | | 2/2005 |
| WO | 2005123686 | A1 | 12/2005 |
| WO | 2006002421 | | 1/2006 |
| WO | 2006007700 | | 1/2006 |
| WO | 2006138512 | | 12/2006 |
| WO | 2008154221 | | 12/2008 |
| WO | 2011106114 | | 9/2011 |

OTHER PUBLICATIONS

Hoehn, H. et al., "Potential antidiabetic agents. Pyrazolo[3,4-b]pyridines", Journal of Medicial Chemistry, 1973, 16(12), 1340-6.
Caplus Accession No, 2006:125585 & JP 2006036762 (Taisho Pharmaceutical Co. Ltd.), Feb. 9, 2006.
Takahashi, Torizo Syntheses of heterocyclic compounds of nitrogen. LXXV. 3-Quinolinecarboxylic acid derivatives.' Yakugaku Zasshi, 1952 72, 1112-14.
Graves, "Discovery of Novel Targets of Quinoline Drugs in the Human Purine Binding Proteome" Molecular Pharmacology 2002 vol. 62, No. 6, 1364-1372.
West, Anthony R., "Solid State Chemistry and its Application", Wiley, New York, 1988, pp. 358 & 365.
Jensen et al., "Synthesis of 4-Quinolone Derivatives", Acta Chemica Scandinavica 49 (1995), pp. 53-56.
Doucet-Personeni et al., "A Structure-Based Design Approach to the Development of Novel, Reversible AChE Inhibitors", J. Med. Chem. 2001, 44, pp. 3203-3215.
Singapore Written Opinion for Application No. 201206956-3 dated Jan. 22, 2014.
Singapore Search Report for Application No. 201206956-3 dated Jan. 22, 2014.
Colombian Office Action issued Apr. 2, 2014 for the application 12-188.315.
Mexican Office Action issued Dec. 3, 2013 for the application MX/a/2012/011386.
Australian Office Action issued Jun. 30, 2013 for the application 2011235069.
Baker at al., Irreversible Enzyme Inhibitors. 192. Hydrophobic Bending to Some Dehydrogenases with 5-Substituted-4-hydroxyquinoline-3-carboxylic Acids, Journal of Medicinal Chemistry, 1972 15(3), p. 237-241.
CAS Registry No. 933710-66-8, 2007.
Davis "Search for New Trypanocides, V. Some Derivatives of 10-Phenyl-4:9-diazaphenanthrene.", Journal of the Chemical Society, 1957 p. 828-836.
Godard et al , "o-Aminoformylquinolines, new heterocyclic synthons," Journal of Heterocyclic Chemistry, 1980 17(3), p. 465-473.
Hirao et al., "Studies on the Synthesis of Quinoline Compounds, IV. Syntheses of of 3,3'-Dicarboxy-1,1'- diethyl-4,4'-dioxo-1,1',4,4'-tetrahydropolymethylenedioxydiquinolines", Memoirs of the Kyushu Institute of Technology, Engineering, 1984, No. 14, p. 29-34.
Lijima et al, "ANDP-2, A Novel Acrinol Degradation Product by Light", Journal of Health Science, 2007. 53(6), p. 745-749.
Kripalani et al., "Biotransformation in the monkey of cartzolate (SQ 65,396), a substituted pyrazolopyridine having anxiolytic activity", Xenobiotica, 1981 11(7), p. 481-486.
Lalezari "Synthesis of 4-Aminothieno [2,3-b]pyridine-5-carboxylic Acids (1), ", Journal of Heterocyclic Chemistry, 1979 16 (3), p. 603-604.
Santilli et al., "2-Oxo-1, 8-naphthyridine-3-carboxylic Acid Derivatives with Potent Gastric Antisecretory Properties", Journal of Medicinal Chemistry, 1987 30 (12), p. 2270-2277.
Schaefer et al., "The synthesis of 4-aminoquinolines by intramolecular Friedel-Crafts reaction", Monatshefte fuer Chemie, 1978 109(3), p. 527-535.
Stanczak et al., "Comparison of pharmacophore cinnoline and quinoline systems on the basis of computer calculation and pharmacological screening of their condensed systems", Pharmazie, 2001 56(6) p. 501-505.
Titkova et al., "Synthesis of 4-substituted 3-carbethoxy [carboxy]-1,5-naphthyridines, their properties and biological activity, Khimiko-Farmatsevticheskii Zhurnal", 1982 16(6), p. 468-470.
Zuleski et at "Tracazolate metabolites in rat tissue; Drug Metabolism and Disposition", 1985, 13(2), p. 139-147.

SWEET FLAVOR MODIFIER

CROSS-REFERENCE TO RELATED APPLICATIONS

This application is a continuation of U.S. Utility application Ser. No. 13/076,632, filed Mar. 31, 2011, and claims the benefit of priority to U.S. Provisional Patent Application No. 61/320,528, filed Apr. 2, 2010 and entitled "SWEET FLAVOR MODIFIER"; and U.S. Provisional Patent Application No. 61/422,341, filed Dec. 13, 2010 and entitled "SWEET FLAVOR MODIFIER". The contents of these applications are hereby incorporated by reference in their entireties for all purposes.

FIELD OF THE INVENTION

The invention relates to compounds useful as sweet flavor modifiers and/or tastants.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to have superior sweet taste enhancing properties and are described in the four patent applications listed below.

(1) U.S. patent application Ser. No. 11/760,592, entitled "Modulation of Chemosensory Receptors and Ligands Associated Therewith", filed Jun. 8, 2007; (2) U.S. patent application Ser. No. 11/836,074, entitled "Modulation of Chemosensory Receptors and Ligands Associated Therewith", filed Aug. 8, 2007; (3) U.S. Patent Application Ser. No. 61/027,410, entitled "Modulation of Chemosensory Receptors and Ligands Associated Therewith", filed Feb. 8, 2008; and (4) International Application No. PCT/US2008/065650, entitled "Modulation of Chemosensory Receptors and Ligands Associated Therewith", filed Jun. 3, 2008. The contents of these applications are herein incorporated by reference in their entirety for all purposes.

The present invention provides novel and inventive sweet taste enhancers with desirable characteristics.

SUMMARY OF THE INVENTION

In one embodiment, the present invention provides a compound having structural Formula (I) or (I'):

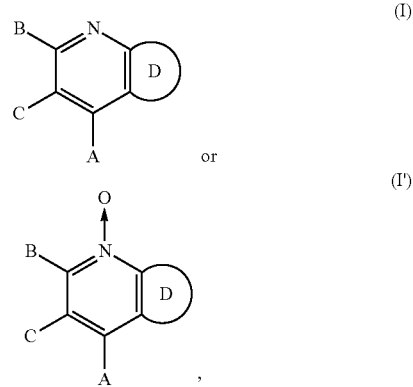

or a tautomer, salt, and/or solvate, wherein:

A is —$OR^1$, —$NR^1C(O)R^2$, —$NHOR^1$, —$NR^1R^2$, —$NR^1CO_2R^2$, —$NR^1C(O)NR^2R^3$, —$NR^1C(S)NR^2R^3$ or —$NR^1C(=NH)NR^2R^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$OR^4$, —$S(O)_aR^4$, —$NR^4R^5$, —$C(O)NR^4R^5$, —$CO_2R^4$, —$NR^4CO_2R^5$, —$NR^4C(O)NR^5R^6$, —$NR^4C(S)NR^5R^6$, —$NR^4C(=NH)NR^5R^6$, —$SO_2NR^4R^5$, —$NR^4SO_2R^5$, —$NR^4SO_2NR^5R^6$, —$B(OR^4)(OR^5)$, —$P(O)(OR^4)(OR^5)$, or —$P(O)(R^4)(OR^5)$;

C is —$OR^7$, —$S(O)_bR^7$, $SO_3R^7$, —$C(O)NR^7R^8$, —$CO_2R^7$, —$NR^7CO_2R^8$, —$NR^7C(O)NR^8R^9$, —$NR^7C(=NH)NR^8R^9$, —$SO_2NR^7R^8$, —$NR^7SO_2R^8$, —$NR^7SO_2NR^8R^9$, —$B(OR^7)(OR^8)$, —$P(O)(OR^7)(OR^8)$, —$P(O)(R^7)(OR^8)$, or heteroaryl (for example, tetrazole);

D is an aryl, substituted aryl, heteroaryl, substituted heteroaryl, cycloalkyl, substituted cycloalkyl, cycloheteroalkyl or substituted cycloheteroalkyl ring wherein the ring is optionally fused to another aryl, substituted aryl, heteroaryl, substituted heteroaryl, cycloalkyl, substituted cycloalkyl, cycloheteroalkyl, or substituted cycloheteroalkyl ring;

a and b are independently 0, 1 or 2; and $R^1$, $R^2$, $R^3$, $R^4$, $R^5$, $R^6$, $R^7$, $R^8$, and $R^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, $R^1$ and $R^2$, $R^2$ and $R^3$, $R^4$ and $R^5$, $R^5$ and $R^6$, $R^7$; and $R^8$, or $R^8$ and $R^9$, together with the atoms to which they are bonded, form a cycloheteroalkyl or substituted cycloheteroalkyl ring.

In another embodiment, the present invention provides an ingestible composition comprising a compound of the present invention and an ingestibly acceptable excipient.

In another embodiment, the present invention provides a flavoring concentrate formulation comprising a compound of the present invention and a carrier.

In another embodiment, the present invention provides a method of modulating the sweet taste of an ingestible composition comprising contacting the ingestible composition or precursors thereof with a compound of the present invention to form a modified ingestible composition.

In another embodiment, the present invention provides a method for preparing a compound of the present invention.

DETAILED DESCRIPTION OF THE INVENTION

These and other embodiments, advantages, and features of the present invention are provided in the sections below. Unless defined otherwise, all technical and scientific terms used herein have the same meaning as commonly understood by one of ordinary skill in the art to which this invention belongs.

DEFINITIONS

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 10 carbon atoms ($C_1$-$C_{10}$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined herein below. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. "Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," or "Carbocyclyl," by itself or as part of another substituent, refers to a saturated or unsaturated cyclic alkyl radical, as defined herein. Similarly, "Cycloalkylene," or "Carbocyclylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," or "Heterocyclylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Compounds" refers to compounds encompassed by structural formulae disclosed herein, such as (I), (II), (IIa), (IIb), (III), (IIIa), (IIIb), (IIIc), and (IIId), and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N \rightarrow O$).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —OS$(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$ where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O- alkyl, -alkylene-heteroaryl, -alkylene-cycloheteroalkyl, -alkylene-C(O)OR$^b$, -alkylene-C(O)NR$^b$R$^b$, and —CH$_2$—CH$_2$—C(O)—CH$_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —R$^a$, halo, —O$^-$, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O), —P(O)(OR$^b$)(OR$^b$), —C(O)R$^b$, —C(S) R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$—NR$^b$C(NR$^b$)R$^b$ and —NR$^b$C(NR$^b$)NR$^c$R$^c$, where R$^a$, R$^b$ and R$^c$ are as previously defined.

Substituent groups useful for substituting nitrogen atoms in heteroalkyl and cycloheteroalkyl groups include, but are not limited to, —R$^a$, —O$^-$, —OR$^b$, —SR$^b$, —S$^-$, —NR$^c$R$^c$, trihalomethyl, —CF$_3$, —CN, —NO, —NO$_2$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O)$_2$, —P(O)(OR$^b$)(O), —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$ where R$^a$, R$^b$ and R$^c$ are as previously defined. Substituent groups from the above lists useful for substituting other specified groups or atoms will be apparent to those of skill in the art.

The substituents used to substitute a specified group can be further substituted, typically with one or more of the same or different groups selected from the various groups specified above.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

An "enhancer" herein refers to a compound, or an ingestibly acceptable salt or solvate thereof, that modulates (increases) the activation of a particular receptor, preferably the chemosensory, e.g., T1R2/T1R3 receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto. Most enhancers, at its ligand enhancing concentration, do not result in substantial activation of the particular receptor by themselves. Usually the ligand enhancing concentrations of an enhancer are concentration levels of the enhancer that increases or enhances the activation of a particular receptor by a ligand without substantially activating the particular receptor by the enhancer itself. In some embodiments, certain enhancers, when used at a concentration higher than the ligand enhancing concentration, can also activate a particular receptor by themselves in addition to modulating (e.g., increase or enhancement) the activation of the receptor. For example, certain enhancers, when used at a concentration higher than the ligand enhancing concentration, can be sweeteners (i.e., sweet flavoring agent/entity) as well.

A "flavor" herein refers to the perception of taste in a subject, which include sweet, sour, salty, bitter and umami. The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "flavor modifier" or "flavor modifying agent" herein refers to a compound or the ingestibly acceptable salt or solvate thereof that modulates, including enhancing or potentiating, and/or inducing, the tastes of a flavoring agent in an animal or a human.

A "flavor enhancer" herein refers to a compound or ingestibly acceptable salt thereof that enhances and/or multiplies the tastes of a flavoring agent, or an ingestible composition comprising the flavoring agent.

A "sweet flavor" refers to the sweet taste typically induced by sugar, such as sucrose, in an animal or a human.

A "sweet flavoring agent", "sweet flavor entity", "sweetener", "sweet compound", or "sweet receptor activating compound" herein refers to a compound or ingestibly acceptable salt thereof that elicits a detectable sweet flavor in a subject, e.g., sucrose or a compound that activates a T1R2/T1R3 receptor in vitro. The subject may be a human or an animal.

A "sweet flavor modifier" or "sweet flavor modifying agent" herein refers to a compound or ingestibly acceptable salt or solvate thereof that modulates, including enhancing or potentiating, inducing, or blocking, the sweet taste of a sweet flavoring agents in an animal or a human. The sweet flavor modifier includes both sweet flavor enhancer and sweet flavoring agent.

A "sweet flavor enhancer" or "sweet flavor enhancing agent" herein refers to an enhancer of a sweet flavor wherein the term enhancer is the same as defined above.

A "sweet receptor activating compound" herein refers to a compound that activates a sweet receptor, such as a T1R2/T1R3 receptor. One example of a sweet receptor activating compound is a sweetener, such as sucrose.

A "sweet receptor modulating compound" herein refers to a compound that modulates (activates, block, or enhances/reduces activation of) a sweet receptor such as a T1R2/T1R3 receptor.

A "sweet receptor enhancing compound" herein refers to a compound that enhances or potentiates the effect of a sweet receptor activating compound, e.g., sucrose.

Although most sweet receptor enhancing compounds or sweet flavor enhancers, at its ligand enhancing concentration of use, do not result in substantial activation of the particular receptor by themselves, some of the sweet receptor enhancing compounds or sweet flavor enhancers, when used at a concentration higher than its ligand enhancing concentration, can also activate a particular receptor by themselves in addition to modulating (increase) the activation of the receptor. For example, some of the sweet receptor enhancing compounds or sweet flavor enhancers, when used at a concentration higher than their ligand enhancing concentrations, can also activate a sweet receptor, such as a T1R2/T1R3 receptor, acting as the receptor agonists.

A "sweet flavor modulating amount" herein refers to an amount of a compound of Formula (I) that is sufficient to alter (either increase or decrease) sweet taste in an ingestible composition, or a precursor thereof, sufficiently to be perceived by a human subject. In many embodiments of the invention, at least about 0.001 ppm of the present compound would need to be present in order for most human subjects to perceive a modulation of the sweet flavor of an ingestible composition comprising the present compound. A broad range of concentration that would typically be employed in order to economically provide a desirable degree of sweet flavor modulation can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor enhancing amount" herein refers to an amount of a compound that is sufficient to enhance the taste of flavoring agents, e.g., sucrose, in a ingestible composition, as perceived by an animal or a human. A broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm. In some embodiments, sweet flavor enhancing amount is the amount corresponding to ligand enhancing concentration(s) of a sweet flavor enhancer of the present invention.

A "sweet receptor modulating amount" herein refers to an amount of a compound that is sufficient to modulate (activate, enhance or block) a sweet taste receptor protein. In many embodiments of the invention, a sweet receptor modulating amount is at least about 1 µM, or at least about 1 nM, or at least about 10 nM, or at least about 100 nM (i.e. about 0.1 µM). A "T1R2/T1R3 receptor modulating or activating amount" is an amount of compound that is sufficient to modulate or activate a T1R2/T1R3 receptor. A "sweet receptor" is a taste receptor that can be modulated by a sweet compound. Preferably a sweet receptor is a G protein coupled receptor, and more preferably the sweet receptor is a T1R2/T1R3 receptor.

Compounds

In one embodiment, the present invention provides a compound having structural Formula (I) or (I'):

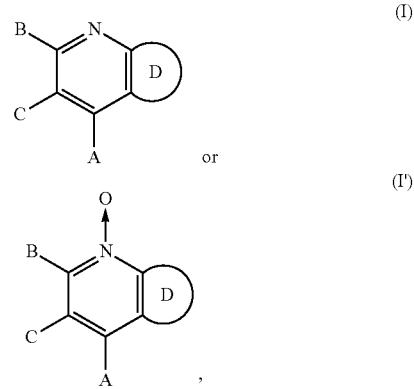

or a tautomer, salt, and/or solvate, wherein:

A is —OR$^1$, —NR$^1$C(O)R$^2$, —NHOR$^1$, —NR$^1$R$^2$, —NR$^1$CO$_2$R$^2$, —NR$^1$C(O)NR$^2$R$^3$, —NR$^1$C(S)NR$^2$R$^3$ or —NR$^1$C(=NH)NR$^2$R$^3$;

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^4$, —S(O)$_a$R$^4$, —NR$^4$R$^5$, —C(O)NR$^4$R$^5$, —CO$_2$R$^4$, —NR$^4$CO$_2$R$^5$, —NR$^4$C(O)NR$^5$R$^6$, —NR$^4$C(S)NR$^5$R$^6$, —NR$^4$C(=NH)NR$^5$R$^6$, —SO$_2$NR$^4$R$^5$, —NR$^4$SO$_2$R$^5$, —NR$^4$SO$_2$NR$^5$R$^6$, —B(OR$^4$)(OR$^5$), —P(O)(OR$^4$)(OR$^5$), or —P(O)(R$^4$)(OR$^5$);

C is —OR$^7$, —S(O)$_b$R$^7$, SO$_3$R$^7$, —C(O)NR$^7$R$^8$, —CO$_2$R$^7$, —NR$^7$CO$_2$R$^8$, —NR$^7$C(O)NR$^8$R$^9$, —NR$^7$C(=NH)NR$^8$R$^9$, —SO$_2$NR$^7$R$^8$, —NR$^7$SO$_2$R$^8$, —NR$^7$SO$_2$NR$^8$R$^9$, —B(OR$^7$)(OR$^8$), —P(O)(OR$^7$)(OR$^8$), —P(O)(R$^7$)(OR$^8$), or heteroaryl (for example, tetrazole);

D is an aryl, substituted aryl, heteroaryl, substituted heteroaryl, cycloalkyl, substituted cycloalkyl, cycloheteroalkyl or substituted cycloheteroalkyl ring wherein the ring is optionally fused to another aryl, substituted aryl, heteroaryl, substituted heteroaryl, cycloalkyl, substituted cycloalkyl, cycloheteroalkyl, or substituted cycloheteroalkyl ring;

a and b are independently 0, 1 or 2; and

R$^1$, R$^2$, R$^3$, R$^4$, R$^5$, R$^6$, R$^7$, R$^8$, and R$^9$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^1$ and R$^2$, R$^2$ and R$^3$, R$^4$ and R$^5$, R$^5$ and R$^6$, R$^7$; and R$^8$, or R$^8$ and R$^9$, together with the atoms to which they are bonded, form a cycloheteroalkyl or substituted cycloheteroalkyl ring.

In one embodiment of the present invention, the Formula (I) is subject to the following provisos:

(a) when D is substituted phenyl; B is hydrogen; C is —CO$_2$R$^7$; R$^7$; is hydrogen or alkyl; A is —NR$^1$R$^2$; and one of R$^1$ and R$^2$ is hydrogen; then the other of R$^1$ and R$^2$ is not substituted arylalkyl; and (b) when D is phenyl or substituted phenyl; C is —CO₂R⁷; R⁷; is alkyl; A is —NR¹R²; and R¹ and R² are both hydrogen; then B is not —CO₂R⁴; wherein R⁴ is alkyl.

In one embodiment of the present invention, the Formula (I) does not include the following compounds:

8-Bromo-4-(4-methoxybenzyl)amino-5-methoxyquinoline-3-carboxylic acid ethyl ester;
4-(4-Methoxybenzyl)amino-5-methoxyquinoline-3-carboxylic acid ethyl ester;
4-(4-Methoxybenzyl)amino-5-methoxyquinoline-3-carboxylic acid;
4-(4-Methoxybenzyl)amino-8-methoxyquinoline-3-carboxylic acid ethyl ester;
4-(4-Methoxybenzyl)amino-8-methoxyquinoline-3-carboxylic acid;
4-Amino-3-ethoxycarbonyl-2-ethoxycarbonylmethylquinoline; and
4-Amino-3-ethoxycarbonyl-2-ethoxycarbonylmethyl-5-methoxyquinoline.

In one embodiment of Formula (I), R¹ and R² are independently hydrogen, alkyl, substituted alkyl, aryl, substituted aryl, arylalkyl, acyl, substituted acyl, heteroalkyl, substituted heteroalkyl, heteroaryl, substituted heteroaryl, heteroarylalkyl or substituted heteroarylalkyl; or alternatively, R¹ and R², R² and R³, R⁴ and R⁵, R⁵ and R⁶, R⁷; and R⁸, or R⁸ and R⁹, together with the atoms to which they are bonded, form a cycloheteroalkyl or substituted cycloheteroalkyl ring.

In one embodiment of Formula (I), when B is substituted alkyl, then the substituent on the alkyl is not —C(O)OR^b; where R^b is alkyl.

In one embodiment of Formula (I), when B is substituted alkyl, then the substituent on the alkyl is selected from the group consisting of —R^a, halo, —O⁻, =O, —OR^b, —SR^b, —S⁻, =S, —NR^cR^c, =NR^b, =N—OR^b, trihalomethyl, —CF₃, —CN, —OCN, —SCN, —NO, —NO₂, =N₂, —N₃, —S(O)₂R^b, —S(O)₂NR^b, —S(O)₂O⁻, —S(O)₂OR^b, —OS(O)₂R^b, —OS(O)₂O⁻, —OS(O)₂OR^b, —P(O)(O⁻)₂, —P(O)(OR^b)(O⁻), —P(O)(OR^b)(OR^b), —C(O)R^b, —C(S)R^b, —C(NR^b)R^b, —C(O)O⁻, —C(S)OR^b, —C(O)NR^cR^c, —C(NR^b)NR^cR^c, —OC(O)R^b, —OC(S)R^b, —OC(O)O⁻, —OC(O)OR^b, —OC(S)OR^b, —NR^bC(O)R^b, —NR^bC(S)R^b, —NR^bC(O)O⁻, —NR^bC(O)OR^b, —NR^bC(S)OR^b, —NR^bC(O)NR^cR^c, —NR^bC(NR^b)R^b and —NR^bC(NR^b)NR^cR^c where R^a is selected from the group consisting of alkyl, cycloalkyl, heteroalkyl, cycloheteroalkyl, aryl, arylalkyl, heteroaryl and heteroarylalkyl; each R^b is independently hydrogen or R^a; and each R^c is independently R^b or alternatively, the two R^cs may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

In one embodiment of the present invention, the compounds of Formula (I) or (I') have a structural Formula (II) or (II'),

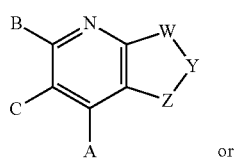

(II)

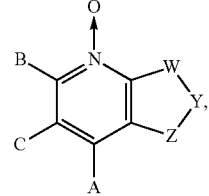

(II')

or a tautomer, salt, and/or solvate, wherein:
Y forms a single bond with either W or Z and a double bond with the other of W or Z;
W is —C(R¹⁰)—, —S—, —N—, —NR¹¹)—, or —O—;
Y is —C(R¹²)— or —N—;
Z is —C(R¹³)—, —S—, —N—, —NR¹⁴)—, or —O—;
R¹⁰ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —OR¹⁵, —S(O)_cR¹⁵, —NR¹⁵R¹⁶, —C(O)NR¹⁵R¹⁶, —CO₂R¹⁵, —SO₂NR¹⁵R¹⁶, —NR¹⁵SO₂R¹⁶, —P(O)(OR¹⁵)(OR¹⁶) or —P(O)(R¹⁵)(OR¹⁶);
R¹² is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —OR¹⁷, —S(O)_dR¹⁷, —OC(O)R¹⁷, —NR¹⁷R¹⁸, —C(O)NR¹⁷R¹⁸, —CO₂R¹⁷, —SO₂NR¹⁷R¹⁸, —NR¹⁷SO₂R¹⁸, —P(O)(OR¹⁷)(OR¹⁸) or —P(O)(R¹⁷)(OR¹⁸);
R¹³ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —OR¹⁹, —S(O)_eR¹⁹, —OC(O)R¹⁹, —NR¹⁹R²⁰, —C(O)NR¹⁹R²⁰, —C(O)R¹⁹, —CO₂R¹⁷, —SO₂NR¹⁹R²⁰, —NR¹⁹SO₂R²⁰, —P(O)(OR¹⁹)(OR²⁰) or —P(O)(R¹⁹)(OR²⁰); or alternatively R¹⁰ and R¹², or R¹² and R¹³, together with the atoms to which are attached, form a cycloalkyl, substituted cycloalkyl, cycloheteroalkyl or substituted cycloheteroalkyl ring;
c, d and e are independently 0, 1, or 2;
R¹¹ and R¹⁴ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and
R¹⁵, R¹⁶, R¹⁷, R¹⁸, R¹⁹, or R²⁰ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R¹⁵ and R¹⁶, R¹⁷ and R¹⁸, or R¹⁹ and R²⁰, together with the atoms to which are attached, form a cycloheteroalkyl or substituted cycloheteroalkyl ring; and
with the following provisos:
(a) when W is —O— or —S— or —NR¹¹—, then Z is —C(R¹³)— or —N—;
(b) when Z is —O— or —S— or —NR¹⁴—, then W is —C(R¹⁰)— or —N—; and
(c) when W is —C(R¹⁰)— or —N—, then Z cannot be —C(R¹³)— or —N—.

In one embodiment of the present invention, the compounds of Formula (II) or (II') have a structural Formula (IIa) or (IIa'),

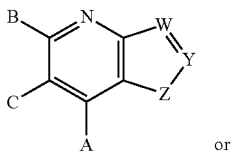
(IIa)

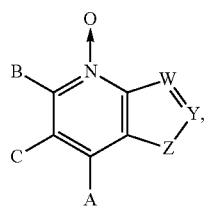
(IIa')

or a tautomer, salt, and/or solvate, wherein, W is —C(R$^{10}$)—, or —N—; Y is —C(R$^{12}$)— or —N—; and Z is —S—, —NR$^{14}$)—, or —O—.

In one embodiment of the present invention, the compounds of Formula (II) or (II') have a structural Formula (IIb) or (IIb'),

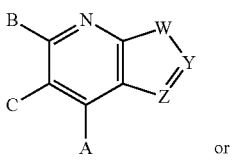
(IIb)

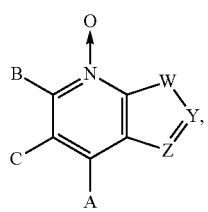
(IIb')

or a tautomer, salt, and/or solvate, wherein, W is —S—, —NR$^{11}$)—, or —O—; Y is —C(R$^{12}$)— or —N—; and Z is —C(R$^{13}$)—, or —N—.

In one embodiment of the present invention, the compounds of Formula (I) or (I') have a structural Formula (III) or (III'),

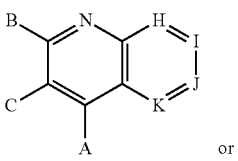
(III)

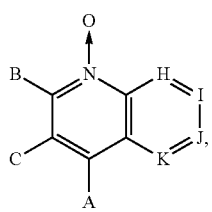
(III')

or a tautomer, salt, and/or solvate thereof, wherein:

H is —C(R$^{21}$)— or —N—;

I is —C(R$^{22}$) or —N—;

J is —C(R$^{23}$)— or —N—;

K is —C(R$^{24}$)— or —N—;

R$^{21}$ is hydrogen, alkyl, substituted alkyl, halo, —CN, —OR$^{25}$;

R$^{22}$ is hydrogen, alkyl, substituted alkyl, halo, —CN, —OR$^{27}$;

R$^{23}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —OR$^{29}$, —S(O)$_f$R$^{29}$, —OC(O)R$^{29}$, —NR$^{29}$R$^{30}$, —C(O)NR$^{29}$R$^{30}$, —CO$_2$R$^{29}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

R$^{24}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —OR$^{31}$, —S(O)$_g$R$^{31}$, —OC(O)R$^{31}$, —NR$^{31}$R$^{32}$, —C(O)NR$^{31}$R$^{32}$, —C(O)R$^{31}$, —CO$_2$R$^{31}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$); or alternatively R$^{23}$ and R$^{24}$, taken together with the atom to which they are attached, form a cycloalkyl, substituted cycloalkyl, cycloheteroalkyl, or substituted cycloheteroalkyl ring;

f and g are independently 0, 1 or 2; and

R$^{25}$, R$^{26}$, R$^{27}$, R$^{28}$, R$^{29}$, R$^{30}$, R$^{31}$, and R$^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively R$^{25}$ and R$^{26}$, R$^{27}$ and R$^{28}$, R$^{29}$ and R$^{30}$, or R$^{31}$ and R$^{32}$, together with the atoms to which they are attached, form a cycloheteroalkyl or substituted cycloheteroalkyl ring;

with the proviso that at most, two of H, I, J and K are —N—.

In one embodiment of Formula (III), one or two of H, I, J and K are —N—.

In one embodiment of Formula (III), H is —N—, I is —C(R$^{22}$)—, J is —C(R$^{23}$)—, and K is —C(R$^{24}$)—.

In one embodiment of Formula (III), H is —C(R$^{21}$)—, I is —N—, J is —C(R$^{23}$)—, and K is —C(R$^{24}$)—.

In one embodiment of Formula (III), H is —C(R$^{21}$)—, I is —C(R$^{22}$)—, J is —N—, and K is —C(R$^{24}$)—.

In one embodiment of Formula (III), H is —C(R$^{21}$)—, I is —C(R$^{22}$), J is —C(R$^{23}$)—, and K is —N—.

In one embodiment of Formula (III), H and I are —N—.

In one embodiment of Formula (III), H and J are —N—.

In one embodiment of Formula (III), H and K are —N—.

In one embodiment of Formula (III), I and J are —N—.

In one embodiment of Formula (III), I and K are —N—.

In one embodiment of Formula (III), J and K are —N—.

In one embodiment of the present invention, the compounds of Formula (III) or (III') have a structural Formula (IIIa) or (IIIa'),

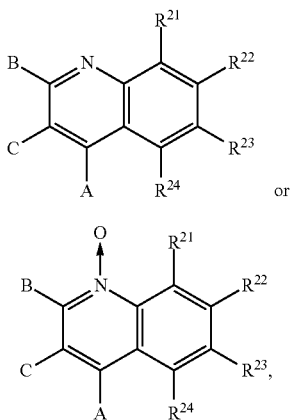

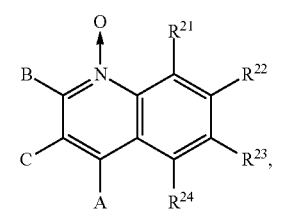

or a tautomer, salt, and/or solvate thereof.

In one embodiment of Formula (IIIa), two or three of $R^{21}$, $R^{22}$, $R^{23}$, and $R^{24}$ are hydrogen.

In one embodiment of Formula (IIIa), $R^{21}$ is hydrogen; $R^{22}$ is hydrogen, alkyl, substituted alkyl, halo, —CN, or —$OR^{27}$; $R^{23}$ is hydrogen, alkyl, substituted alkyl, —CN, —$OR^{29}$, —$S(O)_gR^{29}$, —$OC(O)R^{29}$, —$NR^{29}R^{30}$, —$C(O)NR^{29}R^{30}$, —$C(O)R^{29}$, —$CO_2R^{29}$, —$SO_2NR^{29}R^{30}$, or —$NR^{29}SO_2R^{30}$; $R^{24}$ is hydrogen, alkyl, substituted alkyl, —CN, —$OR^{31}$, —$S(O)_gR^{31}$, —$OC(O)R^{31}$, —$NR^{31}R^{32}$, —$C(O)NR^{31}R^{32}$, —$C(O)R^{31}$, —$CO_2R^{31}$, —$SO_2NR^{31}R^{32}$, or —$NR^{31}SO_2R^{32}$; or alternatively $R^{23}$ and $R^{24}$, taken together with the atoms to which they are attached, form a cycloalkyl, substituted cycloalkyl, cycloheteroalkyl, or substituted cycloheteroalkyl ring; and $R^{27}$, $R^{29}$, $R^{30}$, $R^{31}$, and $R^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively $R^{25}$ and $R^{26}$, $R^{27}$ and $R^{28}$, $R^{29}$ and $R^{30}$, or $R^{31}$ and $R^{32}$, together with the atoms to which they are attached, form a cycloheteroalkyl or substituted cycloheteroalkyl ring.

In one embodiment of Formula (IIIa), $R^{21}$ and $R^{22}$ are all hydrogen.

In one embodiment of Formula (IIIa), $R^{23}$ and $R^{24}$, taken together with the atom to which they are attached, form a cycloalkyl, substituted cycloalkyl, cycloheteroalkyl, or substituted cycloheteroalkyl ring.

In one embodiment of Formula (IIIa), $R^{23}$ and $R^{24}$, taken together with the atom to which they are attached, form a substituted cycloheteroalkyl ring containing one or more substituents selected from the group consisting of —$R^a$, halo, —$O^-$, $=O$, —$OR^b$, —$SR^b$, —$S^-$, $=S$, —$NR^cR^c$, $=NR^b$, $=N-OR^b$, trihalomethyl, —$CF_3$, —CN, —OCN, —SCN, —NO, —$NO_2$, $=N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(O)OR^b$, —$C(S)R^b$, —$C(NR^b)R^b$, —$C(O)O^-$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$—$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S; or alternatively, two of the substituents on the cycloheteroalkyl ring, together with the atoms to which they are bonded, form a cycloalkyl, substituted cycloalkyl, cycloheteroalkyl, or substituted cycloheteroalkyl ring.

In one embodiment of Formula (IIIa), $R^{21}$, $R^{22}$, $R^{23}$, and $R^{24}$ are all hydrogen.

In one embodiment of Formula (IIIa), A is —$OR^1$, —$NR^1C(O)R^2$, —$NHOR^1$, —$NR^1R^2$, —$NR^1$, —$NR^1CO_2R^2$, —$NR^1C(O)NR^2R^3$, —$NR^1CSNR^2R^3$, or —$NR^1C(=NH)NR^2R^3$.

In one embodiment of Formula (IIIa), C is —$S(O)_bR^7$, $SO_3R^7$, —$C(O)NR^7R^8$, —$CO_2R^7$, —$NR^7CO_2R^8$, —$NR^7C(O)NR^8R^9$, —$NR^7C(S)NR^8R^9$, —$NR^7C(=NH)NR^8R^9$, —$SO_2NR^7R^8$, —$NR^7SO_2R^8$, —$NR^7SO_2NR^8R^9$, —$B(OR^7)(OR^8)$, —$P(O)(OR^7)(OR^8)$, or —$P(O)(R^7)(OR^8)$.

In one embodiment of Formula (IIIa), B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl.

In one embodiment of Formula (IIIa), three of $R^{21}$, $R^{22}$, $R^{23}$, and $R^{24}$ are hydrogen; A is —$OR^1$, —$NR^1C(O)R^2$, —$NHOR^1$, —$NR^1R^2$, —$NR^1CO_2R^2$, —$NR^1C(O)NR^2R^3$, —$NR^1C(S)NR^2R^3$, or —$NR^1C(=NH)NR^2R^3$; C is —$S(O)_bR^7$, $SO_3R^7$, —$C(O)NR^7R^8$, —$CO_2R^7$, —$NR^7CO_2R^8$, —$NR^7C(O)NR^8R^9$, —$NR^7C(S)NR^8R^9$, —$NR^7C(=NH)NR^8R^9$, —$SO_2NR^7R^8$, —$NR^7SO_2R^8$, —$NR^7SO_2NR^8R^9$, —$B(OR^7)(OR^8)$, —$P(O)(OR^7)(OR^8)$, or —$P(O)(R^7)(OR^8)$ or tetrazole; B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl.

In one embodiment of the present invention, the compounds of Formula (IIIa) or (IIIa') have a structural Formula (IIIb) or (IIIb'),

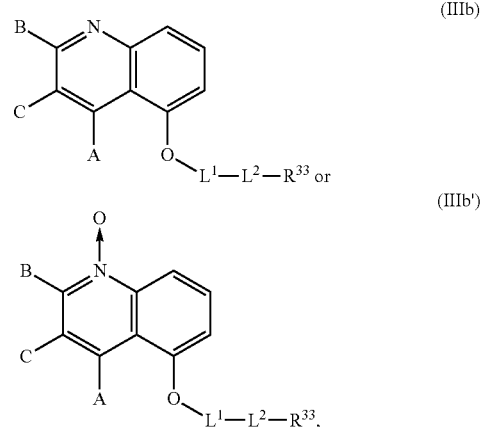

or a tautomer, salt, and/or solvate thereof; wherein
$L^1$ is alkylene or substituted alkylene;
$L^2$ is —$NR^{34}$—, —O—, —S—, —$NR^{34}$—C(O)—, —C(O)—$NR^{34}$—, —O—C(O)—, —C(O)—O—, —$NR^{34}$—C(O)—O—, —O—C(O)—$NR^{34}$—, —$NR^{34}$—C(O)—$NR^{35}$—, —O—C(O)—O—, -heterocyclylene-C(O)—, or -(substituted heterocyclylene)-C(O)—;

$R^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and $R^{34}$ and $R^{35}$ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

In one embodiment of the present invention, the compounds of Formula (IIIb) or (IIIb') have a structural Formula (IIIc), (IIIc'), (IIId), or (IIId'),

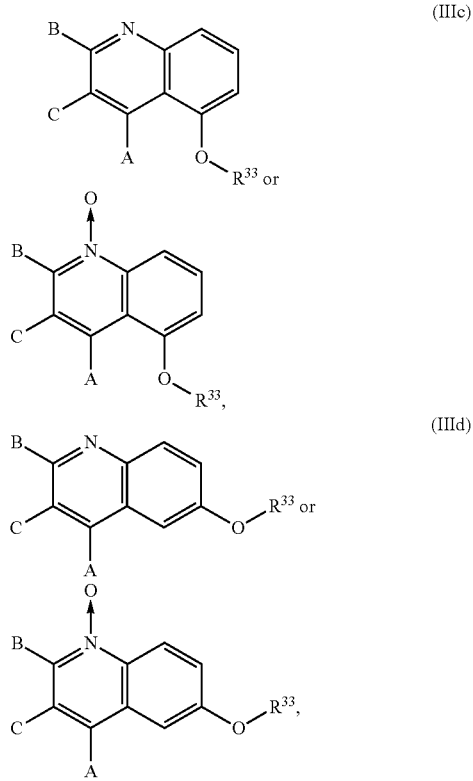

or a tautomer, salt, and/or solvate thereof; wherein $R^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

In one embodiment of Formula (IIIc) or (IIId), $R^{33}$ is alkyl, substituted alkyl, carbocyclyl, substituted carbocyclyl; heterocyclyl, substituted heterocyclyl, heteroalkyl, or substituted heteroalkyl.

In one embodiment of Formula (IIIb), (IIIc), or (IIId), A is —OR$^1$, —NR$^1$C(O)R$^2$, —NHOR$^1$, —NR$^1$R$^2$, —NR$^1$CO$_2$R$^2$, —NR$^1$C(O)NR$^2$R$^3$, —NR$^1$CSNR$^2$R$^3$, or —NR$^1$C(=NH)NR$^2$R$^3$.

In one embodiment of Formula (IIIb), (IIIc), or (IIId), C is —S(O)$_b$R$^7$, SO$_3$R$^7$, —C(O)NR$^7$R$^8$, —CO$_2$R$^7$, —NR$^7$CO$_2$R$^8$, —NR$^7$C(O)NR$^8$R$^9$, —NR$^7$C(S)NR$^8$R$^9$, —NR$^7$C(=NH)NR$^8$R$^9$, —SO$_2$NR$^7$R$^8$, —NR$^7$SO$_2$R$^8$, —NR$^7$SO$_2$NR$^8$R$^9$, —B(OR$^7$)(OR$^8$), —P(O)(OR$^7$)(OR$^8$), or —P(O)(R$^7$)(OR$^8$).

In one embodiment of Formula (IIIb), (IIIc), or (IIId), B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl.

In one embodiment of Formula (IIIb), A is —OR$^1$, —NHOR$^1$, or —NR$^1$R$^2$; B is hydrogen, alkyl, substituted alkyl, aryl, or substituted aryl; C is —SO$_3$R$^7$, —C(O)NR$^7$R$^8$, —CO$_2$R$^7$, —SO$_2$NR$^7$R$^8$, —B(OR$^7$)(OR$^8$), —P(O)(OR$^7$)(OR$^8$), or —P(O)(R$^7$)(OR$^8$); L$^1$ is alkylene or substituted alkylene; L$^2$ is —NR$^{34}$—, —O—, —NR$^{34}$—C(O)—, —C(O)—NR$^{34}$—, —O—C(O)—, —C(O)—O—, -heterocyclylene-C(O)—, or -(substituted heterocyclylene)-C(O)—; $R^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and $R^{34}$ and $R^{35}$ are independently hydrogen, alkyl, or substituted alkyl.

In one embodiment of Formula (IIIc) or (IIId), A is —OR$^1$, —NHOR$^1$, or —NR$^1$R$^2$; B is hydrogen, alkyl, substituted alkyl, aryl, or substituted aryl; C is —SO$_3$R$^7$, —C(O)NR$^7$R$^8$, —CO$_2$R$^7$, —SO$_2$NR$^7$R$^8$, —B(OR$^7$)(OR$^8$), —P(O)(OR$^7$)(OR$^8$), or —P(O)(R$^7$)(OR$^8$); $R^{33}$ is alkyl, substituted alkyl, carbocyclyl, substituted carbocyclyl; heterocyclyl, substituted heterocyclyl, heteroalkyl, or substituted heteroalkyl.

In some specific embodiments of the present invention, the compound is selected from the group consisting of

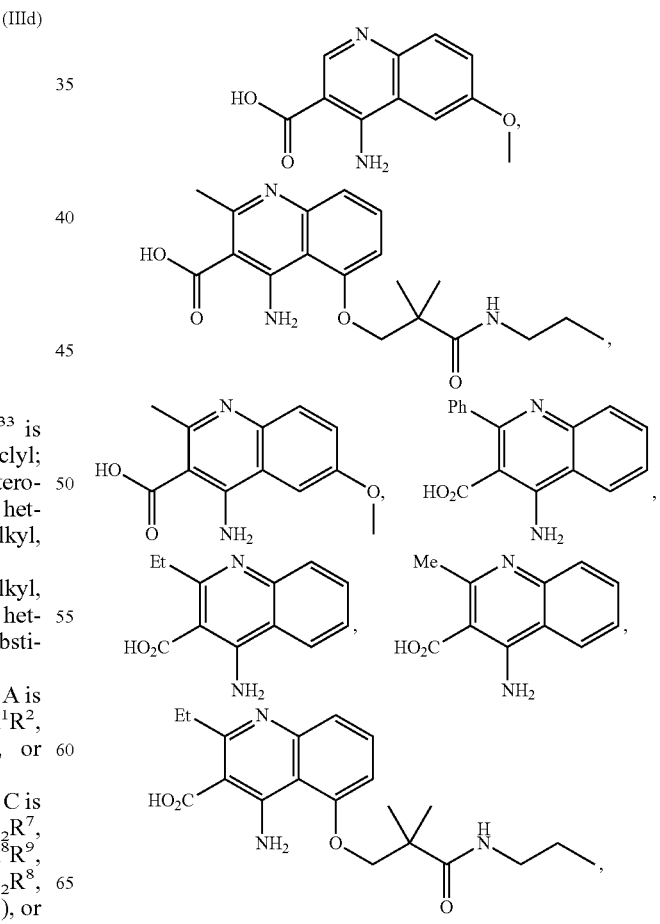

-continued
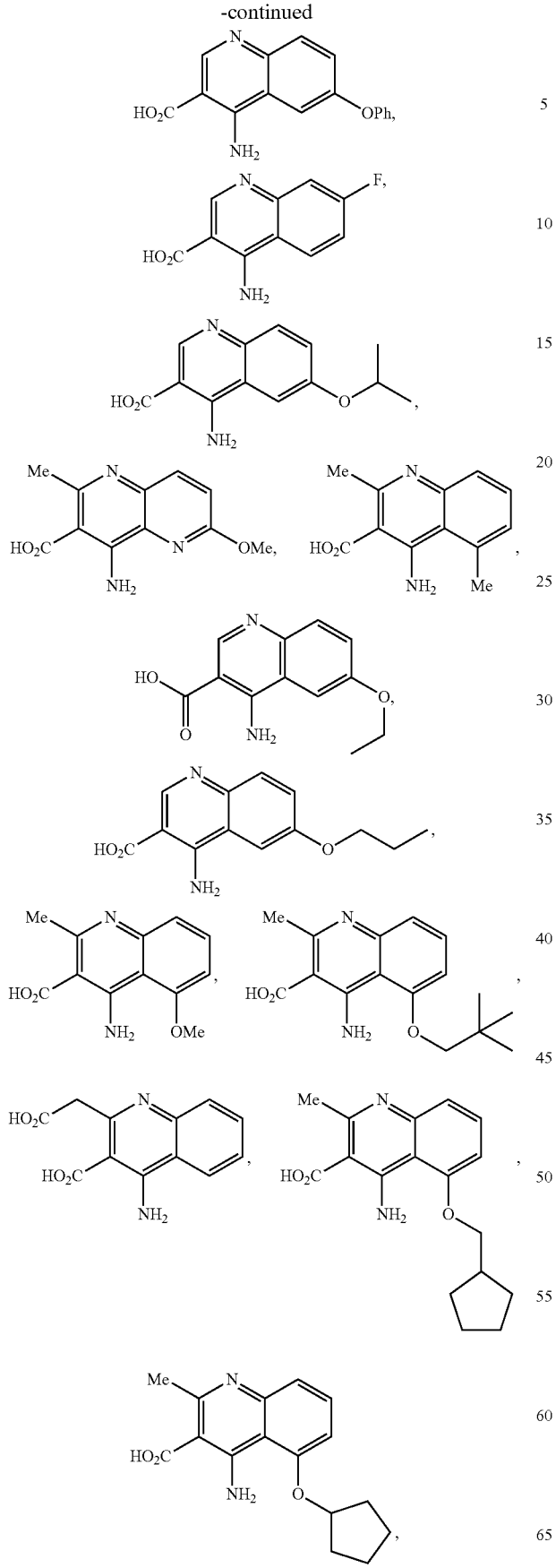
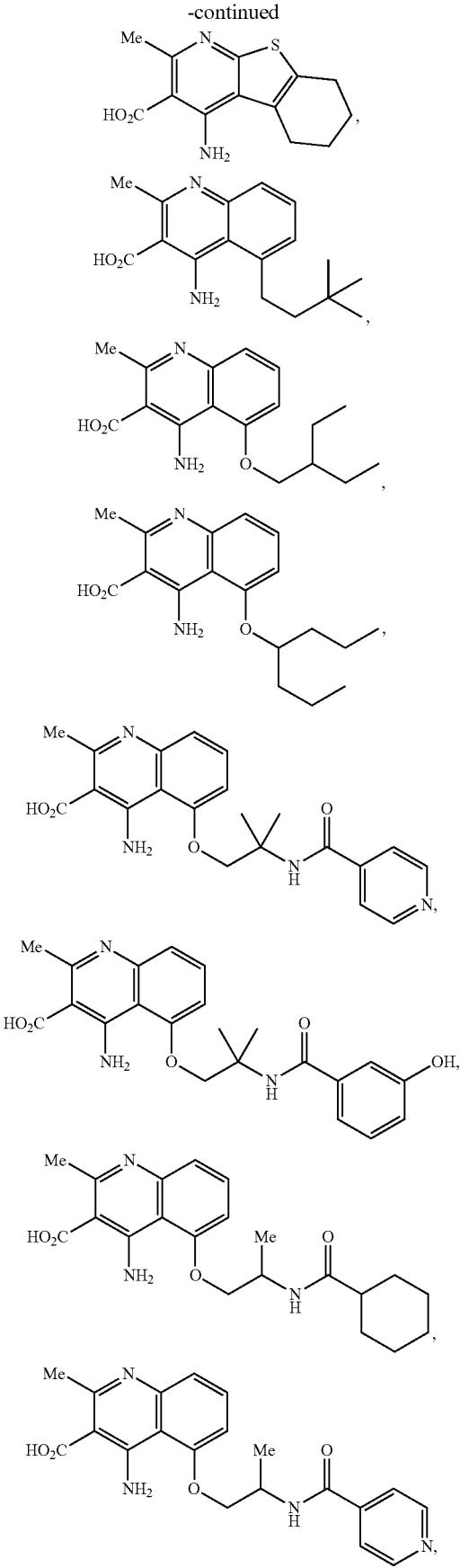

-continued
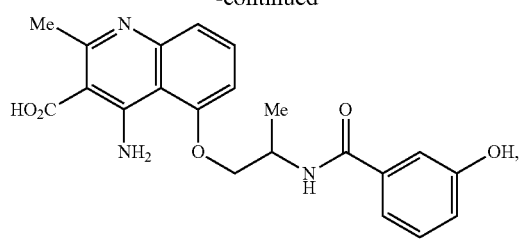
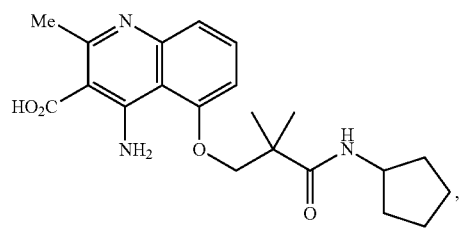
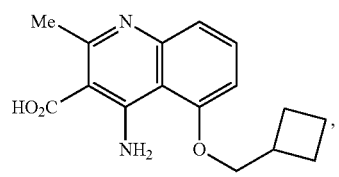
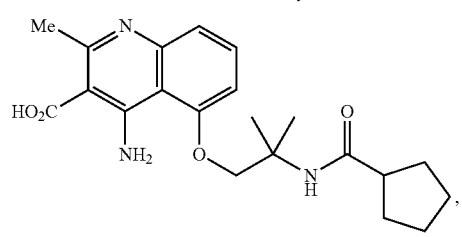
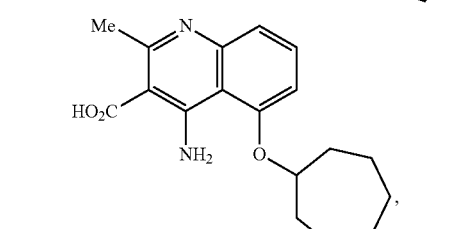
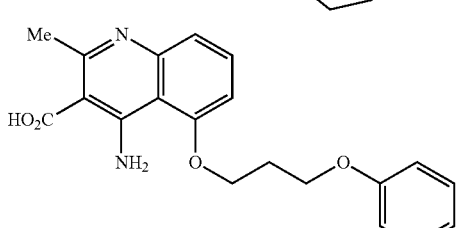
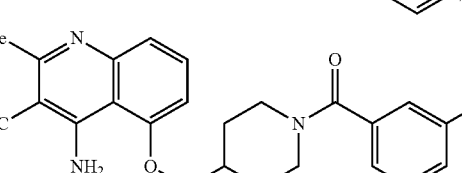
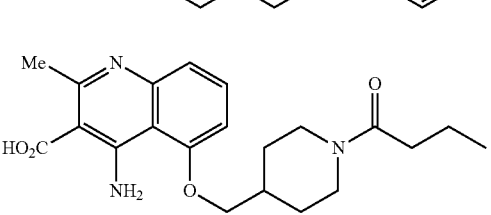
-continued
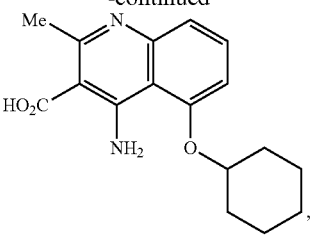
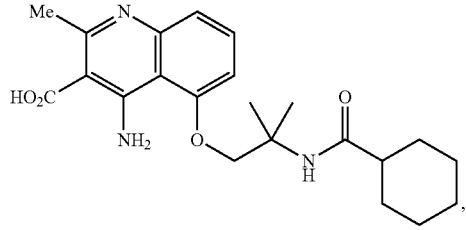
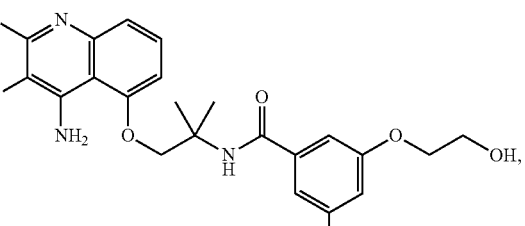
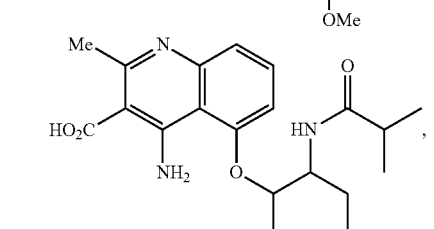
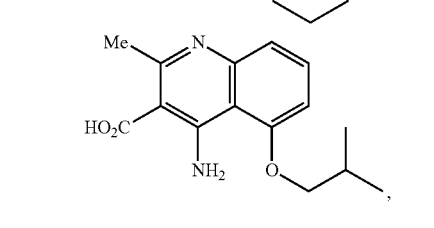
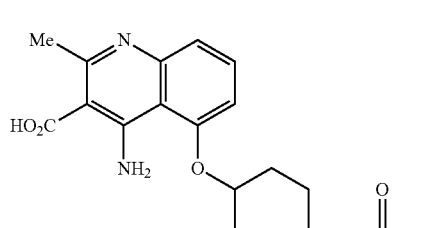
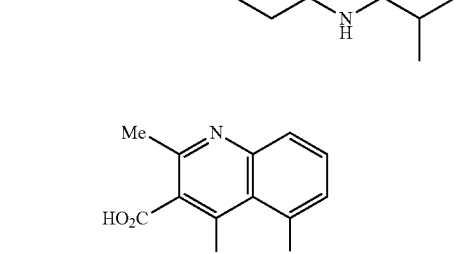

25
-continued
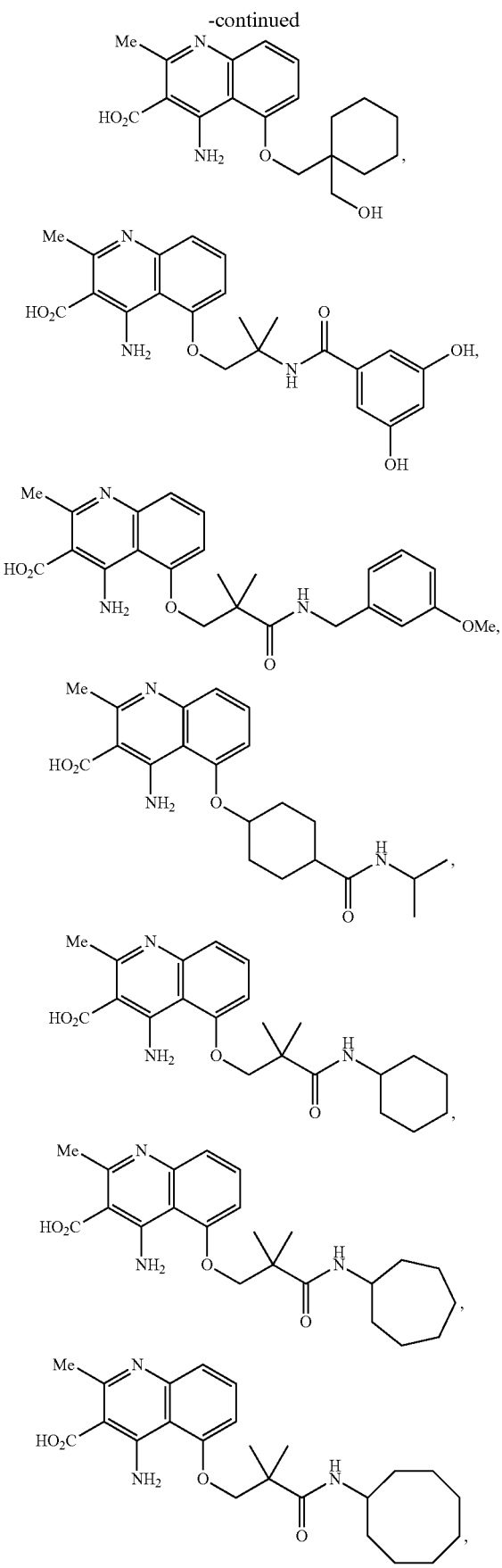
26
-continued
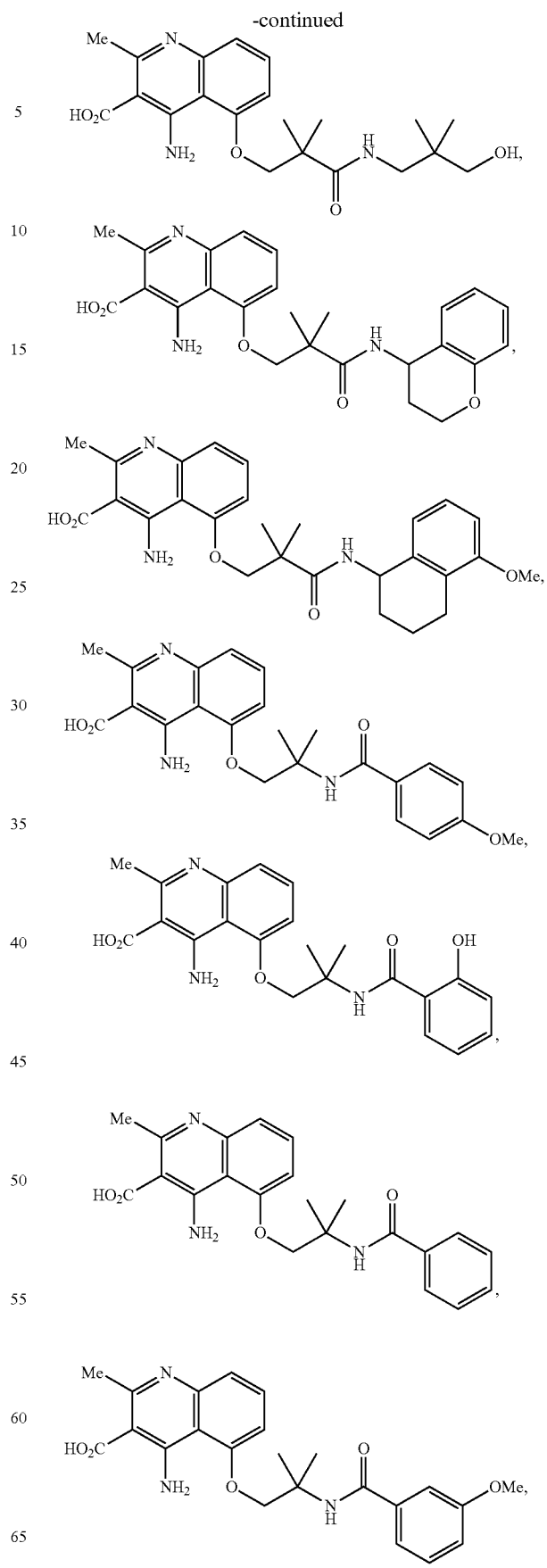

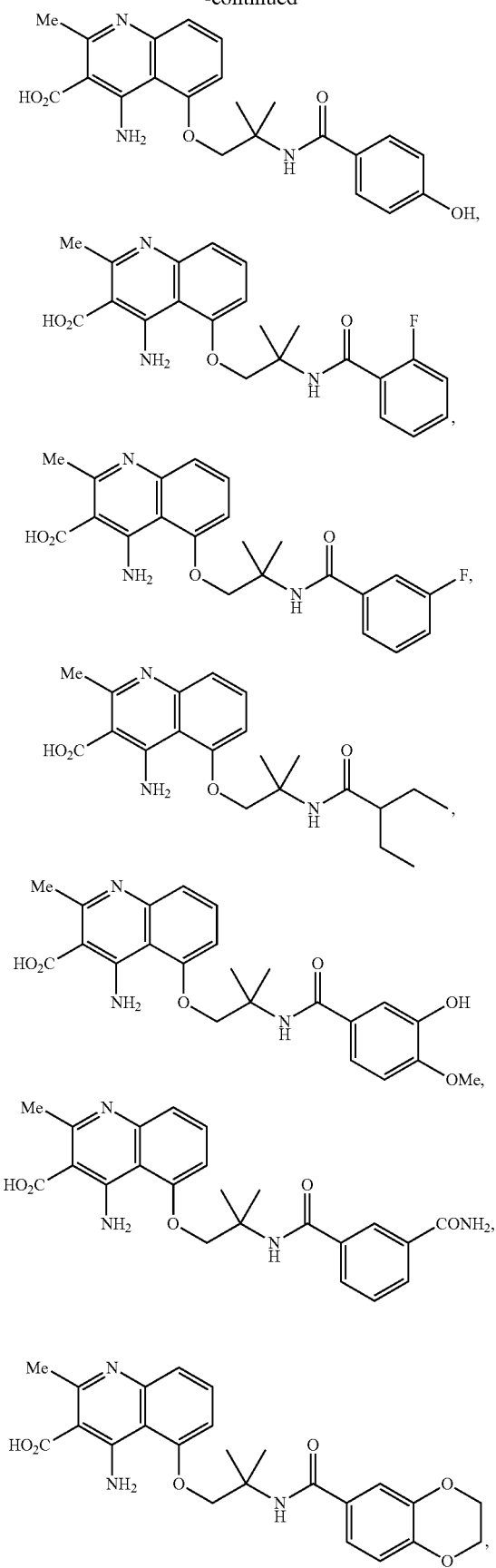
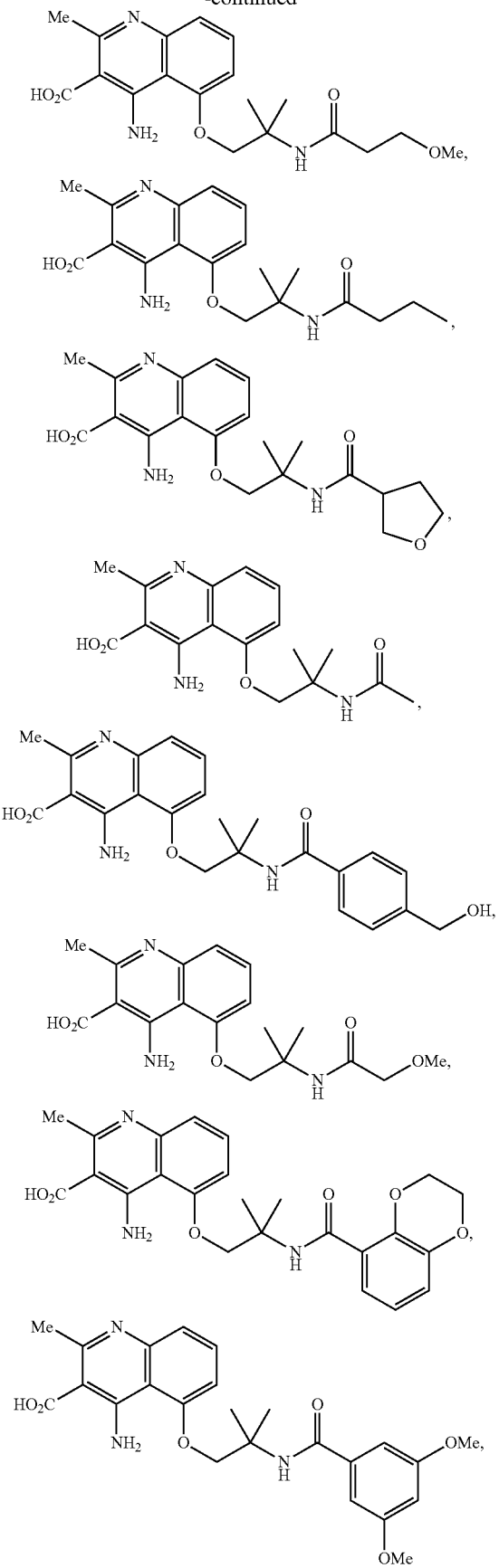

29
-continued
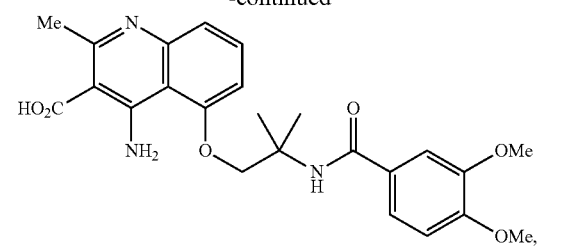
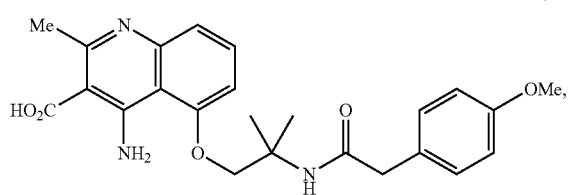
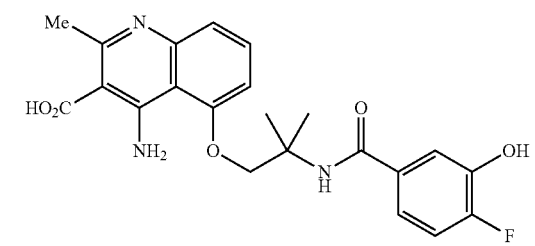
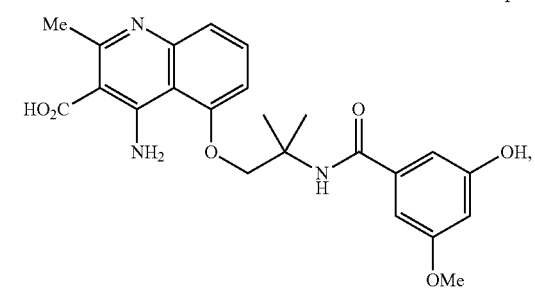
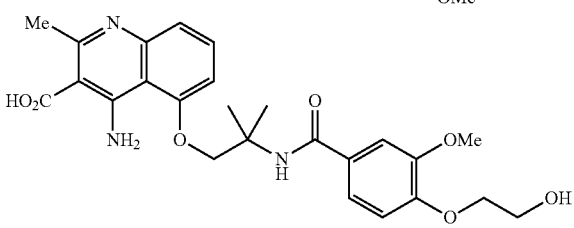
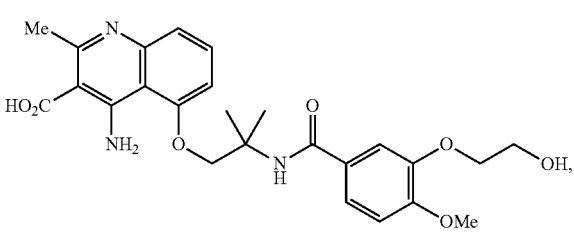
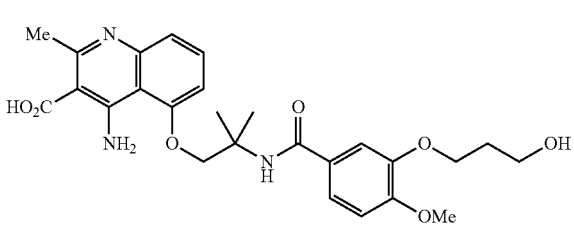
30
-continued
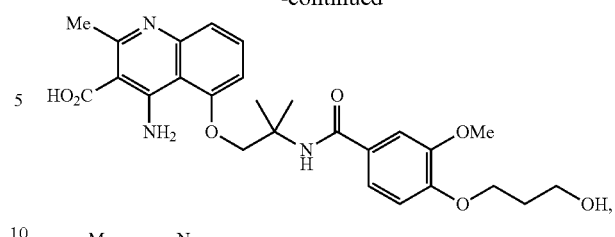
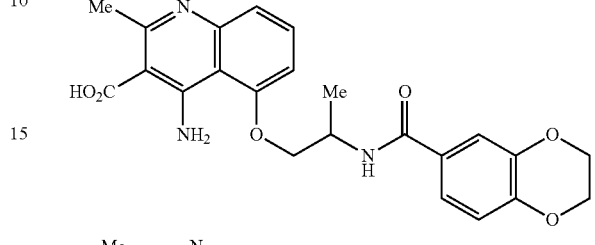
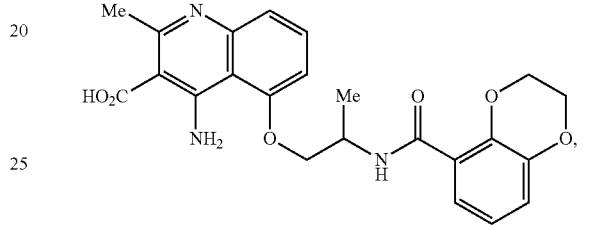
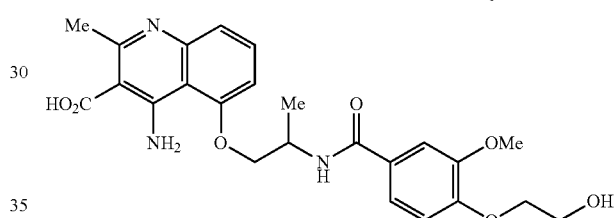
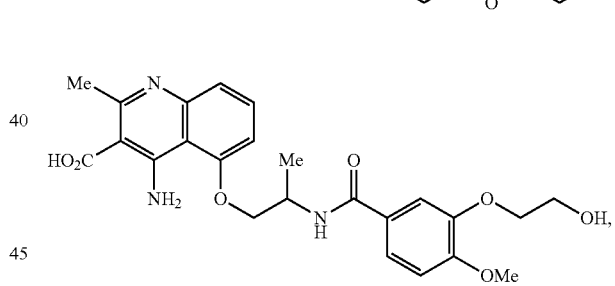
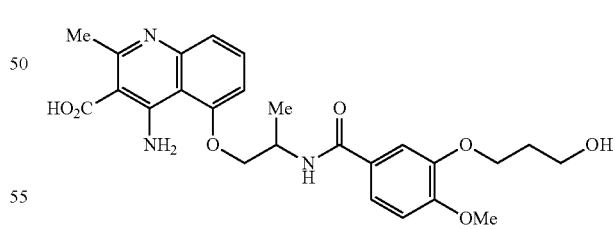
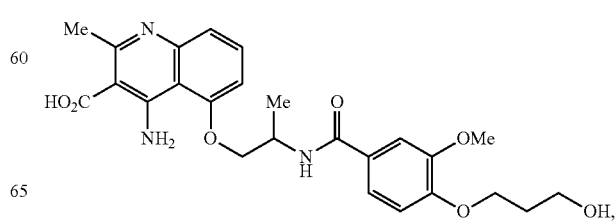

31
-continued
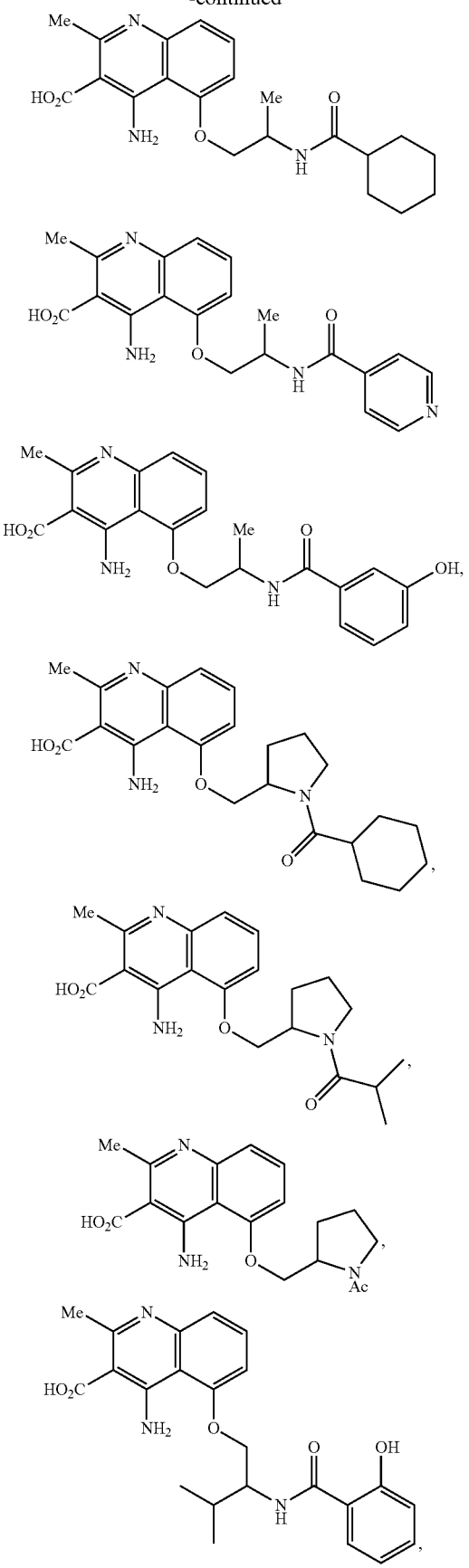
32
-continued
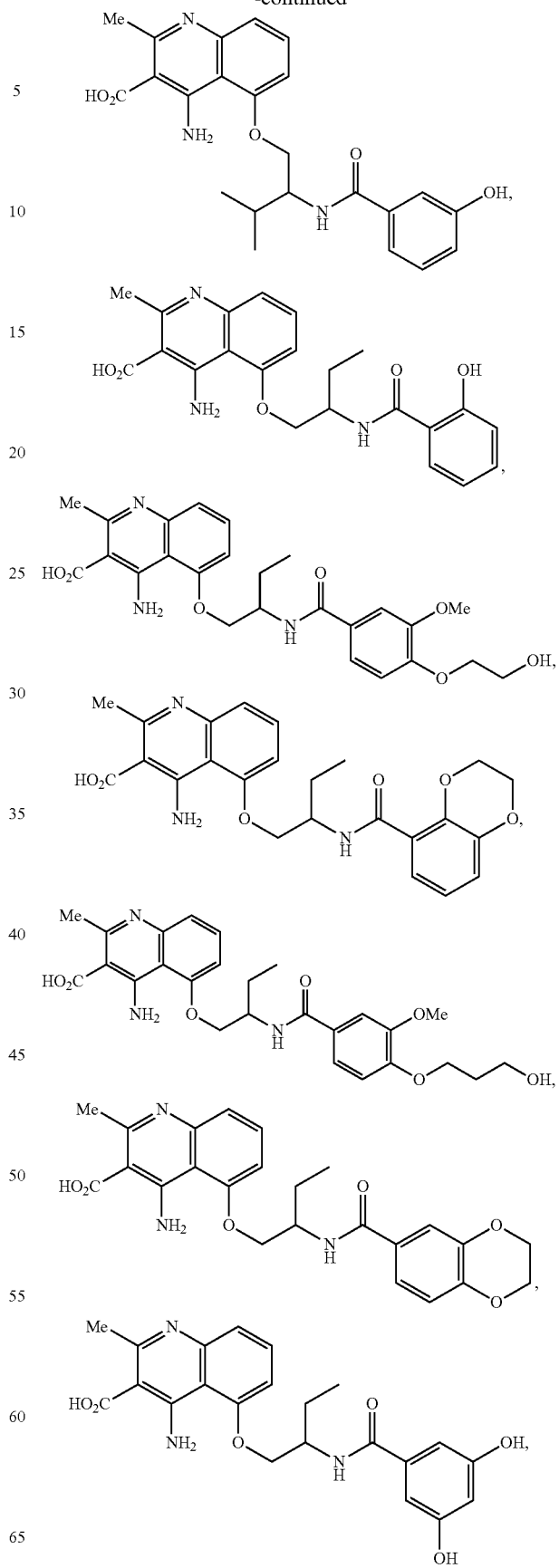

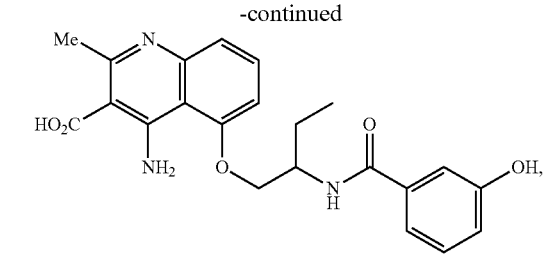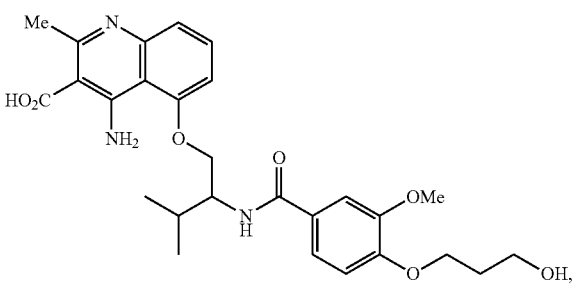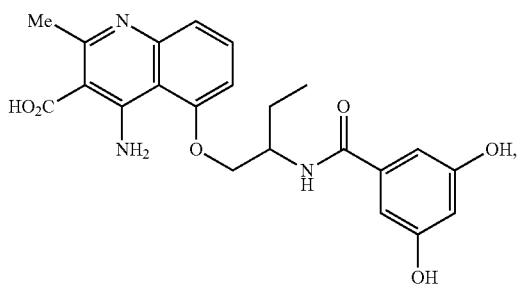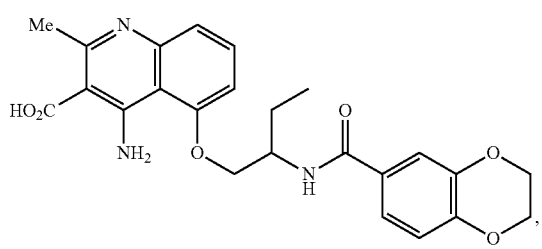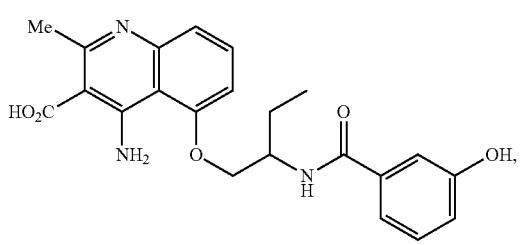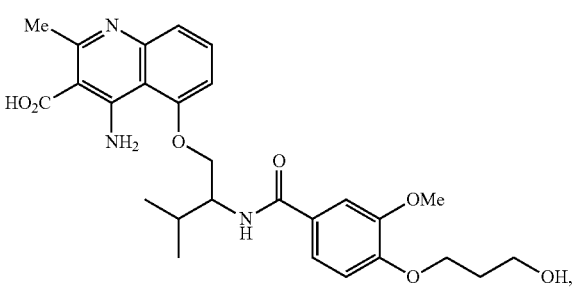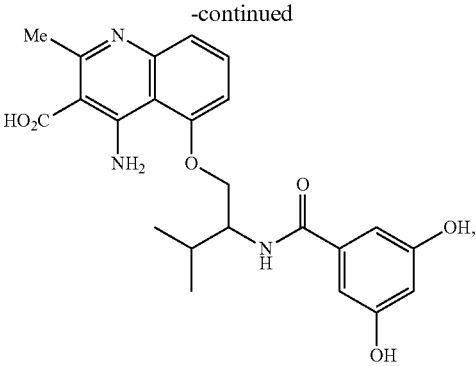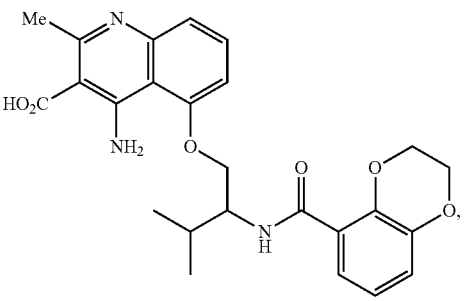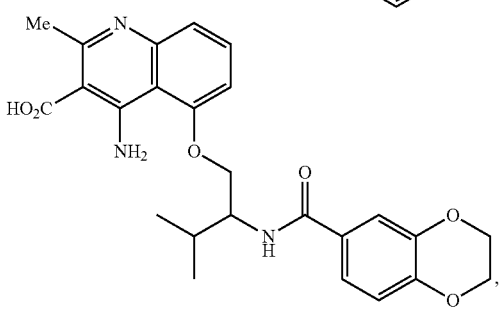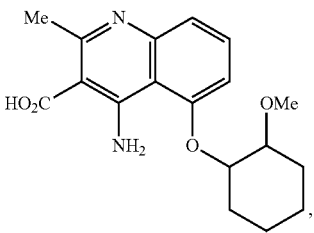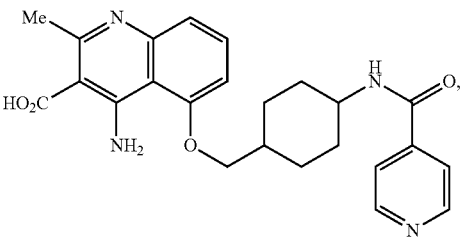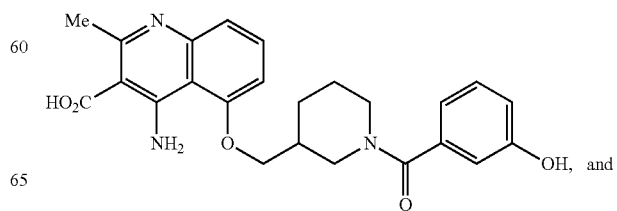

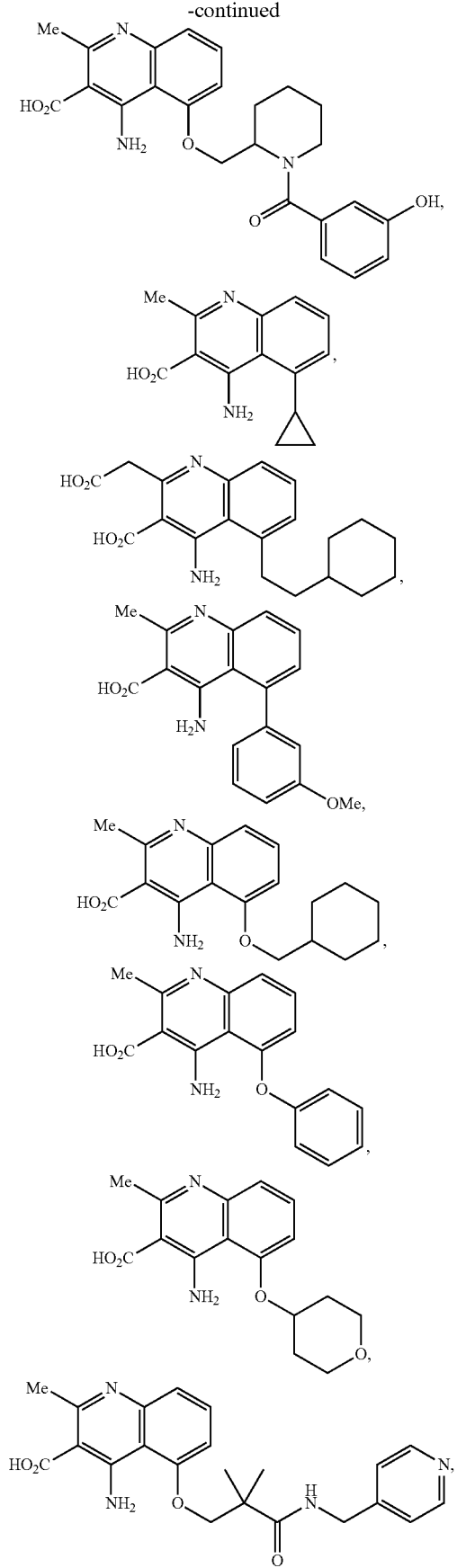
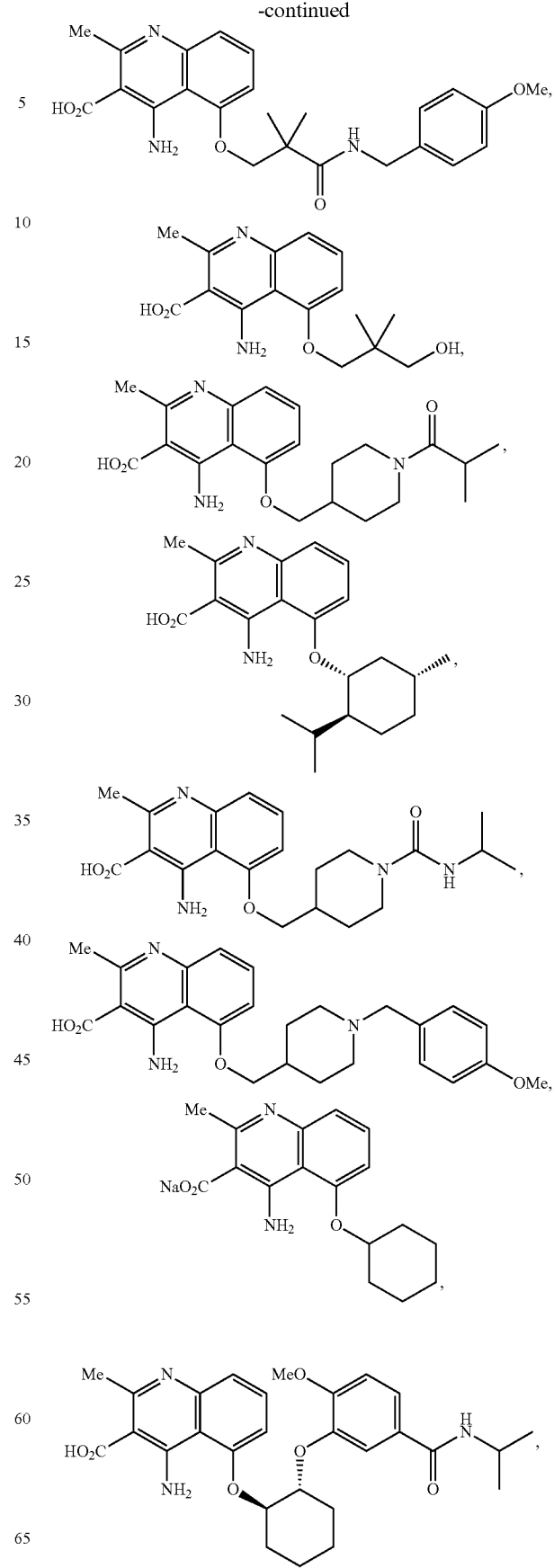

-continued

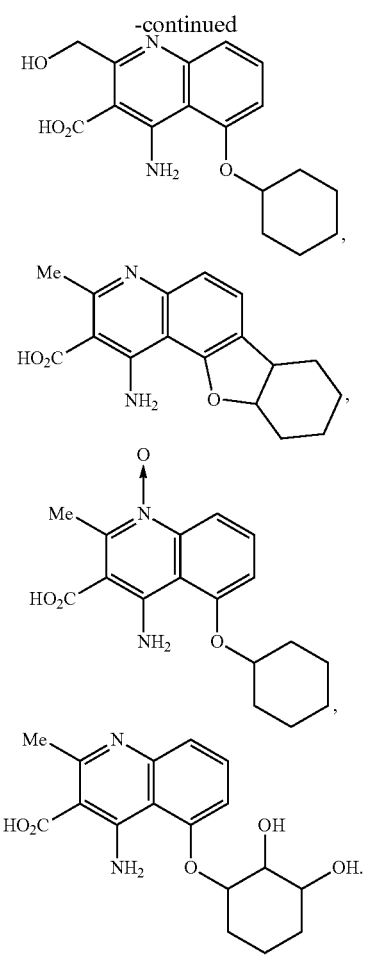

In another embodiment, the present invention provides a method for preparing a compound of Formula (IV):

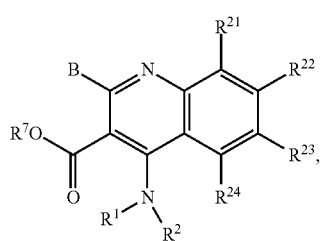

(IV)

wherein

B is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl;

$R^1$, $R^2$, and $R^7$; are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; or alternatively, $R^1$ and $R^2$, together with the atoms to which they are bonded, form a cycloheteroalkyl or substituted cycloheteroalkyl ring;

$R^{21}$ is hydrogen, alkyl, substituted alkyl, halo, —CN, —$OR^{25}$;

$R^{22}$ is hydrogen, alkyl, substituted alkyl, halo, —CN, —$OR^{27}$;

$R^{23}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —$OR^{29}$, —$S(O)_fR^{29}$, —$OC(O)R^{29}$, —$NR^{29}R^{30}$, —$C(O)NR^{29}R^{30}$, —$CO_2R^{29}$, —$SO_2NR^{29}R^{30}$, —$NR^{29}SO_2R^{30}$, —$B(OR^{29})(OR^{30})$, —$P(O)(OR^{29})(OR^{30})$ or —$P(O)(R^{29})(OR^{30})$;

$R^{24}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —$OR^{31}$, —$S(O)_gR^{31}$, —$OC(O)R^{31}$, —$NR^{31}R^{32}$, —$C(O)NR^{31}R^{32}$, —$C(O)R^{31}$, —$CO_2R^{31}$, —$SO_2NR^{31}R^{32}$, —$NR^{31}SO_2R^{32}$, —$B(OR^{31})(OR^{32})$, —$P(O)(OR^{31})(OR^{32})$ or —$P(O)(R^{31})(OR^{32})$; or alternatively $R^{23}$ and $R^{24}$, taken together with the atom to which they are attached, form a cycloalkyl, substituted cycloalkyl, cycloheteroalkyl, or substituted cycloheteroalkyl ring;

f and g are independently 0, 1 or 2; and $R^{25}$, $R^{26}$, $R^{27}$, $R^{28}$, $R^{29}$, $R^{30}$, $R^{31}$, and $R^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; or alternatively $R^{25}$ and $R^{26}$, $R^{27}$ and $R^{28}$, $R^{29}$ and $R^{30}$, or $R^{31}$ and $R^{32}$, together with the atoms to which they are attached, form a cycloheteroalkyl or substituted cycloheteroalkyl ring.

The method comprises reacting a compound of Formula (IVa):

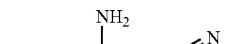

(IVa)

with a compound of Formula (IVb):

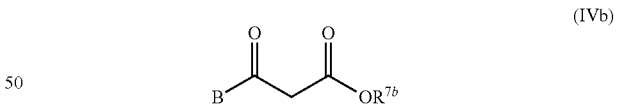

(IVb)

in the presence of a Lewis acid in an anhydrous and non-polar solvent; wherein $R^{7b}$ is alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; and $R^{21}$, $R^{22}$, $R^{23}$, and $R^{24}$, are the same as defined in Formula (IV).

When $R^7$; in Formula (IV) is hydrogen, then the compound may be obtained by hydrolyzing the corresponding compound where $R^7$; is alkyl or substituted alkyl, which in turn can be prepared from the reaction of the compounds of Formulae (IVa) and (IVb). Such a hydrolyzation condition may be basic, acidic, or any condition known to one skilled in the art.

By "Lewis acid", it is meant a compound that is an electron-pair acceptor and therefore able to react with a Lewis base to form a Lewis adduct, by sharing the electron pair furnished by the Lewis base. One illustrative example is that the reaction of trimethylboron (Lewis acid) and ammonia (Lewis base) to give the adduct $Me_3BNH_3$. The Lewis acid suitable for the reaction of compounds of Formulae (IVa) and (IVb) may be any Lewis acid known to one skilled in the art. In one specific embodiment, the Lewis acid is a metal halide, for example, stannic chloride, boron trihalides, or aluminium chloride.

Solvents for carrying out chemical reactions can be broadly classified into two categories: polar and nonpolar. Generally, the dielectric constant of the solvent provides a rough measure of a solvent's polarity. Solvents with a dielectric constant of less than 15 are generally considered to be nonpolar. Examples of nonpolar solvents include, but are not limited to, pentane, cyclopentane, hexane, cyclohexane, benzene, toluene, 1,4-dioxane, chloroform, diethyl ether, and a combination thereof.

In one embodiment of the method, the reaction of the compound of Formula (IVa) and the compound of Formula (IVb) is conducted at least in part at a temperature of about 60° C. or higher. For example, the reaction may be conducted at the room temperature in part and at a temperature of about 60° C. or higher in part. In one embodiment, the temperature of about 60° C. or higher is a temperature of about 70° C. or higher; in another embodiment, the temperature of about 60° C. or higher is a temperature of about 80° C. or higher; in another embodiment, the temperature of about 60° C. or higher is a temperature of about 90° C. or higher; in another embodiment, the temperature of about 60° C. or higher is a temperature of about 100° C. or higher; in another embodiment, the temperature of about 60° C. or higher is a temperature below about 130° C.

In one embodiment of Formula (IV), $R^1$, $R^2$, and $R^7$; are hydrogen.

In one embodiment of Formula (IV), B is alkyl or substituted alkyl.

In one embodiment of Formula (IV), $R^{24}$ is $-OR^{31}$, and $R^{31}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl.

In one embodiment of the invention, the compound of Formula (IV) is represented by Formula (IVc):

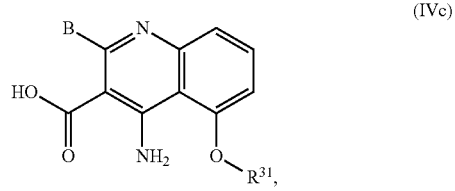

(IVc)

Wherein B is alkyl or substituted alkyl; and $R^{31}$ is alkyl, substituted alkyl, carbocyclyl, and substituted carbocyclyl.

Compositions

The present compounds can be used for one or more methods of the present invention, e.g., modulating or enhancing sweet flavor. In general, the compounds of the present invention, individually or in combination, can be provided in a composition, such as, e.g., an ingestible composition.

The compounds of Formula (I) and its various subgenuses, and their salts and/or solvates, should preferably be comestibly acceptable, e.g., deemed suitable for consumption in food or drink from the perspective of giving unmodified comestible compositions an improved and/or pleasing sweet taste, and would not be significantly toxic or causes unpleasant or undesirable pharmacological or toxicological effects on an animal or human at the typical concentrations they are employed as flavoring agents for the comestible compositions.

The typical method of demonstrating that a flavorant compound is comestibly acceptable is to have the compound tested and/or evaluated by an Expert Panel of the Flavor and Extract Manufacturers Association and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference.

In one embodiment, the compounds of the present invention can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

In one embodiment, the present compound is added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that use sucrose, sucralose and/or other sweeteners.

In general, over the counter (OTC) product and oral hygiene product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral hygiene product include, but are not limited to mouth cleaning strips, toothpaste, toothbrushes, mouthwashes/dental rinses, denture care, mouth fresheners at-home teeth whiteners and dental floss.

In another embodiment, the present compounds are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a sweet receptor modulating amount, a sweet receptor ligand modulating amount, a sweet flavor modulating amount, a sweet flavoring agent amount, or a sweet flavor enhancing amount of one or more of the present compounds will be added to the ingestible composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, enhancing or inhibiting) the sweet taste or other taste properties of other natural or synthetic sweet tastants, and ingestiable compositions made therefrom. In one embodiment, the compounds of the present invention is used or provided in its ligand enhancing concentration(s). For example, a broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In one embodiment, the present invention provides a sweet enhancing composition. The sweet enhancing composition comprises a compound of the present invention in an amount effective to provide sweetening, e.g., sweet flavor enhancing amount in combination with a first amount of sweetener, wherein the sweetening is more than the sweetening provided by the first amount of sweetener without the compound.

In one embodiment, the present invention provides an ingestible composition which comprises the sweet enhancing composition of the present invention. In certain embodiments, the present ingestible composition is in the form of a food or beverage product, a pharmaceutical composition, a nutritional product, a dietary supplement, over-the-counter medication, or oral care product.

In one embodiment, the present invention provides a sweetener replacement composition which comprises one or more compounds of the present invention in an amount effective to provide sweetening, e.g., at a concentration higher than their ligand enhancing concentration in the absence of a sweetener, e.g., sucrose other than the present compound(s).

According to another aspect of the invention, the compounds of the present invention are provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacture in large industrial scales to produce the ready-to-use soft drinks Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) as flavor modifying ingredient, a compound of the present invention; ii) a carrier; and iii) optionally at least one adjuvant. The term "as flavor modifying ingredient" denotes that the compound of the present invention acts as a flavoring agent or a flavor modifying agent (such as a flavor enhancer) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. The present flavoring concentrate formulation can be carbonated or non-carbonated.

The flavoring concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haen, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions oïMethoden der Organischen Chemie (Houben-Weyl), and the like. Many general methods for preparation of starting materials comprising variously substituted heterocyclic, hetereoaryl, and aryl rings (the precursors of Ar, $hAr^1$, and/or $hAr^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entirieties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, 3$^r$ Ed., John Wiley & Sons (1999).

Some exemplary synthetic methods for preparing the present compounds are illustrated in the Schemes 1 to 4 below.

Scheme 1: Preparation of substituted 4-aminoquinoline-3-carboxylate dirivatives (VI) from substituted anilines (I)

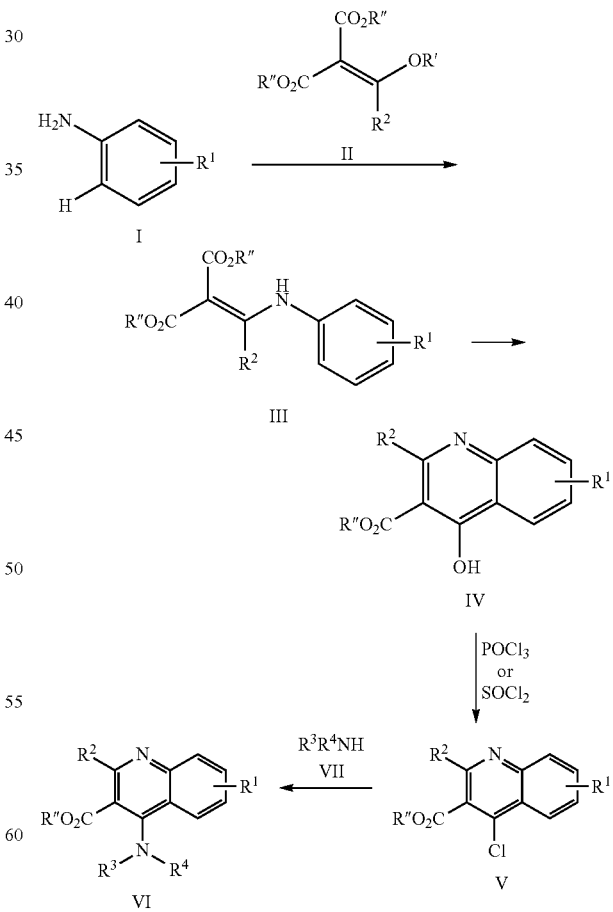

As shown in Scheme 1, substituted 4-aminoquinoline-3-carboxylate derivatives (VI) can be prepared by reacting the corresponding anilines I with 2-(alkoxymethylene)malonates II followed by cyclization of the intermediates III under elevated temperature to provide the hydroxyl intermediates IV that can be treated with POCl$_3$ or SO$_2$Cl$_2$ to provide the corresponding chloride derivatives V that can be further treated with ammonia or amines to give the desired aminoquinolines VI. (Kamal, A. et al. *Bioorg. Med. Chem.* 2005, 13, 2021-2029; Fryer, R. I. et al. *J. Med. Chem.* 1993, 36, 1669-1673; Bi, Y. et al. *Bioorg. Med. Chem. Lett.* 2004, 14, 1577-1580; Li, S. Y. et al. *Bioorg. Med. Chem.* 2006, 14, 7370-7376. Koga, H. et al. *J. Med. Chem.* 1980, 23, 1358-1363.).

Scheme 2: Preparation of substituted 4-aminoquinoline-3-carboxylate derivatives (VI) from substituted 2-aminobenzoic acid derivatives (VIII)

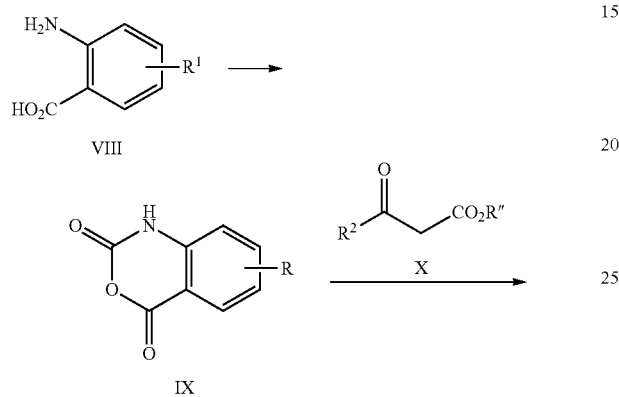

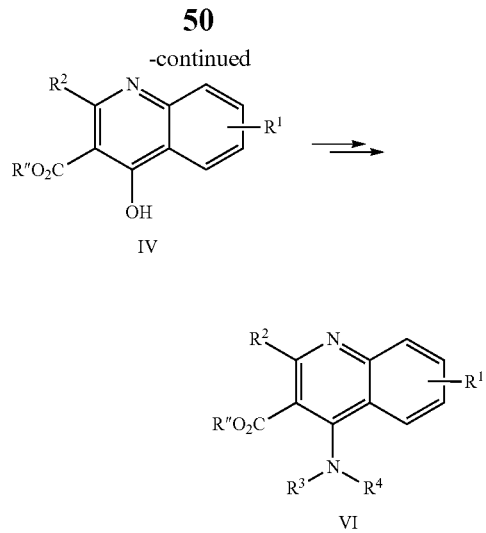

Substituted 4-aminoquinoline-3-carboxylate derivatives (VI) can also be prepared by reacting the corresponding 2-aminobenzoic acids VIII with phosgene or equivalent to provide the isatoic anhydrides IX that can be further reacted with X to give the derivatives IV (Mai, A. et al. *J. Med. Chem.* 2006, 49, 6897-6907. Beutner, G. L. et al. *J. Org. Chem.* 2007, 72, 7058-7061, and references cited therein.), which can be converted to VI as described in Scheme 1.

Scheme 3: Preparation of substituted 4-aminoquinoline-3-carboxylate derivatives (VI) from substituted 2-amino benzonitrile derivatives (XI)

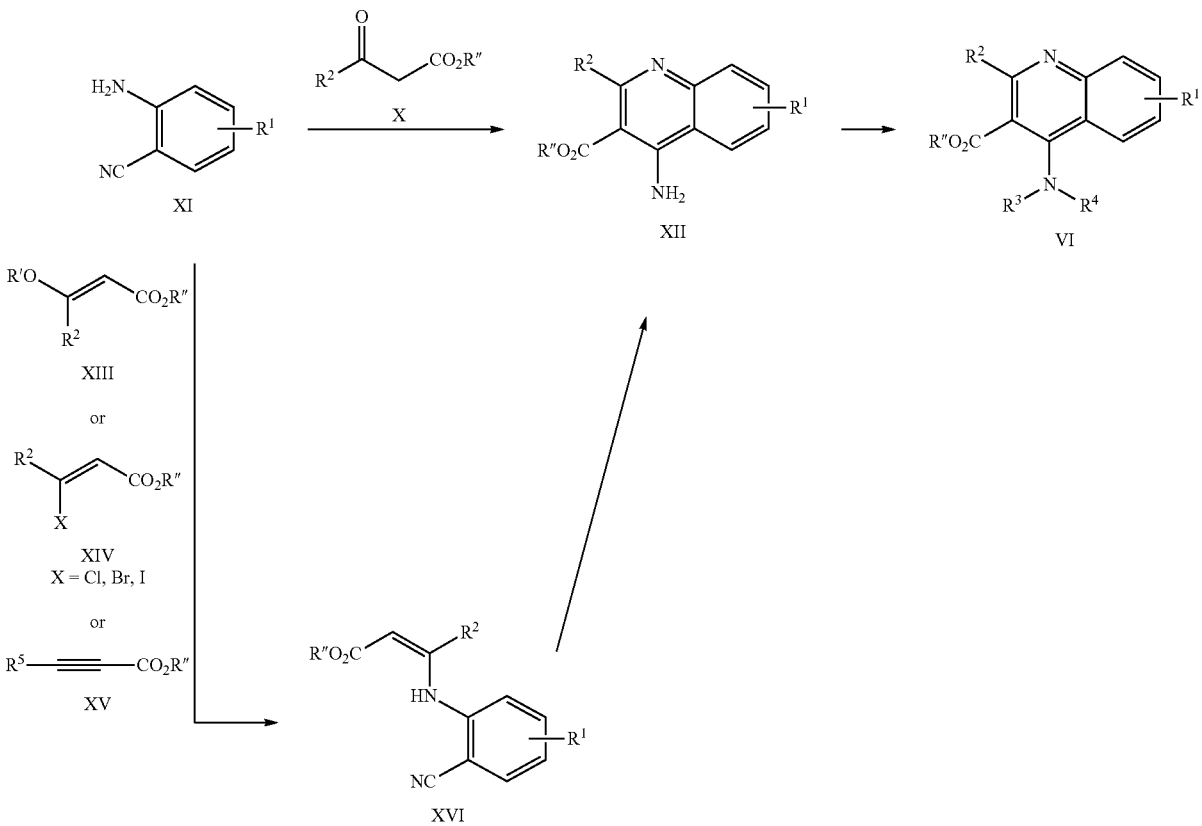

Alternatively, substituted 4-aminoquinoline-3-carboxylate derivatives (VI) can be prepared by reacting the corresponding amino benzonitriles XI with X to provide the amino derivatives XII (Sestili, I. et al. *Eur. J. Med. Chem.* 2004, 39, 1047-1057. Doucet-Personeni, C. et al. *J. Med. Chem.* 2001, 44, 3203-3215. Veronese, A. C. et al. *Tetrahedron* 1995, 51, 12277-12284, and the references cited therein.) that can be further alkylated to give the substituted aminoquinolines VI as shown in Scheme 3. Amino quinolines XII can also be prepared via a Michael addition of the 2-amino benzonitriles XI to various α,β-unsaturated carboxylate derivatives XIII, XIV or XV to provide the adducts XVI (MacNab, H. et al. *Synthesis* 2009, 2171-2174. Vicario, J. L. *Synthesis* 2007, 2065-2092, and references cited therein.) that can be further cyclized to give the amino quinolines XII (Han, G. F. et al. *Synth. Commun.* 2009, 39, 2492-2505. Tabarrini, O. et al. *Bioorg. Med. Chem.* 2001, 9, 2921-2928. Shutske, G. M. et al. *J. Med. Chem.* 1989, 32, 1805-1813, and references cited therein.).

fications and changes can be made to the herein disclosed exemplary embodiments without departing from the spirit and scope of the invention.

Example 1

4-amino-6-methoxyquinoline-3-carboxylic acid

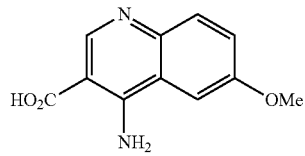 [SMILES: COc1ccc2ncc(C(=O)O)c(N)c2c1]

To a stirred solution of ethyl 4-amino-6-methoxyquinoline-3-carboxylate (Example 1a, 1.23 g, 5.0 mmol) in EtOH

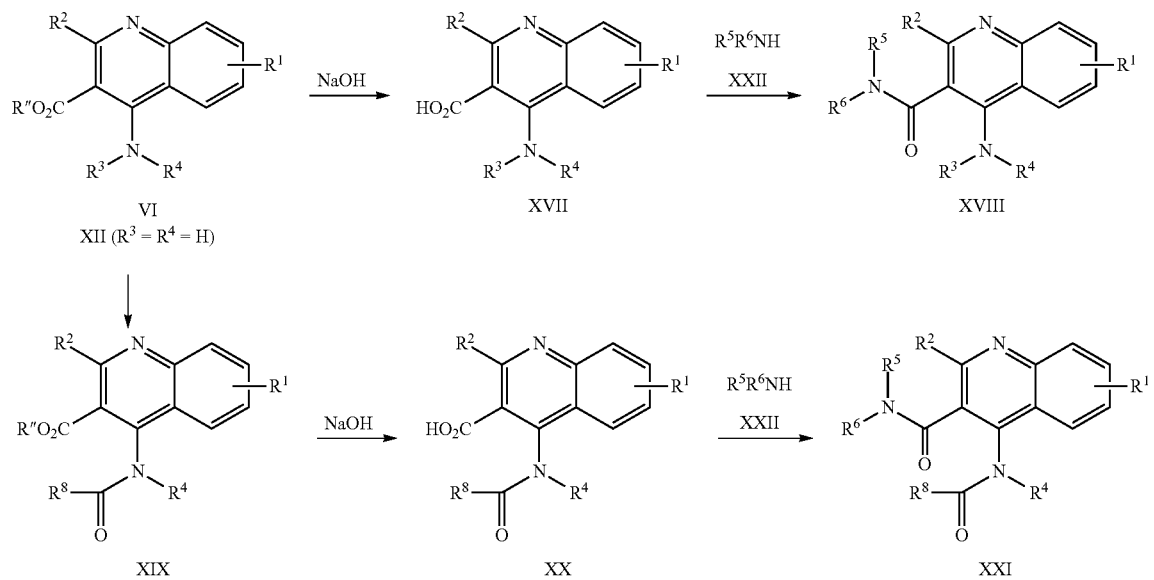

As described in Scheme 4, hydrolysis of 4-aminoquinoline-3-carboxylate derivatives VI or XII in the presence of NaOH provide 4-aminoquinoline-3-carboxylic acids XVII (Zhao, Y. L. et al. *Eur. J. Med. Chem.* 2005, 40, 792-797.) which can be further coupled with amines XXII under standard conditions to give 4-aminoquinoline-3-carboxamide derivatives XVIII. When $R^3$ and/or $R^4$=H, 4-aminoquinoline-3-carboxylates VI or XII can be further functionalized by coupling with acids XXIII to give 4-carboxamidoquinoline-3-carboxylates XIX. Compound XIX can be further hydrolyzed to the acids XX that can be further coupled to the amines XXII to provide amide derivatives XXI.

EXAMPLES

Having now generally described the invention, the same will be more readily understood by reference to the following examples, which are provided by way of illustration and are not intended as limiting. It is understood that various modi- (20.0 mL) was added aqueous NaOH (2.0 N, 5.0 mL) at room temperature. The reaction mixture was then refluxed for 3 hr. The solution was then filtered and washed with water. The filtrate was cooled to 0° C. and neutralized carefully with 1N HCl to pH 7. Most of the EtOH was removed under reduced pressure, and the precipitate was collected by filtration, washed with cold water, and dried under vacuum to give the title compound as an off-white solid (1.01 g, 93%). $^1$H NR (400 MHz, DMSO-$d_6$) δ 3.89 (s, 3H), 6.40 (dd, J=2.8, 9.4 Hz, 1H), 7.73 (d, J=9.4 Hz, 1H), 7.77 (d, J=2.8 Hz, 1H), 8.77 (s, 1H). MS 219 (MH$^+$).

Example 1a ethyl 4-amino-6-methoxyquinoline-3-carboxylate

A mixture of ethyl 4-chloro-6-methoxyquinoline-3-carboxylate (Example 1b, 796 mg, 3.0 mmol) and ammonia (25% aqueous solution, 10 mL) in isopropanol (40 mL) was stirred at 110° C. in a pressure reactor overnight. Most of the solvent was then removed under reduced pressure, and the reaction mixture was diluted with water. The precipitate was collected by filtration, washed with cold water, and dried under vacuum to give the title compound as an off-white solid (680 mg, 92%). $^1$H NR (400 MHz, DMSO-$d_6$) δ 1.33 (t, J=7.0 Hz, 3H), 3.88 (s, 3H), 4.32 (q, J=7.0 Hz, 2H), 7.36 (dd, J=2.8, 8.8 Hz, 1H), 7.72 (d, J=8.8 Hz, 1H), 7.74 (d, J=2.8 Hz, 1H), 8.23 (bs, 2H), 8.77 (s, 1H). MS 247 (MH$^+$).

Example 1b ethyl 4-chloro-6-methoxyquinoline-3-carboxylate

A solution of ethyl 4-hydroxy-6-methoxyquinoline-3-carboxylate (Example 1c, 1.24 g, 5.0 mmol) in POCl$_3$ was refluxed under nitrogen for 3 hrs. The solution was cooled to room temperature and evaporated under reduced pressure. The residue was carefully quenched with ice, and neutralized with 2.0 N NaOH to pH 7. The precipitate was collected by filtration, washed with cold water, and dried under vacuum to give the title compound as a pale-yellow solid (1.29 g, 97%). $^1$H NR (400 MHz, DMSO-$d_6$) δ 1.36 (t, J=7.0 Hz, 3H), 3.96 (s, 3H), 4.41 (q, J=7.0 Hz, 2H), 7.57 (d, J=2.8 Hz, 1H), 7.61 (dd, J=2.8, 8.8 Hz, 1H), 8.05 (d, J=8.8 Hz, 1H), 8.97 (s, 1H). MS 266, 268 (MH$^+$).

Example 1c ethyl 4-hydroxy-6-methoxyquinoline-3-carboxylate

A mixture of 4-methoxyaniline (12.3 g, 100 mmol) and diethyl 2 (21.6 g, 100 mmol) was stirred at 120° C. under nitrogen for 4 hrs. The solution was cooled to room temperature and Ph$_2$O (100 mL) was added. The reaction mixture was refluxed at 260° C. under nitrogen for 8 hrs. The solution was cooled to room temperature and diluted with hexanes. The resultant precipitate was collected by filtration, washed with 25% ethyl acetate in hexanes, and dried under vacuum to give ethyl 4-hydroxy-6-methoxyquinoline-3-carboxylate as a pale-yellow solid (4.21 g, 17%). $^1$H NR (400 MHz, DMSO-$d_6$) δ 1.26 (t, J=7.0 Hz, 3H), 3.83 (s, 3H), 4.19 (q, J=7.0 Hz, 2H), 7.32 (dd, J=3.2, 9.6 Hz, 1H), 7.55 (d, J=3.2 Hz, 1H), 7.56 (d, J=9.6 Hz, 1H), 8.47 (s, 1H), 12.27 (s, 1H). MS 248 (MH$^+$).

Example 2

4-amino-5-(2,2-dimethyl-3-oxo-3-(propylamino)propoxy)-2-methyl-quinoline-3-carboxylic acid

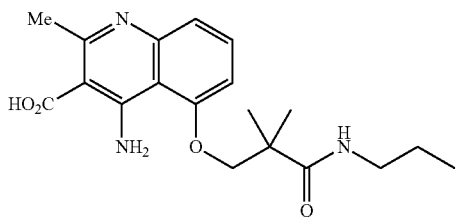 [SMILES: CCCNC(=O)C(C)(C)COc1cccc2nc(C)c(C(=O)O)c(N)c12]

Prepared as in Example 1 from ethyl 4-amino-5-(2,2-dimethyl-3-oxo-3-(propylamino)propoxy)-2-methylquinoline-3-carboxylate (Example 2a) as an off-white solid (41%). $^1$H NR (400 MHz, DMSO-$d_6$) δ 0.73 (t, J=7.6 Hz, 3H), 1.25 (s, 6H), 1.33-1.42 (m, 2H), 2.76 (s, 3H), 3.00-3.05 (m, 2H), 4.16 (s, 2H), 7.01 (d, J=8.0 Hz, 1H), 7.29 (d, J=8.0 Hz, 1H), 7.67 (t, J=8.0 Hz, 1H), 7.89 (t, J=5.8 Hz, 1H), 8.85 (bs, 1H), 12.28 (bs, 1H), 12.78 (bs, 1H). MS 360 (MH$^+$).

Example 2a ethyl 4-amino-5-(2,2-dimethyl-3-oxo-3-(propylamino)propoxy)-2-methylquinoline-3-carboxylate To a solution of 3-(3-amino-2-cyanophenoxy)-2,2-dimethyl-N-propylpropan-amide (Tachdjian, C. et al. PCT Int. Appl. 2008, WO 2008154221, 1.38 g, 5.0 mmol) and ethyl acetoacetate (0.66 g, 5.0 mmol) in dry toluene (150 mL) was added SnCl$_4$ (2.61 g, 10.0 mmol) dropwise via syringe at room temperature under nitrogen. After 1 hr at room temperature, the reaction mixture was refluxed for an additional 5 hrs. The solution was cooled to room temperature and the solvent removed under reduced pressure. The residue was diluted with EtOAc, and aqueous NaOH (2N) was added at room temperature to pH >8. The solution was filtered and the organic layer separated. The aqueous layer was extracted with EtOAc (5×). The combined organic layers was washed with brine, and dried over Na$_2$SO$_4$. After evaporation of the solvent, the residue was purified by chromatography on silica gel (0.5% MeOH in EtOAc) to give the title compound as an off-white solid (1.63 g, 84%). $^1$H NR (400 MHz, DMSO-$d_6$) δ 0.73 (t, J=7.6 Hz, 3H), 1.25 (s, 6H), 1.32 (t, J=7.4 Hz, 3H), 1.35-1.42 (m, 2H), 2.54 (s, 3H), 3.00-3.05 (m, 2H), 4.12 (s, 2H), 4.31 (q, J=7.4 Hz, 2H), 6.87 (d, J=8.0 Hz, 1H), 7.23 (d, J=8.0 Hz, 1H), 7.50 (t, J=8.0 Hz, 1H), 7.80 (t, J=5.6 Hz, 1H), 8.08 (s, 2H). MS 388 (MH$^+$).

Example 3

4-amino-6-methoxy-2-methylquinoline-3-carboxylic acid

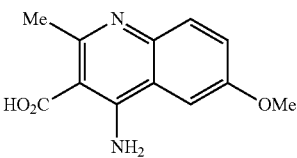 [SMILES: COc1ccc2nc(C)c(C(=O)O)c(N)c2c1]

Prepared as in Example 1 from ethyl 4-amino-6-methoxy-2-methylquinoline-3-carboxylate (Example 3a) as a white solid (87%). $^1$H NR (400 MHz, DMSO-$d_6$) δ 2.83 (s, 3H), 3.90 (s, 3H), 7.57 (dd, J=2.4, 8.2 Hz, 1H), 8.09 (d, J=8.2 Hz, 1H), 8.10 (d, J=2.4 Hz, 1H), 9.39 (s, 1H), 9.67 (s, 1H). MS 233 (MH$^+$).

Example 3a ethyl 4-amino-6-methoxy-2-methylquinoline-3-carboxylate

Prepared as in Example 2a from 2-amino-5-methoxybenzonitrile (Campbell, J. B. et al. Synth. Commun. 1989, 19, 2255-2263.) and ethyl acetoacetate as an off-white solid (92%). $^1$H NMR (400 MHz, DMSO-$d_6$) δ 1.33 (t, J=6.8 Hz, 3H), 2.57 (s, 3H), 3.86 (s, 3H), 4.33 (q, J=6.8 Hz, 2H), 7.28

(dd, J=2.8, 9.2 Hz, 1H), 7.59 (d, J=9.2 Hz, 1H), 7.60 (bs, 2H), 7.63 (d, J=2.8 Hz, 1H). MS 261 (MH+).

Example 4

4-amino-2-phenylquinoline-3-carboxylic acid

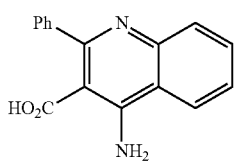 [SMILES: Nc1c(C(=O)O)c(-c2ccccc2)nc2ccccc12]

Prepared as in Example 1 from ethyl 4-amino-2-phenylquinoline-3-carboxylate (Example 4a) as an off-white solid (33%). $^1$H NR (400 MHz, DMSO-$d_6$) δ 7.39-7.52 (m, 7H), 7.79 (m, 3H), 8.33 (d, J=8.0 Hz, 1H), 12.63 (bs, 1H). MS 265 (MH+).

Example 4a ethyl 4-amino-2-phenylquinoline-3-carboxylate

Prepared as in Example 2a from 2-aminobenzonitrile and ethyl 3-oxo-3-phenylpropanoate as a yellow solid (45%). $^1$H NR (400 MHz, DMSO-$d_6$) δ 0.72 (t, J=8.0 Hz, 3H), 3.92 (q, J=8.0 Hz, 2H), 7.44 (m, 5H), 7.50 (m, 1H), 7.61 (bs, 2H), 7.73 (m, 1H), 7.83 (d, J=8.0 Hz, 1H), 8.37 (d, J=8.0 Hz, 1H). MS 293 (MH+).

Example 5

4-amino-2-ethylquinoline-3-carboxylic acid

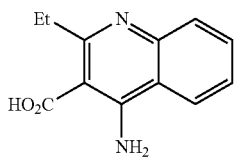 [SMILES: CCc1nc2ccccc2c(N)c1C(=O)O]

Prepared as in Example 2 from methyl 4-amino-2-ethylquinoline-3-carboxylate (Example a) as a white solid (26%). $^1$H NR (400 MHz, DMSO-$d_6$+1 drop $D_2O$) δ 1.24 (t, J=8.0 Hz, 3H), 3.28 (q, J=8.0 Hz, 2H), 7.56 (t, J=8.0 Hz, 1H), 7.78 (d, J=8.0 Hz, 1H), 7.83 (t, J=8.0 Hz, 1H), 8.36 (d, J=8.0 Hz, 1H).). MS 217 (MH+).

Example 5a ethyl 4-amino-2-phenylquinoline-3-carboxylate

Prepared as in Example 2a from 2-aminobenzonitrile and methyl 3-oxopentanoate as a solid (27%). $^1$H NR (400 MHz, DMSO-$d_6$) δ 1.18 (t, J=8.0 Hz, 3H), 2.88 (q, J=8.0 Hz, 2H), 3.86 (s, 3H), 7.40 (m, 1H), 7.44 (bs, 2H), 7.64 (m, 1H), 7.68 (m, 1H), 8.26 (d, J=8.0 Hz, 1H). MS 231 (MH+).

Example 6

4-amino-2-methylquinoline-3-carboxylic acid

Prepared as in Example 1 from ethyl 4-amino-2-methylquinoline-3-carboxylate (Example 6a) as a off-white solid (41%). $^1$H NR (400 MHz, DMSO-$d_6$) δ 1.05 (t, J=8.0 Hz, 3H), 2.84 (s, 3H), 7.56 (bs, 1H), 7.76 (m, 1H), 7.82 (bs, 1H), 8.39 (d, J=8.0 Hz, 1H), 8.99 (bs, 1H), 12.00 (bs, 1H), 12.98 (bs, 1H). MS 203 (MH+).

Example 6a ethyl 4-amino-2-methylquinoline-3-carboxylate

Prepared as in Example 2a from 2-aminobenzonitrile and ethyl 3-oxobutanoate as a yellow solid (32%). $^1$H NR (400 MHz, DMSO-$d_6$) δ 1.33 (t, J=8.0 Hz, 3H), 2.61 (s, 3H), 4.34 (q, J=8.0 Hz, 2H), 7.41 (m, 1H), 7.66 (m, 2H), 7.74 (bs, 2H), 8.27 (d, J=8.0 Hz, 1H). MS 231 (MH+).

Example 7

4-amino-5-(2,2-dimethyl-3-oxo-3-(propylamino) propoxy)-2-ethyl-quinoline-3-carboxylic acid

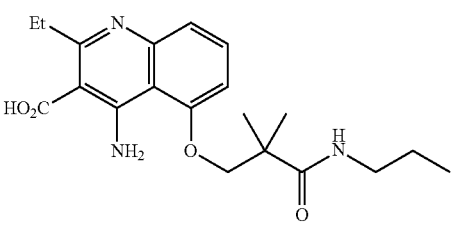 [SMILES: CCCNC(=O)C(C)(C)COc1cccc2nc(CC)c(C(=O)O)c(N)c12]

Prepared as in Example 1 from methyl 4-amino-5-(2,2-dimethyl-3-oxo-3-(propylamino)propoxy)-2-ethylquinoline-3-carboxylate (Example 7a) as a solid (75%). $^1$H NR (400 MHz, DMSO-$d_6$) δ 0.75 (t, J=8.0 Hz, 3H), 1.03 (t, J=8.0 Hz, 3H), 1.27 (s, 6H), 1.39 (m, 2H), 3.04 (q, J=4.0 Hz, 2H), 3.45 (q, J=4.0 Hz, 2H), 4.17 (s, 2H), 7.04 (d, J=8.0 Hz, 1H), 7.32 (d, J=8.0 Hz, 1H), 7.69 (t, J=8.0 Hz, 1H), 7.90 (t, J=4.0 Hz, 1H), 8.89 (bs, 1H), 12.75 (bs, 1H). MS 374 (MH+).

Example 7a methyl 4-amino-5-(2,2-dimethyl-3-oxo-3-(propylamino)propoxy)-2-ethylquinoline-3-carboxylate Prepared as in Example 2a from 3-(3-amino-2-cyanophenoxy)-2,2-dimethyl-N-propylpropan-amide (Tachdjian, C. et al. *PCT Int. Appl.* 2008, WO 2008154221) and methyl 3 as a yellow solid (17%). ¹H NR (400 MHz, DMSO-d₆) δ 0.75 (t, J=8.0 Hz, 3H), 1.17 (t, J=8.0 Hz, 3H), 1.26 (s, 6H), 1.40 (m, 2H), 2.84 (q, J=8.0 Hz, 2H), 3.04 (q, J=8.0 Hz, 2H), 3.85 (s, 3H), 4.13 (s, 2H), 6.88 (d, J=8.0 Hz, 1H), 7.27 (dd, J=8.0 Hz, 1H), 7.51 (t, J=8.0 Hz, 1H), 7.81 (m, 3H). MS 388 (MH⁺).

Example 8

4-amino-6-phenoxyquinoline-3-carboxylic acid

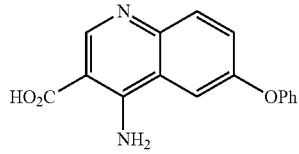 [SMILES: Nc1c(C(=O)O)cnc2ccc(Oc3ccccc3)cc12]

Prepared as in Example 1 from ethyl 4-amino-6-phenoxyquinoline-3-carboxylate (Example 8a) as a off-white solid (50%). ¹H NR (400 MHz, DMSO-d₆) δ 7.07 (d, J=8.0 Hz, 2H), 7.16 (t, J=8.0 Hz, 1H), 7.42 (m, 2H), 7.49 (dd, J=8.0 Hz, 1H), 7.87 (d, J=8.0 Hz, 1H), 8.13 (d, J=4.0 Hz, 1H), 8.86 (s, 1H). MS 281 (MH⁺).

Example 8a ethyl 4-amino-6-phenoxyquinoline-3-carboxylate

Prepared as in Example 1a from ethyl 4-chloro-6-phenoxyquinoline-3-carboxylate (Example 8b) and ammonia as a off-white solid (82%). ¹H NR (400 MHz, DMSO-d₆) δ 1.35 (t, J=8.0 Hz, 3H), 4.35 (q, J=8.0 Hz, 2H), 7.05 (d, J=8.0 Hz, 2H), 7.15 (t, J=8.0 Hz, 1H), 7.40 (m, d, 2H), 7.46 (dd, J=8.0 Hz, 1H), 7.87 (d, J=8.0 Hz, 1H), 8.13 (d, J=4.0 Hz, 1H), 8.27 (bs, 2H), 8.87 (s, 1H). MS 309 (MH⁺).

Example 8b ethyl 4-chloro-6-phenoxyquinoline-3-carboxylate

Prepared as in Example 1b from ethyl 4-hydroxy-6-phenoxyquinoline-3-carboxylate (Example 8c) and POCl₃ as a tan solid (96%). ¹H NR (400 MHz, DMSO-d₆) δ 1.36 (t, J=8.0 Hz, 3H), 4.40 (q, J=8.0 Hz, 2H), 7.23 (d, J=8.0 Hz, 2H), 7.29 (t, J=8.0 Hz, 1H), 7.50 (t, J=8.0 Hz, 2H), 7.63 (d, J=4.0 Hz, 1H), 7.76 (dd, J=8.0 Hz, 1H), 8.21 (d, J=8.0 Hz, 1H), 9.06 (s, 1H). MS 328, 330 (MH⁺).

Example 8c ethyl 4-hydroxy-6-phenoxyquinoline-3-carboxylate

Prepared as in Example 1c from 4-phenoxyaniline and diethyl 2 as a white solid (41%). ¹H NR (400 MHz, DMSO-d₆) δ 1.24 (t, J=8.0 Hz, 3H), 4.18 (q, J=8.0 Hz, 2H), 7.07 (d, J=8.0 Hz, 2H), 7.20 (t, J=8.0 Hz, 1H), 7.43 (t, J=8.0 Hz, 2H), 7.47 (m, 2H), 7.69 (d, J=12.0 Hz, 1H), 12.39 (bs, 1H). MS 310 (MH⁺).

Example 9

4-amino-7-fluoroquinoline-3-carboxylic acid

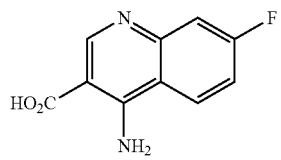 [SMILES: Nc1c(C(=O)O)cnc2cc(F)ccc12]

Prepared as in Example 1 from ethyl 4-amino-7-fluoroquinoline-3-carboxylate (Example 9a) as an off white solid (66%). ¹H NR (CD₃OD, 400 MHz) δ 7.49 (m, 2H), 8.50 (dd, J=10.0, 5.2 Hz, 1H), 8.94 (s, 1H). MS 207 (MH⁺).

Example 9a ethyl 4-amino-7-fluoroquinoline-3-carboxylate

Prepared as in Example 1a from ethyl 4-chloro-7-fluoroquinoline-3-carboxylate (Example 9b) and ammonia as an off white solid (99%). MS 235 (MH⁺).

Example 9b ethyl 4-chloro-7-fluoroquinoline-3-carboxylate

Prepared as in Example 1b from ethyl 7-fluoro-4-hydroxyquinoline-3-carboxylate (Example 9c) and POCl₃ as an off white solid (96%). MS 254, 256 (MH⁺).

Example 9c ethyl 7-fluoro-4-hydroxyquinoline-3-carboxylate

Prepared as in Example 1c from 3-fluoroaniline and diethyl 2 as a brown solid (51%). MS 236 (MH⁺).

Example 10

4-amino-6-isopropoxyquinoline-3-carboxylic acid

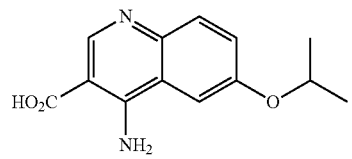 [SMILES: CC(C)Oc1ccc2ncc(C(=O)O)c(N)c2c1]

Prepared as in Example 1 from ethyl 4-amino-6-isopropoxyquinoline-3-carboxylate (Example 10a) as a an off white solid (94%). ¹H NR (400 MHz, DMSO-d₆) δ 1.30 (s, 3H), 1.32 (s, 3H), 4.82 (m, 1H), 7.37 (d, J=9.2 Hz, 1H), 7.72 (d, J=9.2 Hz, 1H), 7.78 (s, 1H), 8.75 (s, 1H). MS 247 (MH+).

Example 10a ethyl 4-amino-6-isopropoxyquinoline-3-carboxylate

Prepared as in Example 1a from ethyl 4-chloro-6-isopropoxyquinoline-3-carboxylate (Example 10b) and ammonia as an off white solid (75%). MS 275 (MH+).

Example 10b 4-chloro-6-isopropoxyquinoline-3-carboxylate

Prepared as in Example 1b from ethyl 4-hydroxy-6-isopropoxyquinoline-3-carboxylate (Example 10c) and POCl₃ as a pale yellow solid (93%). MS 294, 296 (MH+).

Example 10c ethyl 4-hydroxy-6-isopropoxyquinoline-3-carboxylate

Prepared as in Example 1c from 4-isopropoxyaniline and diethyl 2 as a yellow solid (20%). MS 276 (MH+).

Example 11

4-amino-6-methoxy-2-methyl-1,5-naphthyridine-3-carboxylic acid

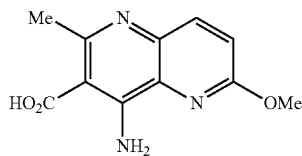 [SMILES: COc1ccc2nc(C)c(C(=O)O)c(N)c2n1]

Prepared as in Example 1 from ethyl 4-amino-6-methoxy-2-methyl-1,5-naphthyridine-3-carboxylate (Example 11a) as an off white solid (56%). ¹H NR (400 MHz, DMSO-d₆) δ 2.68 (s, 3H), 4.02 (s, 3H), 7.21 (d, J=8.8 Hz, 1H), 7.99 (d, J=9.2 Hz, 1H). MS 234 (MH+).

Example 11a ethyl 4-amino-6-methoxy-2-methyl-1,5-naphthyridine-3-carboxylate Prepared as in Example 2a from 3-amino-6-methoxypicolinonitrile (Example 11b) and ethyl 3-oxobutanoate as an off white solid (45%). MS 262 (MH+).

Example 11b 3-amino-6-methoxypicolinonitrile

To a solution of 6-methoxy-3-nitropicolinonitrile (Piersanti, G. et al. *Org. Biomolecular Chem.* 2007, 5, 2567-2571.) (2.0 g, 11.1 mmol) in diglyme (52 mL) was added dropwise a solution of SnCl₂ (6.35 g, 33.5 mmol) in concentrated HCl solution (26 mL) at 0° C. The solution was stirred at 0° C. for 1 hr, then the reaction mixture was neutralized with concentrated NaOH solution, and extracted with EtOAc (2×). The combined organic layers were washed with brine, and dried over Na₂SO₄. After evaporation of the solvent, the residue was purified by chromatography on silica gel (50% EtOAc in hexanes) to give 3-amino-6-methoxypicolinonitrile (966 mg, 58%) as a brown solid. ¹H NR (400 MHz, CDCl₃) δ 3.81 (s, 3H), 4.10 (bs, 2H), 6.81 (d, J=8.0 Hz, 1H), 7.08 (d, J=8.0 Hz, 1H). MS 150 (MH+).

Example 12

4-amino-2,5-dimethylquinoline-3-carboxylic acid

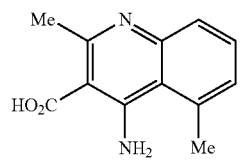 [SMILES: Cc1nc2cccc(C)c2c(N)c1C(=O)O]

Ethyl 4-(4-methoxybenzylamino)-2,5-dimethylquinoline-3-carboxylate (Example 12a, 0.563 g, 1.54 mmol) was dissolved in TFA (8 mL) and the resultant solution was stirred at room temperature for 15 minutes, TFA was then removed under vacuum to give the crude ethyl 4 product, which was dissolved in EtOH (4 mL). To this solution was added NaOH (4.0 N, 3.86 mL) and the reaction mixture was stirred at 100° C. for 1 hr. Water (25 mL) was added, and the solvent was decanted away from insoluble material then acidified with AcOH to pH 5.5. The precipitate was collected by filtration to give the title compound (300 mg, 90%) as a white solid. ¹H NR (400 MHz, DMSO-d₆) δ 2.78 (s, 3H), 2.88 (s, 3H), 7.30 (d, J=7.2 Hz, 1H), 7.58 (d, J=8.0 Hz, 1H), 7.65 (m, 1H), 7.8-8.0 (br, 1H), 12.2-12.9 (br, 2H). MS 217 (MH+).

Example 12a ethyl 4-(4-methoxybenzylamino)-2,5-dimethylquinoline-3-carboxylate A solution of ethyl 4-chloro-2,5-dimethylquinoline-3-carboxylate (Example 12b, 0.518 g, 1.96 mmol) and (4-methoxyphenyl)methanamine (1.15 mL, 8.86 mmol) in toluene (10 mL) and DMF (5 mL) were stirred at 115° C. under nitrogen for 12 hrs. The solvent was removed under vacuum, and the residue was purified by chromatography on silica gel (0% to 50% EtOAc in hexanes) to give the title compound as an oil (563 mg, 79%). ¹H NR (400 MHz, DMSO-d₆) δ 1.24 (t, J=7.6 Hz, 3H), 2.45 (s, 3H), 2.78 (s, 3H), 3.73 (s, 3H), 4.2-4.3 (m, 4H), 6.27 (t, J=6.0 Hz, 1H), 6.88 (d, J=8.4 Hz, 2H), 7.19 (m, 3H), 7.48 (m, 1H), 7.58 (d, J=8.4 Hz, 1H). MS 365 (MH+).

Example 12b ethyl 4-chloro-2,5-dimethylquinoline-3-carboxylate

A solution of 5-methyl-1H-benzo[d][1,3]oxazine-2,4-dione (Example 12c) (1.36 g, 7.68 mmol), ethyl 3-oxobutanoate (1.46 mL, 11.5 mmol), and NaOH (0.046 g, 1.15 mmol) in anhydrous dioxane (10 mL) were refluxed under nitrogen for 15 hrs. The solvent was then removed under vacuum, and the residue was re-dissolved in DMF (15 mL). To this solution was added POCl₃ (1.41 mL, 15.4 mmol), and the reaction mixture was stirred at room temperature for 45 minutes. The reaction was carefully quenched with ice water (150 mL), and extracted with DCM (2×75 mL). The combined organic layers were washed with brine, and dried over $Na_2SO_4$. After evaporation of the solvent, the residue was purified by chromatography on silica gel eluting with 50% EtOAc in hexanes to give the title compound as red oil (520 mg, 26%). $^1$H NMR (400 MHz, DMSO-$d_6$) δ 1.36 (t, J=7.6 Hz, 3H), 2.58 (s, 3H), 2.97 (s, 3H), 4.46 (q, J=7.6 Hz, 2H), 7.51 (d, J=7.2 Hz, 1H), 7.71 (m, 1H), 7.87 (d, J=7.6 Hz, 1H). MS 264, 266 (MH$^+$)

Example 12c 5-methyl-1H-benzo[d][1,3]oxazine-2,4-dione

Trichloromethyl carbonochloridate (2.04 mL, 16.9 mmol) was added to 2-amino-6-methylbenzoic acid (2.13 g, 14.1 mmol) in anhydrous dioxane (32 mL) under nitrogen, then refluxed for 30 minutes. Diethyl ether (100 mL) was added, and the precipitated solid was collected by filtration to give 5-methyl-1H-benzo[d][1,3]oxazine-2,4-dione (1.4 g, 56%) which was used without further purification.

Example 13

4-amino-6-ethoxyquinoline-3-carboxylic acid

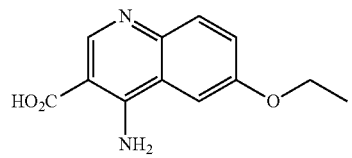 [SMILES: CCOc1ccc2ncc(C(=O)O)c(N)c2c1]

Prepared as in Example 1 from ethyl 4-amino-6-ethoxyquinoline-3-carboxylate (Example 13a) as an off white solid (76%). $^1$H NR (400 MHz, DMSO-$d_6$) δ 1.39 (t, J=7.2 Hz, 3H), 4.18 (q, J=7.2 Hz, 2H), 7.50-7.53 (m, 1H), 7.86 (d, J=8.8 Hz, 1H), 7.95 (d, J=2.0 Hz, 1H), 8.86 (s, 1H), 9.26 (bs, 1H), 9.86 (bs, 1H). MS 233 (MH$^+$).

Example 13a ethyl 4-amino-6-ethoxyquinoline-3-carboxylate

Prepared as in Example 1a from ethyl 4-chloro-6-ethoxyquinoline-3-carboxylate (Example 13b) and ammonia as an off white solid (77%). $^1$H NR (400 MHz, DMSO-$d_6$) δ 1.31-1.40 (m, 6H), 4.15 (q, J=7.2 Hz, 2H), 4.31 (q, J=6.8 Hz, 2H), 7.34 (q, J=6.4 Hz, 1H), 7.69-7.74 (m, 2H), 8.21 (bs, 2H), 8.77 (s, 1H). MS 261 (MH$^+$).

Example 13b ethyl 4-chloro-6-ethoxyquinoline-3-carboxylate

Prepared as in Example 1b from ethyl 6-ethoxy-4-hydroxyquinoline-3-carboxylate (Example 13c) and POCl$_3$ as pale yellow solid (100%). $^1$H NR (400 MHz, DMSO-$d_6$) δ 1.34-1.42 (m, 6H), 4.21 (q, J=7.2 Hz, 2H), 4.40 (q, J=7.2 Hz, 2H), 7.52 (d, J=2.8 Hz, 1H), 7.56-7.59 (m, 1H), 8.02 (d, J=8.8 Hz, 1H), 8.94 (s, 1H). MS 280, 282 (MH$^+$).

Example 13c ethyl 6-ethoxy-4-hydroxyquinoline-3-carboxylate

Prepared as in Example 1c from 4-ethoxyaniline and diethyl 2 as a white solid (26%). $^1$H NR (400 MHz, DMSO-$d_6$) δ 1.24-1.37 (m, 6H), 4.09 (q, J=6.8 Hz, 2H), 4.19 (q, J=7.2 Hz, 2H), 7.29-7.32 (m, 1H), 7.52-7.56 (m, 2H), 8.47 (s, 1H), 12.27 (s, 1H). MS 262 (MH$^+$).

Example 14

4-amino-6-propoxyquinoline-3-carboxylic acid

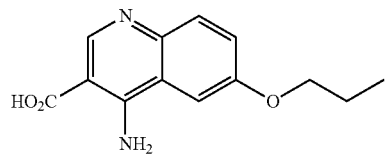 [SMILES: CCCOc1ccc2ncc(C(=O)O)c(N)c2c1]

Prepared as in Example 1 from ethyl 4-amino-6-propoxyquinoline-3-carboxylate (Example 14a) as a white solid (56%). $^1$H NR (400 MHz, DMSO-$d_6$) δ 1.01 (t, J=7.6 Hz, 3H), 1.77-1.82 (m, 2H), 4.06 (t, J=6.8 Hz, 2H), 7.43 (d, J=2.0 Hz, 1H), 7.71-7.78 (m, 2H), 8.77 (s, 1H). MS 247 (MH$^+$).

Example 14a 4-amino-6-propoxyquinoline-3-carboxylate

Prepared as in Example 1a from ethyl 4-chloro-6-propoxyquinoline-3-carboxylate (Example 14b) and ammonia as a white solid. MS 275 (MH$^+$).

Example 14b ethyl 4-chloro-6-propoxyquinoline-3-carboxylate

Prepared as in Example 1b from ethyl 4-hydroxy-6-propoxyquinoline-3-carboxylate (Example 14c) and POCl$_3$ as a pale yellow solid. MS 294, 296 (MH$^+$).

Example 14c ethyl 4-hydroxy-6-propoxyquinoline-3-carboxylate

Prepared as in Example 1c from 4-propoxyaniline and diethyl 2 as a white solid (65%). $^1$H NR (400 MHz, DMSO-$d_6$) δ 0.98 (t, J=7.2 Hz, 3H), 1.25 (t, J=7.2 Hz, 3H), 1.72-1.77 (m, 2H), 3.98 (t, J=6.0 Hz, 2H), 4.16-4.21 (m, 2H), 6.97-6.99 (m, 1H), 7.53-7.56 (m, 2H), 8.47 (d, J=5.2 Hz, 1H), 12.27 (s, 1H). MS 276 (MH$^+$).

Example 15

4-amino-5-methoxy-2-methylquinoline-3-carboxylic acid

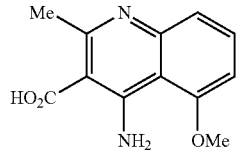 [SMILES: COc1cccc2nc(C)c(C(=O)O)c(N)c12]

Prepared as in Example 1 from ethyl 4-amino-5-methoxy-2-methylquinoline-3-carboxylate (Example 15a) as a off-white solid. $^1$H NR (400 MHz, DMSO-$d_6$) δ 2.49 (s, 3H), 4.05

(s, 3H), 7.19 (d, J=7.6 Hz, 1H), 7.61 (d, J=8.0 Hz, 1H), 7.85 (t, J=8.0 Hz, 1H), 9.49 (s, 1H), 9.85 (s, 1H). MS 233 (MH+).

Example 15a ethyl 4-amino-5-methoxy-2-methylquinoline-3-carboxylate

Prepared as in Example 2a from 2-amino-6-methoxybenzonitrile and ethyl 3 as a pale yellow solid. $^1$H NR (400 MHz, DMSO-$d_6$) δ 1.32 (t, J=7.2 Hz, 3H), 2.55 (s, 3H), 3.96 (s, 3H), 4.30 (q, J=7.2 Hz, 2H), 6.88 (d, J=8.4 Hz, 1H), 7.22 (d, J=7.6 Hz, 1H), 7.52 (t, J=8.0 Hz, 1H), 8.15 (s, 2H). MS 261 (MH+).

Example 16

4-amino-2-methyl-5-(neopentyloxy)quinoline-3-carboxylic acid

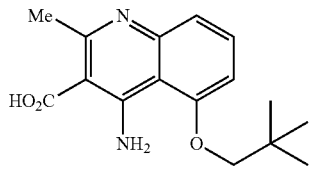 [SMILES: Cc1nc2cccc(OCC(C)(C)C)c2c(N)c1C(=O)O]

Prepared as in Example 1 from ethyl 4-amino-2-methyl-5-(neopentyloxy)quinoline-3-carboxylate (Example 16a) as a white solid. $^1$H NR (400 MHz, DMSO-$d_6$) δ 1.06 (s, 9H), 2.76 (s, 3H), 3.93 (s, 2H), 7.05 (d, J=8.4 Hz, 1H), 7.31 (d, J=8.0 Hz, 1H), 7.66 (t, J=8.0 Hz, 1H). MS 289 (MH+).

Example 16a ethyl 4-amino-2-methyl-5-(neopentyloxy)quinoline-3-carboxylate

Prepared as in Example 2a from 2-amino-6-(neopentyloxy)benzonitrile (Tachdjian, C. et al. PCT Int. Appl. 2008, WO 2008154221) and ethyl 3-oxobutanoate as a white solid (64%). $^1$H NMR (400 MHz, DMSO-$d_6$) δ 1.06 (s, 9H), 1.32 (t, J=6.8 Hz, 3H), 2.54 (s, 3H), 3.86 (s, 2H), 4.31 (q, J=6.8 Hz, 2H). 6.88-6.91 (m, 1H), 7.22-7.25 (m, 1H), 7.50 (t, J=8.0 Hz, 1H), 8.06 (s, 2H). MS 317 (MH+).

Example 17

4-amino-2-(carboxymethyl)quinoline-3-carboxylic acid

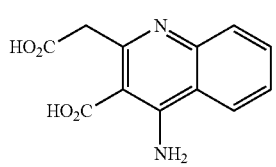 [SMILES: Nc1c(C(=O)O)c(CC(=O)O)nc2ccccc12]

Prepared as in Example 1 from ethyl 4-amino-2-(2-ethoxy-2-oxoethyl)quinoline-3-carboxylate (Example 17a) as a white solid (26%). $^1$H NR (400 MHz, DMSO-$d_6$) δ 3.76 (s, 2H), 7.36 (t, J=8.0 Hz, 1H), 7.58 (t, J=8.0 Hz, 1H), 7.64 (d, J=12.0 Hz, 1H), 7.87 (bs, 2H), 8.17 (d, J=8.0 Hz, 1H). MS 188 (MH+—CH$_2$CO$_2$H).

Example 17a ethyl 4-amino-2-(2-ethoxy-2-oxoethyl)quinoline-3-carboxylate

Prepared as in Example 2a from 2-aminobenzonitrile and diethyl 3-oxopentanedioate as a pale yellow solid (25%). $^1$H NR (400 MHz, DMSO-$d_6$) δ 1.19 (t, J=8.0 Hz, 3H), 1.30 (t, J=8.0 Hz, 3H), 4.08 (m, 4H), 4.28 (q, J=8.0 Hz, 2H), 7.50 (m, 1H), 7.73 (m, 2H), 8.10 (bs, 2H), 8.53 (d, J=8.0 Hz, 1H). MS 303 (MH+).

Example 18

4-amino-5-(cyclopentylmethoxy)-2-methylquinoline-3-carboxylic acid

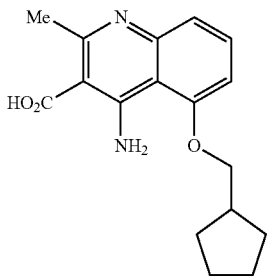 [SMILES: Cc1nc2cccc(OCC3CCCC3)c2c(N)c1C(=O)O]

To a solution of ethyl 4-amino-5-(cyclopentylmethoxy)-2-methylquinoline-3-carboxylate (Example 18a, 16.8 g, 51.2 mmol) in EtOH (100 mL) was added NaOH (2 N, 64 mL) at room temperature. The reaction mixture was refluxed for 4 h. After it was cooled down to room temperature, the reaction solution was filtered to remove any possible solid residue. The filtrate was carefully neutralized with 2N HCl to pH 7 at 0° C. The resultant precipitate was collected by filtration, washed with water, re-dissolved in EtOH (500 mL) and water (30 mL), and treated with activated charcoal (650 mg) at 70° C. for 0.5 h. The charcoal was removed by filtration, and the filtrate was concentrated and stored at 4° C. overnight. The resulting precipitate was collected by filtration, washed with cold 25% EtOH in H$_2$O, and dried under vacuum at 60° C. overnight to give the title compound as an off-white solid (7.5 g, 49%). $^1$H NR (400 MHz, DMSO-$d_6$) δ 1.31-1.37 (m, 2H), 1.53-1.64 (m, 4H), 1.79-1.85 (m, 2H), 2.47-2.50 (m, 1H), 2.75 (s, 3H), 4.11 (d, J=8.8 Hz, 2H), 7.03 (d, J=8.0 Hz, 1H), 7.26 (d, J=8.4 Hz, 1H), 7.66 (t, J=8.0 Hz, 1H), 8.77 (brs, 1H), 12.26 (brs, 1H), 12.75 (brs, 1H). $^1$H NR (400 MHz, CD$_3$OD) δ 1.39-1.49 (m, 2H), 1.63-1.77 (m, 4H), 1.91-1.98 (m, 2H), 2.51-2.61 (m, 1H), 2.78 (s, 3H), 4.16 (d, J=8.0 Hz, 2H), 7.08 (d, J=8.0 Hz, 1H), 7.23 (d, J=8.0 Hz, 1H), 7.72 (t, J=8.0 Hz, 1H). MS 301 (MH+).

Example 18a ethyl 4-amino-5-(cyclopentylmethoxy)-2-methylquinoline-3-carboxylate To a solution of 2-amino-6-(cyclopentylmethoxy)benzonitrile (Tachdjian, C. et al. PCT Int. Appl. 2008, WO 2008154221) (21.63 g, 100.0 mmol) and ethyl acetoacetate (12.6 mL, 100.0 mmol) in anhydrous toluene (300 mL) was added SnCl$_4$ (23.1 mL, 200.0 mmol) over a period of 25 minutes at room temperature under nitrogen. The stirred reaction mixture was then refluxed for 5 h under nitrogen. After it was cooled down to room temperature, the reaction solution was concentrated to remove most of the solvent under reduced pressure. The residue was re-dissolved in EtOAc (3.5 L) and carefully neutralized to pH 8 with aqueous NaOH solution (6.0 N, ~130 mL) at 0° C. The resultant mixture was stirred at room temperature overnight. The precipitate was filtered off, and the organic layer was separated and washed with brine (400 mL), dried over $Na_2SO_4$ and concentrated under reduced pressure. The residue was purified by column chromatography on silica gel eluting with 30% EtOAc in hexanes to give the title compound as a pale yellow solid (24.6 g, 75%). $^1$H NR (400 MHz, DMSO-$d_6$) δ 1.30-1.36 (m, 5H), 1.53-1.65 (m, 4H), 1.81-1.86 (m, 2H), 2.42-2.45 (m, 1H), 2.54 (s, 3H), 4.05 (d, J=7.2 Hz, 2H), 4.31 (q, J=7.2 Hz, 2H), 6.89 (d, J=7.6 Hz, 1H), 7.21-7.23 (m, 1H), 7.50 (t, J=8.0 Hz, 1H), 8.08 (s, 2H). MS 329 (MH$^+$).

Example 19

4-amino-5-(cyclopentyloxy)-2-methylquinoline-3-carboxylic acid

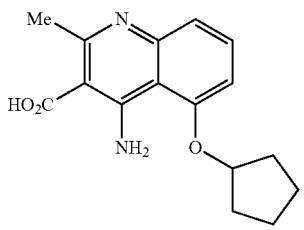 [SMILES: Cc1nc2cccc(OC3CCCC3)c2c(N)c1C(=O)O]

Prepared as in Example 1 from ethyl 4-amino-5-(cyclopentyloxy)-2-methylquinoline-3-carboxylate (Example 19a) as a off white solid (83%). $^1$H NR (400 MHz, DMSO-$d_6$) δ 1.56-1.60 (m, 2H), 1.67-1.70 (m, 2H), 1.83-1.87 (m, 1H), 1.92-1.96 (m, 2H), 2.67 (s, 3H), 5.05-5.07 (m, 1H), 6.93 (d, J=8.4 Hz, 1H), 7.18 (d, J=8.4 Hz, 1H), 7.57 (t, J=8.4 Hz, 1H). MS 287 (MH$^+$).

Example 19a ethyl 4-amino-5-(cyclopentyloxy)-2-methylquinoline-3-carboxylate

Prepared as in Example 2a from 2-amino-6-(cyclopentyloxy)benzonitrile (Tachdjian, C. et al. PCT Int. Appl. 2008, WO 2008154221) and ethyl 3-oxobutanoate as a yellow solid (40%). MS 315 (MH$^+$).

Example 20

4-amino-2,3-butylene-6-methylthieno[2,3-b]pyridine-5-carboxylic acid

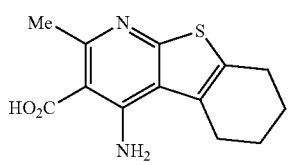 [SMILES: Cc1nc2sc3c(c2c(N)c1C(=O)O)CCCC3]

Prepared as in Example 1 from ethyl 4-amino-2,3-butylene-6-methylthieno[2,3-b]pyridine-5-carboxylate (Example 20a) as a solid. $^1$H NR (400 MHz, DMSO-$d_6$) δ 1.78-1.79 (m, 4H), 2.53 (s, 3H), 2.71-2.72 (m, 2H), 2.94-2.96 (m, 2H), 6.86 (s, 2H). MS 263 (MH$^+$).

Example 20a ethyl 4-amino-2,3-butylene-6-methylthieno[2,3-b]pyridine-5-carboxylate Prepared as in Example 2a from 2-amino-4,5,6,7-tetrahydrobenzo[b]thiophene-3-carbonitrile (Tachdjian, C. et al. PCT Int. Appl. 2008, WO 2008154221) and ethyl 3 as a yellow solid. MS 291 (MH$^+$).

Example 21

4-amino-5-(3,3-dimethylbutyl)-2-methylquinoline-3-carboxylic acid

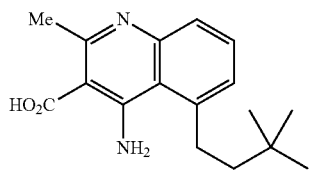 [SMILES: Cc1nc2cccc(CCC(C)(C)C)c2c(N)c1C(=O)O]

Prepared as in Example 1 from ethyl 4-amino-5-(3,3-dimethylbutyl)-2-methylquinoline-3-carboxylate (Example 21a) as a white solid (88%). $^1$H NR (400 MHz, DMSO-$d_6$) δ 0.93 (s, 9H), 1.40 (t, J=8.8 Hz, 2H), 2.75 (s, 3H), 3.17 (t, J=8.4 Hz, 2H), 7.35 (d, J=7.2 Hz, 1H), 7.57 (d, J=8.4 Hz, 1H), 7.66 (t, J=8.0 Hz, 1H), 12.78 (s, 1H). MS 287 (MH$^+$).

Example 21a ethyl 4-amino-5-(3,3-dimethylbutyl)-2-methylquinoline-3-carboxylate

Prepared as in Example 2a from 2-amino-6-(3,3-dimethylbutyl)benzonitrile (Example 21b) and ethyl 3-oxobutanoate as a white solid (95%). $^1$H NR (400 MHz, DMSO-$d_6$) δ 0.93 (s, 9H), 1.32 (t, J=7.2 Hz, 3H), 1.42-1.46 (m, 1H), 2.55 (s, 3H), 3.11-3.15 (m, 2H), 4.33 (q, J=7.2 Hz, 2H), 7.12 (s, 2H), 7.19-7.21 (m, 1H), 7.46-7.52 (m, 2H). MS 315 (MH$^+$).

Example 21b 2-amino-6-(3,3-dimethylbutyl)benzonitrile

A suspension of 2-amino-6-(3,3-dimethylbut-1-ynyl)benzonitrile (Example 21c, 690 mg, 3.48 mmol) and 10% Pd/C (100 mg) in EtOAc/EtOH (1:1, 20 mL) was stirred under an atmosphere of $H_2$ with a balloon at room temperature overnight. The Pd/C was removed by filtration, the filtrate was concentrated, and purified by chromatography on silica gel eluting with 20% EtOAc in hexanes to give the title compound as a light yellow oil (620 mg, 88%). $^1$H NR (400 MHz, DMSO-$d_6$) δ 0.92 (s, 9H), 1.36-1.40 (m, 2H), 2.52-2.56 (m, 2H), 5.88 (s, 2H), 6.45 (d, J=7.6 Hz, 1H), 6.57 (d, J=7.6 Hz, 1H), 7.15 (t, J=8.0 Hz, 1H). MS 203 (MH+).

Example 21c 2-amino-6-(3,3-dimethylbut-1-ynyl)benzonitrile

To a solution of 2-amino-6-bromobenzonitrile (1.97 g, 10.0 mmol), 3,3-dimethylbut-1-yne (2.46 g, 30 mmol), $K_2CO_3$ (2.76 g, 20.0 mmol), and CuI (191 mg, 0.1 mmol) in DME/$H_2O$ (4:1, 50 mL) was added Pd(PPh$_3$)$_4$ (1.16 g, 0.1 mmol) at room temperature under nitrogen. The reaction mixture was refluxed under nitrogen overnight. After it was cooled down to room temperature, the reaction was quenched with brine, extracted with EtOAc. The organic layer was washed with brine, dried over $Na_2SO_4$, and concentrated. The residue was purified by chromatography on silica gel eluting with 20% EtOAc in hexanes to give the title compound as a light brown oil (1.84 g, 93%). $^1$H NR (400 MHz, DMSO-$d_6$) δ 1.27 (s, 9H), 6.10 (s, 2H), 6.59 (d, J=7.2 Hz, 1H), 6.71 (d, J=8.0 Hz, 1H), 7.18-7.22 (m, 1H). MS 199 (MH+).

Example 22

4-amino-5-(2-ethylbutoxy)-2-methylquinoline-3-carboxylic acid

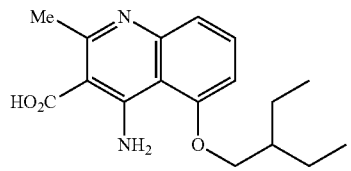 [SMILES: CCC(CC)COc1cccc2nc(C)c(C(=O)O)c(N)c12]

Prepared as in Example 1 from ethyl 4-amino-5-(2-ethylbutoxy)-2-methylquinoline-3-carboxylate (Example 22a) as a white solid (45%). M.p.: 145-151° C. $^1$H NR (400 MHz, DMSO-$d_6$) δ 0.90 (t, J=8 Hz, 6H), 1.48-1.41, (m, 4H), 1.84-1.78 (m, 1H), 2.73 (s, 3H), 4.11 (d, J=8 Hz, 2H), 6.99 (d, J=8 Hz, 1H), 7.32 (d, J=8 Hz, 1H), 7.59 (t, J=8 Hz, 1H), 8.40 (brs, 1H), 11.09 (brs, 1H), 13.91 (brs, 1H). MS 303 (MH+).

Example 22a ethyl 4-amino-5-(2-ethylbutoxy)-2-methylquinoline-3-carboxylate

Prepared as in Example 2a from 2-amino-6-(2-ethylbutoxy)benzonitrile (Example 22b) and ethyl 3-oxobutanoate as a white solid (89%). $^1$H NR (400 MHz, DMSO-$d_6$) δ 0.90 (t, J=8 Hz, 6H), 1.32 (t, J=8 Hz, 3H), 1.48-1.41 (m, 4H), 1.79-1.73 (m, 1H), 2.54 (s, 3H), 4.08 (d, J=4 Hz, 2H), 4.31 (q, J=8 Hz, 2H), 6.92 (dd, J=2, 8 Hz, 1H), 7.23 (dd, J=2, 8 Hz, 1H), 7.50 (t, J=8 Hz, 1H), 8.04 (brs, 1H). MS 331 (MH+).

Example 22b 2-amino-6-(2-ethylbutoxy)benzonitrile

To a solution of 2-ethylbutan-1-ol (1.02 g, 10.0 mmol) in dry THF (60 mL) was carefully added NaH (60% in mineral oil, 480 mg, 12.0 mmol) in small portions at 0° C. under nitrogen. The reaction mixture was stirred at 0° C. under nitrogen for 2 hrs. To this solution was added 2 (1.36 g, 10.0 mmol), and the reaction solution was stirred at 0° C.-RT for 2 hrs, and then at 65° C. overnight under nitrogen. The reaction was cooled down to room temperature then quenched with brine, and extracted with EtOAc (3×). The combined organic layers were washed with brine, dried over $Na_2SO_4$. Filtered and evaporated under reduced pressure. The residue was purified by chromatography on silica gel (eluent: 20% EtOAc in hexanes) to give the title compound as colorless oil (1.29 g, 59%). $^1$H NR (400 MHz, CDCl$_3$) δ 0.93 (t, J=8 Hz, 6H), 1.55-1.43 (m, 4H), 1.73-1.65 (m, 1H), 3.90 (d, J=4 Hz, 2H), 4.10 (brs, 2H), 6.25 (d, J=8 Hz, 1H), 6.34 (d, J=8 Hz, 1H), 7.20 (t, J=8 Hz, 1H).

Example 23

4-amino-5-(heptan-4-yloxy)-2-methylquinoline-3-carboxylic acid

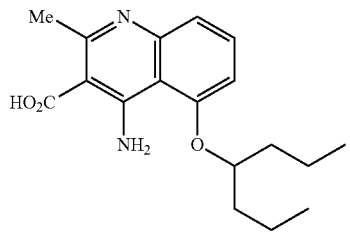 [SMILES: CCCC(CCC)Oc1cccc2nc(C)c(C(=O)O)c(N)c12]

Prepared as in Example 1 from ethyl 4-amino-5-(heptan-4-yloxy)-2-methylquinoline-3-carboxylate (Example 23a) as a white solid (59%). $^1$H NR (400 MHz, DMSO-$d_6$) δ 0.87 (t, J=7.2 Hz, 6H), 1.49-1.25 (m, 4H), 1.84-1.60 (m 4H), 2.74 (s, 3H), 4.74-4.71 (m, 1H), 7.07 (d, J=8.4 Hz, 1H), 7.24 (d, J=8.0 Hz, 1H), 7.64 (t, J=8.4 Hz, 1H), 8.82 (brs, 1H). MS 317 (MH+).

Example 23a ethyl 4-amino-5-(heptan-4-yloxy)-2-methylquinoline-3-carboxylate

Prepared as in Example 2a from 2-amino-6-(heptan-4-yloxy)benzonitrile (Example 23b) and ethyl 3-oxobutanoate as a pale yellow solid (65%). $^1$H NR (400 MHz, DMSO-$d_6$) δ 0.87 (t, J=7.2 Hz, 6H), 1.31 (t, J=7.2 Hz, 3H), 1.47-1.33 (m, 4H), 1.77-1.59 (m, 4H), 2.54 (s, 3H), 4.30 (q, J=7.2 Hz, 2H), 4.67-4.64 (m, 1H), 6.92 (d, J=7.6 Hz, 1H), 7.19 (dd, J=0.8, 8.4 Hz, 1H), 7.49 (t, J=8.0 Hz, 1H), 8.13 (brs, 2H). MS 345 (MH+).

Example 23b 2-amino-6-(heptan-4-yloxy)benzonitrile

Prepared as in Example 22b from heptan-4-ol and 2-amino-6-fluorobenzonitrile as a white solid (24%). $^1$H NR (400 MHz, CDCl$_3$) δ 0.92 (t, J=7.2 Hz, 6H), 1.55-1.31 (m, 8H), 3.88 (s, br, 1H), 4.33-4.27 (m, 1H), 6.26 (d, J=8.0 Hz, 1H), 6.35 (d, J=8.0 Hz, 1H), 7.20 (t, J=8.0 Hz, 1H).

Example 24

4-amino-5-(2-(isonicotinamido)-2-methylpropoxy)-2-methylquinoline-3-carboxylic acid

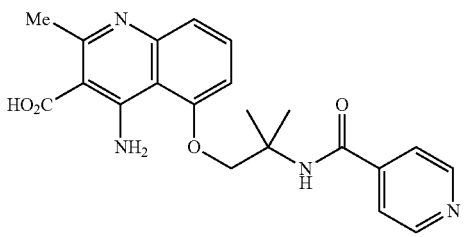 [SMILES: Cc1nc2cccc(OCC(C)(C)NC(=O)c3ccncc3)c2c(N)c1C(=O)O]

Prepared as in Example 1 from ethyl 4-amino-5-(2-(isonicotinamido)-2-methylpropoxy)-2-methylquinoline-3-carboxylate (Example 24a) as a white solid (67%). M.p.: 195-198° C. $^1$H NMR (400 MHz, DMSO-d$_6$) δ 1.51 (s, 6H), 2.75 (s, 3H), 4.48 (s, 2H), 7.07 (d, J=8 Hz, 1H), 7.31 (d, J=8 Hz, 1H), 7.67 (t, J=8 Hz, 1H), 7.70 (dd, J=1, 8 Hz, 2H), 8.50 (s, 1H), 8.67 (dd, J=1, 8 Hz, 2H), 8.76 (brs, 1H), 12.19 (brs, 1H), 12.85 (brs, 1H). MS 395 (MH$^+$).

Example 24a ethyl 4-amino-5-(2-(isonicotinamido)-2-methylpropoxy)-2-methylquinoline-3-carboxylate To a solution of ethyl 4-amino-5-(2-amino-2-methylpropoxy)-2-methylquinoline-3-carboxylate (Example 24b, 1.0 g, 3.15 mmol) in dry DMF (20 mL) was added isonicotinic acid (504 mg, 4.10 mmol), followed by EDCI (783 mg, 4.10 mmol), HOBt (554 mg, 4.10 mmol), and triethylamine (414 mg, 4.10 mmol) at room temperature under nitrogen. After it was stirred at room temperature for 12 hrs, the reaction mixture was concentrated under reduced pressure. The residue was diluted with water, and extracted with EtOAc (3×). The aqueous layer was basified with 2N NaOH to pH 8 and extracted with EtOAc (3×). The combined organic layers were washed with brine, dried over MgSO$_4$, filtered, concentrated, and purified by chromatography on silica gel eluting with 10% MeOH in dichloromethane to give the title compound as a yellow solid (1.1 g, 83%). $^1$H NR (400 MHz, DMSO-d$_6$) δ 1.29 (t, J=4 Hz, 3H), 1.51 (s, 6H), 2.94 (s, 3H), 4.28 (q, J=4 Hz, 2H), 4.42 (s, 2H), 6.93 (dd, J=1, 8 Hz, 1H), 7.24 (dd, J=1, 8 Hz, 2H), 7.52 (t, J=8 Hz, 1H), 7.69 (dd, J=2, 4 Hz, 2H), 8.14 (s, 2H), 8.37 (s, 1H), 8.67 (dd, J=2, 4 Hz, 2H). MS 423 (MH$^+$).

Example 24b ethyl 4-amino-5-(2-amino-2-methylpropoxy)-2-methylquinoline-3-carboxylate Prepared as in Example 2a from benzyl 1-(3-amino-2-cyanophenoxy)-2-methylpropan-2-ylcarbamate (Example 24c) and ethyl 3-oxobutanoate as a yellow-brown solid (91%). $^1$H NR (400 MHz, DMSO-d$_6$) δ 1.15 (s, 6H), 1.31 (t, J=4 Hz, 3H), 2.54 (s, 3H), 3.87 (s, 2H), 4.31 (q, J=4 Hz, 2H), 6.85 (d, J=4 Hz, 1H), 7.21 (d, J=4 Hz, 1H), 7.49 (t, J=8 Hz, 1H), 8.38 (brs, 2H). MS 318 (MH$^+$).

Example 24c benzyl 1-(3-amino-2-cyanophenoxy)-2-methylpropan-2-ylcarbamate

To a solution of 2-amino-6-(2-amino-2-methylpropoxy)benzonitrile (Example 24d, 30.5 g, 148.6 mmol) in THF/H$_2$O (1:1, 400 mL) was added NaHCO$_3$ (24.7 g, 294 mmol), followed by benzyl(2,5-dioxopyrrolidin-1-yl) carbonate (44.0 g, 176 mmol) at room temperature. The reaction was stirred at room temperature for 4 h then the organic layer was separated and the aqueous layer was extracted with EtOAc (2×). The combined organic layers were washed with brine and dried over MgSO$_4$. After filtration, the solvent was evaporated and the crude oil was purified by chromatography on silica gel (eluent: 0-60% EtOAc in hexane) to give the title compound as yellow oil (44.8 g, 89%). $^1$H NR (400 MHz, DMSO-d$_6$) δ 1.30 (s, 6H), 4.02 (s, 2H), 4.96 (s, 2H), 5.98 (s, 2H), 6.14 (d, J=8.0 Hz, 1H), 6.32 (dd, J=0.8, 8.4 Hz, 1H), 7.12 (t, J=8.4 Hz, 1H), 7.38-7.21 (m, 6H). MS 340 (MH$^+$).

Example 24d 2-amino-6-(2-amino-2-methylpropoxy)benzonitrile

To a solution of 2-amino-2-methylpropan-1-ol (14.4 g, 161 mmol) in anhydrous THF (150 mL) was added NaH (6.8 g, 161 mmol, 60% in mineral oil) in small portions at 0° C. under nitrogen. The mixture was stirred at 0° C. for 30 minutes and then stirred at room temperature for another 30 minutes. The solution was cooled down to 0° C. again, and to this solution was added dropwise a solution of 2-amino-6-fluorobenzonitrile (20.0 g, 147 mmol) in anhydrous THF (50 mL). The reaction mixture was then refluxed overnight under nitrogen. The reaction mixture was cooled down to room temperature and carefully quenched with aqueous NH$_4$Cl solution and extracted with ethyl acetate (3×). The combined organic layers were washed with brine, dried over MgSO$_4$, filtered and concentrated. The crude mixture was purified by chromatography on silica gel eluting with 10% MeOH in DCM to give the title compound as yellow solid (23.4 g 71%). $^1$H NR (400 MHz, DMSO-d$_6$) δ 1.08 (s, 6H), 3.15 (s, 2H), 3.64 (s, 2H), 5.98 (s, 2H), 6.13 (d, J=8.0 Hz, 1H), 6.31 (d, J=8.4 Hz, 1H), 7.15 (t, J=8.4 Hz, 1H). MS 236 (MH$^+$).

Example 25

4-amino-5-(2-(3-hydroxybenzamido)-2-methylpropoxy)-2-methylquinoline-3-carboxylic acid

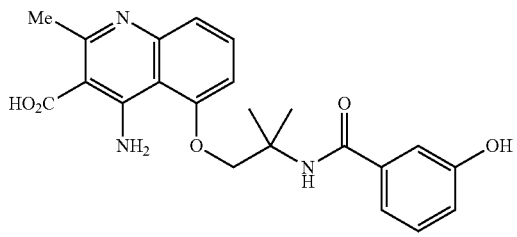 [SMILES: Cc1nc2cccc(OCC(C)(C)NC(=O)c3cccc(O)c3)c2c(N)c1C(=O)O]

Prepared as in Example 1 from ethyl 4-amino-5-(2-(3-hydroxybenzamido)-2-methylpropoxy)-2-methylquinoline- 3-carboxylate (Example 25a) as a white solid (65%). M.p.: 195-198° C. $^1$H NR (400 MHz, DMSO-$d_6$) δ 1.48 (s, 6H), 2.75 (s, 3H), 4.47 (s, 2H), 6.87 (dt, J=8, 4 Hz, 1H), 7.22-7.16 (m, 3H), 7.06 (d, J=8 Hz, 1H), 7.27 (d, J=8 Hz, 1H), 7.67 (t, J=8 Hz, 1H), 8.08 (s, 1H), 8.84 (brs, 1H), 9.69 (s, 1H), 12.12 (brs, 1H), 12.78 (brs, 1H). MS 410 (MH$^+$).

Example 25a ethyl 4-amino-5-(2-(3-hydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-hydroxybenzoic acid as a yellow-brown solid (64%). $^1$H NR (400 MHz, DMSO-$d_6$) δ 1.30 (t, J=4 Hz, 3H), 1.48 (s, 6H), 2.55 (s, 3H), 4.30 (q, J=4 Hz, 2H), 4.41 (s, 2H), 6.85-6.88 (m, 1H), 6.92 (d, J=8 Hz, 1H), 7.25-7.15 (m, 4H), 7.52 (t, J=8 Hz, 1H), 7.98 (s, 1H), 8.19 (s, 2H), 9.59 (s, 1H). MS 438 (MH$^+$).

Example 26

(S)-4-amino-5-(2-(cyclohexanecarboxamido)propoxy)-2-methylquinoline-3-carboxylic acid

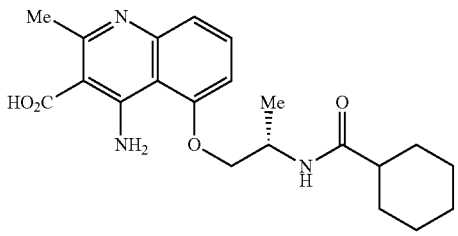 [SMILES: Cc1nc2cccc(OC[C@H](C)NC(=O)C3CCCCC3)c2c(N)c1C(=O)O]

Prepared as in Example 1 from (5)-ethyl 4-amino-5-(2-(cyclohexanecarboxamido)propoxy)-2-methylquinoline-3-carboxylate (Example 26a) as a white solid (53%). $^1$H NR (400 MHz, DMSO-$d_6$) δ 1.25-1.10 (m, 5H), 1.34-1.31 (m, 2H), 1.69-1.62 (m, 5H), 2.11-2.05 (m, 1H), 2.69 (s, 3H), 3.93 (t, J=9.2 Hz, 1H), 4.13 (dd, J=4, 9.6 Hz, 1H), 4.14-4.11 (m, 1H), 6.86 (d, J=8.0 Hz, 1H), 7.28 (d, J=8.4 Hz, 1H), 7.49 (t, J=8.0 Hz, 1H), 7.95 (d, J=8.4 Hz, 1H). MS 386 (MH$^+$).

Example 26a (5)-ethyl 4-amino-5-(2-(cyclohexanecarboxamido)propoxy)-2-methylquinoline-3-carboxylate Prepared as in Example 24a from (S)-ethyl 4-amino-5-(2-aminopropoxy)-2-methylquinoline-3-carboxylate (Example 26b) and cyclohexanecarboxylic acid as brown solid (28%). MS 414 (MH$^+$).

Example 26b (S)-ethyl 4-amino-5-(2-aminopropoxy)-2-methylquinoline-3-carboxylate Prepared as in Example 2a from (S)-benzyl(1-(3-amino-2-cyanophenoxy)propan-2-yl)carbamate (Example 26c) and ethyl 3-oxobutanoate as brown solid. MS 304 (MH$^+$).

Example 26c (S)-benzyl(1-(3-amino-2-cyanophenoxy)propan-2-yl)carbamate

Prepared as in Example 24c from (S)-2-amino-6-(2-aminopropoxy)benzonitrile (Example 26d) as brown solid (86%). $^1$H NR (400 MHz, DMSO-$d_6$) δ 1.12 (d, J=6.4 Hz, 3H), 3.81 (d, J=8.4 Hz, 1H), 3.95-3.92 (m, 1H), 4.99 (s, 2H), 5.36 (s, 2H), 5.96 (s, 2H), 6.20 (d, J=8.0 Hz, 1H), 6.31 (d, J=8.4 Hz, 1H), 7.13 (t, J=8.4 Hz, 1H), 7.44-7.38 (m, 5H). MS 326 (MH$^+$).

Example 26d (S)-2-amino-6-(2-aminopropoxy)benzonitrile

Prepared as in Example 24d from (S)-2-aminopropan-1-ol and 2-amino-6-fluorobenzonitrile as brown solid (73%). $^1$H NR (400 MHz, DMSO-$d_6$) δ 1.01 (d, J=6.5 Hz, 3H), 3.08 (m, 1H), 3.71 (d, J=6.1 Hz, 2H), 5.95 (s, 2H), 6.15 (d, J=8.3 Hz, 1H), 6.2 (d, J=8.3 Hz, 1H), 7.13 (t, J=8.3 Hz, 1H). MS 192 (MH$^+$).

Example 27

(S)-4-amino-5-(2-(isonicotinamido)propoxy)-2-methylquinoline-3-carboxylic acid

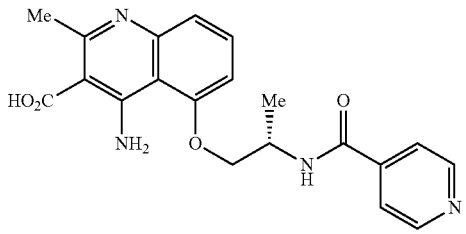 [SMILES: Cc1nc2cccc(OC[C@H](C)NC(=O)c3ccncc3)c2c(N)c1C(=O)O]

Prepared as in Example 1 from (S)-ethyl 4-amino-5-(2-(isonicotinamido)propoxy)-2-methylquinoline-3-carboxylate (Example 27a) as an off-white solid (42%). $^1$H NR (400 MHz, DMSO-$d_6$) δ 1.31 (d, J=6.8 Hz, 3H), 2.66 (s, 3H), 4.14 (t, J=9.2 Hz, 1H), 4.28 (dd, J=3.6, 9.6 Hz, 1H), 4.70-4.55 (m, 1H), 6.92 (d, J=8.0 Hz, 1H), 7.26 (d, J=8.4 Hz, 1H), 7.51 (t, J=8.4 Hz, 1H), 7.75 (dd, J=1.2, 6.0 Hz, 2H), 8.71 (dd, J=1.2, 6.0 Hz, 2H), 8.95 (d, J=8.0 Hz, 1H). MS 409 (MH$^+$).

Example 27a (S)-ethyl 4-amino-5-(2-(isonicotinamido)propoxy)-2-methylquinoline-3-carboxylate Prepared as in Example 24a from (S)-ethyl 4-amino-5-(2-aminopropoxy)-2-methylquinoline-3-carboxylate (Example 26b) and isonicotinic acid as brown solid (36%). MS 409 (MH$^+$).

Example 28

(S)-4-amino-5-(2-(3-hydroxybenzamido)propoxy)-2-methylquinoline-3-carboxylic acid

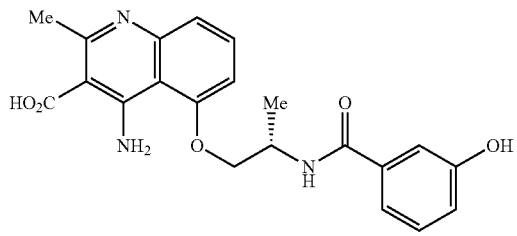 [SMILES: Cc1nc2cccc(OC[C@H](C)NC(=O)c3cccc(O)c3)c2c(N)c1C(=O)O]

Prepared as in Example 1 from (S)-ethyl 4-amino-5-(2-(3-hydroxybenzamido)propoxy)-2-methylquinoline-3-carboxylate (Example 28a) as a white solid (58%). $^1$H NR (400 MHz, DMSO-$d_6$) δ 1.28 (d, J=7.2 Hz, 3H), 2.65 (s, 3H), 4.11 (t, J=8.8 Hz, 1H), 4.22 (dd, J=4.0, 10 Hz, 1H), 4.65-4.55 (m, 1H), 6.88 (d, J=8.0 Hz, 2H), 7.25-7.13 (m, 4H), 7.48 (t, J=8.0 Hz, 1H), 8.49 (d, J=8.0, 1H), 9.93 (brs, 1H). MS 396 (MH$^+$).

Example 28a (5)-ethyl 4-amino-5-(2-(3-hydroxybenzamido)propoxy)-2-methylquinoline-3-carboxylate Prepared as in Example 24a from (5)-ethyl 4-amino-5-(2-aminopropoxy)-2-methylquinoline-3-carboxylate (Example 26b) and 3-hydroxybenzoic acid as brown solid (41%). MS 424 (MH$^+$).

Example 29

4-amino-5-(3-(cyclopentylamino)-2,2-dimethyl-3-oxopropoxy)-2-methylquinoline-3-carboxylic acid

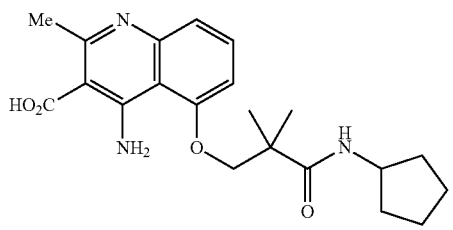 [SMILES: Cc1nc2cccc(OCC(C)(C)C(=O)NC3CCCC3)c2c(N)c1C(=O)O]

Prepared as in Example 1 from ethyl 4-amino-5-(3-(cyclopentylamino)-2,2-dimethyl-3-oxypropoxy)-2-methylquinoline-3-carboxylate (Example 29a) as a white powder (74%). $^1$H NMR (400 MHz, DMSO-$d_6$) δ 1.27 (s, 6H), 1.36-1.46 (m, 4H), 1.57-1.59 (m, 2H), 1.72-1.78 (m, 2H), 2.78 (s, 3H), 4.04 (m, 1H), 4.19 (s, 2H), 7.02 (d, J=8.0 Hz, 1H), 7.33 (d, J=8.0 Hz, 1H), 7.64-7.71 (m, 2H), 8.83 (brs, 1H), 12.25 (brs, 1H), 12.93 (brs, 1H). MS 386 (MH$^+$).

Example 29a ethyl 4-amino-5-(3-(cyclopentylamino)-2,2-dimethyl-3-oxopropoxy)-2-methylquinoline-3-carboxylate Prepared as in Example 2a from 3-(3-amino-2-cyanophenoxy)-N-cyclopentyl-2,2-dimethylpropanamide (Example 29b) and ethyl 3-oxobutanoate as a bright yellow solid (62%). $^1$H NR (400 MHz, DMSO-$d_6$) δ 1.26 (s, 6H), 1.34 (t, J=8.0 Hz, 3H), 1.40-1.46 (m, 4H), 1.57-1.59 (m, 2H), 1.74-1.77 (m, 2H), 2.57 (s, 3H), 4.09 (q, J=4.0 Hz, 1H), 4.15 (s, 2H), 4.33 (q, J=8.0 Hz, 2H), 6.89 (d, J=4.0 Hz, 1H), 7.26 (dd, J=8.0 Hz, 1H), 7.53 (d, J=8.0 Hz, 1H), 7.56 (s, 1H), 8.09 (brs, 2H). MS 414 (MH$^+$).

Example 29b 3-(3-amino-2-cyanophenoxy)-N-cyclopentyl-2,2-dimethylpropanamide Prepared as in Example 22b from N-cyclopentyl-3-hydroxy-2,2-dimethylpropanamide (Example 29c) and 2-amino-6-fluorobenzonitrile as a white solid (45%). $^1$H NR (400 MHz, DMSO-$d_6$) δ 1.19 (s, 6H), 1.40-1.49 (m, 4H), 1.61-1.63 (m, 2H), 1.74-1.79 (m, 2H), 3.95 (s, 2H), 4.03 (m, 1H), 5.98 (s, 2H), 6.19 (d, J=8.0 Hz, 1H), 6.33 (d, J=8.0 Hz, 1H), 7.17 (t, J=8.0 Hz, 1H), 7.23 (d, J=8.0 Hz, 1H). MS 302 (MH$^+$).

Example 29c

N-cyclopentyl-3-hydroxy-2,2-dimethylpropanamide

Prepared as in Example 24a from hydroxypivalic acid and cyclopentyl amine as an orange oil (32%). $^1$H NR (400 MHz, DMSO-$d_6$) δ 1.00 (s, 6H), 1.32-1.40 (m, 2H), 1.43-1.49 (m, 2H), 1.57-1.65 (m, 2H), 1.73-1.81 (m, 2H), 3.34 (d, J=4.0 Hz, 2H), 3.98 (m, 1H), 4.87 (t, J=4.0 Hz, 1H), 7.22 (d, J=4.0 Hz, 1H). MS 186 (MH$^+$).

Example 30

4-Amino-5-(cyclobutylmethoxy)-2-methylquinoline-3-carboxylic acid

Prepared as in Example 1 from ethyl 4-amino-5-(cyclobutylmethoxy)-2-methylquinoline-3-carboxylate (Example 30a) as a white powder (51%). $^1$H NR (400 MHz, DMSO-$d_6$) δ 1.84-1.99 (m, 4H), 2.10-2.15 (m, 2H), 2.77 (s, 3H), 2.92 (m, 1H), 4.23 (d, J=8.0 Hz, 2H), 7.05 (d, J=8.0 Hz, 1H), 7.29 (d, J=8.0 Hz, 1H), 7.68 (t, J=8.0 Hz, 1H), 8.71 (brs, 1H), 12.23 (brs, 1H), 12.81 (brs, 1H). MS 287 (MH$^+$).

Example 30a ethyl 4-amino-5-(cyclobutylmethoxy)-2-methylquinoline-3-carboxylate Prepared as in Example 2a from 2-amino-6-(cyclobutylmethoxy)benzonitrile (Tachdjian, C. et al. PCT Int. Appl. 2008, WO 2008154221) and ethyl 3-oxobutanoate as an orange solid (26%). $^1$H NR (400 MHz, DMSO-$d_6$) δ 1.32 (t, J=8.0 Hz, 3H), 1.83-1.90 (m, 4H), 2.10-2.13 (m, 2H), 2.59 (s, 3H), 2.86 (m, 1H), 4.16 (d, J=4.0 Hz, 2H), 4.32 (q, J=8.0 Hz, 2H), 6.90 (d, J=8.0 Hz, 1H), 7.23 (d, J=8.0 Hz, 1H), 7.51 (t, J=8.0 Hz, 1H), 8.05 (brs, 2H). MS 315 (MH⁺).

Example 31

4-amino-5-(2-(cyclopentanecarboxamido)-2-methylpropoxy)-2-methylquinoline-3-carboxylic acid

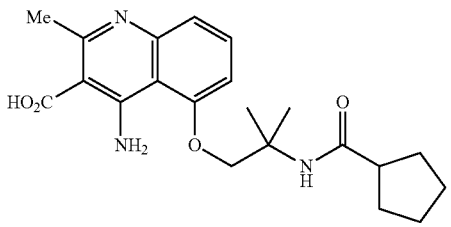 [SMILES: Cc1nc2cccc(OCC(C)(C)NC(=O)C3CCCC3)c2c(N)c1C(=O)O]

Prepared as in Example 1 from ethyl 4-amino-5-(2-(cyclopentanecarboxamido)-2-methylpropoxy)-2-methylquinoline-3-carboxylate (Example 31a) as an off-white solid (68%). ¹H NR (400 MHz, DMSO-d₆) δ 1.36 (s, 6H), 1.43-1.51 (m, 6H), 1.65-1.69 (m, 2H), 2.58 (m, 1H), 2.78 (m, 3H), 4.37 (s, 2H), 7.04 (m, 1H), 7.29 (d, J=8.0 Hz, 1H), 7.68 (m, 1H), 7.80 (s, 1H), 8.84 (brs, 1H), 12.42 (brs, 1H), 12.73 (brs, 1H). MS 386 (MH⁺).

Example 31a ethyl 4-amino-5-(2-(cyclopentanecarboxamido)-2-methylpropoxy)-2-methylquinoline-3-carboxylate Prepared as in Example 24a from ethyl 4-amino-5-(2-amino-2-methylpropoxy)-2-methylquinoline-3-carboxylate (Example 24b) and cyclopentane carboxylic acid as a yellow solid (33%). ¹H NR (400 MHz, DMSO-d₆) δ 1.34 (t, J=4.0 Hz, 3H), 1.37 (s, 6H), 1.42-1.53 (m, 6H), 1.64-1.69 (m, 2H), 2.58 (m, 1H), 2.62 (s, 3H), 4.32 (s, 2H), 4.35 (m, 2H), 6.96 (m, 1H), 7.28 (d, J=8.0 Hz, 1H), 7.58 (m, 1H), 7.66 (s, 1H), 8.41 (d, 2H). MS 414 (MH⁺).

Example 32

4-Amino-5-(cycloheptyloxy)-2-methylquinoline-3-carboxylic acid

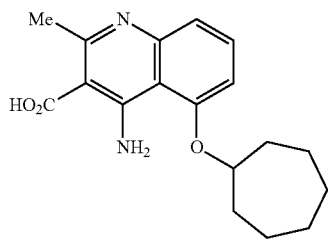 [SMILES: Cc1nc2cccc(OC3CCCCCC3)c2c(N)c1C(=O)O]

Prepared as in Example 1 from ethyl 4-amino-5-(cycloheptyloxy)-2-methylquinoline-3-carboxylate (Example 32a) as a light yellow solid (34%). ¹H NR (400 MHz, DMSO-d₆) δ 1.49-1.65 (m, 8H), 1.83-1.89 (m, 2H), 2.04-2.09 (m, 2H), 2.74 (s, 3H), 4.85 (m, 1H), 7.03 (d, J=8.0 Hz, 1H), 7.23 (d, J=8.0 Hz, 1H), 7.65 (t, J=8.0 Hz, 1H), 8.82 (brs, 1H), 12.24 (brs, 1H), 12.64 (brs, 1H). MS 315 (MH⁺).

Example 32a ethyl 4-amino-5-(cycloheptyloxy)-2-methylquinoline-3-carboxylate Prepared as in Example 2a from 2-amino-6-(cycloheptyloxy)benzonitrile (Example 32b) and ethyl 3-oxobutanoate as a bright yellow solid (72%). ¹H NR (400 MHz, DMSO-d₆) δ 1.32 (t, J=8.0 Hz, 3H), 1.49-1.65 (m, 8H), 1.78-1.87 (m, 2H), 2.04-2.10 (m, 2H), 2.53 (s, 3H). 4.31 (q, J=8.0 Hz, 2H), 4.79 (m, 1H), 6.89 (d, J=8.0 Hz, 1H), 7.20 (d, J=8.0 Hz, 1H), 7.49 (t, J=8.0 Hz, 1H), 8.14 (brs, 2H). MS 343 (MH⁺).

Example 32b 2-amino-6-(cycloheptyloxy)benzonitrile

Prepared as in Example 22b from cycloheptanol and 2-amino-6-fluorobenzonitrile as yellow oil (11%). ¹H NR (400 MHz, DMSO-d₆) δ 1.42-1.71 (m, 10H), 1.88-1.93 (m, 2H), 4.56 (m, 1H), 5.95 (s, 2H), 6.20 (d, J=8.0 Hz, 1H), 6.30 (d, J=8.0 Hz, 1H), 7.15 (t, J=8.0 Hz, 1H). MS 231 (MH⁺).

Example 33

4-Amino-2-methyl-5-(3-phenoxypropoxy)quinoline-3-carboxylic acid

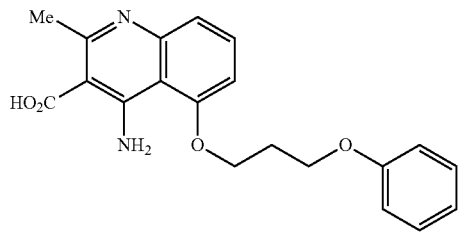 [SMILES: Cc1nc2cccc(OCCCOc3ccccc3)c2c(N)c1C(=O)O]

Prepared as in Example 1 from ethyl 4-amino-2-methyl-5-(3-phenoxypropoxy)quinoline-3-carboxylate (Example 33a) as a yellow solid (90%). ¹H NR (400 MHz, DMSO-d₆) δ 2.35 (m, 2H), 2.77 (s, 3H), 4.19 (t, J=4.0 Hz, 2H), 4.42 (t, J=4.0 Hz, 2H), 6.91-6.96 (m, 3H), 7.09 (d, J=8.0 Hz, 1H), 7.26-7.30 (m, 3H), 7.70 (t, J=8.0 Hz, 1H), 8.96 (brs, 1H), 12.24 (brs, 1H), 12.75 (brs, 1H). MS 353 (MH⁺).

Example 33a ethyl 4-amino-2-methyl-5-(3-phenoxypropoxy)quinoline-3-carboxylate Prepared as in Example 2a from 2-amino-6-(3-phenoxypropoxy)benzonitrile (Example 33b) and ethyl 3-oxobutanoate as a yellow solid (47%). ¹H NR (400 MHz, DMSO-d₆) δ 1.33 (t, J=8.0 Hz, 3H), 2.34 (m, 2H), 2.57 (s, 3H), 4.19 (t, J=4.0 Hz, 2H), 4.33 (q, J=8.0 Hz, 2H), 4.37 (t, J=4.0 Hz, 2H), 6.91-6.97 (m, 4H), 7.24-7.29 (m, 3H), 7.53 (t, J=8.0 Hz, 1H), 8.17 (s, 2H). MS 381 (MH⁺).

Example 33b 2-amino-6-(3-phenoxypropoxy)benzonitrile

Prepared as in Example 22b from 3-phenoxy-1-propanol and 2-amino-6-fluorobenzonitrile as a yellow oil (93%). ¹H NR (400 MHz, DMSO-d$_6$) δ 2.14 (m, 2H), 4.10-4.16 (m, 4H), 5.98 (s, 2H), 6.23 (d, J=8.0 Hz, 1H), 6.33 (d, J=8.0 Hz, 1H), 6.89-6.94 (m, 5H), 7.16 (t, J=8.0 Hz, 1H).

Example 34

44-Amino-5-((1-(3-hydroxybenzoyl)piperidin-4-yl)methoxy)-2-methylquinoline-3-carboxylic acid

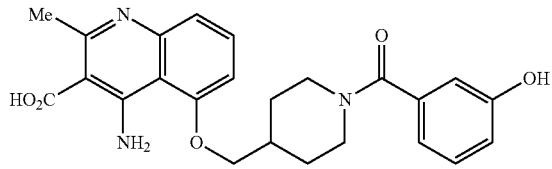 [SMILES: Cc1nc2cccc(OCC3CCN(C(=O)c4cccc(O)c4)CC3)c2c(N)c1C(=O)O]

Prepared as in Example 1 from ethyl 4-amino-5-((1-(3-hydroxybenzoyl)piperidin-4-yl)methoxy)-2-methylquinoline-3-carboxylate (Example 34a) as an orange powder (23%). $^1$H NMR (400 MHz, DMSO-d$_6$) δ 1.24 (brs, 2H), 1.79-1.88 (m, 2H), 2.29 (m, 1H), 2.77 (s, 3H), 3.07 (brs, 2H), 3.65 (brs, 1H), 4.17 (d, J=8.0 Hz, 2H), 4.50 (brs, 1H), 6.74-6.83 (m, 3H), 7.07 (d, J=8.0 Hz, 1H), 7.23 (t, J=8.0 Hz, 1H), 7.29 (d, J=8.0 Hz, 1H), 7.69 (t, J=8.0 Hz, 1H), 8.74 (brs, 1H), 9.75 (s, 1H), 12.25 (brs, 1H), 12.71 (brs, 1H). MS 436 (MH$^+$).

Example 34a ethyl 4-amino-5-((1-(3-hydroxybenzoyl)piperidin-4-yl)methoxy)-2-methylquinoline-3-carboxylate Prepared as in Example 2a from 2-amino-6-((1-(3-hydroxybenzoyl)piperidin-4-yl)methoxy)benzonitrile (Example 34b) and ethyl 3-oxobutanoate as a yellow solid (49%). $^1$H NMR (400 MHz, DMSO-d$_6$) δ 1.24 (m, 2H), 1.31 (t, J=4.0 Hz, 3H), 1.77-1.89 (m, 2H), 2.22 (brs, 1H), 2.55 (s, 3H), 2.79 (brs, 1H), 3.04 (brs, 1H), 3.64 (brs, 1H), 4.10 (m, 2H), 4.32 (q, J=8.0 Hz, 2H), 4.49 (brs, 1H), 6.71-6.82 (m, 3H), 6.93 (d, J=8.0 Hz, 1H), 7.19-7.25 (m, 2H), 7.52 (t, J=8.0 Hz, 1H), 8.06 (brs, 2H), 9.64 (s, 1H). MS 464 (MH$^+$).

Example 34b 2-amino-6-((1-(3-hydroxyenzoyl)piperidin-4-yl)methoxy)benzonitrile Prepared as in Example 24a from 2-amino-6-(piperidin-4-ylmethoxy)benzonitrile (Example 34c) and 3-hydroxybenzoic acid as an orange glass (66%). $^1$H NR (400 MHz, DMSO-d$_6$) δ 1.29 (m, 2H), 1.66-1.92 (m, 2H), 2.06 (m, 1H), 2.80 (brs, 1H), 3.05 (brs, 1H), 3.62 (brs, 1H), 3.91 (d, J=8.0 Hz, 2H), 4.49 (brs, 1H), 5.99 (s, 2H), 6.22 (d, J=8.0 Hz, 1H), 6.34 (d, J=8.0 Hz, 1H), 6.72-6.83 (m, 3H), 7.15-7.24 (m, 2H), 9.65 (s, 1H). MS 352 (MH$^+$).

Example 34c 2-amino-6-(piperidin-4-ylmethoxy)benzonitrile

To a solution of tert-butyl 4-((3-amino-2-cyanophenoxy)methyl)piperidine-1-carboxylate (Example 34d, 1.33 g, 4.0 mmol) in EtOAc (20 mL) was added dropwise aqueous HCl solution (12 N, 6.6 mL) at 0° C. The reaction mixture was stirred at room temperature overnight. The solvent was removed under reduced pressure to give the title compound (100%) as a brown solid, which is pure enough and used directly in the next step without further purification. MS 232 (MH$^+$).

Example 34d 2 tert-butyl 4-((3-amino-2-cyanophenoxy)methyl)piperidine-1-carboxylate Prepared as in Example 22b from N-Boc-4-piperidinemethanol and 2-amino-6-fluorobenzonitrile as an off-white solid (37%). $^1$H NR (400 MHz, DMSO-d$_6$) δ 1.15-1.21 (m, 2H), 1.40 (s, 9H), 1.74 (m, 2H), 1.99 (brs, 1H), 2.74 (brs, 2H), 3.87 (d, J=4.0 Hz, 2H), 3.96 (m, 2H), 5.99 (s, 2H), 6.21 (d, J=8.0 Hz, 1H), 6.33 (d, J=8.0 Hz, 1H), 7.17 (t, J=8.0 Hz, 1H). MS 232 (MH$^+$-Boc).

Example 35

4-Amino-5-((1-butyrylpiperidin-4-yl)methoxy)-2-methylquinoline-3-carboxylic acid

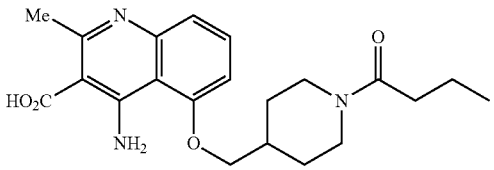 [SMILES: CCCC(=O)N1CCC(COc2cccc3nc(C)c(C(=O)O)c(N)c23)CC1]

Prepared as in Example 1 ethyl 4-amino-5-((1-butyrylpiperidin-4-yl)methoxy)-2-methylquinoline-3-carboxylate (Example 35a) as a white solid (61%). $^1$H NR (400 MHz, DMSO-d$_6$) δ 0.87 (t, J=8.0 Hz, 3H), 1.05-1.22 (m, 2H), 1.50 (m, 2H), 1.80 (m, 2H), 2.24-2.31 (m, 3H), 2.65 (s, 3H), 3.02 (2H), 3.88-3.92 (m, 1H), 4.11 (m, 2H), 4.44 (m, 1H), 7.05 (m, 1H), 7.26 (d, J=8.0 Hz, 1H), 7.69 (m, 1H), 8.76 (brs, 1H), 12.33 (brs, 1H), 12.65 (brs, 1H). MS 386 (MH$^+$).

Example 35a ethyl 4-amino-5-((1-butyrylpiperidin-4-yl)methoxy)-2-methylquinoline-3-carboxylate Prepared as in Example 24a from ethyl 4-amino-2-methyl-5-(piperidin-4-ylmethoxy)quinoline-3-carboxylate (Example 35b) and butyric acid as a yellow oil (50%). MS 414 (MH$^+$).

Example 35b ethyl 4-amino-2-methyl-5-(piperidin-4-ylmethoxy)quinoline-3-carboxylate Prepared as in Example 2a from benzyl 4-((3-amino-2-cyanophenoxy)methyl)piperidine-1-carboxylate (Example 35c) and ethyl 3-oxobutanoate as an orange solid (25%). $^1$H NR (400 MHz, DMSO-d$_6$) δ 1.29-1.37 (m, 5H), 1.77-1.80 (m, 2H), 2.07 (brs, 1H), 2.53 (s, 3H), 2.55-2.65 (m, 3H), 3.06-3.09 (m, 2H), 4.06 (d, J=8.0 Hz, 2H), 4.32 (q, J=8.0 Hz, 2H), 6.92 (d, J=8.0 Hz, 1H), 7.24 (d, J=8.0 Hz, 1H), 7.51 (t, J=8.0 Hz, 1H), 8.08 (s, 2H). MS 344 (MH+).

Example 35c 4-((3-amino-2-cyanophenoxy)methyl)piperidine-1-carboxylate

Prepared as in Example 22b from 1-N-Cbz-4-(hydroxymethyl)piperidine and 2-amino-6-fluoro-benzonitrile as a yellow oil (18%). $^1$H NR (400 MHz, DMSO-d$_6$) δ 1.20-1.25 (m, 2H), 1.75-1.78 (m, 2H), 1.96 (brs, 1H), 3.88 (d, J=8.0 Hz, 2H), 3.99-4.04 (m, 4H), 5.07 (s, 2H), 5.99 (s, 2H), 6.21 (d, J=8.0 Hz, 1H), 6.34 (d, J=8.0 Hz, 1H), 7.17 (t, J=8.0 Hz, 1H), 7.29-7.40 (m, 5H). MS 366 (MH+).

Example 36

4-amino-5-(cyclohexyloxy)-2-methylquinoline-3-carboxylic acid

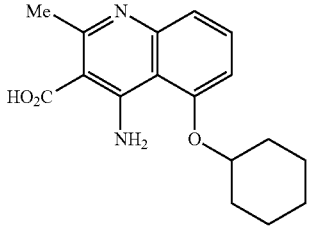 [SMILES: Cc1nc2cccc(OC3CCCCC3)c2c(N)c1C(=O)O]

To a solution of ethyl 4-amino-5-(cyclohexyloxy)-2-methylquinoline-3-carboxylate (Example 36a, 110 g, 0.335 mol) in EtOH (450 mL) was added a solution of NaOH (33.5 g, 0.837 mol) in water (200 mL) at room temperature. The reaction mixture was then refluxed overnight. The reaction solution was cooled down to 0° C. and carefully neutralized with 4N HCl to pH 7. The resultant solution was concentrated under reduced pressure to remove most of the EtOH. The precipitate was collected by filtration, and re-dissolved in EtOH (4 L) at 65° C. and treated with activated charcoal (5 g) for 0.5 h. The charcoal was removed by filtration over celite, and the filtrate was concentrated. The precipitate was collected by filtration, washed with cold water, and dried under vacuum at 60° C. overnight to give the title compound as a white solid (100 g, 99%). M.p.: 220.0-221.5° C. $^1$H NR (400 MHz, DMSO-d$_6$) δ 1.28-1.72 (m, 8H), 2.00-2.04 (m, 2H), 2.75 (s, 3H), 4.69-4.71 (m, 1H), 7.10-7.12 (d, J=8.0 Hz, 1H), 7.24-7.26 (d, J=8.0 Hz, 1H), 7.65 (t, J=8.0 Hz, 1H), 12.80 (brs, 1H). MS 301 (MH+). Elemental Analysis Calculated (Found) for $C_{17}H_{20}N_2O_3$: C, 67.98% (67.74%); H, 6.71% (7.01%); N, 9.33% (9.40%).

Example 36a ethyl 4-amino-5-(cyclohexyloxy)-2-methylquinoline-3-carboxylate

A solution of ethyl 3-oxobutanoate (29.9 g, 0.230 mol) in anhydrous toluene (200 mL) was added to a solution of 2-amino-6-(cyclohexyloxy)benzonitrile (Example 36b, 49.8 g, 0.230 mol) in anhydrous toluene (1000 mL) under nitrogen in a 3 L round bottom flask sitting in an oil bath at room temperature. SnCl$_4$ (53.9 mL, 0.461 mol) was added slowly over a period of approximately 1 h. The oil bath temperature was then raised to 110° C. and the reaction mixture was stirred at that temperature for 2.5 h. It was then cooled down to 5° C., still under nitrogen, and the toluene was decanted away from the immiscible viscous oil at the bottom of the flask. The viscous oil was further concentrated under vacuum at 60° C., re-dissolved in boiling ethyl acetate (1 L), and transferred to a 4 liter Erlenmeyer flask. The solution was diluted with more EtOAc (1.5 L), cooled down to -15° C., and neutralized with NaOH (3 N, 500 mL). The organic layer was separated, and the aqueous emulsion was extracted once more with ethyl acetate. The insoluble tin salts were filtered out from the aqueous layer, then both the salts and aqueous filtrate were washed once more with ethyl acetate. The combined organic layers were dried over MgSO$_4$, concentrated, and passed through a silica column using 0% to 60% ethyl acetate in hexanes. The product was purified by recrystallization from EtOAc to give the title compound as an off-white solid (64.3 g, 85%). $^1$H NR (400 MHz, DMSO-d$_6$) δ 1.28-1.34 (m, 1H), 1.32 (t, 3H), 1.37-1.45 (m, 2H), 1.51-1.63 (m, 3H), 1.67-1.71 (m, 2H), 1.99-2.03 (m, 2H), 2.54 (s, 3H), 4.28-4.33 (q, J=6.8 Hz, 2H), 4.64 (m, 1H), 6.95-6.97 (d, J=7.6 Hz, 1H), 7.19-7.21 (d, J=8.4 Hz, 1H), 7.65 (t, J=8.4 Hz, 1H), 8.15 (brs, 2H). MS 329 (MH+).

Example 36b 2-amino-6-(cyclohexyloxy)benzonitrile

To a solution of cyclohexanol (19.1 g, 0.191 mol) in anhydrous THF (500 mL) was added NaH (7.6 g, 40% in mineral oil, 0.191 mol) in small portions at 0° C. under nitrogen. The mixture was stirred at room temperature for 1 h and a solution of 2-amino-6-fluorobenzonitrile (20.0 g, 0.15 mol) in anhydrous THF (150 mL) was added drop-wise at room temperature. The reaction mixture was heated to reflux overnight then cooled to room temperature and most of the THF removed under reduced pressure. Ice water (100 mL) was added to the concentrated reaction mixture followed by EtOAc (500 mL). The organic layer was separated and successively washed with water and brine, dried over Na$_2$SO$_4$, filtered and evaporated under reduced pressure. The residue was purified by chromatography on silica gel eluting with 25-30% EtOAc in hexanes to give 2-amino-6-(cyclohexyloxy)benzonitrile as a light yellow oil (17.9 g, 56%). $^1$H NR (400 MHz, CDCl$_3$) δ 1.32-1.43 (m, 3H), 1.51-1.55 (m, 1H), 1.62-1.69 (m, 2H), 1.79-1.95 (m, 4H), 4.31-4.36 (m, 3H), 6.23-6.27 (m, 2H), 7.18 (d, J=8.0 Hz, 1H). MS 329 (WO.

Example 36b 2-amino-6-(cyclohexyloxy)benzonitrile

Alternative Methode a)
To a solution of 2-(cyclohexyloxy)-6-nitrobenzonitrile (Example 36c, 50.0 g, 0.20 mol) in THF/AcOH (1:1 by volume, 500 mL) was added iron powder (34.0 g, 0.61 mol) in one portion at room temperature under nitrogen. The reaction mixture was refluxed for 40 min under nitrogen and cooled down to room temperature and EtOAc (2 L) was added. The precipitate that formed was filtered off and washed with EtOAc. The organic layer was separated and washed successively with water (2×300 mL), aqueous NaOH (1.0 N, 2×300 mL), saturated Na$_2$CO$_3$ solution (300 mL), brine (300 mL), dried over Na$_2$SO$_4$ filtered and evaporated under reduced pressure. The residue was purified by chromatography on silica gel eluting with 25% EtOAc in hexanes to give 2-amino-6-(cyclohexyloxy)benzonitrile as a pale yellow oil (45.0 g, 94%), which solidified after storage overnight at room temperature.

Alternative Methode b):

A 3-L 3-neck round bottom flask was first purged with nitrogen. 10% Pd/C (2.81 g) was then added under nitrogen, followed successively by 2 (Example 36c, 43.2 g, 0.175 mol), anhydrous methanol (389 mL), and acetic acid (80.4 mL). A reflux condenser, a dropping funnel containing a solution of ammonium formate (49.8 g, 0.790 mol) in anhydrous methanol (498 mL), thermometer, nitrogen inlet and nitrogen outlet were attached. Ammonium formate solution (75 mL) was added at room temperature, then the reaction was slowly heated to a maximum of 42° C. The mixture was monitored carefully until initiation of the reaction was observed (an evolution of gas occurred with roughly a 10° C. exotherm). Initiation of the reaction often took up to 40 minutes before starting. The remaining of the ammonium formate solution was then added at a rate which maintained an internal reaction temperature of 40° C. to 48° C. After the addition was complete, the reaction mixture was stirred for another 10 minutes at 45° C., then cooled down to room temperature. The Pd/C was filtered out using a Teflon filter, and the solvent was evaporated. Ice water (1 L) was added to the residue, then the water was decanted and discarded. The residue was dissolved in diethyl ether, washed with water, then saturated sodium bicarbonate solution, then dried with magnesium sulfate and concentrated. The product was then purified on silica gel using isocratic DCM to give the product as a yellow oil (31.5 g, 83%).

Example 36c 2-(cyclohexyloxy)-6-nitrobenzonitrile

To a solution of cyclohexanol (46.8 grams, 0.467 mol) in anhydrous THF (1 L) was added sodium hydride (20.3 grams, 0.508 mol) at −40° C. under nitrogen. The reaction mixture was allowed to warm slowly to room temperature and stir for another 1 hour. It was then cooled down to −55° C. and 2,6-dinitrobenzonitrile (78.4 g, 0.406 mol) was added. The reaction was stirred at room temperature overnight, then cooled down to −20° C., and citric acid (23.4 grams, 0.122 mol) was added. The mixture was then poured into ice water (5 L) which contained citric acid (7.8 g, 0.041 mol), stirred for 15 minutes, and the precipitated product was collected by filtration. The crude product was recrystallized from isopropanol (750 mL, heated to boiling, then cooled down to 0° C.), filtered, washed with isopropanol (300 mL), then air dried to give 84.4 g yellow solid. The solid was dissolved in dichloromethane (169 mL) and filtered through a plug of alumina to give the title compound as a pale yellow solid (83.2 g, 83.2%). $^1$H NR (400 MHz, DMSO-$d_6$) δ 1.4 (m, 4H), 1.6 (m, 2H), 1.7 (m, 2H), 1.9 (m, 2H), 4.75 (m, 1H), 7.79 (dd, J=2.0, 8.0 Hz, 1H), 7.84-7.91 (m, 2H).

Example 37

4-amino-5-(2-(cyclohexanecarboxamido)-2-methylpropoxy)-2-methylquinoline-3-carboxylic acid

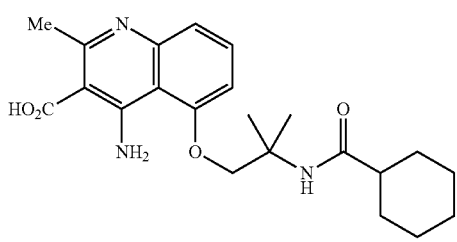 [SMILES: Cc1nc2cccc(OCC(C)(C)NC(=O)C3CCCCC3)c2c(N)c1C(=O)O]

Prepared as in Example 1 from ethyl 4-amino-5-(2-(cyclohexanecarboxamido)-2-methylpropoxy)-2-methylquinoline-3-carboxylate (Example 37a) as a white powder (78%). $^1$H NMR (400 MHz, DMSO-$d_6$) δ 1.11-1.22 (m, 5H), 1.33 (s, 6H), 1.56-1.62 (m, 5H), 2.14 (m, 1H), 2.78 (s, 3H), 4.34 (s, 2H), 7.01 (d, J=8.4 Hz, 1H), 7.30 (d, J=8.4 Hz, 1H), 7.66 (t, J=8.4 Hz, 1H), 7.74 (s, 1H). MS 400 (MH$^+$).

Example 37a ethyl 4-amino-5-(2-(cyclohexanecarboxamido)-2-methylpropoxy)-2-methylquinoline-3-carboxylate Prepared as in Example 2a from N-(1-(3-amino-2-cyanophenoxy)-2-methylpropan-2-yl)cyclohexanecarboxamide (Example 37b) and ethyl 3-oxobutanoate as a bright yellow solid (55%). MS 428 (MH$^+$).

Example 37b

N-(1-(3-amino-2-cyanophenoxy)-2-methylpropan-2-yl)cyclohexanecarboxamide

Prepared as in Example 22b from N-(1-hydroxy-2-methylpropan-2-yl)cyclohexanecarboxamide (Example 37c) and 2-amino-6-fluorobenzonitrile as an off-white solid (29%). MS 316 (MH$^+$).

Example 37c

N-(1-hydroxy-2-methylpropan-2-yl)cyclohexanecarboxamide

Prepared as in Example 24a from cyclohexanecarboxylic acid and 2-amino-2-methylpropan-1-ol as a colorless oil (15%). MS 200 (MH$^+$).

Example 38

4-amino-5-(2-(3-(2-hydroxyethoxy)-5-methoxybenzamido)-2-methylpropoxy)-2-methylquinoline-3-carboxylic acid

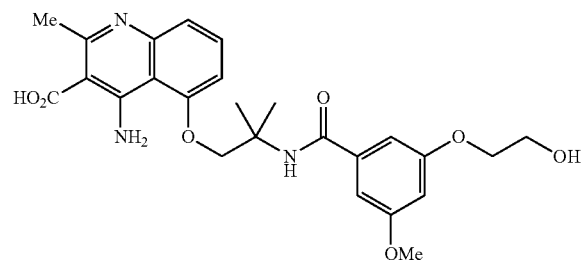 [SMILES: COc1cc(OCCO)cc(C(=O)NC(C)(C)COc2cccc3nc(C)c(C(=O)O)c(N)c23)c1]

To a solution of 4-amino-5-(2-(3-(2-(benzyloxy)ethoxy)-5-methoxybenzamido)-2-methylpropoxy)-2-methylquinoline-3-carboxylic acid (Example 38a, 237 mg, 0.5 mmol) in EtOH/EtOAc (1:1, 20 mL) was added 10% Pd/C (wet, 50 mg). The suspension was then stirred under an atmosphere of hydrogen at room temperature overnight. The Pd/C was filtered off, and the filtrate was concentrated. The residue was purified by HPLC (eluent: 10-100% MeOH in H$_2$O) to give the title compound as an off-white solid (152 mg, 63%). $^1$H NR (400 MHz, DMSO-$d_6$) δ 1.49 (s, 6H), 2.75 (s, 3H), 3.68 (t, J=5.2 Hz, 2H), 3.73 (s, 3H), 3.99 (t, J=5.2 Hz, 1H), 4.47 (s, 2H), 6.57 (s, 1H), 6.88 (s, 1H), 6.96 (s, 1H), 7.06 (d, J=7.6 Hz, 1H), 7.28 (d, J=8 Hz, 1H), 7.67 (t, J=8 Hz, 1H), 8.14 (s, 1H). MS 484 (MH$^+$).

Example 38a 4-amino-5-(2-(3-(2-(benzyloxy)ethoxy)-5-methoxy-benzamido)-2-methylpropoxy)-2-methylquinoline-3-carboxylic acid Prepared as in Example 1 from ethyl 4-amino-5-(2-(3-(2-hydroxyethoxy)-5-methoxybenzamido)-2-methylpropoxy)-2-methylquinoline-3-carboxylate (Example 38b) as a white powder (95%). MS 574 (MH$^+$).

Example 38b ethyl 4-amino-5-(2-(3-(2-hydroxyethoxy)-5-methoxy-benzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-(2-(benzyloxy)ethoxy)-5-methoxybenzoic acid (Example 39c) as a pale-brown solid (90%). MS 602 (MH$^+$).

Example 38c 3-(2-(benzyloxy)ethoxy)-5-methoxybenzoic

Prepared as in Example 1 from methyl 3-(2-(benzyloxy)ethoxy)-5-methoxybenzoate
(Example 38d) as a white solid (64%). $^1$H NR (400 MHz, DMSO-d$_6$) δ 3.83 (s, 3H), 3.84 (t, J=4.8 Hz, 2H), 4.18 (t, J=4.8 Hz, 2H), 4.65 (s, 2H), 6.74 (s, 1H), 7.25-7.37 (m, 7H).

Example 38d methyl 3-(2-(benzyloxy)ethoxy)-5-methoxybenzoate

To a solution of methyl 3-hydroxy-5-methoxybenzoate (Chakraporty, T. K. and Reddy, G. V. *J. Org. Chem.*, 57, 1992, 5462.) (3.3 g, 18.1 mmol) in dry DMF (30 mL) was added K$_2$CO$_3$ (6.3 g, 45.3 mmol) at room temperature. The reaction was stirred at room temperature for 10 minutes then ((2-bromoethoxy)methyl)benzene (3.4 mL, 21.7 mmol) was added and the mixture stirred at 160° C. for 2 hrs. The reaction was cooled down to room temperature and diluted with EtOAc, washed with water and brine, and dried over MgSO$_4$, filtered and concentrated to give the crude product (90%) which was used in the next step without further purification.

Example 39

4-amino-5-((2-isobutyramidocyclohexyl)oxy)-2-methylquinoline-3-carboxylic acid

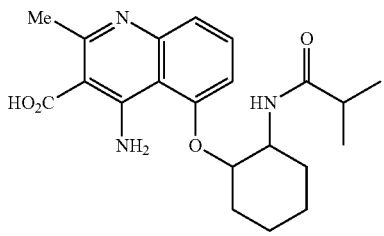 [SMILES: Cc1nc2cccc(OC3CCCCC3NC(=O)C(C)C)c2c(N)c1C(=O)O]

Prepared as in Example 1 from ethyl 4-amino-5-((2-isobutyramidocyclohexyl)oxy)-2-methylquinoline-3-carboxylate (Example 39a) as a white powder (90%). $^1$H NR (400 MHz, DMSO-d$_6$) δ 0.83 (d, J=6.4 Hz, 3H), 0.93 (d, J=6.4 Hz, 3H), 1.42 (m, 3H), 1.65 (m, 4H), 1.96 (m, 1H), 2.40 (m, 1H), 2.76 (s, 3H), 4.13 (m, 1H), 4.99 (m, 1H), 7.07 (d, J=8.4 Hz, 1H), 7.25 (d, J=8.4 Hz, 1H), 7.63 (t, J=8 hz, 1H), 7.93 (d, J=7.6 Hz, 1H). MS 386 (MH$^+$).

Example 39a ethyl 4-amino-5-((2-isobutyramidocyclohexyl)oxy)-2-methylquinoline-3-carboxylate Prepared as in Example 2a from N-(2-(3-amino-2-cyanophenoxy)cyclohexyl)isobutyramide (Example 39b) and ethyl 3-oxobutanoate as a yellow solid (63%). MS 414 (MH$^+$).

Example 39b

N-(2-(3-amino-2-cyanophenoxy)cyclohexyl)isobutyramide

Prepared as in Example 22b from N-(2-hydroxycyclohexyl)isobutyramide (Example 39c) and 2-amino-6-fluorobenzonitrile as a brown solid (70%). MS 302 (MH$^+$).

Example 39c

N-(2-hydroxycyclohexyl)isobutyramide

Prepared as in Example 24a from isobutyric acid and 2-aminocyclohexanol as a colorless oil (53%). MS 186 (MH$^+$).

Example 40

4-amino-5-((4-isobutyramidocyclohexyl)oxy)-2-methylquinoline-3-carboxylic acid

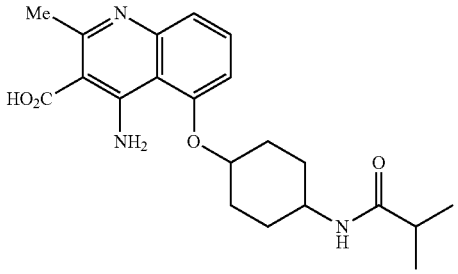 [SMILES: Cc1nc2cccc(OC3CCC(NC(=O)C(C)C)CC3)c2c(N)c1C(=O)O]

Prepared as in Example 1 from ethyl 4-amino-5-((4-isobutyramidocyclohexyl)oxy)-2-methylquinoline-3-carboxylate (Example 40a) as a white powder (87%). $^1$H NR (400 MHz, DMSO-d$_6$) δ 0.97 (d, J=7.2 Hz, 6H), 1.34-1.37 (m, 2H), 1.65-1.68 (m, 2H), 1.81-1.84 (m, 2H), 2.13-2.16 (m, 2H), 2.33 (m, 1H), 2.75 (s, 3H), 3.58 (m, 1H), 4.84 (m, 1H), 7.15 (d, J=8.4 Hz, 1H), 7.23 (d, J=8 Hz, 1H), 7.65 (d, J=7.6 Hz, 2H). MS 386 (MH$^+$).

Example 40a ethyl 4-amino-5-((4-isobutyramidocyclohexyl)oxy)-2-methylquinoline-3-carboxylate Prepared as in Example 2a from N-(4-(3-amino-2-cyanophenoxy)cyclohexyl)isobutyramide (Example 40b) and ethyl 3-oxobutanoate as a yellow solid (57%). MS 414 (MH$^+$).

Example 40b

N-(4-(3-amino-2-cyanophenoxy)cyclohexyl)isobutyramide

Prepared as in Example 22b from N-(4-hydroxycyclohexyl)isobutyramide (Example 40c) and 2-amino-6-fluorobenzonitrile as an off-white solid (99%). MS 302 (MH$^+$).

Example 40c

N-(4-hydroxycyclohexyl)isobutyramide

Prepared as in Example 24a from isobutyric acid and 4-aminocyclohexanol as a colorless oil (44%). MS 186 (MH$^+$).

Example 41

4-amino-5-isobutoxy-2-methylquinoline-3-carboxylic acid

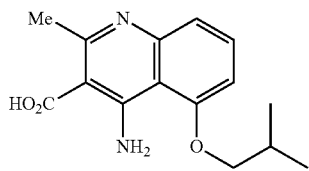 [SMILES: Cc1nc2cccc(OCC(C)C)c2c(N)c1C(=O)O]

To a solution of ethyl 4-amino-5-isobutoxy-2-methylquinoline-3-carboxylate (Example 41a, 18.0 g, 59.53 mmol) in EtOH (150 mL) was added aqueous NaOH solution (3 N, 50 mL) and the reaction mixture was refluxed overnight. It was then cooled down to room temperature and the solution was filtered to remove any possible solid residue. The filtrate was carefully neutralized with 6N HCl to pH 7 at 0° C. The resultant precipitate was collected by filtration, washed with water, re-dissolved in EtOH (700 mL) and water (20 mL), and treated with activated charcoal (650 mg) at 70° C. for 0.5 h. The charcoal was removed by filtration, and the filtrate was concentrated and stored at 4° C. overnight. The resulting precipitate was collected by filtration, washed with cold H$_2$O, and dried under vacuum at 60° C. overnight to give the title compound as a white solid (4.24 g, 26%). M.p.: 203.7° C. $^1$H NR (400 MHz, DMSO-d$_6$) δ 1.01-1.02 (m, 6H), 2.19-2.24 (m, 1H), 2.77 (s, 3H), 4.05 (d, J=6.4 Hz, 2H), 7.08 (d, J=8.0 Hz, 1H), 7.33 (d, J=8.0 Hz, 1H), 7.71 (t, J=8.0 Hz, 1H), 8.9 (brs, 1H), 11.45 (brs, 1H), 13.2 (brs, 1H). MS 275 (MH$^+$). Elemental Analysis Calculated (Found) for C$_{15}$H$_{18}$N$_2$O$_3$·0.75 H$_2$O: C, 62.59% (62.23%); H, 6.83% (7.25%); N, 9.76% (9.73%).

Example 41a ethyl 4-amino-5-isobutoxy-2-methylquinoline-3-carboxylate

To a solution of 2-amino-6-isobutoxybenzonitrile (Example 41b, 16.4 g, 86.32 mmol) and ethyl acetoacetate (10.9 mL, 86.32 mmol) in anhydrous toluene (200 mL) was added SnCl$_4$ (19.9 mL, 172.63 mmol) over a period of 15 minutes at room temperature under nitrogen. The stirred reaction mixture was then refluxed for 3.5 h under nitrogen. After it was cooled down to room temperature, the reaction solution was concentrated to remove most of the solvent under reduced pressure. The residue was re-dissolved in EtOAc (3 L) and carefully neutralized to pH 8 with aqueous NaOH solution (6.0 N, ~110 mL) at 0° C. The resultant mixture was stirred at room temperature overnight. The precipitate was filtered off, and the organic layer was separated and washed with brine (400 mL), dried over Na$_2$SO$_4$ and concentrated under reduced pressure. The residue was purified by column chromatography on silica gel eluting with 50% EtOAc in hexanes to give the title compound as a white solid (18.0 g, 69%). MS 303 (MH$^+$).

Example 41b 2-amino-6-isobutoxybenzonitrile

To a solution of 2-isobutoxy-6-nitrobenzonitrile (Example 41c, 34.3 g, 0.156 mol) in AcOH/THF (1:1 by volume, 250 mL) was added iron powder (17.36 g, 0.311 mol) in one portion. The stirred suspension was heated to reflux for 30 minutes. After it was cooled down to room temperature, the reaction solution was diluted with EtOAc (1 L). The solid was removed by filtration, and the filtrate was washed subsequently with water (300 mL×2), 1N NaOH (300 mL), saturated Na$_2$CO$_3$ aqueous solution (300 mL), brine (300 mL), and dried over Na$_2$SO$_4$. After evaporation of the solvent, the residue was purified by chromatography on silica gel eluting with 20% EtOAc in hexanes to give the title compound as a yellow oil (16.4 g, 83%). $^1$H NMR (400 MHz, DMSO-d$_6$) δ 0.96 (d, J=6.8 Hz, 6H), 1.96-2.02 (m, 1H), 3.75 (d, J=6.4 Hz, 2H), 5.96 (s, 2H), 6.17 (d, J=8.4 Hz, 1H), 6.30 (d, J=8.4 Hz, 1H), 7.15 (t, J=8.8 Hz, 1H). MS 191 (MH$^+$).

Example 41b

Alternative procedure: 2-amino-6-isobutoxybenzonitrile

Sodium hydride (60% suspension in oil, 25.0 g, 0.625 mol) was suspended in anhydrous THF (1000 mL) under nitrogen and heated to an internal temperature of 40° C. to 45° C. 2 (61.2 mL, 0.661 mol) was then added slowly and portionwise. The mixture was heated at 40° C. to 45° C. for 1 hour, then cooled to 35° C. 2-amino-6-fluorobenzonitrile (50.0 g, 0.367 mol) was added and refluxed for 21 hours. The mixture was cooled to r.t., then ice (250 g), ice water (750 mL), and hexanes (1000 mL) was added. Insoluble solids were filtered out and the organic layer was separated. The aqueous layer was extracted once more with a mixture of diethyl ether (250 mL) and hexanes (250 mL). The combined organic layer was washed twice with a solution of citric acid (53 g) in water (500 mL), then washed with 80% brine (300 mL), then dried with magnesium sulfate, filtered and concentrated under reduced pressure. The residue was dissolved in methanol (500 mL), and the immiscible oil carried through from the sodium hydride suspension was separated off in a reparatory funnel. The solvent was evaporated under vacuum, and the residue was washed with hexanes (250 mL), after which the product 2 was obtained as a viscous oil (46 grams, yield: 66%). $^1$H NR (400 MHz, DMSO-d$_6$) δ 7.16 (t, J=8.0 Hz, 1H), 6.33 (d, J=8.0 Hz, 1H), 6.17 (d, J=8.0 Hz, 1H), 5.97 (s, 2H), 3.75 (d, J=7.2 Hz, 2H), 2.00 (m, 1H), 0.97 (d, J=6.8 Hz, 6H) ppm. MS 191 (MH$^+$).

Example 41c 2-isobutoxy-6-nitrobenzonitrile

To a solution of 2-methylpropan-1-ol (9.6 mL, 0.104 mol) in anhydrous THF (200 mL) was added NaH (60% in mineral oil, 4.565 g, 0.114 mol) in small portions at 0° C. under N$_2$. After it was stirred at room temperature for 30 min, the reaction mixture was cooled down to −70° C. and 2,6-dinitrobenzonitrile (20.0 g, 0.104 mol) was added portionwise. After the addition was complete, the reaction mixture was stirred at −70° C.-RT overnight, then poured into ice water (600 mL). The resultant precipitate was collected by filtration and rinsed with water, hexane, and air dried to provide 2-isobutoxy-6-nitrobenzonitrile as a light yellow solid (34.3 g, 100%). $^1$H NMR (400 MHz, DMSO-d$_6$) δ 1.0 (d, J=6.8 Hz, 6H), 2.04-2.11 (m, 1H), 4.02 (d, J=6.8 Hz, 2H), 7.69-7.71 (m, 1H), 7.84-7.90 (m, 2H). MS 221 (MH$^+$).

Example 42

4-amino-5-isopropoxy-2-methylquinoline-3-carboxylic acid

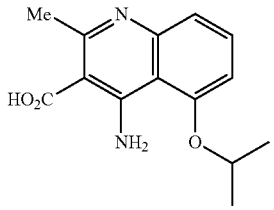 [SMILES: Cc1nc2cccc(OC(C)C)c2c(N)c1C(=O)O]

Prepared as in Example 1 from ethyl 4-amino-5-isopropoxy-2-methylquinoline-3-carboxylate (Example 42a) as a white solid (71%). $^1$H NR (400 MHz, DMSO-d$_6$) δ 1.4 (d, J=6.4 Hz, 6H), 2.73 (s, 3H), 4.87-4.93 (m, 1H), 7.01 (d, J=8.0 Hz, 1H), 7.27 (d, J=8.0 Hz, 1H), 7.60 (t, J=8.4 Hz, 1H). MS 261 (MH$^+$).

Example 42a ethyl 4-amino-5-isopropoxy-2-methylquinoline-3-carboxylate

Prepared as in Example 2a from 2-amino-6-isopropoxybenzonitrile (Tachdjian, C. et al. PCT Int. Appl. 2008, WO 2008154221) and ethyl 3-oxobutanoate as an off-white solid (32%). $^1$H NMR (400 MHz, DMSO-d$_6$) δ 1.32 (t, J=7.6 Hz, 3H), 1.38 (d, J=6.0 Hz, 6H), 2.54 (s, 3H), 4.3 (q, J=7.2 Hz, 2H), 4.83-4.89 (m, 1H), 6.93 (d, J=8.0 Hz, 1H), 7.20 (d, J=8.0 Hz, 1H), 7.50 (t, J=8.4 Hz, 1H), 8.14 (s, 2H). MS 289 (MH$^+$).

Example 43

4-amino-5-((1-(hydroxymethyl)cyclohexyl)methoxy)-2-methylquinoline-3-carboxylic acid

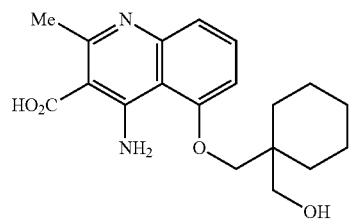 [SMILES: Cc1nc2cccc(OCC3(CO)CCCCC3)c2c(N)c1C(=O)O]

Prepared as in Example 1 from ethyl 4-amino-5-((1-(hydroxymethyl)cyclohexyl)methoxy)-2-methylquinoline-3-carboxylate (Example 43a) as an off-white solid (49%). $^1$H NR (400 MHz, DMSO-d$_6$) δ 1.37-1.48 (m, 10H), 2.75 (s, 3H), 3.50 (s, 2H), 4.03 (s, 2H), 5.08 (brs, 1H), 7.06 (d, J=8.4 Hz, 1H), 7.25 (d, J=8.8 Hz, 1H), 7.66 (t, J=8.4 Hz, 1H), 9.39 (brs, 1H), 12.17 (brs, 1H), 12.74 (brs, 1H). MS 345 (MH$^+$).

Example 43a ethyl 4-amino-5-((1-(hydroxymethyl)cyclohexyl)methoxy)-2-methylquinoline-3-carboxylate Prepared as in Example 2a from (1-((3-amino-2-cyanophenoxy)methyl)cyclohexyl)methyl acetate (Tachdjian, C. et al. PCT Int. Appl. 2008, WO 2008154221) and ethyl 3 as an off-white solid (60%). MS 373 (MH$^+$).

Example 44

4-amino-5-(2-(3,5-dihydroxybenzamido)-2-methylpropoxy)-2-methylquinoline-3-carboxylic acid

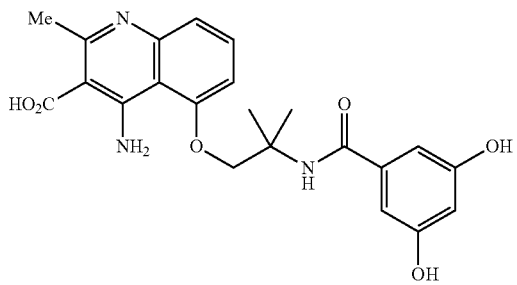 [SMILES: Cc1nc2cccc(OCC(C)(C)NC(=O)c3cc(O)cc(O)c3)c2c(N)c1C(=O)O]

Prepared as in Example 1 from ethyl 4-amino-5-(2-(3,5-dihydroxybenzamido)-2-methylpropoxy)-2-methylquinoline-3-carboxylate (Example 44a) as a white solid (73%). $^1$H NMR (400 MHz, DMSO-d$_6$) δ 1.46 (s, 6H), 2.75 (s, 3H), 4.44 (s, 2H), 6.3-6.31 (m, 1H), 6.61 (s, 2H), 7.04 (d, J=8.0 Hz, 1H), 7.27 (d, J=8.4 Hz, 1H), 7.66 (t, J=8.0 Hz, 1H), 7.98 (s, 1H), 8.79 (brs, 1H), 9.48 (s, 2H). MS 426 (MH$^+$).

Example 44a ethyl 4-amino-5-(2-(3,5-dihydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3,5-dihydroxybenzoic acid as a yellow-brown solid (15%). MS 454 (MH+).

Example 45

4-amino-5-((4-(isopropylcarbamoyl)cyclohexyl)oxy)-2-methylquinoline-3-carboxylic acid

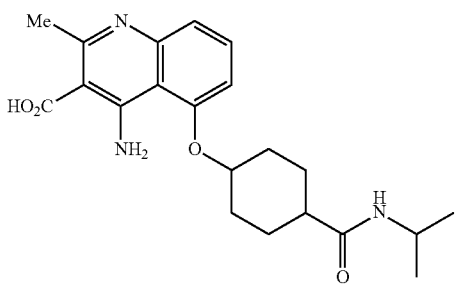 [SMILES: Cc1nc2cccc(OC3CCC(C(=O)NC(C)C)CC3)c2c(N)c1C(=O)O]

Prepared as in Example 1 from ethyl 4-amino-5-(4-(isopropylcarbamoyl)cyclohexyl)oxy)-2-methylquinoline-3-carboxylate (Example 45a) as a white powder (71%). $^1$H NR (400 MHz, DMSO-$d_6$) δ 1.01 (d, J=6.4 Hz, 6H), 1.59-1.68 (m, 6H), 2.06-2.09 (m, 2H), 2.2-2.22 (m, 1H), 2.76 (s, 3H), 3.77-3.83 (m, 1H), 4.96 (s, 1H), 7.06 (d, J=8.0 Hz, 1H), 7.26 (d, J=8.4 Hz, 1H), 7.58 (d, J=8.0 Hz, 1H), 7.65 (t, J=8.4 Hz, 1H), 8.79 (brs, 1H), 12.84 (brs, 2H). MS 386 (MH+).

Example 45a ethyl 4-amino-5-((4-(isopropylcarbamoyl)cyclohexyl)oxy)-2-methylquinoline-3-carboxylate Prepared as in Example 2a from 4-(3-amino-2-cyanophenoxy)-N-isopropylcyclohexanecarboxamide (Example 45b) and ethyl 3-oxobutanoate as a yellow solid (56%). MS 414 (MH+).

Example 45b 4-(3-amino-2-cyanophenoxy)-N-isopropylcyclohexanecarboxamide

Prepared as in Example 22b from 4-hydroxy-N-isopropylcyclohexanecarboxamide (Example 45c) and 2-amino-6-fluorobenzonitrile as an off-white solid (17%). $^1$H NR (400 MHz, DMSO-$d_6$) δ 1.01 (d, J=6.4 Hz, 6H), 1.47-1.57 (m, 4H), 1.67-1.77 (m, 2H), 1.89-1.93 (m, 2H), 2.08-2.15 (m, 1H), 3.75-3.84 (m, 1H), 4.57 (brs, 1H), 5.93 (s, 2H), 6.19 (d, J=8.0 Hz, 1H), 6.28 (d, J=8.0 Hz, 1H), 7.13 (t, J=8.0 Hz, 1H), 7.48 (d, J=8.0 Hz, 1H). MS 302 (MH+).

Example 45c 4-hydroxy-N-isopropylcyclohexanecarboxamide

Prepared as in Example 24a from 4-hydroxycyclohexanecarboxylic acid and propan-2-amine as a colorless oil (68%). MS 186 (MH+).

Example 46

4-amino-5-(3-((3-methoxybenzyl)amino)-2,2-dimethyl-3-oxopropoxy)-2-methylquinoline-3-carboxylic acid

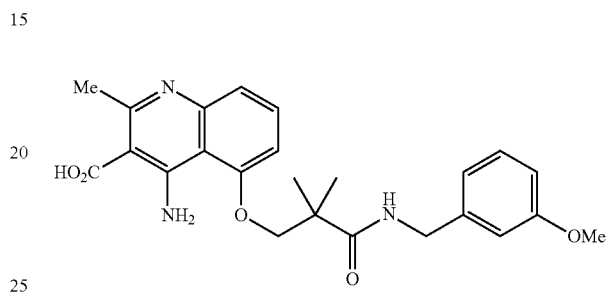

Prepared as in Example 1 from ethyl 4-amino-5-(3-((3-methoxybenzyl)amino)-2,2-dimethylpropanamide (Example 46a) as a white powder (58%). M.p.: 172~174° C. $^1$H NR (400 MHz, DMSO-$d_6$) δ 1.31 (s, 6H), 2.76 (s, 3H), 3.53 (s, 3H), 4.21 (s, 2H), 4.27 (d, J=5.6 Hz, 2H), 6.64 (dd, J=8.0, 2.4 Hz, 1H), 6.69 (m, 1H), 6.72 (d, J=8.0 Hz, 1H), 6.98-7.10 (m, 2H), 7.28 (d, J=8.0 Hz, 1H), 7.66 (t, J=8.0 Hz, 1H), 8.47 (t, J=5.6 Hz, 1H), 8.77 (brs, 1H), 12.26 (brs, 1H), 12.79 (brs, 1H). MS 438 (MH+).

Example 46a ethyl 4-amino-5-(3-((3-methoxybenzyl)amino)-2,2-dimethyl-3-oxopropoxy)-2-methylquinoline-3-carboxylate Prepared as in Example 2a from 3-(3-amino-2-cyanophenoxy)-N-(3-methoxybenzyl)-2,2-dimethylpropanamide (Example 46b) and ethyl 3-oxobutanoate as a yellow solid (42%). MS 466 (MH+).

Example 46b 3-(3-amino-2-cyanophenoxy)-N-(3-methoxybenzyl)-2,2-dimethylpropanamide Prepared as in Example 22b from 3-hydroxy-N-(3-methoxybenzyl)-2,2-dimethylpropanamide (Example 46c) and 2-amino-6-fluorobenzonitrile as a white solid (41%). MS 354 (MH+).

Example 46c 3-hydroxy-N-(3-methoxybenzyl)-2,2-dimethylpropanamide

Prepared as in Example 24a from 3-hydroxy-2,2-dimethylpropanoic acid and (3 as an orange oil (41%). MS 238 (MH+).

Example 47

4-amino-5-(3-(cyclohexylamino)-2,2-dimethyl-3-oxopropoxy)-2-methylquinoline-3-carboxylic acid

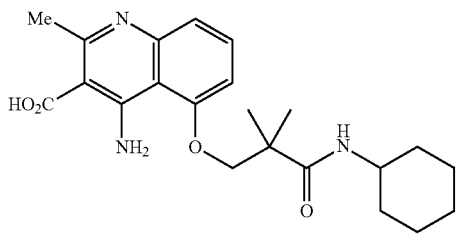 [SMILES: Cc1nc2cccc(OCC(C)(C)C(=O)NC3CCCCC3)c2c(N)c1C(=O)O]

Prepared as in Example 1 from ethyl 4-amino-5-(3-(cyclohexylamino)-2,2-dimethyl-3-oxopropoxy)-2-methylquinoline-3-carboxylate (Example 47a) as an off-white solid (13%). MS 400 (MH$^+$).

Example 47a ethyl 4-amino-5-(3-(cyclohexylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclohexanamine as a yellow-brown solid (46%). MS 428 (MH$^+$).

Example 47b 3-((4-amino-3-(ethoxycarbonyl)-2-methylquinolin-5-yl)oxy)-2,2-dimethylpropanoic acid Prepared as in Example 2a from benzyl 3-(3-amino-2-cyanophenoxy)-2,2-dimethylpropanoate (Example 47c) and ethyl 3-oxobutanoate as a brown solid (80%). MS 192 (MH$^+$).

Example 47c 3-(3-amino-2-cyanophenoxy)-2,2-dimethylpropanoate

To a solution of benzyl 3-(2-cyano-3-nitrophenoxy)-2,2-dimethylpropanoate (Example 47d, 200 mg, 0.56 mmol) in AcOH (5 mL) was added iron powder (158 mg, 2.82 mmol) at room temperature. The reaction mixture was then stirred at 90° C. for 1 h. The reaction mixture was was cooled to room temperature then diluted with AcOEt. The precipitate was filtered off and the filtrate was successively washed with 1N NaOH and brine, then dried over Na$_2$SO$_4$, filtered and evaporated. The residue was purified by chromatography on silica gel (eluent: 40% EtOAc in hexanes) to give a title compound as a colorless oil (187 mg, 100%). MS 325 (MH$^+$).

Example 47d benzyl 3-(2-cyano-3-nitrophenoxy)-2,2-dimethylpropanoate

To a solution of benzyl 3-hydroxy-2,2-dimethylpropanoate (Yang, D. et al. *J. Am. Chem. Soc.* 2002, 124, 9966. 6.68 g, 32.1 mmol) in dry THF (200 mL) was carefully added NaH (60% in mineral oil, 3.5 g, 87.5 mmol) in small portions at 0° C. under nitrogen. The reaction mixture was stirred at 0° C. under nitrogen for 2 hrs. To this solution was added 2,6-dinitrobenzonitrile (6.19 g, 32.1 mmol), and the reaction solution was stirred at 0° C.-RT under nitrogen overnight. The reaction mixture was quenched with brine, and extracted with EtOAc (3×). The combined organic layers were washed with brine, dried over Na$_2$SO$_4$. After evaporation of the solvent, the residue was purified by chromatography on silica gel eluting (Elunet: 20% EtOAc in hexanes) to give the title compound as a brown solid (10.0 g, 87%). MS 355 (MH$^+$).

Example 48

4-amino-5-(3-(cycloheptylamino)-2,2-dimethyl-3-oxopropoxy)-2-methylquinoline-3-carboxylic acid

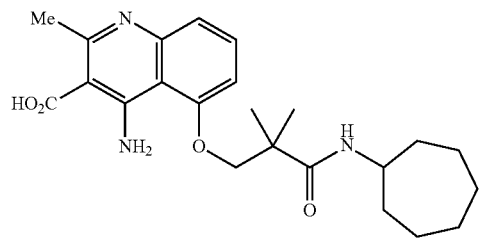 [SMILES: Cc1nc2cccc(OCC(C)(C)C(=O)NC3CCCCCC3)c2c(N)c1C(=O)O]

Prepared as in Example 1 from ethyl 4-amino-5-(3-(cycloheptylamino)-2,2-dimethyl-3-oxopropoxy)-2-methylquinoline-3-carboxylate (Example 48a) as an off-white solid (12%). MS 414 (MH$^+$).

Example 48a ethyl 4-amino-5-(3-(cycloheptylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cycloheptanamine as a brown solid (43%). MS 456 (MH$^+$).

Example 49

4-amino-5-(3-(cyclooctylamino)-2,2-dimethyl-3-oxopropoxy)-2-methylquinoline-3-carboxylic acid

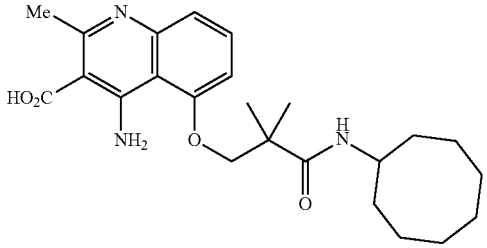 [SMILES: Cc1nc2cccc(OCC(C)(C)C(=O)NC3CCCCCCC3)c2c(N)c1C(=O)O]

Prepared as in Example 1 from ethyl 4-amino-5-(3-(cyclooctylamino)-2,2-dimethyl-3-oxopropoxy)-2-methylquinoline-3-carboxylate (Example 49a) as an off-white solid (11%). MS 428 (MH$^+$).

Example 49a ethyl 4-amino-5-(3-(cyclooctylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and cyclooctanamine as a brown solid (46%). MS 456 (MH+).

Example 50

4-amino-5-(3-((3-hydroxy-2,2-dimethylpropyl)amino)-2,2-dimethyl-3-oxopropoxy)-2-methylquinoline-3-carboxylic acid

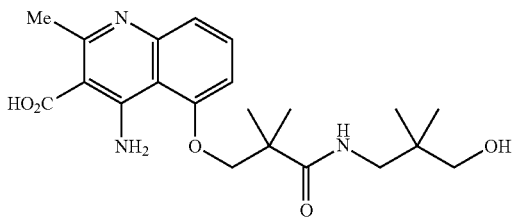 [SMILES: Cc1nc2cccc(OCC(C)(C)C(=O)NCC(C)(C)CO)c2c(N)c1C(=O)O]

Prepared as in Example 1 from ethyl 4-amino-5-(3-((3-hydroxy-2,2-dimethylpropyl)amino)-2,2-dimethyl-3-oxopropoxy)-2-methylquinoline-3-carboxylate (Example 50a) as an off-white solid (87%). $^1$H NR (400 MHz, DMSO-$d_6$) δ 0.71 (s, 6H), 1.28 (s, 6H), 2.74 (s, 3H), 2.97 (d, J=6.0 Hz, 2H), 3.0 (s, 2H), 4.57 (brs, 1H), 6.99 (d, J=8.4 Hz, 1H), 7.27 (d, J=8.0 Hz, 1H), 7.65 (t, J=8.4 Hz, 1H), 7.77 (t, J=6.4 Hz, 1H), 8.78 (brs, 1H), 12.04 (brs, 1H), 12.82 (brs, 1H). MS 404 (MH+).

Example 50a ethyl 4-amino-5-(3-((3-hydroxy-2,2-dimethylpropyl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and 3-amino-2,2-dimethylpropan-1-ol as a brown solid (40%). MS 432 (MH+).

Example 51

4-amino-5-(3-(chroman-4-ylamino)-2,2-dimethyl-3-oxopropoxy)-2-methylquinoline-3-carboxylic acid

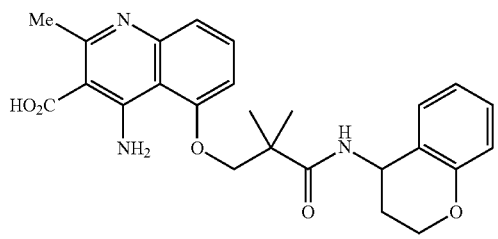 [SMILES: Cc1nc2cccc(OCC(C)(C)C(=O)NC3CCOc4ccccc43)c2c(N)c1C(=O)O]

Prepared as in Example 1 from ethyl 4-amino-5-(3-(chroman-4-ylamino)-2,2-dimethyl-3-oxopropoxy)-2-methylquinoline-3-carboxylate (Example 51a) as an off-white solid (80%). $^1$H NMR (400 MHz, DMSO-$d_6$) δ 1.31 (d, J=4.0 Hz, 6H), 1.80-2.00 (m, 2H), 2.76 (s, 3H), 4.05-4.19 (m, 2H), 4.24 (s, 2H), 5.10 (q, J=6.8 Hz, 1H), 6.51 (t, J=7.6 Hz, 1H), 6.89 (d, J=8.4 Hz, 1H), 6.94 (d, J=8.0 Hz, 1H), 7.01 (dd, J=15.0, 8.4 Hz, 2H), 7.30 (d, J=8.8 Hz, 1H), 7.66 (t, J=8.4 Hz, 1H), 8.26 (d, J=8.8 Hz, 1H), 8.77 (brs, 1H), 12.31 (brs, 1H), 12.86 (brs, 1H). MS 450 (MH+).

Example 51a ethyl 4-amino-5-(3-(chroman-4-ylamino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and chroman-4-amine (Lu, Y. et al. PCT Int. Appl. 2008, WO 2008043019) as a brown solid (37%). MS 478 (MH+).

Example 52

4-amino-5-(3-((5-methoxy-1,2,3,4-tetrahydronaphthalen-1-yl)amino)-2,2-dimethyl-3-oxopropoxy)-2-methylquinoline-3-carboxylic acid

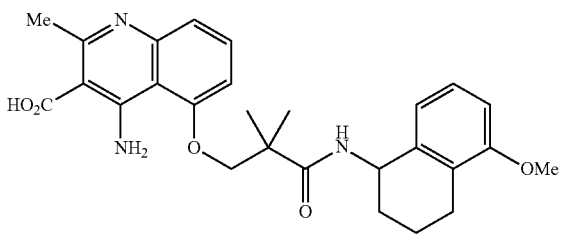 [SMILES: COc1cccc2c1CCCC2NC(=O)C(C)(C)COc1cccc2nc(C)c(C(=O)O)c(N)c12]

Prepared as in Example 1 from ethyl 4-amino-5-(3-((5-methoxy-1,2,3,4-tetrahydronaphthalen-1-yl)amino)-2,2-dimethyl-3-oxopropoxy)-2-methylquinoline-3-carboxylate (Example 52a) as an off-white solid (69%). $^1$H NR (400 MHz, DMSO-$d_6$) δ 1.30 (d, J=4.0 Hz, 6H), 1.52-1.87 (m, 4H), 2.75 (s, 3H), 4.22 (s, 2H), 4.95-5.05 (m, 1H), 6.59 (d, J=7.2 Hz, 1H), 6.67-6.75 (m, 2H), 6.97 (d, J=8.4 Hz, 1H), 7.28 (d, J=8.0 Hz, 2H), 7.64 (t, J=8.4 Hz, 1H), 8.13 (d, J=8.8 Hz, 1H), 8.74 (brs, 1H), 12.22 (brs, 1H), 12.80 (brs, 1H). MS 478 (MH+).

Example 52a ethyl 4-amino-5-(3-((5-methoxy-1,2,3,4-tetrahydronaphthalen-1-yl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and 5-methoxy-1,2,3,4-tetrahydronaphthalen-1-amine as a brown solid (40%). MS 506 (MH+).

Example 53

4-amino-5-(2-(4-methoxybenzamido)-2-methylpropoxy)-2-methylquinoline-3-carboxylic acid

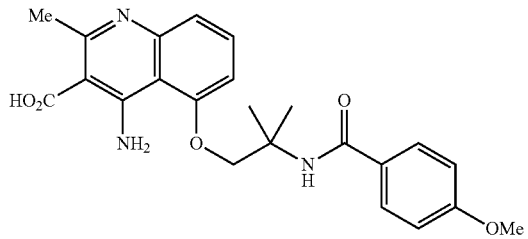 [SMILES: COc1ccc(C(=O)NC(C)(C)COc2cccc3nc(C)c(C(=O)O)c(N)c23)cc1]

Prepared as in Example 1 from ethyl 4-amino-5-(2-(4-methoxybenzamido)-2-methylpropoxy)-2-methylquinoline-3-carboxylate (Example 53a) as a white solid. MS 424 (MH$^+$).

Example 53a ethyl 4-amino-5-(2-(4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-methoxybenzoic acid as a brown solid. MS 452 (MH$^+$).

Example 54

4-amino-5-(2-(2-hydroxybenzamido)-2-methylpropoxy)-2-methylquinoline-3-carboxylic acid

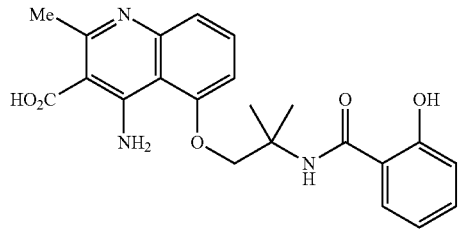

Prepared as in Example 1 from ethyl 4-amino-5-(2-(2-hydroxybenzamido)-2-methylpropoxy)-2-methylquinoline-3-carboxylate (Example 54a) as an off-white solid. MS 410 (MH$^+$).

Example 54a ethyl 4-amino-5-(2-(2-hydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2-hydroxybenzoic acid as a brown solid. MS 438 (MH$^+$).

Example 55

4-amino-5-(2-(3-methoxybenzamido)-2-methylpropoxy)-2-methylquinoline-3-carboxylic acid

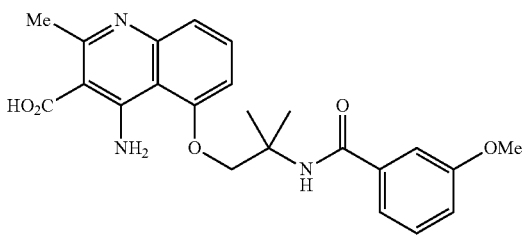 [SMILES: COc1cccc(C(=O)NC(C)(C)COc2cccc3nc(C)c(C(=O)O)c(N)c23)c1]

Prepared as in Example 1 from ethyl 4-amino-5-(2-(3-methoxybenzamido)-2-methylpropoxy)-2-methylquinoline-3-carboxylate (Example 55a) as a white solid. MS 424 (MH$^+$).

Example 55a ethyl 4-amino-5-(2-(3-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-methoxybenzoic acid as a brown solid. MS 452 (MH$^+$).

Example 56

4-amino-5-(2-benzamido-2-methylpropoxy)-2-methylquinoline-3-carboxylic acid

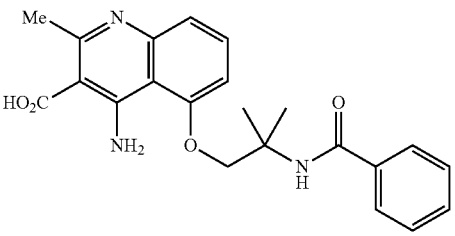 [SMILES: Cc1nc2cccc(OCC(C)(C)NC(=O)c3ccccc3)c2c(N)c1C(=O)O]

Prepared as in Example 1 from ethyl 4-amino-5-(2-benzamido-2-methylpropoxy)-2-methylquinoline-3-carboxylate (Example 56a) as a white solid. MS 394 (MH$^+$).

Example 56a ethyl 4-amino-5-(2-benzamido-2-methylpropoxy)-2-methylquinoline-3-carboxylate Prepared as in Example 24a from 4-amino-5-(2-amino-2-methylpropoxy)-2-methylquinoline-3-carboxylate (Example 24b) and benzoic acid as a brown solid. MS 422 (MH$^+$).

Example 57

4-amino-5-(2-(4-hydroxybenzamido)-2-methylpropoxy)-2-methylquinoline-3-carboxylic acid

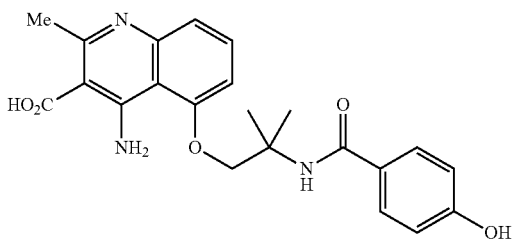 [SMILES: Cc1nc2cccc(OCC(C)(C)NC(=O)c3ccc(O)cc3)c2c(N)c1C(=O)O]

Prepared as in Example 1 from ethyl 4-amino-5-(2-(4-hydroxybenzamido)-2-methylpropoxy)-2-methylquinoline-3-carboxylate (Example 57a) as an off-white solid. MS 410 (MH$^+$).

Example 57a ethyl 4-amino-5-(2-(4-hydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-hydroxybenzoic acid as a brown solid. MS 438 (MH$^+$).

Example 58

4-amino-5-(2-(2-fluorobenzamido)-2-methylpropoxy)-2-methylquinoline-3-carboxylic acid

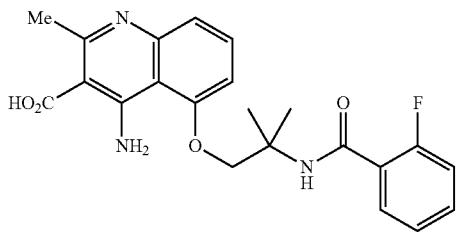

Prepared as in Example 1 from ethyl 4-amino-5-(2-(2-fluorobenzamido)-2-methylpropoxy)-2-methylquinoline-3-carboxylate (Example 58a) as an off-white solid. MS 412 (MH$^+$).

Example 58a ethyl 4-amino-5-(2-(2-fluorobenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2-fluorobenzoic acid as a brown solid. MS 440 (MH$^+$).

Example 59

4-amino-5-(2-(3-fluorobenzamido)-2-methylpropoxy)-2-methylquinoline-3-carboxylic acid

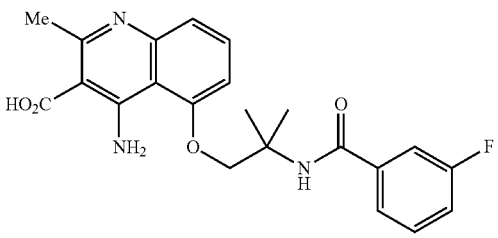 [SMILES: Cc1nc2cccc(OCC(C)(C)NC(=O)c3cccc(F)c3)c2c(N)c1C(=O)O]

Prepared as in Example 1 from ethyl 4-amino-5-(2-(3-fluorobenzamido)-2-methylpropoxy)-2-methylquinoline-3-carboxylate (Example 59a) as an off-white solid. MS 412 (MH$^+$).

Example 59a ethyl 4-amino-5-(2-(3-fluorobenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-fluorobenzoic acid as a brown solid. MS 440 (MH$^+$).

Example 60

4-amino-5-(2-(3-hydroxy-4-methoxybenzamido)-2-methylpropoxy)-2-methylquinoline-3-carboxylic acid

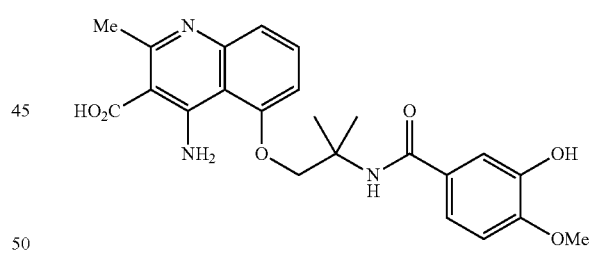

Prepared as in Example 1 from ethyl 4-amino-5-(2-(3-hydroxy-4-methoxybenzamido)-2-methylpropoxy)-2-methylquinoline-3-carboxylate (Example 60a) as an off-white solid. MS 440 (MH$^+$).

Example 60a ethyl 4-amino-5-(2-(3-hydroxy-4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-hydroxy-4-methoxybenzoic acid as a brown solid. MS 468 (MH$^+$).

Example 61

4-amino-5-(2-(3-carbamoylbenzamido)-2-methyl-propoxy)-2-methylquinoline-3-carboxylic acid

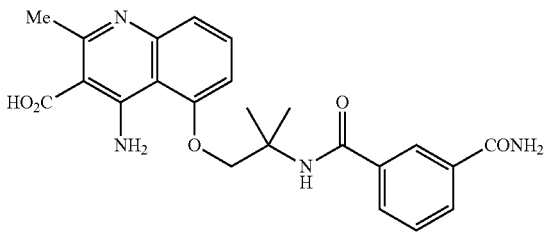 [SMILES: Cc1nc2cccc(OCC(C)(C)NC(=O)c3cccc(C(N)=O)c3)c2c(N)c1C(=O)O]

Prepared as in Example 1 from ethyl 4-amino-5-(2-(3-carbamoylbenzamido)-2-methylpropoxy)-2-methylquinoline-3-carboxylate (Example 61a) as an off-white solid. MS 437 (MH⁺).

Example 61a ethyl 4-amino-5-(2-(3-carbamoylbenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-carbamoylbenzoic acid as a brown solid. MS 465 (MH⁺).

Example 62

4-amino-5-(2-(2,3-dihydrobenzo[b][1,4]dioxine-6-carboxamido)-2-methylpropoxy)-2-methylquinoline-3-carboxylic acid

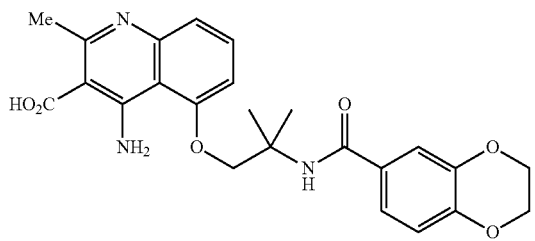 [SMILES: Cc1nc2cccc(OCC(C)(C)NC(=O)c3ccc4c(c3)OCCO4)c2c(N)c1C(=O)O]

Prepared as in Example 1 from ethyl 4-amino-5-(2-(2,3-dihydrobenzo[b][1,4]dioxine-6-carboxamido)-2-methylpropoxy)-2-methylquinoline-3-carboxylate (Example 62a) as a pale-yellow solid (18%). ¹H NR (400 MHz, DMSO-d₆) δ 1.49 (s, 6H), 2.76 (s, 3H), 4.25 (m, 4H), 4.48 (s, 2H), 6.87 (d, J=8.8 Hz, 1H), 7.06 (d, J=7.6 Hz, 1H), 7.39-7.26 (m, 3H), 7.67 (t, J=7.2 Hz, 1H), 7.99 (s, 1H), 8.83 (brs, 1H), 12.31 (brs, 1H), 12.71 (brs, 1H). MS 452 (MH⁺).

Example 62a ethyl 4-amino-5-(2-(2,3-dihydrobenzo[b][1,4]dioxine-6-carboxamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2,3-dihydrobenzo[b][1,4]dioxine-6-carboxylic acid as a brown solid (60%). MS 480 (MH⁺).

Example 63

4-amino-5-(2-(2-ethylbutanamido)-2-methylpropoxy)-2-methylquinoline-3-carboxylic acid

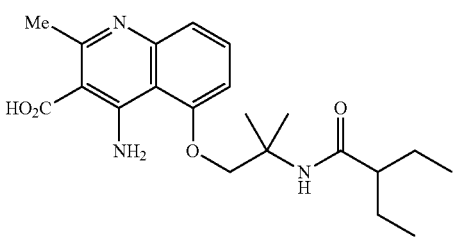 [SMILES: CCC(CC)C(=O)NC(C)(C)COc1cccc2nc(C)c(C(=O)O)c(N)c12]

Prepared as in Example 1 from ethyl 4-amino-5-(2-(2-ethylbutanamido)-2-methylpropoxy)-2-methylquinoline-3-carboxylate (Example 63a) as an off-white solid. MS 388 (MH⁺).

Example 63a ethyl 4-amino-5-(2-(2-ethylbutanamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2-ethylbutanoic acid as a brown solid. MS 416 (MH⁺).

Example 64

4-amino-5-(2-(3-methoxypropanamido)-2-methylpropoxy)-2-methylquinoline-3-carboxylic acid

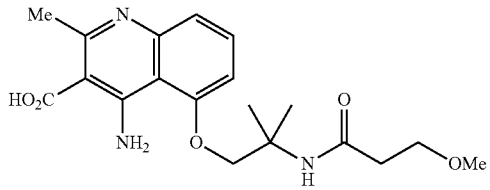 [SMILES: COCCC(=O)NC(C)(C)COc1cccc2nc(C)c(C(=O)O)c(N)c12]

Prepared as in Example 1 from ethyl 4-amino-5-(2-(3-methoxypropanamido)-2-methylpropoxy)-2-methylquinoline-3-carboxylate (Example 64a) as an off-white solid. MS 376 (MH⁺).

Example 64a ethyl 4-amino-5-(2-(3-methoxypropanamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-methoxypropanoic acid as a brown solid. MS 404 (MH⁺).

Example 65

4-amino-5-(2-butyramido-2-methylpropoxy)-2-methylquinoline-3-carboxylic acid

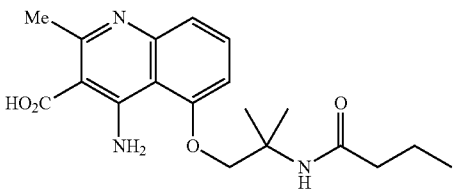 [SMILES: CCCC(=O)NC(C)(C)COc1cccc2nc(C)c(C(=O)O)c(N)c12]

Prepared as in Example 1 from ethyl 4-amino-5-(2-butyramido-2-methylpropoxy)-2-methylquinoline-3-carboxylate (Example 65a) as an off-white solid. MS 360 (MH$^+$).

Example 65a ethyl 4-amino-5-(2-butyramido-2-methylpropoxy)-2-methylquinoline-3-carboxylate Prepared as in Example 24a from 4-amino-5-(2-amino-2-methylpropoxy)-2-methylquinoline-3-carboxylate (Example 24b) and butyric acid as a brown solid. MS 388 (MH$^+$).

Example 66

4-amino-2-methyl-5-(2-methyl-2-(tetrahydrofuran-3-carboxamido)propoxy)quinoline-3-carboxylic acid

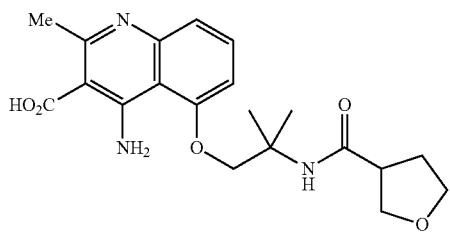 [SMILES: Cc1nc2cccc(OCC(C)(C)NC(=O)C3CCOC3)c2c(N)c1C(=O)O]

Prepared as in Example 1 from ethyl 4-amino-2-methyl-5-(2-methyl-2-(tetrahydrofuran-3-carboxamido)propoxy)quinoline-3-carboxylate (Example 66a) as an off-white solid. MS 388 (MH$^+$).

Example 66a ethyl 4-amino-2-methyl-5-(2-methyl-2-(tetrahydrofuran-3-carboxamido)propoxy)quinoline-3-carboxylate Prepared as in Example 24a from 4-amino-5-(2-amino-2-methylpropoxy)-2-methylquinoline-3-carboxylate (Example 24b) and tetrahydrofuran-3-carboxylic acid as a brown solid. MS 416 (MH$^+$).

Example 67

4-amino-5-(2-(4-(hydroxymethyl)benzamido)-2-methylpropoxy)-2-methylquinoline-3-carboxylic acid

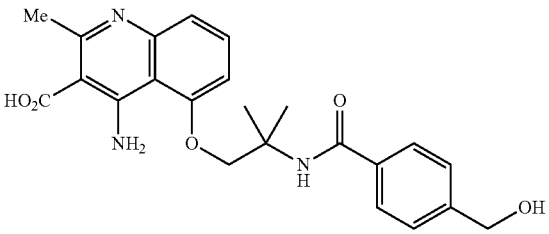 [SMILES: Cc1nc2cccc(OCC(C)(C)NC(=O)c3ccc(CO)cc3)c2c(N)c1C(=O)O]

Prepared as in Example 1 from ethyl 4-amino-5-(2-(4-(hydroxymethyl)benzamido)-2-methylpropoxy)-2-methylquinoline-3-carboxylate (Example 67a) as an off-white solid. MS 424 (MH$^+$).

Example 67a ethyl 4-amino-5-(2-(4-(hydroxymethyl)benzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-(hydroxymethyl)benzoic acid as a brown solid. MS 452 (MH$^+$).

Example 68

4-amino-5-(2-(2-methoxyacetamido)-2-methylpropoxy)-2-methylquinoline-3-carboxylic acid

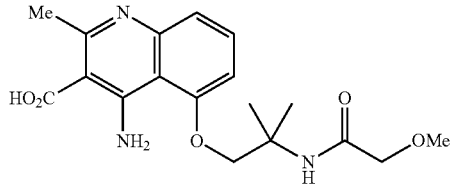 [SMILES: COCC(=O)NC(C)(C)COc1cccc2nc(C)c(C(=O)O)c(N)c12]

Prepared as in Example 1 from ethyl 4-amino-5-(2-(2-methoxyacetamido)-2-methylpropoxy)-2-methylquinoline-3-carboxylate (Example 68a) as an off-white solid. MS 362 (MH$^+$).

Example 68a ethyl 4-amino-5-(2-(2-methoxyacetamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2-methoxyacetic acid as a brown solid. MS 390 (MH$^+$).

Example 69

5-(2-acetamido-2-methylpropoxy)-4-amino-2-methylquinoline-3-carboxylic acid

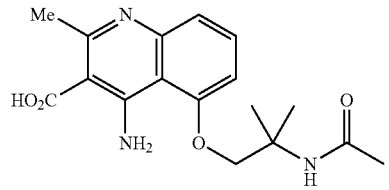 [SMILES: CC(=O)NC(C)(C)COc1cccc2nc(C)c(C(=O)O)c(N)c12]

Prepared as in Example 1 from ethyl 5-(2-acetamido-2-methylpropoxy)-4-amino-2-methylquinoline-3-carboxylate (Example 69a) as an off-white solid. MS 332 (MH+).

Example 69a ethyl 5-(2-acetamido-2-methylpropoxy)-4-amino-2-methylquinoline-3-carboxylate Prepared as in Example 24a from 4-amino-5-(2-amino-2-methylpropoxy)-2-methylquinoline-3-carboxylate (Example 24b) and acetic acid as a brown solid. MS 390 (MH+).

Example 70

4-amino-5-(2-(2,3-dihydrobenzo[b][1,4]dioxine-5-carboxamido)-2-methylpropoxy)-2-methylquinoline-3-carboxylic acid

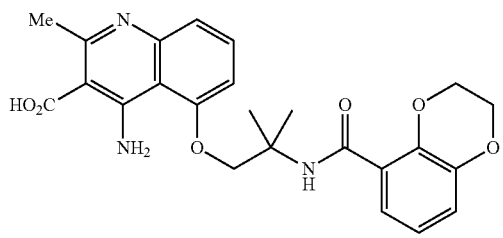 [SMILES: Cc1nc2cccc(OCC(C)(C)NC(=O)c3cccc4c3OCCO4)c2c(N)c1C(=O)O]

Prepared as in Example 1 from ethyl 4-amino-5-(2-(2,3-dihydrobenzo[b][1,4]dioxine-5-carboxamido)-2-methylpropoxy)-2-methylquinoline-3-carboxylate (Example 70a) as an off-white solid. MS 452 (MH+).

Example 70a ethyl 4-amino-5-(2-(2,3-dihydrobenzo[b][1,4]dioxine-5-carboxamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2,3-dihydrobenzo[b][1,4]dioxine-5-carboxylic acid as a brown solid. MS 480 (MH+).

Example 71

4-amino-5-(2-(3,5-dimethoxybenzamido)-2-methylpropoxy)-2-methylquinoline-3-carboxylic acid

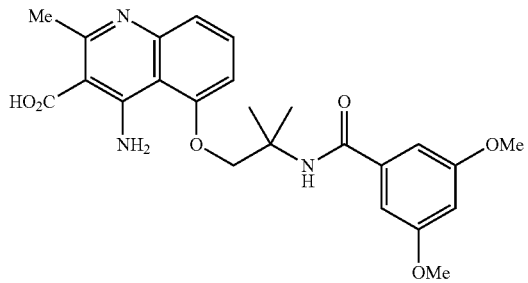 [SMILES: COc1cc(OC)cc(C(=O)NC(C)(C)COc2cccc3nc(C)c(C(=O)O)c(N)c23)c1]

Prepared as in Example 1 from ethyl 4-amino-5-(2-(3,5-dimethoxybenzamido)-2-methylpropoxy)-2-methylquinoline-3-carboxylate (Example 71a) as an off-white solid. MS 454 (MH+).

Example 71a ethyl 4-amino-5-(2-(3,5-dimethoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3,5-dimethoxybenzoic acid as a brown solid. MS 482 (MH+).

Example 72

4-amino-5-(2-(3,4-dimethoxybenzamido)-2-methylpropoxy)-2-methylquinoline-3-carboxylic acid

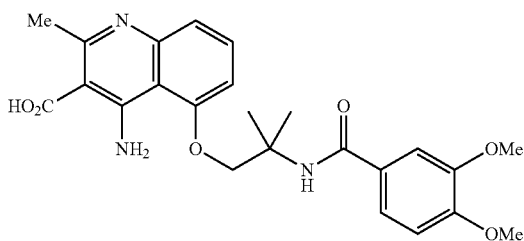 [SMILES: COc1ccc(C(=O)NC(C)(C)COc2cccc3nc(C)c(C(=O)O)c(N)c23)cc1OC]

Prepared as in Example 1 from ethyl 4-amino-5-(2-(3,4-dimethoxybenzamido)-2-methylpropoxy)-2-methylquinoline-3-carboxylate (Example 72a) as an off-white solid. MS 454 (MH+).

Example 72a ethyl 4-amino-5-(2-(3,4-dimethoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3,4-dimethoxybenzoic acid as a brown solid. MS 482 (MH+).

Example 73

4-amino-5-(2-(2-(4-methoxyphenyl)acetamido)-2-methylpropoxy)-2-methylquinoline-3-carboxylic acid

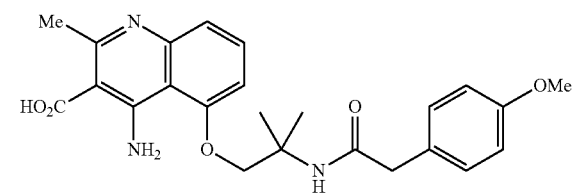 [SMILES: COc1ccc(CC(=O)NC(C)(C)COc2cccc3nc(C)c(C(=O)O)c(N)c23)cc1]

Prepared as in Example 1 from ethyl 4-amino-5-(2-(2-(4-methoxyphenyl)acetamido)-2-methylpropoxy)-2-methylquinoline-3-carboxylate (Example 73a) as an off-white solid. MS 438 (MH+).

Example 73a ethyl 4-amino-5-(2-(2-(4-methoxyphenyl)acetamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 2-(3,4-dimethoxyphenyl)acetic acid as a brown solid. MS 466 (MH$^+$).

Example 74

4-amino-5-(2-(4-fluoro-3-hydroxybenzamido)-2-methylpropoxy)-2-methylquinoline-3-carboxylic acid

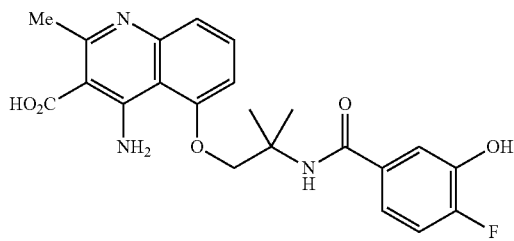 [SMILES: Cc1nc2cccc(OCC(C)(C)NC(=O)c3ccc(F)c(O)c3)c2c(N)c1C(=O)O]

Prepared as in Example 1 from ethyl 4-amino-5-(2-(4-fluoro-3-hydroxybenzamido)-2-methylpropoxy)-2-methylquinoline-3-carboxylate (Example 74a) as an off-white solid. MS 428 (MH$^+$).

Example 74a ethyl 4-amino-5-(2-(4-fluoro-3-hydroxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-fluoro-3-hydroxybenzoic acid as a brown solid. MS 456 (MH$^+$).

Example 75

4-amino-5-(2-(3-hydroxy-5-methoxybenzamido)-2-methylpropoxy)-2-methylquinoline-3-carboxylic acid

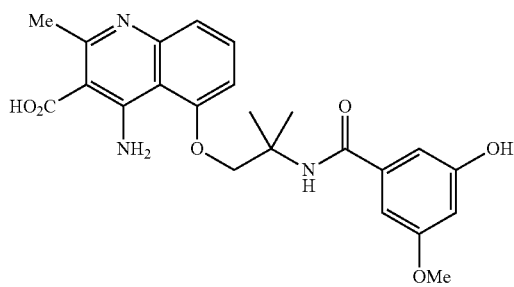 [SMILES: COc1cc(O)cc(C(=O)NC(C)(C)COc2cccc3nc(C)c(C(=O)O)c(N)c23)c1]

Prepared as in Example 1 from ethyl 4-amino-5-(2-(3-hydroxy-5-methoxybenzamido)-2-methylpropoxy)-2-methylquinoline-3-carboxylate (Example 75a) as an off-white solid. MS 440 (MH$^+$).

Example 75a ethyl 4-amino-5-(2-(3-hydroxy-5-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-hydroxy-5-methoxybenzoic acid as a brown solid. MS 468 (MH$^+$).

Example 76

4-amino-5-(2-(4-(2-hydroxyethoxy)-3-methoxybenzamido)-2-methylpropoxy)-2-methylquinoline-3-carboxylic acid

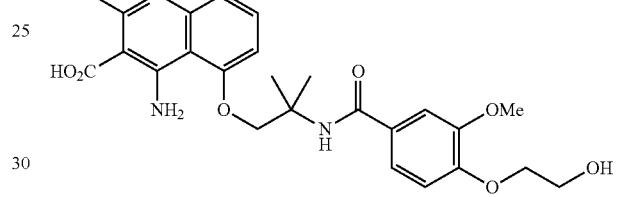

Prepared as in Example 1 from ethyl 4-amino-5-(2-(4-(2-hydroxyethoxy)-3-methoxybenzamido)-2-methylpropoxy)-2-methylquinoline-3-carboxylate (Example 76a) as an off-white solid. MS 484 (MH$^+$).

Example 76a ethyl 4-amino-5-(2-(4-(2-hydroxyethoxy)-3-methoxybenzamido)-2-methyl-propoxy)-2-methylquinoline-3-carboxylate Prepared as in Example 24a from 4-amino-5-(2-amino-2-methylpropoxy)-2-methylquinoline-3-carboxylate (Example 24b) and 4-(2-hydroxyethoxy)-3-methoxybenzoic acid (Uto, Y. et al. *Bioorg. Med. Chem. Lett.* 2009, 19, 4151.) as a brown solid. MS 512 (MH$^+$).

Example 77

4-amino-5-(2-(3-(2-hydroxyethoxy)-4-methoxybenzamido)-2-methylpropoxy)-2-methylquinoline-3-carboxylic acid

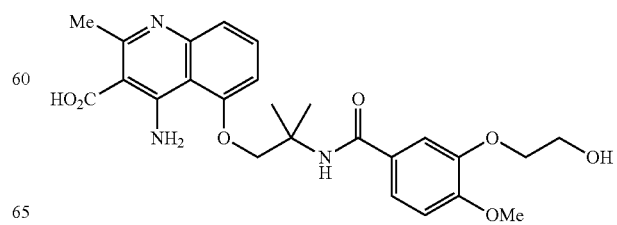

Prepared as in Example 1 from ethyl 4-amino-5-(2-(3-(2-hydroxyethoxy)-4-methoxybenzamido)-2-methylpropoxy)-2-methylquinoline-3-carboxylate (Example 77a) as an off-white solid. MS 484 (MH+).

Example 77a ethyl 4-amino-5-(2-(3-(2-hydroxyethoxy)-4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-(2-hydroxyethoxy)-4-methoxybenzoic acid as a brown solid. MS 512 (MH+).

Example 78

4-amino-5-(2-(3-(3-hydroxypropoxy)-4-methoxybenzamido)-2-methylpropoxy)-2-methylquinoline-3-carboxylic acid

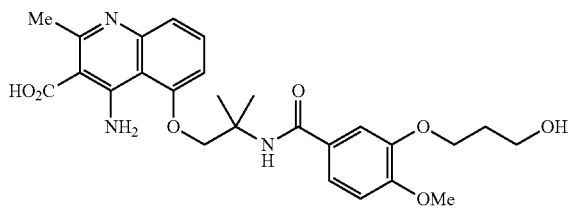 [SMILES: COc1ccc(C(=O)NC(C)(C)COc2cccc3nc(C)c(C(=O)O)c(N)c23)cc1OCCCO]

Prepared as in Example 1 from ethyl 4-amino-5-(2-(3-(3-hydroxypropoxy)-4-methoxybenzamido)-2-methylpropoxy)-2-methylquinoline-3-carboxylate (Example 78a) as an off-white solid. MS 498 (MH+).

Example 78a ethyl 4-amino-5-(2-(3-(3-hydroxypropoxy)-4-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 3-(3-hydroxypropoxy)-4-methoxybenzoic acid as a brown solid. MS 526 (MH+).

Example 79

4-amino-5-(2-(4-(3-hydroxypropoxy)-3-methoxybenzamido)-2-methylpropoxy)-2-methylquinoline-3-carboxylic acid

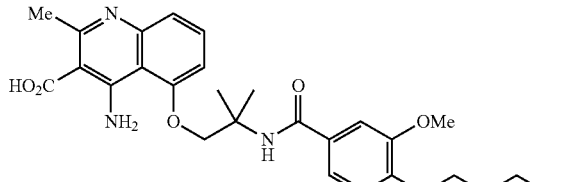

Prepared as in Example 1 from ethyl 4-amino-5-(2-(4-(3-hydroxypropoxy)-3-methoxybenzamido)-2-methylpropoxy)-2-methylquinoline-3-carboxylate (Example 79a) as an off-white solid. MS 498 (MH+).

Example 79a ethyl 4-amino-5-(2-(4-(3-hydroxypropoxy)-3-methoxybenzamido)-2-methylpropoxy)-2-methylquinoline-3-carboxylate Prepared as in Example 24a from 4-amino-5-(2-amino-2-methylpropoxy)-2-methylquinoline-3-carboxylate (Example 24b) and 4-(3-hydroxypropoxy)-3-methoxybenzoic acid (Baraldi, P. G. et al. *J. Med. Chem.* 1999, 42, 5131.) as a brown solid. MS 526 (MH+).

Example 80

(S)-4-amino-5-(2-(2,3-dihydrobenzo[b][1,4]dioxine-6-carboxamido)propoxy)-2-methylquinoline-3-carboxylic acid

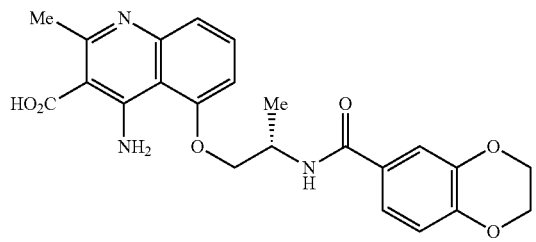 [SMILES: Cc1nc2cccc(OC[C@H](C)NC(=O)c3ccc4c(c3)OCCO4)c2c(N)c1C(=O)O]

Prepared as in Example 1 from (S)-ethyl 4-amino-5-(2-(2,3-dihydrobenzo[b][1,4]dioxine-6-carboxamido)propoxy)-2-methylquinoline-3-carboxylate (Example 80a) as an off-white solid. MS 438 (MH+).

Example 80a (S)-ethyl 4-amino-5-(2-(2,3-dihydrobenzo[b][1,4]dioxine-6-carboxamido)propoxy)-2-methylquinoline-3-carboxylate Prepared as in Example 24a from (S)-ethyl 4-amino-5-(2-aminopropoxy)-2-methylquinoline-3-carboxylate (Example 26b) and 2,3-dihydrobenzo[b][1,4]dioxine-6-carboxylic acid as brown solid. MS 466 (MH+).

Example 81

(S)-4-amino-5-(2-(2,3-dihydrobenzo[b][1,4]dioxine-5-carboxamido)propoxy)-2-methylquinoline-3-carboxylic acid

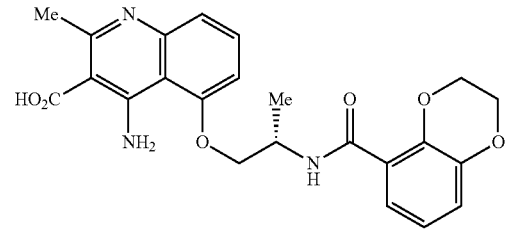 [SMILES: Cc1nc2cccc(OC[C@H](C)NC(=O)c3cccc4c3OCCO4)c2c(N)c1C(=O)O]

Prepared as in Example 1 from (S)-ethyl 4-amino-5-(2-(2,3-dihydrobenzo[b][1,4]dioxine-5-carboxamido)propoxy)-2-methylquinoline-3-carboxylate (Example 81a) as an off-white solid. MS 438 (MH+).

Example 81a (S)-ethyl 4-amino-5-(2-(2,3-dihydrobenzo[b][1,4]dioxine-5-carboxamido)propoxy)-2-methylquinoline-3-carboxylate Prepared as in Example 24a from (S)-ethyl 4-amino-5-(2-aminopropoxy)-2-methylquinoline-3-carboxylate (Example 26b) and 2,3-dihydrobenzo[b][1,4]dioxine-5-carboxylic acid as brown solid. MS 466 (MH$^+$).

Example 82

(S)-4-amino-5-(2-(4-(2-hydroxyethoxy)-3-methoxybenzamido)propoxy)-2-methylquinoline-3-carboxylic acid

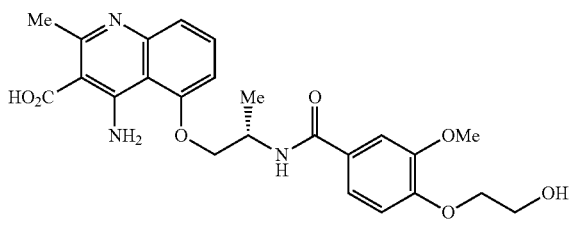

Prepared as in Example 1 from (S)-ethyl 4-amino-5-(2-(4-(2-hydroxyethoxy)-3-methoxybenzamido)propoxy)-2-methylquinoline-3-carboxylate (Example 82a) as an off-white solid. MS 470 (MH$^+$).

Example 82a (S)-ethyl 4-amino-5-(2-(4-(2-hydroxyethoxy)-3-methoxybenzamido)propoxy)-2-methylquinoline-3-carboxylate Prepared as in Example 24a from (S)-ethyl 4-amino-5-(2-aminopropoxy)-2-methylquinoline-3-carboxylate (Example 26b) and 4-(2-hydroxyethoxy)-3-methoxybenzoic acid (Uto, Y. et al. *Bioorg. Med. Chem. Lett.* 2009, 19, 4151.) as a brown solid. MS 498 (MH$^+$).

Example 83

(S)-4-amino-5-(2-(3-(2-hydroxyethoxy)-4-methoxybenzamido)propoxy)-2-methylquinoline-3-carboxylic acid

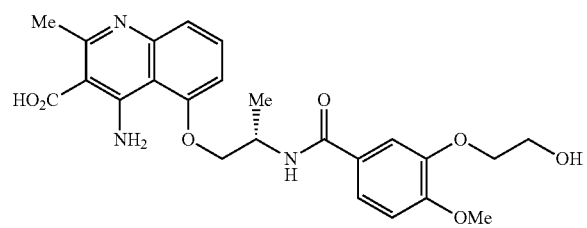 [SMILES: COc1ccc(C(=O)N[C@@H](C)COc2cccc3nc(C)c(C(=O)O)c(N)c23)cc1OCCO]

Prepared as in Example 1 from (S)-ethyl 4-amino-5-(2-(3-(2-hydroxyethoxy)-4-methoxybenzamido)propoxy)-2-methylquinoline-3-carboxylate (Example 83a) as an off-white solid. MS 470 (MH$^+$).

Example 83a (S)-ethyl 4-amino-5-(2-(3-(2-hydroxyethoxy)-4-methoxybenzamido)propoxy)-2-methylquinoline-3-carboxylate Prepared as in Example 24a from (S)-ethyl 4-amino-5-(2-aminopropoxy)-2-methylquinoline-3-carboxylate (Example 26b) and 3-(2-hydroxyethoxy)-4-methoxybenzoic acid as a brown solid. MS 498 (MH$^+$).

Example 84

(S)-4-amino-5-(2-(3-(3-hydroxypropoxy)-4-methoxybenzamido)propoxy)-2-methylquinoline-3-carboxylic acid

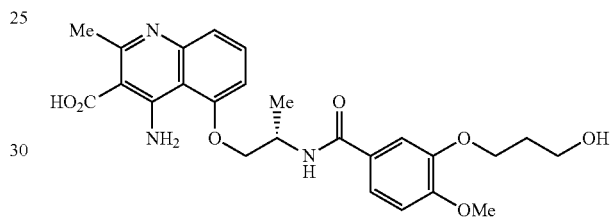

Prepared as in Example 1 from (S)-ethyl 4-amino-5-(2-(3-(3-hydroxypropoxy)-4-methoxybenzamido)-propoxy)-2-methylquinoline-3-carboxylate (Example 84a) as an off-white solid. MS 484 (MH$^+$).

Example 84a (S)-ethyl 4-amino-5-(2-(3-(3-hydroxypropoxy)-4-methoxybenzamido)propoxy)-2-methylquinoline-3-carboxylate Prepared as in Example 24a from (S)-ethyl 4-amino-5-(2-aminopropoxy)-2-methylquinoline-3-carboxylate (Example 26b) and 3-(3-hydroxypropoxy)-4-methoxybenzoic acid as a brown solid. MS 512 (MH$^+$).

Example 85

(S)-4-amino-5-(2-(4-(3-hydroxypropoxy)-3-methoxybenzamido)propoxy)-2-methylquinoline-3-carboxylic acid

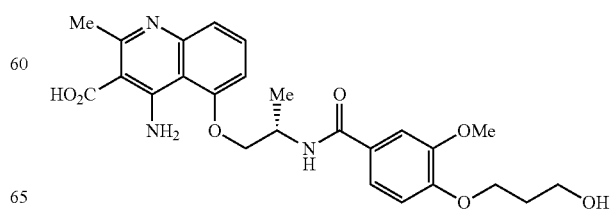

Prepared as in Example 1 from (S)-ethyl 4-amino-5-(2-(4-(3-hydroxypropoxy)-3-methoxybenzamido)propoxy)-2-methylquinoline-3-carboxylate (Example 85a) as an off-white solid. MS 484 (MH⁺).

Example 85a (S)-ethyl 4-amino-5-(2-(4-(3-hydroxypropoxy)-3-methoxybenzamido)propoxy)-2-methylquinoline-3-carboxylate Prepared as in Example 24a from (S)-ethyl 4-amino-5-(2-aminopropoxy)-2-methylquinoline-3-carboxylate (Example 26b) and 4-(3-hydroxypropoxy)-3-methoxybenzoic acid (Baraldi, P. G. et al. *J. Med. Chem.* 1999, 42, 5131.) as a brown solid. MS 512 (MH⁺).

Example 86

(R)-4-amino-5-(2-(cyclohexanecarboxamido)propoxy)-2-methylquinoline-3-carboxylic acid (SID 47687595)

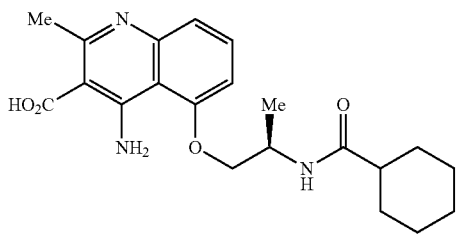 [SMILES: Cc1nc2cccc(OC[C@@H](C)NC(=O)C3CCCCC3)c2c(N)c1C(=O)O]

Prepared as in Example 1 from (R)-ethyl 4-amino-5-(2-(cyclohexanecarboxamido)propoxy)-2-methylquinoline-3-carboxylate (Example 86a) as a white solid (43%). ¹H NR (400 MHz, DMSO-d₆) δ 1.25-1.10 (m, 5H), 1.34-1.31 (m, 2H), 1.69-1.62 (m, 5H), 2.11-2.05 (m, 1H), 2.69 (s, 3H), 3.93 (t, J=9.2 Hz, 1H), 4.13 (dd, J=4, 9.6 Hz, 1H), 4.14-4.11 (m, 1H), 6.86 (d, J=8.0 Hz, 1H), 7.28 (d, J=8.4 Hz, 1H), 7.49 (t, J=8.0 Hz, 1H), 7.95 (d, J=8.4 Hz, 1H). MS 386 (MH⁺).

Example 86a (R)-ethyl 4-amino-5-(2-(cyclohexanecarboxamido)propoxy)-2-methylquinoline-3-carboxylate Prepared as in Example 24a from (R)-ethyl 4-amino-5-(2-aminopropoxy)-2-methylquinoline-3-carboxylate (Example 86b) and cyclohexanecarboxylic acid as brown solid (31%). MS 414 (MH⁺).

Example 86b (R)-ethyl 4-amino-5-(2-aminopropoxy)-2-methylquinoline-3-carboxylate Prepared as in Example 2a from (R)-benzyl(1-(3-amino-2-cyanophenoxy)propan-2-yl)carbamate (Example 86c) and ethyl 3-oxobutanoate as brown solid. MS 304 (MH⁺).

Example 86c (R)-benzyl(1-(3-amino-2-cyanophenoxy)propan-2-yl)carbamate

Prepared as in Example 24c from (R)-2-amino-6-(2-aminopropoxy)benzonitrile (Example 86d) as brown solid (79%). ¹H NR (400 MHz, DMSO-d₆) δ 1.12 (d, J=6.4 Hz, 3H), 3.81 (d, J=8.4 Hz, 1H), 3.95-3.92 (m, 1H), 4.99 (s, 2H), 5.36 (s, 2H), 5.96 (s, 2H), 6.20 (d, J=8.0 Hz, 1H), 6.31 (d, J=8.4 Hz, 1H), 7.13 (t, J=8.4 Hz, 1H), 7.44-7.38 (m, 5H). MS 326 (MH⁺).

Example 86d (R)-2-amino-6-(2-aminopropoxy)benzonitrile

Prepared as in Example 24d from (R)-2-aminopropan-1-ol and 2-amino-6-fluorobenzonitrile as brown solid (81%). ¹H NR (400 MHz, DMSO-d₆) δ 1.01 (d, J=6.5 Hz, 3H), 3.08 (m, 1H), 3.71 (d, J=6.1 Hz, 2H), 5.95 (s, 2H), 6.15 (d, J=8.3 Hz, 1H), 6.2 (d, J=8.3 Hz, 1H), 7.13 (t, J=8.3 Hz, 1H). MS 192 (MH⁺).

Example 87

(R)-4-amino-5-(2-(isonicotinamido)propoxy)-2-methylquinoline-3-carboxylic acid

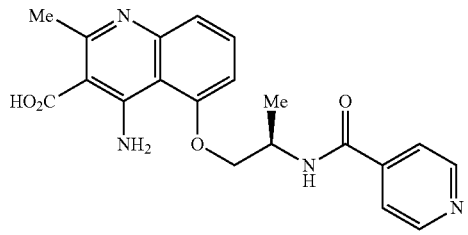 [SMILES: Cc1nc2cccc(OC[C@@H](C)NC(=O)c3ccncc3)c2c(N)c1C(=O)O]

Prepared as in Example 1 from (R)-ethyl 4-amino-5-(2-(isonicotinamido)propoxy)-2-methylquinoline-3-carboxylate (Example 87a) as an off-white solid (32%). ¹H NR (400 MHz, DMSO-d₆) δ 1.31 (d, J=6.8 Hz, 3H), 2.66 (s, 3H), 4.14 (t, J=9.2 Hz, 1H), 4.28 (dd, J=3.6, 9.6 Hz, 1H), 4.70-4.55 (m, 1H), 6.92 (d, J=8.0 Hz, 1H), 7.26 (d, J=8.4 Hz, 1H), 7.51 (t, J=8.4 Hz, 1H), 7.75 (dd, J=1.2, 6.0 Hz, 2H), 8.71 (dd, J=1.2, 6.0 Hz, 2H), 8.95 (d, J=8.0 Hz, 1H). MS 409 (MH⁺).

Example 87a (R)-ethyl 4-amino-5-(2-(isonicotinamido)propoxy)-2-methylquinoline-3-carboxylate Prepared as in Example 24a from (R)-ethyl 4-amino-5-(2-aminopropoxy)-2-methylquinoline-3-carboxylate (Example 86b) and isonicotinic acid as brown solid (41%). MS 409 (MH⁺).

Example 88

(R)-4-amino-5-(2-(3-hydroxybenzamido)propoxy)-2-methylquinoline-3-carboxylic acid

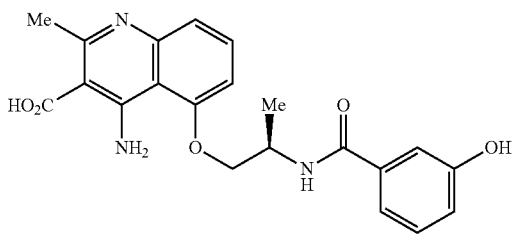 [SMILES: Cc1nc2cccc(OC[C@@H](C)NC(=O)c3cccc(O)c3)c2c(N)c1C(=O)O]

Prepared as in Example 1 from (R)-ethyl 4-amino-5-(2-(3-hydroxybenzamido)propoxy)-2-methylquinoline-3-carboxylate (Example 88a) as a white solid (51%). ¹H NR (400 MHz, DMSO-d₆) δ 1.28 (d, J=7.2 Hz, 3H), 2.65 (s, 3H), 4.11 (t, J=8.8 Hz, 1H), 4.22 (dd, J=4.0, 10 Hz, 1H), 4.65-4.55 (m, 1H), 6.88 (d, J=8.0, 2H), 7.25-7.13 (m, 4H), 7.48 (t, J=8.0 Hz, 1H), 8.49 (d, J=8.0, 1H), 9.93 (brs, 1H). MS 396 (MH⁺).

Example 88a (R)-ethyl 4-amino-5-(2-(3-hydroxybenzamido)propoxy)-2-methylquinoline-3-carboxylate Prepared as in Example 24a from (R)-ethyl 4-amino-5-(2-aminopropoxy)-2-methylquinoline-3-carboxylate (Example 86b) and 3-hydroxybenzoic acid as brown solid (36%). MS 424 (MH⁺).

Example 89

(S)-4-amino-5-((1-(cyclohexanecarbonyl)pyrrolidin-2-yl)methoxy)-2-methylquinoline-3-carboxylic acid (SID 47039333)

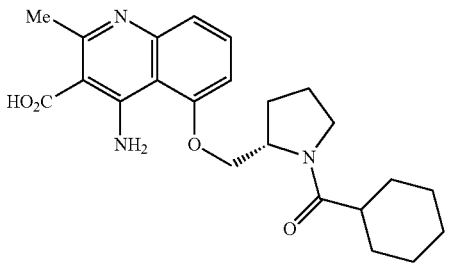 [SMILES: Cc1nc2cccc(OC[C@@H]3CCCN3C(=O)C3CCCCC3)c2c(N)c1C(=O)O]

Prepared as in Example 1 from (S)-ethyl 4-amino-5-((1-(cyclohexanecarbonyl)pyrrolidin-2-yl)methoxy)-2-methylquinoline-3-carboxylate (Example 89a) as an off-white solid (31%). ¹H NMR (400 MHz, DMSO-d₆) δ 1.34-1.11 (m, 5H), 1.72-1.51 (m, 5H), 2.08-1.79 (m, 5H), 2.44-2.35 (m 1H), 2.52 (s, 3H), 3.55-3.45 (m, 2H), 4.02 (dd, J=6.8, 9.2 Hz, 1H), 4.17 (dd, J=4.8, 10.0 Hz, 1H), 4.45-4.38 (m, 1H), 6.75 (d, J=7.2 Hz), 7.11 (d, J=7.6 Hz, 1H), 7.27 (t, J=8.0 Hz, 1H). MS 412 (MH⁺).

Example 89a (S)-ethyl 4-amino-5-((1-(cyclohexanecarbonyl)pyrrolidin-2-yl)methoxy)-2-methylquinoline-3-carboxylate Prepared as in Example 24a from (S)-ethyl 4-amino-2-methyl-5-(pyrrolidin-2-ylmethoxy)-quinoline-3-carboxylate (Example 89b) and cyclohexanecarboxylic acid as brown solid (46%). MS 440 (MH⁺).

Example 89b (S)-ethyl 4-amino-2-methyl-5-(pyrrolidin-2-ylmethoxy)quinoline-3-carboxylate Prepared as in Example 2a from (S)-benzyl 2-((3-amino-2-cyanophenoxy)methyl)pyrrolidine-1-carboxylate (Example 89c) and ethyl 3-oxobutanoate as brown solid. MS 330 (MH⁺).

Example 89c (S)-benzyl 2-((3-amino-2-cyanophenoxy)methyl)pyrrolidine-1-carboxylate Prepared as in Example 24c from (S)-2-amino-6-(pyrrolidin-2-ylmethoxy)benzonitrile (Example 89d) as brown solid (79%). MS 351 (MH⁺).

Example 89d (S)-2-amino-6-(pyrrolidin-2-ylmethoxy)benzonitrile

Prepared as in Example 24d from (S)-pyrrolidin-2-ylmethanol and 2-amino-6-fluorobenzonitrile as brown solid (51%). MS 218 (MH⁺).

Example 90

(S)-4-amino-5-((1-isobutyrylpyrrolidin-2-yl)methoxy)-2-methylquinoline-3-carboxylic acid

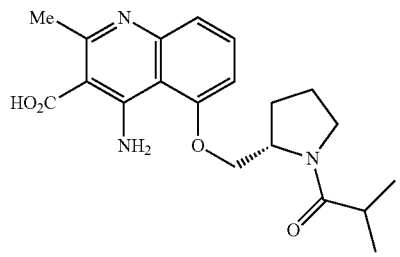 [SMILES: Cc1nc2cccc(OC[C@@H]3CCCN3C(=O)C(C)C)c2c(N)c1C(=O)O]

Prepared as in Example 1 from (S)-ethyl 4-amino-5-((1-isobutyrylpyrrolidin-2-yl)methoxy)-2-methylquinoline-3-carboxylate (Example 90a) as an off-white solid (39%). ¹H NR (400 MHz, DMSO-d₆) δ 0.99 (dd, J=2.0, 6.8 Hz, 6H), 2.05-1.83 (m, 4H), 2.65 (s, 3H), 3.53 (t, J=7.2 Hz, 2H), 4.08 (dd, J=6.8, 10.0 Hz, 1H), 4.20 (dd, J=6.0, 10.0 Hz, 1H), 4.54 (m, 1H), 6.99 (d, J=8.0 Hz, 1H), 7.21 (d, J=8.4 Hz, 1H), 7.50 (t, J=8.0 Hz, 1H). MS 344 (MH⁺).

Example 90a (S)-ethyl 4-amino-5-((1-isobutyrylpyrrolidin-2-yl)-methoxy)-2-methylquinoline-3-carboxylate Prepared as in Example 24a from (S)-ethyl 4-amino-2-methyl-5-(pyrrolidin-2-ylmethoxy)-quinoline-3-carboxylate (Example 89b) and isobutyric acid as brown solid (46%). MS 400 (MH⁺).

Example 91

(S)-5-((1-acetylpyrrolidin-2-yl)methoxy)-4-amino-2-methylquinoline-3-carboxylic acid

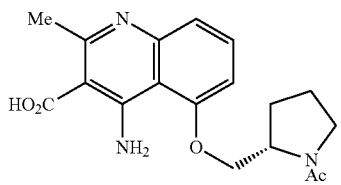

Prepared as in Example 1 from (S)-ethyl 5-((1-acetylpyrrolidin-2-yl)methoxy)-4-amino-2-methylquinoline-3-carboxylate (Example 91a) as an off-white solid (23%). $^1$H NR (400 MHz, DMSO-$d_6$) δ 1.98 (s, 3H), 2.03-1.82 (m, 4H), 2.71 (s, 3H), 3.48 (t, J=6.0 Hz, 2H), 4.05 (dd, J=6.4, 10.0 Hz, 1H), 4.22 (dd, J=6.8, 10.0 Hz, 1H), 4.54-4.46 (m, 1H), 6.99 (d, J=8.0 Hz, 1H), 7.34 (d, J=8.0 Hz, 1H), 7.54 (t, J=10.0 Hz, 1H). MS 344 (MH$^+$).

Example 91a (S)-ethyl 5-((1-acetylpyrrolidin-2-yl)methoxy)-4-amino-2-methylquinoline-3-carboxylate Prepared as in Example 24a from (S)-ethyl 4-amino-2-methyl-5-(pyrrolidin-2-ylmethoxy)-quinoline-3-carboxylate (Example 89b) and acetic anhydride as brown solid (31%). MS 372 (MH$^+$).

Example 92

(R)-4-amino-5-((1-(cyclohexanecarbonyl)pyrrolidin-2-yl)methoxy)-2-methylquinoline-3-carboxylic acid

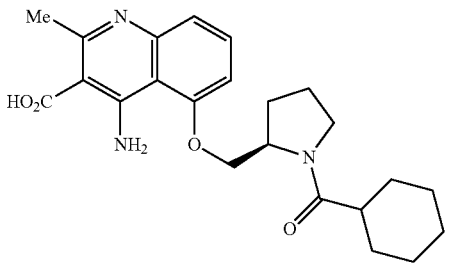 [SMILES: Cc1nc2cccc(OC[C@H]3CCCN3C(=O)C3CCCCC3)c2c(N)c1C(=O)O]

Prepared as in Example 1 from (R)-ethyl 4-amino-5-((1-(cyclohexanecarbonyl)pyrrolidin-2-yl)methoxy)-2-methylquinoline-3-carboxylate (Example 92a) as an off-white solid (37%). $^1$H NMR (400 MHz, DMSO-$d_6$) δ 1.34-1.11 (m, 5H), 1.72-1.51 (m, 5H), 2.08-1.79 (m, 5H), 2.44-2.35 (m 1H), 2.52 (s, 3H), 3.55-3.45 (m, 2H), 4.02 (dd, J=6.8, 9.2 Hz, 1H), 4.17 (dd, J=4.8, 10.0 Hz, 1H), 4.45-4.38 (m, 1H), 6.75 (d, J=7.2 Hz), 7.11 (d, J=7.6 Hz, 1H), 7.27 (t, J=8.0 Hz, 1H). MS 412 (MH$^+$).

Example 92a (R)-ethyl 4-amino-5-((1-(cyclohexanecarbonyl)pyrrolidin-2-yl)methoxy)-2-methylquinoline-3-carboxylate Prepared as in Example 24a from (R)-ethyl 4-amino-2-methyl-5-(pyrrolidin-2-ylmethoxy)-quinoline-3-carboxylate (Example 92b) and cyclohexanecarboxylic acid as brown solid (39%). MS 440 (MH$^+$).

Example 92b (R)-ethyl 4-amino-2-methyl-5-(pyrrolidin-2-ylmethoxy)quinoline-3-carboxylate Prepared as in Example 2a from (R)-benzyl 2-((3-amino-2-cyanophenoxy)methyl)pyrrolidine-1-carboxylate (Example 92c) and ethyl 3-oxobutanoate as brown solid. MS 330 (MH$^+$).

Example 92c (R)-benzyl 2-((3-amino-2-cyanophenoxy)methyl)pyrrolidine-1-carboxylate Prepared as in Example 24c from (R)-2-amino-6-(pyrrolidin-2-ylmethoxy)benzonitrile (Example 92d) as brown solid (71%). MS 351 (MH$^+$).

Example 92d (R)-2-amino-6-(pyrrolidin-2-ylmethoxy)benzonitrile

Prepared as in Example 24d from (R)-pyrrolidin-2-ylmethanol and 2-amino-6-fluorobenzonitrile as brown solid (57%). MS 218 (MH$^+$).

Example 93

(R)-4-amino-5-((1-isobutyrylpyrrolidin-2-yl)methoxy)-2-methylquinoline-3-carboxylic acid

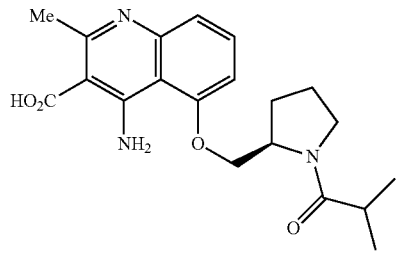 [SMILES: Cc1nc2cccc(OC[C@H]3CCCN3C(=O)C(C)C)c2c(N)c1C(=O)O]

Prepared as in Example 1 from (R)-ethyl 4-amino-5-((1-isobutyrylpyrrolidin-2-yl)methoxy)-2-methylquinoline-3-carboxylate (Example 93a) as an off-white solid (44%). $^1$H NR (400 MHz, DMSO-$d_6$) δ 0.99 (dd, J=2.0, 6.8 Hz, 6H), 2.05-1.83 (m, 4H), 2.65 (s, 3H), 3.53 (t, J=7.2 Hz, 2H), 4.08 (dd, J=6.8, 10.0 Hz, 1H), 4.20 (dd, J=6.0, 10.0 Hz, 1H), 4.54 (m, 1H), 6.99 (d, J=8.0 Hz, 1H), 7.21 (d, J=8.4 Hz, 1H), 7.50 (t, J=8.0 Hz, 1H). MS 344 (MH$^+$).

Example 93a (R)-ethyl 4-amino-5-((1-isobutyrylpyrrolidin-2-yl)methoxy)-2-methylquinoline-3-carboxylate Prepared as in Example 24a from (R)-ethyl 4-amino-2-methyl-5-(pyrrolidin-2-ylmethoxy)quinoline-3-carboxylate (Example 92b) and isobutyric acid as brown solid (39%). MS 400 (MH$^+$).

Example 94

(R)-5-((1-acetylpyrrolidin-2-yl)methoxy)-4-amino-2-methylquinoline-3-carboxylic acid

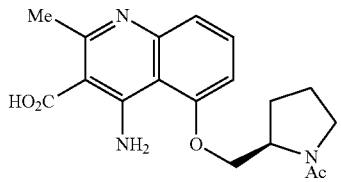

Prepared as in Example 1 from (R)-ethyl 5-((1-acetylpyrrolidin-2-yl)methoxy)-4-amino-2-methylquinoline-3-carboxylate (Example 94a) as an off-white solid (19%). $^1$H NR (400 MHz, DMSO-$d_6$) δ 1.98 (s, 3H), 2.03-1.82 (m, 4H), 2.71 (s, 3H), 3.48 (t, J=6.0 Hz, 2H), 4.05 (dd, J=6.4, 10.0 Hz, 1H), 4.22 (dd, J=6.8, 10.0 Hz, 1H), 4.54-4.46 (m, 1H), 6.99 (d, J=8.0 Hz, 1H), 7.34 (d, J=8.0 Hz, 1H), 7.54 (t, J=10.0 Hz, 1H). MS 344 (MH$^+$).

Example 94a (R)-ethyl 5-((1-acetylpyrrolidin-2-yl)methoxy)-4-amino-2-methylquinoline-3-carboxylate Prepared as in Example 24a from (R)-ethyl 4-amino-2-methyl-5-(pyrrolidin-2-ylmethoxy)quinoline-3-carboxylate (Example 92b) and acetic anhydride as brown solid (28%). MS 372 (MH$^+$).

Example 95

(S)-4-amino-5-(2-(2-hydroxybenzamido)-3-methylbutoxy)-2-methylquinoline-3-carboxylic acid

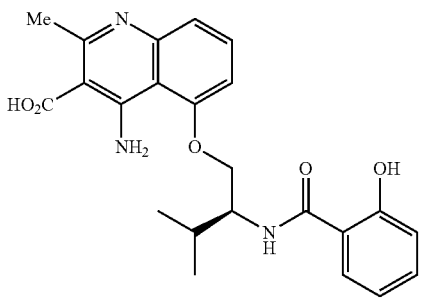 [SMILES: Cc1nc2cccc(OC[C@@H](NC(=O)c3ccccc3O)C(C)C)c2c(N)c1C(=O)O]

Prepared as in Example 1 from (5)-ethyl 4-amino-5-(2-(2-hydroxybenzamido)-3-methylbutoxy)-2-methylquinoline-3-carboxylate (Example 95a) as a white solid (82%). MS 424 (MH$^+$).

Example 95a (5)-ethyl 4-amino-5-(2-(2-hydroxybenzamido)-3-methylbutoxy)-2-methylquinoline-3-carboxylate Prepared as in Example 24a from (5)-ethyl 4-amino-5-(2-amino-3-methylbutoxy)-2-ylmethoxy)quinoline-3-carboxylate (Example 95b) and 2-hydroxybenzoic acid as brown solid (56%). MS 452 (MH$^+$).

Example 95b (S)-ethyl 4-amino-5-(2-amino-3-methylbutoxy)-2-methylquinoline-3-carboxylate Prepared as in Example 2a from (S)-benzyl 1-(3-amino-2-cyanophenoxy)-3-methylbutan-2-ylcarbamate (Example 95c) and ethyl 3-oxobutanoate as brown solid (79%). MS 332 (MH$^+$).

Example 95c (S)-benzyl 1-(3-amino-2-cyanophenoxy)-3-methylbutan-2-ylcarbamate Prepared as in Example 24c from (S)-2-amino-6-(2-amino-3-methylbutoxy)benzonitrile (Example 95d) as brown solid (82%). MS 354 (MH$^+$).

Example 95d (S)-2-amino-6-(2-amino-3-methylbutoxy)benzonitrile

Prepared as in Example 24d from (S)-2-amino-3-methylbutan-1-ol and 2-amino-6-fluorobenzonitrile as brown solid (71%). MS 220 (MH$^+$).

Example 96

(S)-4-amino-5-(2-(3-hydroxybenzamido)-3-methylbutoxy)-2-methylquinoline-3-carboxylic acid

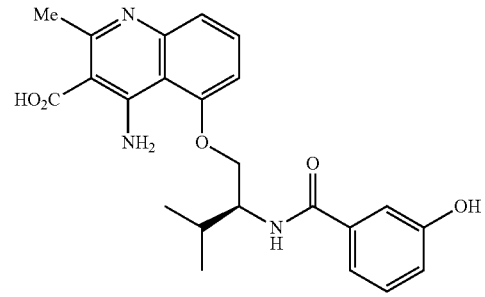 [SMILES: Cc1nc2cccc(OC[C@@H](NC(=O)c3cccc(O)c3)C(C)C)c2c(N)c1C(=O)O]

Prepared as in Example 1 from (S)-ethyl 4-amino-5-(2-(3-hydroxybenzamido)-3-methylbutoxy)-2-methylquinoline-3-carboxylate (Example 96a) as a white solid (83%). MS 424 (MH$^+$).

Example 96a (S)-ethyl 4-amino-5-(2-(3-hydroxybenzamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 3-hydroxybenzoic acid as brown solid (35%). MS 452 (MH$^+$).

Example 97

(S)-4-amino-5-(2-(2-hydroxybenzamido)butoxy)-2-methylquinoline-3-carboxylic acid

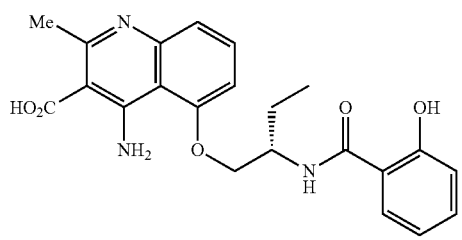 [SMILES: CC[C@@H](COc1cccc2nc(C)c(C(=O)O)c(N)c12)NC(=O)c1ccccc1O]

Prepared as in Example 1 from (S)-ethyl 4-amino-5-(2-(2-hydroxybenzamido)butoxy)-2-methylquinoline-3-carboxylate (Example 97a) as an off-white solid (78%). MS 410 (MH$^+$).

Example 97a (S)-ethyl 4-amino-5-(2-(2-hydroxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 2-hydroxybenzoic acid as brown solid (46%). MS 438 (MH$^+$).

Example 97b (S)-ethyl 4-amino-5-(2-aminobutoxy)-2-methylquinoline-3-carboxylate

Prepared as in Example 2a from (S)-benzyl 1-(3-amino-2-cyanophenoxy)butan-2-ylcarbamate (Example 97c) and ethyl 3-oxobutanoate as brown solid (75%). MS 318 (MH$^+$).

Example 97c (S)-benzyl 1-(3-amino-2-cyanophenoxy)butan-2-ylcarbamate

Prepared as in Example 24c from (S)-2-amino-6-(2-aminobutoxy)benzonitrile (Example 97d) as brown solid (87%). MS 340 (MH$^+$).

Example 97d (S)-2-amino-6-(2-aminobutoxy)benzonitrile

Prepared as in Example 24d from (S)-2-aminobutan-1-ol and 2-amino-6-fluorobenzonitrile as brown solid (73%). MS 206 (MH$^+$).

Example 98

(S)-4-amino-5-(2-(4-(2-hydroxyethoxy)-3-methoxybenzamido)butoxy)-2-methylquinoline-3-carboxylic acid

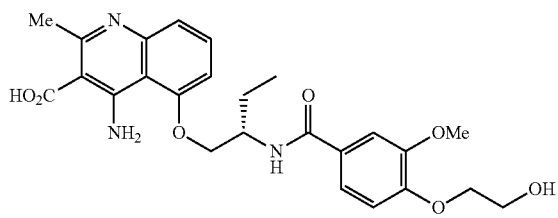 [SMILES: CC[C@@H](COc1cccc2nc(C)c(C(=O)O)c(N)c12)NC(=O)c1ccc(OCCO)c(OC)c1]

Prepared as in Example 1 from (S)-ethyl 4-amino-5-(2-(4-(2-hydroxyethoxy)-3-methoxybenzamido)butoxy)-2-methylquinoline-3-carboxylate (Example 98a) as an off-white solid (83%). MS 484 (MH$^+$).

Example 98a (S)-ethyl 4-amino-5-(2-(4-(2-hydroxyethoxy)-3-methoxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 4-(2-hydroxyethoxy)-3-methoxybenzoic acid (Uto, Y. et al. *Bioorg. Med. Chem. Lett.* 2009, 19, 4151.) as brown solid (38%). MS 512 (MH$^+$).

Example 99

(S)-4-amino-5-(2-(2,3-dihydrobenzo[b][1,4]dioxine-5-carboxamido)butoxy)-2-methylquinoline-3-carboxylic acid

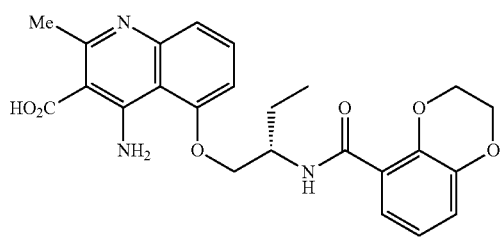 [SMILES: CC[C@@H](COc1cccc2nc(C)c(C(=O)O)c(N)c12)NC(=O)c1cccc2c1OCCO2]

Prepared as in Example 1 from (S)-ethyl 4-amino-5-(2-(2,3-dihydrobenzo[b][1,4]dioxine-5-carboxamido)butoxy)-2-methylquinoline-3-carboxylate (Example 99a) as an off-white solid (78%). MS 452 (MH$^+$).

Example 99a (S)-ethyl 4-amino-5-(2-(2,3-dihydrobenzo[b][1,4]dioxine-5-carboxamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 2,3-dihydrobenzo[b][1,4]dioxine-5-carboxylic acid as brown solid (40%). MS 480 (MH$^+$).

Example 100

(S)-4-amino-5-(2-(4-(3-hydroxypropoxy)-3-methoxybenzamido)butoxy)-2-methylquinoline-3-carboxylic acid

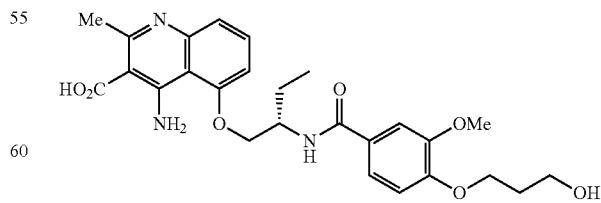

Prepared as in Example 1 from (S)-ethyl 4-amino-5-(2-(4-(3-hydroxypropoxy)-3-methoxybenzamido)butoxy)-2-methylquinoline-3-carboxylate (Example 100a) as an off-white solid (79%). MS 498 (MH$^+$).

Example 100a (S)-ethyl 4-amino-5-(2-(4-(3-hydroxypropoxy)-3-methoxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 4-(3-hydroxypropoxy)-3-methoxybenzoic acid (Baraldi, P. G. et al. *J. Med. Chem.* 1999, 42, 5131.) as brown solid (41%). MS 526 (MH$^+$).

Example 101

(S)-4-amino-5-(2-(3,5-dihydroxybenzamido)butoxy)-2-methylquinoline-3-carboxylic acid

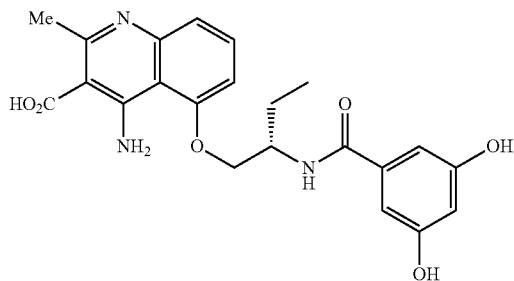 [SMILES: CC[C@@H](COc1cccc2nc(C)c(C(=O)O)c(N)c12)NC(=O)c1cc(O)cc(O)c1]

Prepared as in Example 1 from (S)-ethyl 4-amino-5-(2-(3,5-dihydroxybenzamido)butoxy)-2-methylquinoline-3-carboxylate (Example 101a) as an off-white solid (69%). MS 426 (MH$^+$).

Example 101a (S)-ethyl 4-amino-5-(2-(3,5-dihydroxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 3,5-dihydroxybenzoic acid as brown solid (37%). MS 454 (MH$^+$).

Example 102

(S)-4-amino-5-(2-(2,3-dihydrobenzo[b][1,4]dioxine-6-carboxamido)butoxy)-2-methylquinoline-3-carboxylic acid

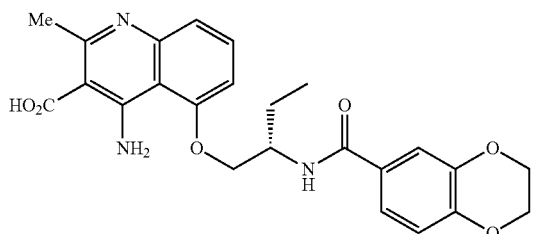

Prepared as in Example 1 from (S)-ethyl 4-amino-5-(2-(2,3-dihydrobenzo[b][1,4]dioxine-6-carboxamido)butoxy)-2-methylquinoline-3-carboxylate (Example 102a) as an off-white solid (71%). MS 452 (MH$^+$).

Example 102a (S)-ethyl 4-amino-5-(2-(2,3-dihydrobenzo[b][1,4]dioxine-6-carboxamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 2,3-dihydrobenzo[b][1,4]dioxine-6-carboxylic acid as brown solid (46%). MS 480 (MH$^+$).

Example 103

(S)-4-amino-5-(2-(3-hydroxybenzamido)butoxy)-2-methylquinoline-3-carboxylic acid

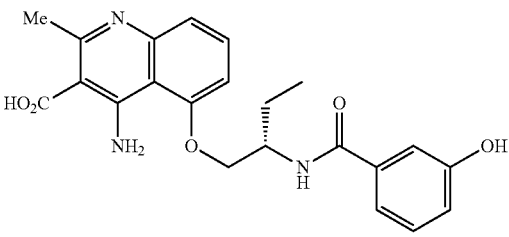 [SMILES: CC[C@@H](COc1cccc2nc(C)c(C(=O)O)c(N)c12)NC(=O)c1cccc(O)c1]

Prepared as in Example 1 from (S)-ethyl 4-amino-5-(2-(3-hydroxybenzamido)butoxy)-2-methylquinoline-3-carboxylate (Example 103a) as an off-white solid (72%). MS 410 (MH$^+$).

Example 103a (S)-ethyl 4-amino-5-(2-(3-hydroxybenzamido)butoxy)-2-methylquinoline-3-carboxylate Prepared as in Example 24a from (S)-ethyl 4-amino-5-(2-aminobutoxy)-2-methylquinoline-3-carboxylate (Example 97b) and 3-hydroxybenzoic acid as brown solid (49%). MS 438 (MH$^+$).

Example 104

(S)-4-amino-5-(2-(4-(3-hydroxypropoxy)-3-methoxybenzamido)-3-methylbutoxy)-2-methylquinoline-3-carboxylic acid

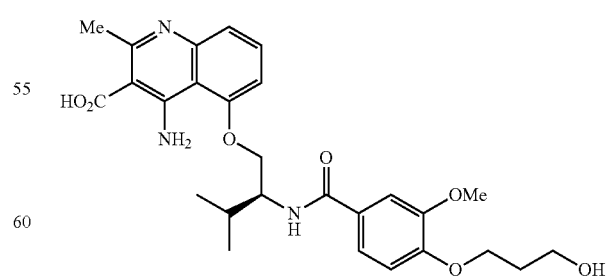

Prepared as in Example 1 from (S)-ethyl 4-amino-5-(2-(4-(3-hydroxypropoxy)-3-methylbutoxy)-2-methylquinoline-3-carboxylate (Example 104a) as an off-white solid (69%). MS 512 (MH$^+$).

Example 104a (S)-ethyl 4-amino-5-(2-(4-(3-hydroxypropoxy)-3-methoxybenzamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 4-(3-hydroxypropoxy)-3-methoxybenzoic acid (Baraldi, P. G. et al. *J. Med. Chem.* 1999, 42, 5131.) as brown solid (29%). MS 540 (MH+).

Example 105

(S)-4-amino-5-(2-(3,5-dihydroxybenzamido)-3-methylbutoxy)-2-methylquinoline-3-carboxylic acid

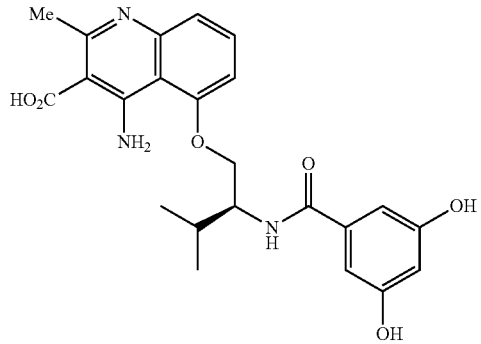 [SMILES: Cc1nc2cccc(OC[C@@H](NC(=O)c3cc(O)cc(O)c3)C(C)C)c2c(N)c1C(=O)O]

Prepared as in Example 1 from (S)-ethyl 4-amino-5-(2-(3,5-dihydroxybenzamido)-3-methylbutoxy)-2-methylquinoline-3-carboxylate (Example 105a) as a white solid (72%). MS 440 (MH+).

Example 105a (S)-ethyl 4-amino-5-(2-(3,5-dihydroxybenzamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 3,5-dihydroxybenzoic acid as brown solid (29%). MS 468 (MH+).

Example 106

(S)-4-amino-5-(2-(2,3-dihydrobenzo[b][1,4]dioxine-5-carboxamido)-3-methylbutoxy)-2-methylquinoline-3-carboxylic acid

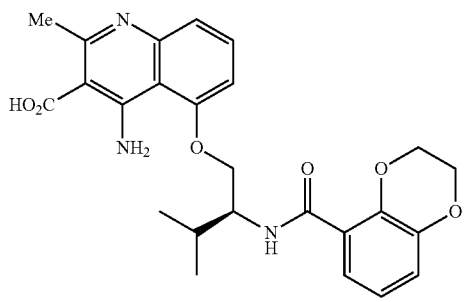 [SMILES: Cc1nc2cccc(OC[C@@H](NC(=O)c3cccc4c3OCCO4)C(C)C)c2c(N)c1C(=O)O]

Prepared as in Example 1 from (S)-ethyl 4-amino-5-(2-(2,3-dihydrobenzo[b][1,4]dioxine-5-carboxamido)-3-methylbutoxy)-2-methylquinoline-3-carboxylate (Example 106a) as a white solid (81%). MS 466 (MH+).

Example 106a (S)-ethyl 4-amino-5-(2-(2,3-dihydrobenzo[b][1,4]dioxine-5-carboxamido)-3-methylbutoxy)-2-methylquinoline-3-carboxylate Prepared as in Example 24a from (S)-ethyl 4-amino-5-(2-amino-3-methylbutoxy)-2-methylquinoline-3-carboxylate (Example 95b) and 2,3-dihydrobenzo[b][1,4]dioxine-5-carboxylic acid as brown solid (36%). MS 494 (MH+).

Example 107

(S)-4-amino-5-(2-(2,3-dihydrobenzo[b][1,4]dioxine-6-carboxamido)-3-methylbutoxy)-2-methylquinoline-3-carboxylic acid

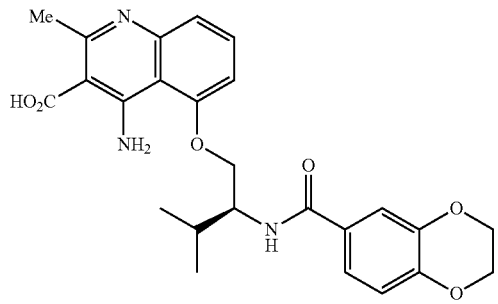 [SMILES: Cc1nc2cccc(OC[C@@H](NC(=O)c3ccc4c(c3)OCCO4)C(C)C)c2c(N)c1C(=O)O]

Prepared as in Example 1 from (S)-ethyl 4-amino-5-(2-(2,3-dihydrobenzo[b][1,4]dioxine-6-carboxamido)-3-methylbutoxy)-2-methylquinoline-3-carboxylate (Example 107a) as an off-white solid (76%). MS 466 (MH+).

Example 107a (5)-ethyl 4-amino-5-(2-(2,3-dihydrobenzo[b][1,4]dioxine-6-carboxamido)-3-methylbutoxy)-2-methylquinoline-3-carboxylate Prepared as in Example 24a from (5)-ethyl 4-amino-5-(2-amino-3-methylbutoxy)-2-methylquinoline-3-carboxylate (Example 95b) and 2,3-dihydrobenzo[b][1,4]dioxine-6-carboxylic acid as brown solid (29%). MS 494 (MH+).

Example 108

4-amino-5-((4-(isonicotinamido)cyclohexyl)methoxy)-2-methylquinoline-3-carboxylic acid

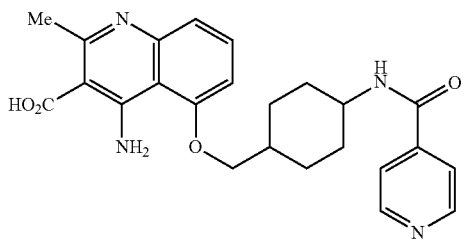 [SMILES: Cc1nc2cccc(OCC3CCC(NC(=O)c4ccncc4)CC3)c2c(N)c1C(=O)O]

Prepared as in Example 1 from ethyl 4-amino-5-((4-(isonicotinamido)cyclohexyl)methoxy)-2-methylquinoline-3-carboxylate (Example 108a) as an off-white solid (43%). $^1$H NMR (400 MHz, DMSO-$d_6$) δ 1.52-2.01 (m, 8H), 2.13 (m, 1H), 2.74 (s, 3H), 3.99 (m, 1H), 4.18 (d, J=6.8 Hz, 2H), 7.05 (d, J=8.0 Hz, 1H), 7.26 (d, J=8.0 Hz, 1H), 7.66 (t, J=8.4 Hz, 1H), 7.71 (d, J=6.0 Hz, 2H), 8.40 (d, J=6.8 Hz, 1H), 8.71 (d, J=6.0 Hz, 2H), 12.70 (brs, 1H). MS 435 (MH$^+$).

Example 108a ethyl 4-amino-5-((4-(isonicotinamido)cyclohexyl)methoxy)-2-methylquinoline-3-carboxylate Prepared as in Example 2a from N-(4-((3-Amino-2-cyanophenoxy)methyl)cyclohexyl)isonicotinamide (Example 108b) and ethyl 3-oxobutanoate as a yellow solid (25%). MS 463 (MH$^+$).

Example 108b

N-(4-((3-Amino-2-cyanophenoxy)methyl)cyclohexyl)isonicotinamide

Prepared as in Example 22b from N-(4-(Hydroxymethyl)cyclohexyl)isonicotinamide (Example 108c) and 2-amino-6-fluorobenzonitrile as a colorless oil (6%). MS 351 (MH$^+$).

Example 108c

N-(4-(Hydroxymethyl)cyclohexyl)isonicotinamide

Prepared as in Example 24a from (4-Aminocyclohexyl)methanol and isonicotinic acid as a yellow oil (100%). MS 235 (MH$^+$).

Example 109

4-amino-5-((2-methoxycyclohexyl)oxy)-2-methylquinoline-3-carboxylic acid

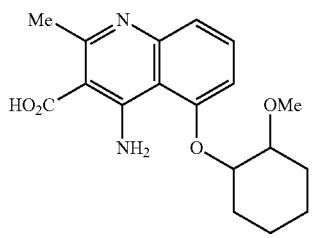 [SMILES: COC1CCCCC1Oc1cccc2nc(C)c(C(=O)O)c(N)c12]

Prepared as in Example 1 from ethyl 4-amino-5-((2-methoxycyclohexyl)oxy)-2-methylquinoline-3-carboxylate (Example 109a) as a white solid (79%). $^1$H NR (400 MHz, DMSO-$d_6$) δ 1.20-1.68 (m, 6H), 2.16 (m, 2H), 2.78 (s, 3H), 3.34 (s, 3H), 3.58 (m, 1H), 4.50 (m, 1H), 7.17 (d, J=8.4 Hz, 1H), 7.29 (d, J=8.4 Hz, 1H), 7.67 (t, J=8.8 Hz, 1H), 8.92 (brs, 1H), 12.14 (brs, 1H), 12.86 (brs, 1H). MS 331 (MH$^+$).

Example 109a ethyl 4-amino-5-((2-methoxycyclohexyl)oxy)-2-methylquinoline-3-carboxylate Prepared as in Example 2a from 2-Amino-6-(2-methoxycyclohexyloxy)benzonitrile (Example 109b) and ethyl 3-oxobutanoate as a pale yellow oil (16%). MS 359 (MH$^+$).

Example 109b

2-Amino-6-(2-methoxycyclohexyloxy)benzonitrile

Prepared as in Example 22b from 2-methoxycyclohexanol and 2-amino-6-fluorobenzonitrile as a yellow oil (34%). MS 247 (MH$^+$).

Example 110

4-amino-5-((1-(3-hydroxybenzoyl)piperidin-3-yl)methoxy)-2-methylquinoline-3-carboxylic acid

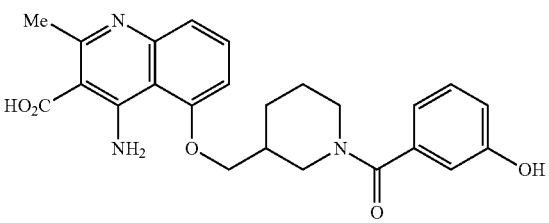 [SMILES: Cc1nc2cccc(OCC3CCCN(C(=O)c4cccc(O)c4)C3)c2c(N)c1C(=O)O]

Prepared as in Example 1 from ethyl 4-amino-5-((1-(3-hydroxybenzoyl)piperidin-3-yl)methoxy)-2-methylquinoline-3-carboxylate (Example 110a) as a white solid (35%). MS 436 (MH$^+$).

Example 110a ethyl 4-amino-5-((1-(3-hydroxybenzoyl)piperidin-3-yl)methoxy)-2-methylquinoline-3-carboxylate Prepared as in Example 24a from ethyl 4-amino-2-methyl-5-(piperidin-3-ylmethoxy)quinoline-3-carboxylate (Example 110b) and 3-hydroxybenzoic acid as a white solid (34%). MS 464 (MH$^+$).

Example 110b ethyl 4-amino-2-methyl-5-(piperidin-3-ylmethoxy)quinoline-3-carboxylate Prepared as in Example 2a from benzyl 3-((3-amino-2-cyanophenoxy)methyl)piperidine-1-carboxylate (Example 110c) and ethyl 3-oxobutanoate as a yellow oil (21%). MS 344 (MH$^+$).

Example 110c benzyl 3-((3-amino-2-cyanophenoxy)methyl)piperidine-1-carboxylate

Prepared as in Example 24c from 2-amino-6-(piperidin-3-ylmethoxy)benzonitrile (Example 110d) as a yellow solid (70%).

Example 110d 2-amino-6-(piperidin-3-ylmethoxy)benzonitrile

Prepared as in Example 24d from 3-piperidinemethanol and 2-amino-6-fluoro-benzonitrile as a light yellow solid (27%). MS 232 (MH$^+$).

Example 111

4-amino-5-((1-(3-hydroxybenzoyl)piperidin-2-yl)methoxy)-2-methylquinoline-3-carboxylic acid

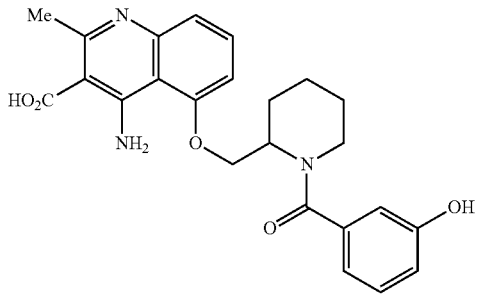 [SMILES: Cc1nc2cccc(OCC3CCCCN3C(=O)c3cccc(O)c3)c2c(N)c1C(=O)O]

Prepared as in Example 1 from ethyl 4-amino-5-((1-(3-hydroxybenzoyl)piperidin-2-yl)methoxy)-2-methylquinoline-3-carboxylate (Example 111a) as an off-white solid (35%). $^1$H NMR (400 MHz, DMSO-$d_6$) δ 1.25-1.89 (m, 6H), 2.74 (s, 3H), 3.44 (m, 2H), 4.27 (m, 1H), 4.75 (m, 2H), 5.29 (m, 1H), 6.64-6.73 (m, 2H), 6.78 (d, J=7.2 Hz, 1H), 7.18 (m, 2H), 7.26 (d, J=8.4 Hz, 1H), 7.68 (m, 1H), 8.87 (brs, 1H), 9.73 (brs, 1H), 11.96 (brs, 1H), 12.70 (brs, 1H). MS 436 (MH$^+$).

Example 111a ethyl 4-amino-5-((1-(3-hydroxybenzoyl)piperidin-2-yl)methoxy)-2-methylquinoline-3-carboxylate Prepared as in Example 24a from ethyl 4-amino-2-methyl-5-(piperidin-2-ylmethoxy)quinoline-3-carboxylate (Example 111b) and 3-hydroxybenzoic acid as a white solid (28%). MS 464 (MH$^+$).

Example 111b ethyl 4-amino-2-methyl-5-(piperidin-2-ylmethoxy)quinoline-3-carboxylate Prepared as in Example 2a from benzyl 2-((3-amino-2-cyanophenoxy)methyl)piperidine-1-carboxylate (Example 111c) and ethyl 3-oxobutanoate as a colorless oil (13%). MS 344 (MH$^+$).

Example 111c benzyl 2-((3-amino-2-cyanophenoxy)methyl)piperidine-1-carboxylate Prepared as in Example 24c from 2-amino-6-(piperidin-2-ylmethoxy)benzonitrile (Example 111d) as a yellow solid (100%). MS 366 (MH$^+$).

Example 111d

2-Amino-6-(piperidin-2-ylmethoxy)benzonitrile

Prepared as in Example 24d from 2-piperidinemethanol and 2-amino-6-fluoro-benzonitrile as a light yellow solid (64%). MS 232 (MH$^+$).

Example 112

4-amino-5-cyclopropyl-2-methylquinoline-3-carboxylic acid

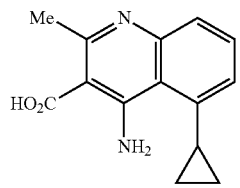 [SMILES: Cc1nc2cccc(C3CC3)c2c(N)c1C(=O)O]

Prepared as in Example 1 from ethyl 4-amino-5-cyclopropyl-2-methylquinoline-3-carboxylate (Example 112a) as a white solid (85%). $^1$H NR (400 MHz, MeOH-$d_4$) δ 1.03 (m, 2H), 1.31 (m, 2H), 2.53 (m, 1H), 2.81 (s, 3H), 7.50 (m, 1H), 7.58 (m, 1H), 7.73 (m, 1H). MS 243 (MH$^+$).

Example 112a ethyl 4-amino-5-cyclopropyl-2-methylquinoline-3-carboxylate

Prepared as in Example 2a from 2-amino-6-cyclopropylbenzonitrile (Tachdjian, C. et al. PCT Int. Appl. 2008, WO 2008154221) and ethyl 3-oxobutanoate as a pale yellow solid (80%). MS 271 (MH$^+$).

Example 113

4-amino-2-(carboxymethyl)-5-(2-cyclohexylethyl)quinoline-3-carboxylic acid

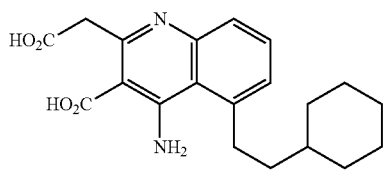 [SMILES: Nc1c(C(=O)O)c(CC(=O)O)nc2cccc(CCC3CCCCC3)c12]

Prepared as in Example 1 from ethyl 4-amino-5-(2-cyclohexylethyl)-2-(2-ethoxy-2-oxoethyl)quinoline-3-carboxylate (Example 113a) as an orange solid (69%). $^1$H NR (400 MHz, DMSO-$d_6$) δ 0.89-0.92 (m, 2H), 1.14-1.29 (m, 4H), 1.44-1.49 (m, 2H), 1.56-1.66 (m, 4H), 1.73-1.76 (m, 1H), 3.15 (t, J=8.0 Hz, 2H), 3.70 (s, 2H), 7.09-7.11 (m, 1H), 7.38-7.42 (m, 1H), 7.46-7.51 (m, 2H). MS 338 (MH$^+$—H$_2$O).

Example 113a ethyl 4-amino-5-(2-cyclohexylethyl)-2-(2-ethoxy-2-oxoethyl)quinoline-3-carboxylate Prepared as in Example 2a from 2-amino-6-(2-cyclohexylethyl)benzonitrile (Example 113b) and diethyl 3-oxopentanedioate as an orange solid (33%). $^1$H NR (400 MHz, DMSO-$d_6$) δ 0.87-0.96 (m, 2H), 1.14-1.22 (m, 7H), 1.27-1.32 (m, 4H), 1.47-1.52 (m, 2H), 1.61-1.68 (m, 4H), 1.74-1.77 (m, 2H), 3.21-3.25 (m, 2H), 4.03 (s, 2H), 4.09 (q, J=8.0 Hz, 2H), 4.27 (q, J=8.0 Hz, 2H), 7.27 (t, J=4.0 Hz, 1H), 7.57 (d, J=8.0 Hz, 2H), 7.63 (brs, 2H). MS 413 (MH$^+$).

Example 113b 2-amino-6-(2-cyclohexylethyl)benzonitrile

Prepared as in Example 21b from 2-amino-6-(cyclohexylethynyl)benzonitrile (Example 113c) as an orange solid (36%). $^1$H NR (400 MHz, DMSO-d$_6$) δ 0.90-0.95 (m, 2H), 1.16-1.24 (m, 4H), 1.41-1.46 (m, 2H), 1.60-1.75 (m, 5H), 2.58-2.62 (m, 2H), 5.90 (s, 2H), 6.48 (d, J=8.0 Hz, 1H), 6.61 (d, J=8.0 Hz, 1H), 7.18 (t, J=4.0 Hz, 1H). MS 229 (MH$^+$).

Example 113c 2-amino-6-(cyclohexylethynyl)benzonitrile

Prepared as in Example 21c from ethynylcyclohexane and 2-amino-6-bromobenzonitrile as a brown oil (100%). $^1$H NR (400 MHz, DMSO-d$_6$) δ 1.24-1.77 (m, 10H), 2.70 (m, 1H), 6.13 (s, 2H), 6.64 (d, J=8.0 Hz, 1H), 6.74 (d, J=8.0 Hz, 1H), 7.22 (t, J=8.0 Hz, 1H). MS 225 (MH$^+$).

Example 114

4-amino-5-(3-methoxyphenyl)-2-methylquinoline-3-carboxylic acid

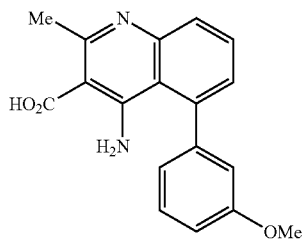 [SMILES: COc1cccc(-c2cccc3nc(C)c(C(=O)O)c(N)c23)c1]

Prepared as in Example 1 from ethyl 4-amino-5-(3-methoxyphenyl)-2-methylquinoline-3-carboxylate (Example 114a) as an off-white solid (38%). MS 309 (MH$^+$).

Example 114a ethyl 4-amino-5-(3-methoxyphenyl)-2-methylquinoline-3-carboxylate Prepared as in Example 2a from 3-amino-3'-methoxy-[1,1'-biphenyl]-2-carbonitrile (Example 114b) and ethyl 3-oxobutanoate as a pale yellow solid (55%). MS 337 (MH$^+$).

Example 114b 3-amino-3'-methoxy-[1,1'-biphenyl]-2-carbonitrile

To a stirred solution of 2-amino-6-bromobenzonitrile (195 mg, 1.0 mmol) and (3 acid (300 mg, 2 mmol) in dioxane (2 mL) was added aqueous potassium carbonate (2.0 mmol, 0.7 mL). The reaction solution was degassed by bubbling N$_2$ for 2 minutes. Palladium tetrakistriphenylphosphine (5% mol) was added to the reaction mixture and the reaction vessel was placed in a microwave reactor and irradiated at 165° C. for 20 minutes. The precipitate was removed by filtration and the filtrate concentrated. The residue was purified by HPLC (acetonitrile/water; 10-90% gradient, 25 minutes) to give the title compound as an off-white solid (180 mg, 80%). MS 225 (MH$^+$).

Example 115

4-amino-5-(cyclohexylmethoxy)-2-methylquinoline-3-carboxylic acid

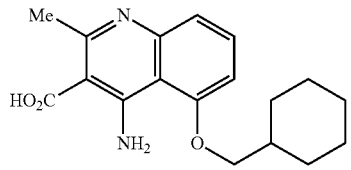 [SMILES: Cc1nc2cccc(OCC3CCCCC3)c2c(N)c1C(=O)O]

Prepared as in Example 1 from ethyl 4-amino-5-(cyclohexylmethoxy)-2-methylquinoline-3-carboxylate (Example 115a) as a white solid (84%). $^1$H NR (400 MHz, DMSO-d$_6$) δ 1.03-1.29 (m, 5H), 1.63-1.82 (m, 5H), 1.94 (m, 1H), 2.75 (s, 3H), 4.06 (d, J=6.4 Hz, 2H), 7.03 (d, J=8.0 Hz, 1H), 7.26 (d, J=8.4 Hz, 1H), 7.66 (t, J=8.4 Hz, 1H). MS 315 (MH$^+$).

Example 115a ethyl 4-amino-5-(cyclohexylmethoxy)-2-methylquinoline-3-carboxylate Prepared as in Example 2a from 2-amino-6-(cyclohexylmethoxy)benzonitrile (Example 115b) and ethyl 3-oxobutanoate as a pale yellow solid (47%). $^1$H NR (400 MHz, MeOD) δ 1.12-1.37 (m, 6H), 1.42 (t, J=4.0 Hz, 3H), 1.73-2.01 (m, 5H), 2.68 (s, 3H), 4.06 (d, J=4.0 Hz, 2H), 4.42 (q, J=8.0 Hz, 2H), 6.96 (d, J=8.0 Hz, 1H), 7.32 (d, J=8.0 Hz, 1H), 7.58 (t, J=8.0 Hz, 1H). MS 343 (MH$^+$).

Example 115b 2-amino-6-(cyclohexylmethoxy)benzonitrile

Prepared as in Example 22b from cyclohexylmethanol and 2-amino-6-fluorobenzonitrile as a colorless oil (50%). $^1$H NR (400 MHz, CDCl$_3$) δ 1.07-1.09 (m, 2H), 1.28-1.32 (m, 3H), 1.75-1.90 (m, 6H), 3.79 (d, J=6.4 Hz, 2H), 4.37 (s, 2H), 6.20 (d, J=8.4 Hz, 1H), 6.28 (d, J=8.4 Hz, 1H), 7.19 (t, J=8.4 Hz, 1H). MS 231 (MH$^+$).

Example 116

4-amino-5-(cyclohexylmethoxy)-2-methylquinoline-3-carboxylic acid

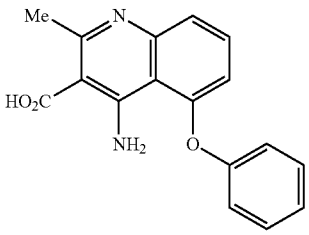 [SMILES: Cc1nc2cccc(Oc3ccccc3)c2c(N)c1C(=O)O]

Prepared as in Example 1 from ethyl 4-amino-2-methyl-5-phenoxyquinoline-3-carboxylate (Example 116a) as an off-white solid (47%). $^1$H NR (400 MHz, DMSO-d$_6$) δ 2.77 (s, 3H), 6.60 (d, J=4.0 Hz, 1H), 7.23 (d, J=8.0 Hz, 2H), 7.30 (t, J=8.0 Hz, 1H), 7.40 (dd, J=8.0 Hz, 1H), 7.49 (t, J=8.0 Hz, 2H), 7.60 (t, J=8.0 Hz, 1H), 8.81 (brs, 1H), 12.20 (brs, 1H), 12.81 (brs, 1H). MS 295 (MH$^+$).

Example 116a ethyl 4-amino-2-methyl-5-phenoxyquinoline-3-carboxylate

Prepared as in Example 2a from 2-amino-6-phenoxybenzonitrile and ethyl 3 as a yellow oil (72%). [1]H NR (400 MHz, DMSO-$d_6$) δ 1.32 (t, J=8.0 Hz, 3H), 2.59 (s, 3H), 4.33 (q, J=8.0 Hz, 2H), 6.61 (dd, J=8.0 Hz, 1H), 7.16 (d, J=4.0 Hz, 2H), 7.25 (t, J=8.0 Hz, 1H), 7.39-7.52 (m, 4H), 7.93 (brs, 2H). MS 323 (MH$^+$).

Example 117

4-amino-5-(3-((4-methoxybenzyl)amino)-2,2-dimethyl-3-oxopropoxy)-2-methylquinoline-3-carboxylic acid

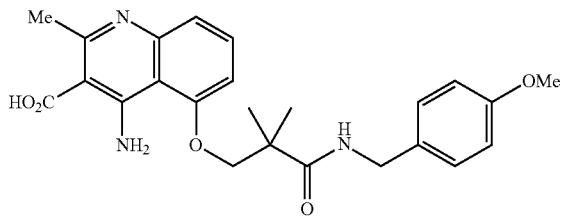 [SMILES: COc1ccc(CNC(=O)C(C)(C)COc2cccc3nc(C)c(C(=O)O)c(N)c23)cc1]

Prepared as in Example 1 from ethyl 4-amino-5-(3-((4-methoxybenzyl)amino)-2,2-dimethyl-3-oxopropoxy)-2-methylquinoline-3-carboxylate (Example 117a) as an off-white solid (38%). MS 438 (MH$^+$).

Example 117a ethyl 4-amino-5-(3-((4-methoxybenzyl)amino)-2,2-dimethyl-3-oxopropoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and (4-methoxyphenyl)methanamine as a yellow solid (100%). MS 466 (MH$^+$).

Example 118

4-amino-2-methyl-5-((tetrahydro-2H-pyran-4-yl)oxy)quinoline-3-carboxylic acid

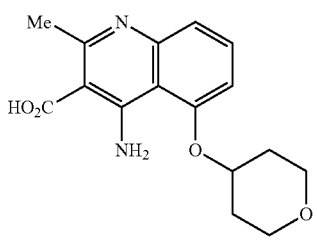 [SMILES: Cc1nc2cccc(OC3CCOCC3)c2c(N)c1C(=O)O]

Prepared as in Example 1 from ethyl 4-amino-2-methyl-5-((tetrahydro-2H-pyran-4-yl)oxy)quinoline-3-carboxylate (Example 118a) as an off-white solid (80%). [1]H NR (400 MHz, DMSO-$d_6$) δ 1.81 (m, 2H), 2.06 (m, 2H), 2.75 (s, 3H), 3.87 (m, 2H), 4.91 (m, 1H), 7.15 (d, J=8.0 Hz, 1H), 7.26 (d, J=8.0 Hz, 1H), 7.65 (t, J=8.0 Hz, 1H). MS 303 (MH$^+$).

Example 118a ethyl 4-amino-2-methyl-5-((tetrahydro-2H-pyran-4-yl)oxy)quinoline-3-carboxylate Prepared as in Example 2a from 2-amino-6-((tetrahydro-2H-pyran-4-yl)oxy)benzonitrile (Example 118b) and ethyl 3-oxobutanoate as a pale yellow solid (51%). MS 331 (MH$^+$).

Example 118b 2-amino-6-((tetrahydro-2H-pyran-4-yl)oxy)benzonitrile

Prepared as in Example 22b from tetrahydro-2H-pyran-4-ol and 2-amino-6-fluorobenzonitrile as a colorless oil (48%). [1]H NR (400 MHz, CDCl$_3$) δ 1.87 (m, 2H), 2.00 (m, 2H), 3.63 (m, 2H), 4.00 (m, 2H), 4.42 (s, 2H), 4.58 (m, 1H), 6.23 (d, J=8.4 Hz, 1H), 6.30 (d, J=8.4 Hz, 1H), 7.20 (t, J=8.4 Hz, 1H). MS 219 (MH$^+$).

Example 119

4-amino-5-(2,2-dimethyl-3-oxo-3-((pyridin-4-ylmethyl)amino)propoxy)-2-methylquinoline-3-carboxylic acid

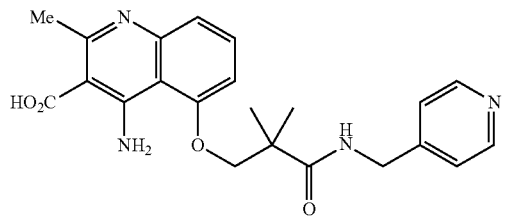 [SMILES: Cc1nc2cccc(OCC(C)(C)C(=O)NCc3ccncc3)c2c(N)c1C(=O)O]

Prepared as in Example 1 from ethyl 4-amino-5-(2,2-dimethyl-3-oxo-3-((pyridin-4-ylmethyl)amino)propoxy)-2-methylquinoline-3-carboxylate (Example 119a) as an off-white solid (44%). MS 409 (MH$^+$).

Example 119a ethyl 4-amino-5-(2,2-dimethyl-3-oxo-3-((pyridin-4-ylmethyl)amino)propoxy)-2-methylquinoline-3-carboxylate Prepared as in Example 24a from 3-((4-amino-3-(ethoxycarbonyl)-2-methylquinolin-5-yl)oxy)-2,2-dimethylpropanoic acid (Example 47b) and pyridin-4-ylmethanamine as a brown solid (43%). MS 437 (MH$^+$).

Example 120

4-amino-5-(3-hydroxy-2,2-dimethylpropoxy)-2-methylquinoline-3-carboxylic acid

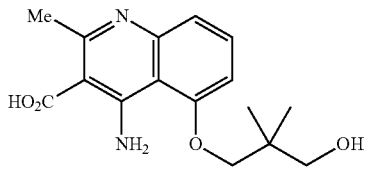 [SMILES: Cc1nc2cccc(OCC(C)(C)CO)c2c(N)c1C(=O)O]

Prepared as in Example 1 from ethyl 4-amino-5-(3-hydroxy-2,2-dimethylpropoxy)-2-methylquinoline-3-carboxylate (Example 120a) as an off-white solid (33%). $^1$H NR (400 MHz, DMSO-$d_6$) δ 0.98 (s, 6H), 2.75 (s, 3H), 3.37 (s, 2H), 3.97 (s, 2H), 5.12 (brs, 1H), 7.01 (d, J=8.4 Hz, 1H), 7.25 (d, J=7.6 Hz, 1H), 7.66 (t, J=8.0 Hz, 1H), 9.27 (brs, 1H), 12.23 (brs, 1H), 12.73 (brs, 1H). MS 305 (MH$^+$).

Example 120a ethyl 4-amino-5-(3-hydroxy-2,2-dimethylpropoxy)-2-methylquinoline-3-carboxylate Prepared as in Example 2a from 3-(3-amino-2-cyanophenoxy)-2,2-dimethylpropyl acetate (Tachdjian, C. et al. PCT Int. Appl. 2008, WO 2008154221) and ethyl 3-oxobutanoate as a pale yellow solid (26%). MS 333 (MH$^+$).

Example 121

4-amino-5-((1-isobutyrylpiperidin-4-yl)methoxy)-2-methylquinoline-3-carboxylic acid

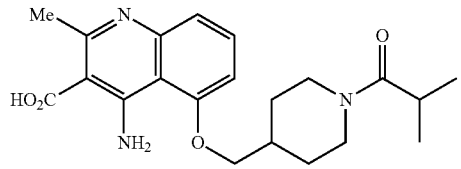 [SMILES: Cc1nc2cccc(OCC3CCN(C(=O)C(C)C)CC3)c2c(N)c1C(=O)O]

Prepared as in Example 1 from ethyl 4-amino-5-((1-isobutyrylpiperidin-4-yl)methoxy)-2-methylquinoline-3-carboxylate (Example 121a) as a white solid (38%). $^1$H NR (400 MHz, DMSO-$d_6$) δ 0.99 (m, 6H), 1.13-1.23 (m, 2H), 1.78-1.89 (m, 2H), 2.26 (brs, 1H), 2.51 (m, 1H), 2.78 (brs, 3H), 2.88 (m, 1H), 3.06 (t, J=12.0 Hz, 1H), 4.02 (d, J=12.0 Hz, 1H), 4.41 (m, 2H), 4.44 (d, J=12.0 Hz, 1H), 7.07 (brs, 1H), 7.28 (d, J=8.0 Hz, 1H), 7.70 (brs, 1H), 8.76 (brs, 1H), 12.37 (brs, 1H), 12.67 (brs, 1H). MS 386 (MH$^+$).

Example 121a ethyl 4-amino-5-((1-isobutyrylpiperidin-4-yl)methoxy)-2-methylquinoline-3-carboxylate Prepared as in Example 2a from 2-amino-6-((1-(4-methoxybenzyl)piperidin-4-yl)methoxy)benzonitrile (Example 121b) and ethyl 3-oxobutanoate as a yellow oil (36%). $^1$H NMR (400 MHz, DMSO-$d_6$) δ 0.97 (m, 6H), 1.32 (t, J=8.0 Hz, 3H), 1.79-1.88 (m, 3H), 2.15-2.18 (m, 2H), 2.55 (s, 3H), 2.86 (m, 1H), 3.04 (m, 1H), 4.00 (m, 2H), 4.07 (d, J=4.0 Hz, 2H), 4.32 (q, J=8.0 Hz, 2H), 4.46 (m, 1H), 6.91 (d, J=8.0 Hz, 1H), 7.24 (d, J=8.0 Hz, 1H), 7.51 (t, J=8.0 Hz, 1H), 8.07 (brs, 2H). MS 414 (MH$^+$).

Example 121b 2-amino-6-((1-(4-methoxybenzyl)piperidin-4-yl)methoxy)benzonitrile

Prepared as in Example 22b from 1-(4-(hydroxymethyl)piperidin-1-yl)-2-methylpropan-1-one (Example 121c) and 2-amino-6-fluorobenzonitrile as a pale yellow solid (21%). $^1$H NR (400 MHz, DMSO-$d_6$) δ 0.99 (m, 6H), 1.13-1.24 (m, 2H), 1.74-1.81 (m, 2H), 1.99 (m, 1H), 2.55 (m, 1H), 2.84 (m, 1H), 3.01 (m, 1H), 3.88 (m, 2H), 4.02 (m, 1H), 4.46 (m, 1H), 5.99 (s, 2H), 6.22 (d, J=8.0 Hz, 1H), 6.34 (d, J=8.0 Hz, 1H), 7.17 (t, J=8.0 Hz, 1H). MS 302 (MH$^+$).

Example 121c 1-(4-(hydroxymethyl)piperidin-1-yl)-2-methylpropan-1-one

Prepared as in Example 24a from isobutyric acid and piperidin-4-ylmethanol as a colorless oil (36%). MS 186 (MH$^+$).

Example 122

4-amino-5-(((1R,2S,5R)-2-isopropyl-5-methylcyclohexyl)oxy)-2-methylquinoline-3-carboxylic acid

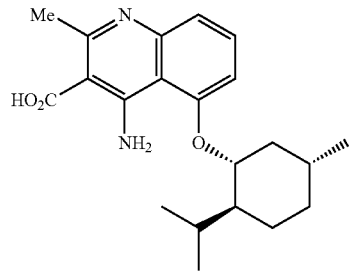 [SMILES: Cc1nc2cccc(O[C@@H]3C[C@H](C)CC[C@H]3C(C)C)c2c(N)c1C(=O)O]

Prepared as in Example 1 from ethyl 4-amino-5-(((1R,2S,5R)-2-isopropyl-5-methylcyclohexyl)oxy)-2-methylquinoline-3-carboxylate (Example 122a) as a white solid (64%). $^1$H NMR (400 MHz, DMSO-$d_6$) δ 0.70 (d, J=6.8 Hz, 3H), 0.89 (t, J=7.6 Hz, 6H), 0.9-1.0 (m, 2H), 1.04 (m, 2H), 1.50-1.82 (m, 5H), 1.95-2.05 (m, 1H), 2.05-2.20 (m, 1H), 2.72 (s, 3H), 4.52 (t-d, J=10.4, 4.4 Hz, 1H), 7.13 (d, J=8.0 Hz, 1H), 7.21 (d, J=8.0 Hz, 1H), 7.61 (t, J=8.0 Hz, 1H), 8.68 (brs, 1H), 11.72 (brs, 1H), 12.73 (brs, 1H). MS 357 (MH$^+$).

Example 122a ethyl 4-amino-5-(((1R,2S,5R)-2-isopropyl-5-methylcyclohexyl)oxy)-2-methylquinoline-3-carboxylate Prepared as in Example 2a from 2-amino-6-(((1R,2S,5R)-2-isopropyl-5-methylcyclohexyl)oxy)benzonitrile (Example 122b) and ethyl 3-oxobutanoate as a pale yellow solid (43%). MS 385 (MH$^+$).

Example 122b 2-amino-6-(((1R,2S,5R)-2-isopropyl-5-methylcyclohexyl)oxy)benzonitrile Prepared as in Example 22b from (1R,2S,5R)-2-isopropyl-5-methylcyclohexanol and 2 as a white solid (51%). MS 273 (MH$^+$).

Example 123

4-amino-5-(2-(3-(2-hydroxyethoxy)-5-methoxybenzamido)-2-methylpropoxy)-2-methylquinoline-3-carboxylic acid hydrochloride

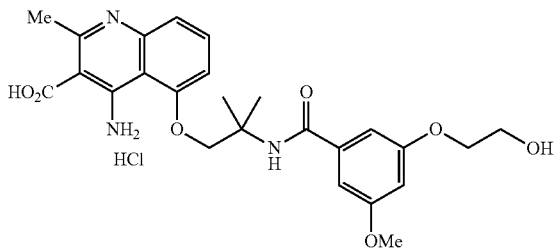 [SMILES: COc1cc(OCCO)cc(C(=O)NC(C)(C)COc2cccc3nc(C)c(C(=O)O)c(N)c23)c1 ; Cl]

To a stirred suspension of 4-amino-5-(2-(3-(2-hydroxyethoxy)-5-methoxybenzamido)-2-methylpropoxy)-2-methylquinoline-3-carboxylate acid (Example 38, 263 mg, 0.544 mmol) in EtOH (2 mL) was added HCl in EtOH (1.25 N, 479 uL, 1.1 equiv.). The mixture was stirred at room temperature until it became a clear solution (0.5 h). The solution was concentrated under reduced pressure to give the title compound as a white solid, which was further purified by recrystallization from EtOH/H$_2$O and dried under vacuum overnight (248 mg, 87%). $^1$H NR (400 MHz, DMSO-d$_6$) δ 1.51 (s, 6H), 2.80 (s, 3H), 3.68 (t, J=5.2 Hz, 2H), 3.74 (s, 3H), 3.97 (t, J=5.2 Hz, 1H), 4.53 (s, 2H), 6.59 (s, 1H), 6.92 (s, 1H), 6.94 (s, 1H), 7.27 (d, J=8.0 Hz, 1H), 7.57 (d, J=8.4 Hz, 1H), 7.86 (t, J=8.4 Hz, 1H), 8.03 (s, 1H), 9.40 (s, 1H), 9.98 (s, 1H). 484 (MH$^+$—HCl).

Example 124

4-amino-5-(cyclopentylmethoxy)-2-methylquinoline-3-carboxylic acid hydrochloride

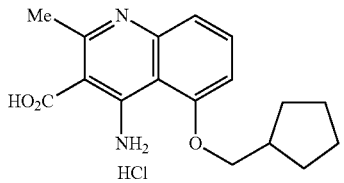 [SMILES: Cc1nc2cccc(OCC3CCCC3)c2c(N)c1C(=O)O ; Cl]

Prepared as in Example 123 from 4-amino-5-(cyclopentylmethoxy)-2-methylquinoline-3-carboxylic acid (Example 18) as a white solid (100%). $^1$H NR (400 MHz, DMSO-d$_6$) δ 1.29-1.37 (m, 2H), 1.51-1.66 (m, 4H), 1.82-1.90 (m, 2H), 2.43-2.51 (m, 1H), 2.81 (s, 3H), 4.18 (d, J=7.2 Hz, 2H), 7.24 (d, J=8.4 Hz, 1H), 7.60 (d, J=8.4 Hz, 1H), 7.84 (t, J=8.4 Hz, 1H), 9.25 (brs, 1H), 9.86 (brs, 1H). MS 301 (MH$^+$—HCl).

Example 125

4-amino-5-((1-(4-methoxybenzyl)piperidin-4-yl)methoxy)-2-methylquinoline-3-carboxylic acid

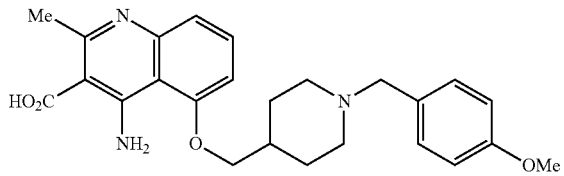 [SMILES: COc1ccc(CN2CCC(COc3cccc4nc(C)c(C(=O)O)c(N)c34)CC2)cc1]

Prepared as in Example 1 from ethyl 4-amino-5-((1-(4-methoxybenzyl)piperidin-4-yl)methoxy)-2-methylquinoline-3-carboxylate (Example 125a) as a white solid (23%). $^1$H NR (400 MHz, DMSO-d$_6$) δ 1.67 (brs, 2H), 2.09 (m, 2H), 2.31 (brs, 1H), 2.92 (brs, 2H), 3.48 (brs, 2H), 3.82 (s, 3H), 4.15 (brs, 2H), 4.25 (d, J=8.0 Hz, 2H), 7.02 (d, J=8.0 Hz, 2H), 7.14 (d, J=8.0 Hz, 1H), 7.30 (d, J=8.0 Hz, 1H), 7.42 (d, J=8.0 Hz, 2H), 7.76 (t, J=8.0 Hz, 1H). MS 436 (MH$^+$).

Example 125a ethyl 4-amino-5-((1-(4-methoxybenzyl)piperidin-4-yl)methoxy)-2-methylquinoline-3-carboxylate Prepared as in Example 2a from 2-amino-6-((1-(4-methoxybenzyl)piperidin-4-yl)methoxy)benzonitrile (Example 125b) and ethyl 3-oxobutanoate as an off-white solid (30%). $^1$H NR (400 MHz, DMSO-d$_6$) δ 1.29-1.33 (m, 5H), 1.74 (m, 2H), 1.92 (m, 3H), 2.54 (s, 3H), 2.83 (m, 2H), 3.38 (s, 2H), 3.71 (s, 3H), 4.04 (d, J=8.0 Hz, 2H), 4.31 (q, J=8.0 Hz, 2H), 6.86 (d, J=8.0 Hz, 2H), 6.90 (d, J=8.0 Hz, 1H), 7.19 (d, J=8.0 Hz, 2H), 7.23 (d, J=8.0 Hz, 1H), 7.50 (t, J=8.0 Hz, 1H), 8.04 (brs, 2H). MS 464 (MH$^+$).

Example 125b 2-amino-6-((1-(4-methoxybenzyl)piperidin-4-yl)methoxy)benzonitrile Prepared as in Example 22b from (1-(4-methoxybenzyl)piperidin-4-yl)methanol (Example 125c) and 2-amino-6-fluorobenzonitrile as an orange solid (19%). MS 352 (MH$^+$).

Example 125c (1-(4-methoxybenzyl)piperidin-4-yl)methanol

To a solution of 4-piperidinemethanol (2.28 g, 19.78 mmol) and 4-methoxybenzaldehyde (2.30 mL, 19.77 mmol) in THF/DCE (1:1 by volume, 100 mL) was added acetic acid (1 mL), followed by NaBH(OAc)$_3$ (16.76 g, 79.08 mmol) in small portions. The reaction mixture was stirred at room temperature overnight under N$_2$. The reaction was diluted with DCM and basified to pH=10 with 2 N NaOH solution. The organic layer was separated, dried over Na$_2$SO$_4$, filtered and evaporated under reduced pressure. The residue was purified by chromatography on silica gel (Eluent: 60% EtOAc in hexanes) to give the title compound as a pale yellow oil (2.13 g, 46%). $^1$H NR (400 MHz, DMSO-d$_6$) δ 1.04-1.13 (m, 2H), 1.28-1.32 (m, 1H), 1.58-1.61 (m, 2H), 1.79-1.86 (m, 2H), 2.75-2.77 (m, 2H), 3.22 (t, J=8.0 Hz, 2H), 3.34 (s, 2H), 3.72 (s, 3H), 4.38 (t, J=4.0 Hz, 1H), 6.85 (d, J=8.0 Hz, 2H), 7.16 (d, J=8.0 Hz, 2H). MS 236 (MH$^+$).

Example 126

4-amino-5-((4-(isopropylcarbamoyl)cyclohexyl)methoxy)-2-methylquinoline-3-carboxylic acid

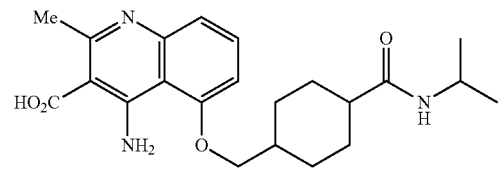 [SMILES: Cc1nc2cccc(OCC3CCC(C(=O)NC(C)C)CC3)c2c(N)c1C(=O)O]

Prepared as in Example 1 from ethyl 4-amino-5-(4-(isopropylcarbamoyl)cyclohexyl)methoxy)-2-methylquinoline-3-carboxylate (Example 126a) as a yellow solid (76%). ¹H NR (400 MHz, DMSO-d₆) δ 1.00 (d, J=6.8 Hz, 6H), 1.15-2.32 (m, 10H), 2.75 (s, 3H), 3.82 (o, J=7.6 Hz, 1H), 4.16 (d, J=6.8 Hz, 2H), 7.07 (br d, J=7.2 Hz, 1H), 7.25 (d, J=8.0 Hz, 1H), 7.49 (d, J=7.6 Hz, 1H), 7.67 (br t, 1H), 8.77 (s, 1H), 12.23 (s, 1H), 12.66 (s, 1H). MS 400 (MH⁺).

Example 126a ethyl 4-amino-5-((4-(isopropylcarbamoyl)cyclohexyl)methoxy)-2-methylquinoline-3-carboxylate Prepared as in Example 2a from 4-((3-amino-2-cyanophenoxy)methyl)-N-isopropylcyclohexanecarboxamide (Example 126b) and ethyl 3-oxobutanoate as a pale yellow solid (37%). ¹H NR (400 MHz, DMSO-d₆) δ 1.01 (d, J=6.4 Hz, 6H), 1.32 (t, J=7.2 Hz, 3H), 1.38-1.81 (m, 8H), 1.88 (m, 1H), 2.25 (m, 1H), 2.55 (s, 3H), 3.82 (bro, J=7.6 Hz, 1H), 4.10 (d, J=6.4 Hz, 2H), 4.31 (q, J=7.6 Hz, 2H), 6.93 (d, J=7.6 Hz, 1H), 7.22 (d, J=8.8 Hz, 1H), 7.50 (m, 2H), 8.09 (s, 2H). MS 428 (MH⁺).

Example 126b 4-((3-amino-2-cyanophenoxy)methyl)-N-isopropylcyclohexanecarboxamide Prepared as in Example 21b from 4-((2-cyano-3-nitrophenoxy)methyl)-N-isopropylcyclohexanecarboxamide (Example 126c) as a yellow solid (81%). ¹H NR (400 MHz, DMSO-d₆) δ 0.99 (d, J=5.6 Hz, 6H), 1.22-1.99 (m, 9H), 2.17 (m, 1H), 3.80 (m, 1H), 3.88 (d, J=7.2 Hz, 2H), 5.94 (brs, 2H), 6.18 (t, J=8.0 Hz, 1H), 6.23 (d, J=8.0 Hz, 1H), 6.31 (d, J=8.8 Hz, 1H), 7.44 (s, 1H). MS 316 (F).

Example 126c 4-((2-cyano-3-nitrophenoxy)methyl-N-isopropylcyclohexanecarboxamide To a solution of 4-(hydroxymethyl)-N-isopropylcyclohexanecarboxamide (Example 126d, 480 mg, 2.41 mmol) in dry THF (10 mL) was added NaH (60% in mineral oil, 116 mg, 4.82 mmol) in small portions at 0° C. under N₂. The reaction mixture was stirred at 0° C. under N₂ for 2 h. To this solution was added 2,6-dinitrobenzonitrile (465 mg, 2.41 mmol), and the reaction mixture was stirred at 0° C.-RT for another 2 h, and then at 60° C. overnight under N₂ and cooled down to room temperature. The reaction was quenched with brine, and extracted with EtOAc (3×). The combined organic layers were washed with brine, dried over Na₂SO₄, filtered, and evaporated under reduced pressure. The residue was purified by chromatography on silica gel (eluent: 50% EtOAc in hexanes) to give the title compound as yellow solid (594 mg, 71%). ¹H NR (400 MHz, DMSO-d₆) δ 1.00 (d, J=7.6 Hz, 6H), 1.22-2.08 (m, 9H), 2.19 (m, 1H), 3.79 (m, 1H), 4.15 (d, J=7.6 Hz, 2H), 7.45 (brs, 1H), 7.78 (d, J=7.2 Hz, 1H), 7.88 (m, 2H). MS 346 (H⁺).

Example 126d 4-(hydroxymethyl)-N-isopropylcyclohexanecarboxamide

Prepared as in Example 24a from 4-(hydroxymethyl)cyclohexanecarboxylic acid and propan-2-amine as a colorless oil (57%). ¹H NR (400 MHz, DMSO-d₆) δ 1.00 (d, J=7.6 Hz, 6H), 1.22-2.08 (m, 9H), 2.12 (m, 1H), 3.28 (t, J=7.6 Hz, 2H), 3.79 (m, 1H), 4.34 (s, 1H), 7.43 (s, 1H). MS 200 (MH⁺).

Example 127

4-amino-5-(cyclohexyloxy)-2-methylquinoline-3-carboxylic acid hydrochloride

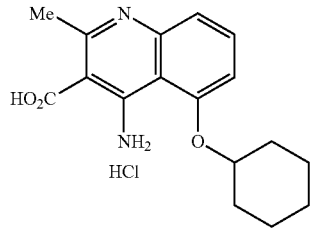

To a suspension of 4-amino-5-(cyclohexyloxy)-2-methylquinoline-3-carboxylic acid (Example 36, 1.0 g, 3.33 mmol) in ethanol (10 mL) was added 1.25 M solution of HCl in ethanol (2.93 mL, 3.66 mmol). The clear solution was stirred for 30 minutes and evaporated to dryness to provide 4-amino-5-(cyclohexyloxy)-2-methylquinoline-3-carboxylic acid hydrochloride (1.12 g, 100%) as a white solid. ¹H NR (400 MHz, DMSO-d₆) δ 1.30 (m, 1H), 1.39-1.47 (m, 2H), 1.53-1.72 (m, 5H), 2.01-2.05 (m, 2H), 2.82 (s, 3H), 4.78-4.82 (m, 1H), 7.29-7.31 (d, J=8.0 Hz, 1H), 7.61-7.63 (d, J=8.0 Hz, 1H), 7.82 (t, J=8.4 Hz, 1H), 9.30 (bs, 1H), 9.93 (bs, 1H). MS 301 (MH⁺—HCl).

Example 128 sodium 4-amino-5-(cyclohexyloxy)-2-methylquinoline-3-carboxylate

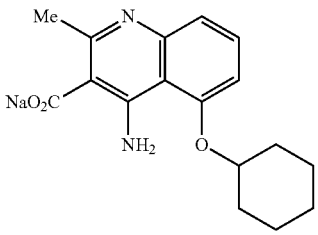

To a solution of 4-amino-5-(cyclohexyloxy)-2-methylquinoline-3-carboxylic acid (Example 36, 1.0 g, 3.33 mmol) in ethanol (20 mL) was added a solution of NaHCO₃ (294 mg, 3.50 mmol) in water (15 mL). The mixture was stirred and warmed up to 60° C. until the solution become clear then evaporated to dryness to provide sodium 4-amino-5-(cyclohexyloxy)-2-methylquinoline-3-carboxylate (1.07 g, 100%) as a white solid. ¹H NR (400 MHz, DMSO-d₆) δ 1.25-1.45 (m, 3H), 1.50-1.70 (m, 5H), 1.53-1.72 (m, 5H), 1.98-2.00 (m, 2H), 2.64 (s, 3H), 4.59-4.63 (m, 1H), 6.87-6.89

(d, J=7.6 Hz, 1H), 7.20-7.22 (d, J=8.0 Hz, 1H), 7.42 (t, J=8.0 Hz, 1H). MS 301 (MH++H—Na).

Example 129

(±)-4-amino-5-β2-(5-(isopropylcarbamoyl)-2-methoxyphenoxy)cyclohexyl)oxy)-2-methylquinoline-3-carboxylic acid

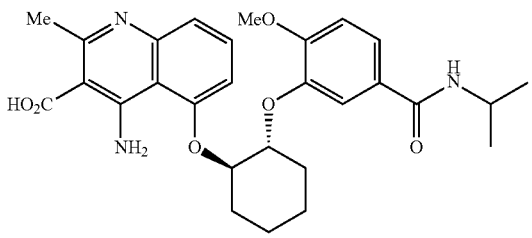 [SMILES: COc1ccc(C(=O)NC(C)C)cc1O[C@@H]1CCCC[C@H]1Oc1cccc2nc(C)c(C(=O)O)c(N)c12]

Prepared as in Example 1 from (±)-ethyl 4-amino-5-(2-(5-(isopropylcarbamoyl)-2-methoxyphenoxy)cyclohexyl)oxy)-2-methylquinoline-3-carboxylate (Example 129a) as a white solid (34%). $^1$H NR (400 MHz, DMSO-$d_6$) δ 1.15 (d, J=8.0 Hz, 6H), 1.35-1.51 (m, 3H), 1.63-1.73 (m, 3H), 2.09 (d, J=12.0 Hz, 1H), 2.24 (d, J=12.0 Hz, 1H), 2.72 (s, 3H), 3.56 (s, 3H), 3.99-4.07 (m, 1H), 4.71-4.78 (m, 2H), 6.85 (d, J=8.0 Hz, 1H), 7.24 (d, J=12.0 Hz, 2H), 7.42 (dd, J=8.0 Hz, 1H), 7.46 (d, J=8.0 Hz, 1H), 7.66 (t, J=8.0 Hz, 1H), 8.03 (d, J=8.0 Hz, 1H), 8.64 (brs, 1H), 12.00 (brs, 1H), 12.61 (brs, 1H). MS 508 (MH+).

Example 129a (±)-ethyl 4-amino-5-(2-(5-(isopropylcarbamoyl)-2-methoxyphenoxy)cyclohexyl)oxy)-2-methylquinoline-3-carboxylate Prepared as in Example 2a from (±)-3-(2-(3-amino-2-cyanophenoxy)cyclohexyl)oxy)-N-isopropyl-4-methoxybenzamide (Example 129b) and ethyl 3-oxobutanoate as a yellow solid (78%). MS 536 (MH+).

Example 129b (±)-3-(2-(3-amino-2-cyanophenoxy)cyclohexyl)oxy)-N-isopropyl-4-methoxybenzamide Prepared as in Example 21b from (±)-3-(2-(2-cyano-3-nitrophenoxy)cyclohexyl)oxy)-N-isopropyl-4-methoxybenzamide (Example 129c) as a brown oil (29%). $^1$H NR (400 MHz, DMSO-$d_6$) δ 1.13-1.19 (m, 6H), 1.42-1.66 (m, 6H), 2.02-2.07 (m, 2H), 3.74 (s, 3H), 4.08 (m, 1H), 4.47 (m, 1H), 4.57 (m, 1H), 5.93 (brs, 2H), 6.32 (d, J=8.0 Hz, 1H), 6.38 (d, J=8.0 Hz, 1H), 7.00 (d, J=8.0 Hz, 1H), 7.17 (t, J=8.0 Hz, 1H), 7.48-7.50 (m, 2H), 7.98 (d, J=8.0 Hz, 1H). MS 424 (MH+).

Example 129c (±)-3-((2-(2-cyano-3-nitrophenoxy)cyclohexyl)oxy)-N-isopropyl-4-methoxybenzamide Prepared as in Example 126c from (±)-3-((2-hydroxycyclohexyl)oxy)-N-isopropyl-4-methoxybenzamide (Example 129d) and 2,6-dinitrobenzonitrile as a brown solid (100%). MS 454 (MH+).

Example 129d (±)-3-((2-hydroxycyclohexyl)oxy)-N-isopropyl-4-methoxybenzamide Prepared as in Example 24a from (±)-3-((2-hydroxycyclohexyl)oxy)-4-methoxybenzoic acid (Example 129e) and propan-2-amine as a white solid (80%). $^1$H NR (400 MHz, DMSO-$d_6$) δ 1.14 (d, J=8.0 Hz, 6H), 1.25-1.30 (m, 4H), 1.61 (m, 2H), 1.85 (m, 2H), 3.56 (m, 1H), 3.79 (s, 3H), 4.03-4.12 (m, 2H), 4.81 (d, J=4.0 Hz, 1H), 6.98 (d, J=8.0 Hz, 1H), 7.45-7.49 (m, 2H), 8.01 (d, J=8.0 Hz, 1H). MS 308 (MH+).

Example 129e (±)-3-((2-hydroxycyclohexyl)oxy)-4-methoxybenzoic acid

Prepared as in Example 1 from (±)-ethyl 3-((2-hydroxycyclohexyl)oxy)-4-methoxybenzoate (Example 129f) as a white solid (100%). $^1$H NR (400 MHz, DMSO-$d_6$) δ 1.23-1.25 (m, 4H), 1.59 (brs, 2H), 1.88 (m, 2H), 3.53 (m, 1H), 3.72 (s, 3H), 3.92 (m, 1H), 4.73 (d, J=4.0 Hz, 1H), 6.82 (d, J=8.0 Hz, 1H), 7.39 (dd, J=4.0 Hz, 1H), 7.48 (d, J=4.0 Hz, 1H).

Example 129f (±)-ethyl 3-((2-hydroxycyclohexyl)oxy)-4-methoxybenzoate

To a solution of methyl 3-hydroxy-4-methoxybenzoate (210 mg, 1.15 mmol) and cyclohexane oxide (466 uL, 4.61 mmol) in ethanol (11 mL) was added $K_2CO_3$ (637 mg, 4.61 mmol) at room temperature. The reaction mixture was then refluxed overnight then cooled down to room temperature, and evaporated under reduced pressure until a small amount of ethanol remained. The solution was diluted with DCM and successively washed with 1N HCl and brine, dried over $Na_2SO_4$ filtered and evaporated under reduced pressure. The residue was purified by chromatography on silica gel (Eluent: 0-20% EtOAc/Hexanes) to afford (±)-ethyl 3-((2 as a colorless oil (307 mg, 91%). $^1$H NR (400 MHz, DMSO-$d_6$) δ 1.16-1.34 (m, 7H), 1.61 (m, 2H), 1.84-1.94 (m, 2H), 3.55 (m, 1H), 3.83 (s, 3H), 4.03 (m, 1H), 4.28 (q, J=8.0 Hz, 2H), 4.85 (d, J=4.0 Hz, 1H), 7.05 (d, J=12.0 Hz, 1H), 7.55-7.58 (m, 2H).

Example 130

4-amino-5-(cyclohexyloxy)-2-(hydroxymethyl)quinoline-3-carboxylic acid

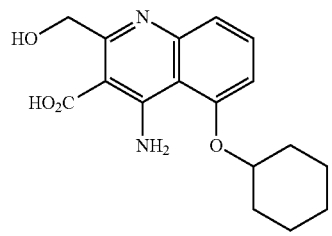 [SMILES: Nc1c(C(=O)O)c(CO)nc2cccc(OC3CCCCC3)c12]

Prepared as in Example 1 from 9-amino-8-(cyclohexyloxy)furo[3,4-b]quinolin-1(3H)-one (Example 130a) as a tan powder (44%). $^1$H NR (400 MHz, DMSO-d$_6$) δ 1.27-1.46 (m, 2H), 1.53-1.71 (m, 6H), 2.00-2.04 (m, 2H), 4.70 (m, 1H), 4.87 (s, 2H), 7.10 (d, J=8.0 Hz, 1H), 7.58 (d, J=8.0 Hz, 1H), 7.64 (t, J=8.0 Hz, 1H), 8.74 (brs, 1H), 11.90 (brs, 1H). MS 317 (MH$^+$).

Example 130a 9-amino-8-(cyclohexyloxy)furo[3,4-b]quinolin-1(3H)-one

Prepared as in Example 2a from 2-amino-6-(cyclohexyloxy)benzonitrile (Example 36b) and ethyl 4-chloro-3-oxobutanoate as an orange solid (29%). $^1$H NR (400 MHz, DMSO-d$_6$) δ 1.30-1.72 (m, 8H), 2.04-2.08 (m, 2H), 4.70 (m, 1H), 5.26 (s, 2H), 7.09 (d, J=8.0 Hz, 1H), 7.36 (d, J=8.0 Hz, 1H), 7.64 (m, 2H), 8.14 (brs, 1H). MS 299 (MH$^+$).

Example 131

1-amino-3-methyl-6b,7,8,9,10,10a-hexahydrobenzofuro[2,3-f]quinoline-2-carboxylic acid

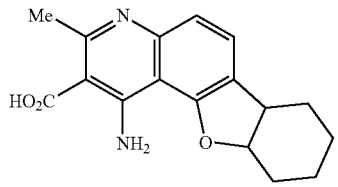 [SMILES: Cc1nc2ccc3c(c2c(N)c1C(=O)O)OC1CCCCC31]

Prepared as in Example 1 from ethyl 1-amino-3-methyl-6b,7,8,9,10,10a-hexahydrobenzofuro[2,3-f]quinoline-2-carboxylate (Example 131a) as an off-white solid (28%). $^1$H NR (400 MHz, DMSO-d$_6$) δ 1.35-1.48 (m, 4H), 1.87-1.97 (m, 4H), 2.76 (s, 3H), 3.38 (m 1H), 5.03 (m 1H), 7.20 (d, J=8 Hz, 1H), 7.61 (d, J=8 Hz, 1H). MS 299 (MH$^+$).

Example 131a ethyl 1-amino-3-methyl-6b,7,8,9,10,10a-hexahydrobenzofuro[2,3-f]quinoline-2-carboxylate Prepared as in Example 2a from 2-amino-6-(cyclohex-2-en-1-yloxy)benzonitrile (Example 131b) and ethyl 3-oxobutanoate as a pale yellow solid (11%). MS 327 (MH$^+$).

Example 131b 2-amino-6-(cyclohex-2-en-1-yloxy)benzonitrile

Prepared as in Example 22b from cyclohex-2-enol and 2-amino-6-fluorobenzonitrile as a colorless oil (78%). $^1$H NR (400 MHz, CDCl$_3$) δ 1.64 (m, 1H), 1.96 (m, 4H), 2.15 (m, 1H), 4.39 (s, 2H), 4.82 (m, 1H), 5.87 (m, 1H), 5.98 (m, 1H), 6.30 (d, 2H), 7.20 (t, 1H). MS 215 (MH$^+$).

Example 132

4-amino-3-carboxy-5-(cyclohexyloxy)-2-methylquinoline 1-oxide

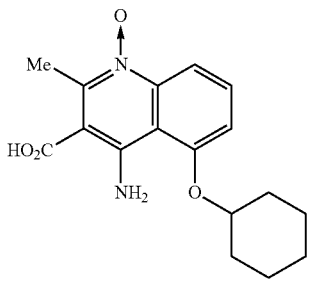 [SMILES: Cc1c(C(=O)O)c(N)c2c(OC3CCCCC3)cccc2[n+]1[O-]]

Prepared as in Example 1 from 4-(N-acetylacetamido)-5-(cyclohexyloxy)-3-(ethoxycarbonyl)-2-methylquinoline 1-oxide (Example 132a) as a white solid (38%). $^1$H NR (400 MHz, DMSO-d$_6$) δ 1.31-1.68 (m, 8H), 1.98-2.04 (m, 2H), 2.69 (s, 3H), 4.71 (m, 1H), 7.20 (d, J=8.0 Hz, 1H), 7.67 (t, J=8.0 Hz, 1H), 7.87 (d, J=8.0 Hz, 1H), 8.75 (brs, 2H). MS 317 (MH$^+$).

Example 132a 4-(N-acetylacetamido)-5-(cyclohexyloxy)-3-(ethoxycarbonyl)-2-methylquinoline 1-oxide To a solution of ethyl 4-(N-acetylacetamido)-5-(cyclohexyloxy)-2-methylquinoline-3-carboxylate (Example 132b, 100 mg, 0.24 mmol) in DCE (5 mL) was added mCPBA (163 mg, 0.73 mmol). The reaction mixture was stirred at room temperature overnight under N$_2$. The solvent was removed under reduce pressure, and the residue was purified by chromatography on silica gel eluting with 0-100% EtOAc/Hexanes gradient to give the title compound as an orange oil (100 mg, 97%). MS 429 (MH$^+$).

Example 132b ethyl 4-(N-acetylacetamido)-5-(cyclohexyloxy)-2-methylquinoline-3-carboxylate To a solution of ethyl 4-amino-5-(cyclohexyloxy)-2-methylquinoline-3-carboxylate (Example 36a, 700 mg, 2.13 mmol) and Et$_3$N (891 uL, 6.39 mmol) in DCM (20 mL) was added acetyl chloride (455 uL, 6.39 mmol) at 0° C., and the reaction mixture was stirred at 0° C.-RT overnight. The reaction was diluted with DCM and washed successively with 10% citric acid, saturated NaHCO$_3$, H$_2$O, and brine, dried over Na$_2$SO$_4$, filtered and evaporated under reduced pressure. The residue was purified by chromatography on silica gel eluting with 0-40% EtOAc/Hexanes gradient to afford the title compound as a yellow oil (100 mg, 11%). MS 413 (MH+).

Example 133

4-amino-5-((2,3-dihydroxycyclohexyl)oxy)-2-methylquinoline-3-carboxylic acid

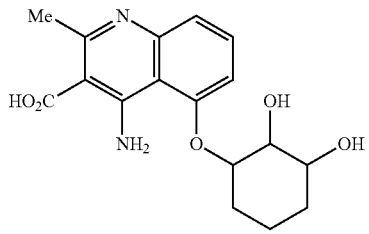 [SMILES: Cc1nc2cccc(OC3CCCC(O)C3O)c2c(N)c1C(=O)O]

Prepared as in Example 1 from 3-((4-amino-3-(ethoxycarbonyl)-2-methylquinolin-5-yl)oxy)cyclohexane-1,2-diyl diacetate (Example 133a) as a white solid (74%). $^1$H NR (400 MHz, DMSO-d$_6$) δ 1.42-1.50 (m, 3H), 1.66-1.70 (m, 2H), 2.12-2.15 (m, 1H), 2.74 (s, 3H), 3.71-3.73 (m, 1H), 3.90 (s, 1H), 4.60-4.62 (m, 1H), 4.71 (brs, 1H), 5.18 (brs, 1H), 7.06 (d, J=8 Hz, 1H), 7.24 (d, J=8 Hz, 1H), 7.60 (t, J=8.4 Hz, 1H). MS 333 (MH+).

Example 133a 3-((4-amino-3-(ethoxycarbonyl)-2-methylquinolin-5-yl)oxy)cyclohexane-1,2-diyl diacetate Prepared as in Example 2a from 3-(3-amino-2-cyanophenoxy)cyclohexane-1,2-diyl diacetate (Example 133b) and ethyl 3-oxobutanoate as a pale yellow solid (32%). MS 445 (MH+).

Example 133b 3-(3-amino-2-cyanophenoxy)cyclohexane-1,2-diyl diacetate

Prepared as in Example 21b from 3-(2-cyano-3-nitrophenoxy)cyclohexane-1,2-diyl diacetate (Example 133c) as a white solid (84%). MS 333 (MH+).

Example 133c 3-(2-cyano-3-nitrophenoxy)cyclohexane-1,2-diyl diacetate

Prepared as in Example 132b from 2-((2,3-dihydroxycyclohexyl)oxy)-6-nitrobenzonitrile (Example 133d) and acetyl chloride as a white solid (19%). MS 363 (MH+).

Example 133d 2-((2,3-dihydroxycyclohexyl)oxy)-6-nitrobenzonitrile

To a solution of 2-(cyclohex-2-en-1-yloxy)-6-nitrobenzonitrile (Example 133e, 5.3 g, 21.7 mmol) in THF/H$_2$O (1:1 by volume, 110 mL) was added OsO$_4$ (110.3 mg, 0.434 mmol) at room temperature. After it was stirred for 30 minutes, NaClO$_3$ (2.71 g, 26.04 mmol) was added in small portions over a period of 1 h, and the reaction mixture was stirred at room temperature for 48 h. The reaction was carefully quenched with aqueous sodium bisulfite solution, and extracted with EtOAc (3×). The combined organic layers were washed with brine, dried over MgSO$_4$, filtered, and evaporated. The residue was purified by chromatography on silica gel eluting with 80-100% EtOAc in hexanes to give the title compound as a brown solid (3.88 g, 64%). MS 279 (MH+).

Example 133e 2-(cyclohex-2-en-1-yloxy)-6-nitrobenzonitrile

Prepared as in Example 126c from cyclohex-2-enol and 2,6-dinitrobenzonitrile as a brown solid (90%). MS 245 (MH+).

Biological Tests

Experiment 1

Screening for Sweet Enhancers hT1R2/R3-HEK293 Gal5 cells were seeded in 384-well-clear bottom plates (Fisher) at a density of ~32,000 cells/well and grown overnight. On the day of the experiment, hT1R2/R3 Gal5 were loaded with the calcium indicator Fluo3AM (4 mM) (Invitrogen, Carlsbad, Calif.) in D-PBS (Invitrogen, Carlsbad, Calif.) using a Multidrop. Cells were incubated for 1 hour at room temperature and excess dye was washed out with D-PBS using an EMBLA cell washer (Molecular Devices, Sunnyvale, Calif.), leaving a residual volume of 25 ml/well. Sweeteners and test compounds were prepared at 4× final concentration and mixed 1:1 in a 384-well Greiner plate (bringing the sweeteners and test compounds concentrations down to 2× final concentration). After 30 minutes of rest time at room temperature, Fluo3AM-loaded cell plates, and the sweetener/compound plate mixture were loaded into a Fluorometric Imaging Plate Reader (FLIPR) (Molecular Devices, Sunnyvale, Calif.). Imaging was performed using a 480 nm excitation and a 535 emission and was initiated with the acquisition of the baseline fluorescence for a period of 7 seconds. Then, the cells were stimulated on line with addition of 25 ml stimuli/well. Subsequent images were acquired every other second for a period of 2 minutes. Raw fluorescence counts were then normalized in each well (using custom made data import software) by calculating delta F/f values (maximum fluorescent count obtained after stimulation-minimal fluorescent count obtained before stimulation/minimal fluorescent count obtained before stimulation). EC$_{50}$s were determined using a non-linear regression algorithm (GraphPad PRISM, San Diego, Calif.), where the Hill slope, bottom asymptotes and top asymptotes were allow to vary. Enhancement properties of test compounds were quantified by determining the magnitude of the leftward shift in the sweeteners EC$_{50}$ values (or an EC$_{50}$ ratio): the value of the EC$_{50}$ measured in the absence of the enhancer divided by the value of the EC$_{50}$ measured in the presence of the enhancer). The present compounds have been tested and shown sweet taste enhancing activities for sucrose as shown in Table A, Table B and C below. Specifically, the EC50 ratio of the test compounds for sucrose enhancement are all greater than about 2 at about 50 μM. The compounds listed in Table A, Table B and C below are Examples described above. For example, Compound Q in Table A is Example 7.

TABLE A

| Compound | EC$_{50}$ Ratio (50 μM) |
|---|---|
| J | 7.5 |
| C | 37.5 |
| E | 15.5 |
| S | 1.8 |
| U | 1.6 |
| K | 6.9 |
| Q | 3.4 |
| I | 9.7 |
| N | 5.1 |
| O | 5 |
| T | 1.7 |
| L | 6.7 |
| F | 13.6 |
| M | 5.7 |
| H | 9.9 |
| D | 21.5 |
| P | 4.2 |
| A | 43.6 (3 μM) |
| B | 37.9 |
| R | 2.5 |
| G | 10.7 |

TABLE B

| Compound | EC$_{50}$ Ratio (50 μM) | Compound | EC$_{50}$ Ratio (50 μM) |
|---|---|---|---|
| V | 21.5 | E2 | 9.7 |
| A1 | 10.2 | E3 | 15.8 |
| O1 | 25.2 | H1 | 3.7 |
| H3 | 60.4 | W2 | 21.1 |
| P1 | 45.9 | U3 | 15.9 |
| B1 | 22.8 | L3 | 17.3 |
| W | 73.8 | B3 | 9.9 |
| I3 | 317.1 | V1 | 21.6 |
| K3 | 29.8 | I1 | 4.7 |
| C4 | 14.6 | J1 | 13.7 |
| R1 | 55.8 | B2 | 7.7 |
| D4 | 23.5 | P2 | 24.7 |
| Q1 | 45.2 | C3 | 17.6 |
| X | 32.5 | F4 | 23.7 |
| C1 | 48.4 | D3 | 173.0 |
| E4 | 176.7 | G4 | 49.2 |
| R3 | 16.7 | M3 | 13.1 |
| J3 | 28.6 | V2 | 20.4 |
| G3 | 40.8 | V3 | 51.0 |
| B4 | 111.7 | G2 | 6.7 |
| Y2 | 23.3 | W1 | 4.5 |
| M2 | 13.4 | K1 | 6.7 |
| D1 | 19.7 | F2 | 3.8 |
| Y | 21.7 | X3 | 3.6 |
| Z | 6.4 | N3 | 3.4 |
| N2 | 25.7 | W3 | 5.7 |
| Q3 | 17.1 | Q2 | 4.4 |
| T1 | 12.9 | L1 | 6.4 |
| E1 | 21.1 | H2 | 3.2 |
| S1 | 49.0 | U2 | 93.8 |
| L2 | 31.7 | I2 | 6.0 |
| F3 | 5.2 | Z3 | 33.6 |
| A3 | 88.3 | X1 | 83.1 |
| Z2 | 34.6 | M1 | 37.0 |
| F1 | 27.0 | N1 | 56.7 |
| K2 | 63.1 | Y3 | 24.5 |
| D2 | 21.2 | A4 | 86.6 |
| T3 | 23.9 | P3 | 9.9 |
| X2 | 55.5 | R2 | 22.0 |
| J2 | 13.7 | Z1 | 50.9 |
| G1 | 3.9 | A2 | 21.9 |
| U1 | 8.1 | Y1 | 108.9 |
| C2 | 19.1 | T2 | 6.2 |
| O2 | 11.3 | O3 | 5.9 |
|  |  | S2 | 3.8 |

TABLE C

| Compound | Sucrose EC$_{50}$ Ratio (50 μM) |
|---|---|
| L4 | 27.8 |
| C5 | 23.8 |
| M4 | 2.9 |
| I4 | 0.9 |
| B5 | 72.7 |
| W4 | 6.0 |
| K4 | 13.7 |
| N4 | 3.4 |
| X4 | 4.9 |
| O4 | 23.0 |
| J4 | 9.2 |
| V4 | 27.9 |
| Y4 | 103.2 |
| P4 | 37.5 |
| R4 | 9.3 |
| H4 | 3.1 |
| S4 | 5.6 |
| Q4 | 17.4 |
| T4 | 23.7 |

The present compounds have been tested and shown sweet taste enhancing activities for sucralose as shown in Table D below. Specifically, the EC50 ratio of the test compounds for sucralose enhancement are all greater than about 2 at about 10 μM.

TABLE D

| Compound | Sucralose EC$_{50}$ Ratio (10 μM) | Compound | Sucralose EC$_{50}$ Ratio (10 μM) | Compound | Sucralose EC$_{50}$ Ratio (10 μM) |
|---|---|---|---|---|---|
| C | 2.0 | T1 | 3.6 | M3 | 4.3 |
| D | 4.0 | E1 | 4.2 | V2 | 3.1 |
| A | 17.0 | S1 | 5.2 | V3 | 5.9 |
| B | 2.5 | L2 | 4.1 | K1 | 2.0 |
| G | 2.2 | F3 | 1.4 | F2 | 2.2 |
| V | 6.7 | A3 | 10.9 | W3 | 2.1 |
| A1 | 3.4 | Z2 | 10.8 | U2 | 5.0 |
| O1 | 2.6 | F1 | 4.3 | Z3 | 3.1 |
| H3 | 12.5 | K2 | 7.6 | X1 | 7.7 |
| P1 | 12.9 | D2 | 2.9 | M1 | 3.1 |
| B1 | 4.2 | T3 | 3.4 | N1 | 4.4 |
| W | 9.9 | X2 | 9.3 | Y3 | 2.9 |
| I3 | 12.9 | J2 | 3.6 | A4 | 6.0 |
| K3 | 8.4 | U1 | 2.0 | P3 | 2.2 |
| C4 | 6.0 | C2 | 3.7 | R2 | 3.4 |

TABLE D-continued

| Compound | Sucralose EC$_{50}$ Ratio (10 μM) | Compound | Sucralose EC$_{50}$ Ratio (10 μM) | Compound | Sucralose EC$_{50}$ Ratio (10 μM) |
|---|---|---|---|---|---|
| R1 | 16.5 | O2 | 2.8 | Z1 | 3.6 |
| D4 | 1.4 | E2 | 4.0 | A2 | 2.2 |
| Q1 | 13.4 | E3 | 3.4 | Y1 | 19.1 |
| X | 5.9 | H1 | 1.6 | T2 | 2.4 |
| C1 | 18.1 | W2 | 5.7 | L4 | 3.4 |
| E4 | 10.7 | U3 | 4.5 | I4 | 6.8 |
| R3 | 5.1 | L3 | 7.2 | B5 | 6.8 |
| J3 | 5.9 | B3 | 2.9 | K4 | 3.4 |
| G3 | 23.8 | V1 | 6.1 | O4 | 7.6 |
| B4 | 8.0 | I1 | 6.1 | J4 | 2.2 |
| Y2 | 2.6 | J1 | 4.3 | V4 | 6.0 |
| M2 | 5.4 | B2 | 3.6 | Y4 | 10.3 |
| D1 | 8.3 | P2 | 3.4 | U4 | 8.3 |
| Y | 4.6 | C3 | 3.2 | P4 | 11.4 |
| N2 | 7.2 | F4 | 4.1 | S4 | 1.9 |
| S3 | 6.8 | D3 | 11.0 | Q4 | 2.5 |
| Q3 | 4.0 | G4 | 7.5 | T4 | 3.2 |

Experiment 2

Sweet Flavor and Sweet Flavor Enhancement Measurement Using Human Panelists Conducting a Scaling Test Test samples containing experimental compounds were compared to a dose-response curve for perceived sweetness intensity of sweeteners (sucralose, sucrose, fructose and other sweeteners) concentrations to determine equivalent sweetness intensity.

A group of eight or more panelists tasted solutions including sweeteners at various concentrations, as well as the experimental compound both with and without added sweetener. Panelists then rated sweetness intensity of all samples on a structured horizontal line scale, anchored from 0 to 15, where 0 equals no sweetness and 15 equals equivalent sweetness to a 15% sucrose sample. Scores for sweetness intensity were averaged across panelists. Then using the average scores and/or equation of the line for the sweetener dose-response curve, equivalent sweetness concentrations were determined for the samples containing experimental compounds.

Subjects had been previously familiarized with the key attribute taste and were trained to use the 0 to 15 point line scale. Subjects refrained from eating or drinking (except water) for at least 1 hour prior to the test. Subjects ate a cracker and rinsed with water several times to clean the mouth.

Sweetener solutions are provided at a wide range of concentrations such as 100 ppm, 200 ppm, 300 ppm, 400 ppm, and 500 ppm for sucralose, or between 0% and 12% for sucrose or fructose, in order to create a dose-response curve. Samples containing experimental compound were prepared both alone and in a 100 ppm sucralose solution or a 6% sucrose or fructose solution. All samples were made up in low sodium buffer pH 7.1. In order to aid dispersion, solutions can be made up in 0.1% ethanol.

The solutions were dispensed in 20 ml volumes into 1 oz. sample cups and served to the subjects at room temperature. All samples were presented in randomized counterbalanced order to reduce response bias. Further, two sessions of testing may be used to check panel precision.

Subjects tasted each sample individually and rate sweetness intensity on the line scale prior to tasting the next sample. All samples were expectorated. Subjects may retaste the samples but can only use the volume of sample given. Subjects must rinse with water between samples. Eating an unsalted cracker between samples may be required depending on the samples tasted.

The scores for each sample were averaged across subjects and standard error was calculated. The dose-response curve was plotted graphically, and this may be used to ensure the panel is rating accurately; i.e., increasing the concentration of sucralose should correspond to increased average scores for sweetness. A 2-way ANOVA (factors being samples and panelists) and multiple comparison tests (such as Tukey's Honestly Significant Difference test) can be used to determine differences among samples and/or panelists. A 3-way ANOVA, with sessions as the third factor, can be used to determine if there is any difference in the ratings between sessions.

The results of human taste tests with Compound J are found below. Compound J is one of the examples described above. Table 1 indicates that 45 μM Compound J in 6% sucrose has sweetness equivalent to about 9-10% sucrose.

TABLE 1

Average Sweetness, n = 28 (14 Panelists × 2 rep).
Tukey's Value = 0.986 (α = 0.05).

| Treatment | Average | SD | St Er | Tukey (5%) |
|---|---|---|---|---|
| 6% Sucrose | 6.6 | 1.1 | 0.2 | a |
| 8% Sucrose | 8.2 | 1.1 | 0.2 | b |
| 9% Sucrose | 9.2 | 0.9 | 0.2 | bc |
| 6% Sucrose + 45 uM Compound J | 9.4 | 1.9 | 0.4 | c |
| 10% Sucrose | 9.7 | 1.7 | 0.3 | c |
| 12% Sucrose | 10.9 | 1.5 | 0.3 | d |

The results of human taste tests with Compound C are found below. Compound C is one of the examples described above. Table 1__1 indicates that 25 μM Compound C in 6% sucrose has sweetness equivalent to about 9-10% sucrose.

TABLE 1__1

Average Sweetness, n = 24 (12 Panelists × 2 rep).
Tukey's Value = 0.912 (α = 0.05).

| Treatment | Average | SD | St Er | Tukey (5%) |
|---|---|---|---|---|
| 6% Sucrose | 6.5 | 1.1 | 0.2 | a |
| 8% Sucrose | 8.2 | 0.7 | 0.1 | b |

TABLE 1__1-continued

Average Sweetness, n = 24 (12 Panelists × 2 rep).
Tukey's Value = 0.912 (α = 0.05).

| Treatment | Average | SD | St Er | Tukey (5%) |
|---|---|---|---|---|
| 9% Sucrose | 8.4 | 1.8 | 0.4 | b |
| 6% Sucrose + 25 uM Compound C | 9.1 | 1.0 | 0.2 | bc |
| 10% Sucrose | 9.5 | 0.7 | 0.1 | c |

The results of human taste tests with Compound O1 are found below. Compound O1 is one of the examples described above. Table 1__2 indicates that 25 µM Compound O1 in 6% sucrose has sweetness equivalent to about 10% sucrose.

TABLE 1__2

Average Sweetness, n = 26 (13 Panelists × 2 rep).
Tukey's Value = 0.733 (α = 0.05).

| Treatment | Average | SD | St Er | Tukey (5%) |
|---|---|---|---|---|
| 6% Sucrose | 6.3 | 0.7 | 0.1 | a |
| 8% Sucrose | 8.2 | 1.0 | 0.2 | b |
| 9% Sucrose | 8.6 | 1.1 | 0.2 | bc |
| 10% Sucrose | 9.2 | 1.0 | 0.2 | c |
| 6% Sucrose + 25 uM Compound O1 | 9.2 | 1.1 | 0.2 | c |

The results of human taste tests with Compound W are found below. Compound W is one of the examples described above. Table 1__3 indicates that 25 µM Compound W in 6% sucrose has sweetness equivalent to about 10% sucrose.

TABLE 1__3

Average Sweetness, n = 28 (14 Panelists × 2 rep).
Tukey's Value = 0.619 (α = 0.05).

| Treatment | Average | SD | St Er | Tukey (5%) |
|---|---|---|---|---|
| 6% Sucrose | 6.2 | 0.5 | 0.1 | a |
| 8% Sucrose | 8.1 | 1.0 | 0.2 | b |
| 9% Sucrose | 8.5 | 0.9 | 0.2 | b |
| 6% Sucrose + 25 uM Compound W | 9.2 | 0.9 | 0.2 | c |
| 10% Sucrose | 9.5 | 1.0 | 0.2 | c |

The results of human taste tests with Compound I3 are found below. Compound I3 is one of the examples described above. Table 1__4 indicates that 21 µM Compound I3 in 6% sucrose has sweetness equivalent to about 10% sucrose.

TABLE 1__4

Average Sweetness, n = 28 (14 Panelists × 2 rep). Tukey's
Value = 0.785 (α = 0.05).

| Treatment | Average | SD | ST Er | Tukey (5%) |
|---|---|---|---|---|
| 6% Sucrose | 6.1 | 0.4 | 0.1 | a |
| 8% Sucrose | 7.8 | 0.9 | 0.2 | b |
| 9% Sucrose | 8.6 | 1.0 | 0.2 | c |
| 10% Sucrose | 9.0 | 0.9 | 0.2 | cd |
| 6% Sucrose + 21 uM Compound I3 | 9.5 | 1.0 | 0.2 | d |

The results of human taste tests with Compound C1 are found below. Compound C1 is one of the examples described above. Table 1__5 indicates that 13 µM Compound C1 in 6% sucrose has sweetness equivalent to about 10% sucrose and that 33 µM Compound C1 in 6% sucrose has sweetness equivalent to about 12% sucrose. Table 1__6 indicates that 33 µM Compound C1 in 50 ppm sucralose has sweetness equivalent to about between 100 ppm sucralose and 200 ppm sucralose.

TABLE 1_5

Average Sweetness, n = 26 (13 Panelists × 2 rep). Tukey's
Value = 1.311 (α = 0.05).

| Treatment | Average | SD | ST Er | Tukey (5%) |
|---|---|---|---|---|
| 6% Sucrose | 6.4 | 0.7 | 0.1 | a |
| 8% Sucrose | 7.9 | 1.7 | 0.3 | b |
| 10% Sucrose | 9.6 | 1.5 | 0.3 | c |
| 6% Sucrose + 13 uM Compound C1 | 9.6 | 1.7 | 0.3 | c |
| 12 Sucrose% | 10.9 | 1.4 | 0.3 | cd |
| 6% Sucrose + 33 uM Compound C1 | 11.0 | 1.7 | 0.3 | d |

TABLE 1_6

Average Sweetness, n = 30 (15 Panelists × 2 rep). Tukey's
Value = 0.911 (α = 0.05).

| Treatment | Average | SD | ST Er | Tukey (5%) |
|---|---|---|---|---|
| 50 ppm sucralose | 3.9 | 1.1 | 0.2 | a |
| 100 ppm sucralose | 5.9 | 1.6 | 0.3 | b |
| 50 ppm sucralose + 33 uM Compound C1 | 7.5 | 2.4 | 0.4 | c |
| 200 ppm sucralose | 8.7 | 1.8 | 0.3 | d |
| 300 ppm sucralose | 10.2 | 1.7 | 0.3 | e |

The results of human taste tests with Compound B4 are found below. Compound B4 is one of the examples described above. Table 1__7 indicates that 36.5 µM Compound B4 in 6% sucrose has sweetness equivalent to about 10-12% sucrose. Table 1__8 indicates that 36.5 µM Compound B4 in 50 ppm sucralose has sweetness equivalent to about 100 ppm.

TABLE 1_7

Average Sweetness, n = 27 (14 Panelists × 1 rep & 13 Panelists ×
1 rep). Tukey's Value = 1.138 (α = 0.05).

| Treatment | Average | SD | ST Er | Tukey (5%) |
|---|---|---|---|---|
| 6% Sucrose | 6.6 | 1.3 | 0.2 | a |
| 8% Sucrose | 8.4 | 1.5 | 0.3 | b |
| 10% Sucrose | 10.3 | 1.2 | 0.2 | c |
| 6% Sucrose + 36.4 uM Compound B4 | 10.5 | 1.4 | 0.3 | c |
| 12% Sucrose | 10.9 | 1.2 | 0.3 | c |

TABLE 1_8

Average Sweetness, n = 26 (13 Panelists × 2 rep). Tukey's
Value = 0.985 (α = 0.05).

| Treatment | Average | SD | ST Er | Tukey (5%) |
|---|---|---|---|---|
| 50 ppm sucralose | 3.9 | 0.6 | 0.1 | a |
| 100 ppm sucralose | 5.5 | 1.1 | 0.2 | b |
| 50 ppm sucralose + 36.5 uM Compound B4 | 6.2 | 2.0 | 0.4 | b |
| 200 ppm sucralose | 9.1 | 1.9 | 0.4 | c |
| 300 ppm sucralose | 10.2 | 1.8 | 0.4 | d |

Experiment 3

Sweet Flavor and Sweet Flavor Enhancement Measurement Using Human Panelists Conducting a Paired Comparison Test Test samples containing experimental compounds are presented in pairs to the panelist and they are asked to determine which of the sample is sweeter. A group of 10-16 or more panelists participated in each test. Subjects refrained from eating or drinking (except water) for at least 1 hour prior to the test. Subjects rinsed with water several times to clean the mouth.

All samples are prepared with ethanol to ensure dispersion of the compound in solution. This includes samples without compound; all solutions are balanced for 0.1% ethanol.

Samples are also prepared with low sodium buffer (pH 7.1) in place of water. Buffer contains 0.952 g of KCl, 5.444 g of $Na_2HPO_4$, and 0.952 g of $KH_2PO_4$ in 40 L of DIUF water. Sample volumes are usually 20 ml.

In one paired comparison test, the panelist is presented with two different samples and asked to identify the sample which is sweeter. The samples within a paired comparison test are presented in a randomized, counterbalanced order. Panelists have up to a 1 minute delay between taste tests to clear the mouth of any tastes.

Binomial probability tables are used to determine the probability of the correct number of responses occurring for each test at alpha=0.05

The results of human taste tests with Compound J are found below. Table 2 indicates that panelists perceived 6% sucrose+45 uM Compound J as being not significantly different in sweetness than a solution of 10% sucrose (p>0.05). Table 3 indicates that 45 μM Compound J alone has little or no sweetness on its own.

TABLE 2

Sample selected as sweeter by panelists, n = 42 (14 panelists × 3 rep).

| Samples | Total |
| --- | --- |
| 10% Sucrose | 17 |
| 6% Sucrose + 45 uM Compound J | 25 |
| Total | 42 |
| 6% Sucrose + 45 uM Compound J (p-value) | 0.360 |

TABLE 3

Sample selected as sweeter by panelists, n = 48 (16 panelists × 3 rep).

| Samples | Total |
| --- | --- |
| 1% Sucrose | 47 |
| LSB + 45 uM Compound J | 1 |
| Total | 48 |
| LSB + 45 uM Compound J (p-value) | <0.001 |

The results of human taste tests with Compound A are found below. Table 2_1 indicates that panelists perceived 6% sucrose+25 uM Compound A as being not significantly different in sweetness than a solution of 10% sucrose (p>0.05). Table 3_1 indicates that 25 μM Compound A alone has little or no sweetness on its own.

TABLE 2_1

Sample selected as sweeter by panelists, n = 16 (16 panelists × 3 rep).

| Samples | Total |
| --- | --- |
| 10% sucrose | 28 |
| 6% sucrose + 25 uM Compound A | 20 |
| Total | 48 |
| 10% sucrose (p-value) | 0.312 |

TABLE 3_1

Sample selected as sweeter by panelists, n = 15 (15 panelists × 3 rep).

| Samples | Total |
| --- | --- |
| 1% sucrose | 44 |
| LSB + 25 uM Compound A | 1 |
| Total | 45 |
| 1% sucrose (p-value) | <0.001 |

The results of human taste tests with Compound C1 are found below. Table 2_2 indicates that panelists perceived 6% sucrose+33 uM Compound C1 as being not significantly different in sweetness than a solution of 12% sucrose (p>0.05). Table 3_2 indicates that 33 μM Compound C1 alone has little or no sweetness on its own.

TABLE 2_2

Sample selected as sweeter by panelists, n = 30 (15 panelists × 2 reps).

| Samples | Total |
| --- | --- |
| 12% Sucrose | 17 |
| 6% Sucrose + 33 uM Compound C1 | 13 |
| Total | 30 |
| 12% Sucrose (p-value) | 0.585 |

TABLE 3_2

Sample selected as sweeter by panelists, n = 22 (11 panelists × 2 reps).

| Samples | Total |
| --- | --- |
| 1% Sucrose | 18 |
| LSB + 33 uM Compound C1 | 4 |
| Total | 22 |
| 1% Sucrose selected (p-value) | 0.004 |

The results of human taste tests with Compound I3 are found below. Table 2_3 indicates that panelists perceived 6% sucrose+25 uM Compound I3 as being not significantly different in sweetness than a solution of 12% sucrose (p>0.05). Table 3_3 indicates that 25 μM Compound I3 alone has little or no sweetness on its own.

TABLE 2_3

| Sample selected as sweeter by panelists, n = 42 (14 panelists × 3 reps). | |
|---|---|
| Samples | Total |
| 12% Sucrose | 18 |
| 6% Sucrose + 25 uM Compound I3 | 24 |
| Total | 42 |
| 12% Sucrose (p-value) | 0.441 |

TABLE 3_3

| Sample selected as sweeter by panelists, n = 42 (14 panelists × 3 reps). | |
|---|---|
| Samples | Total |
| 1% Sucrose | 36 |
| LSB + 25 uM Compound I3 | 6 |
| gTotal | 42 |
| 1% Sucrose selected (p-value) | <0.001 |

The results of human taste tests with Compound B4 are found below. Table 2_4 indicates that panelists perceived 6% sucrose+36.5 uM Compound B4 as being not significantly different in sweetness than a solution of 10% sucrose (p>0.05). Table 3_4 indicates that 36.5 μM Compound B4 alone has little or no sweetness on its own.

TABLE 2_4

| Sample selected as sweeter by panelists, n = 26 (13 panelists × 2 reps). | |
|---|---|
| Samples | Total |
| 10% Sucrose | 10 |
| 6% Sucrose + 36.5 uM Compound B4 | 16 |
| Total | 26 |
| 6% Sucrose + 36.5 uM Compound B4 (p-value) | 0.327 |

TABLE 3_4

| Sample selected as sweeter by panelists, n = 45 (15 panelists × 3 reps). | |
|---|---|
| Samples | Total |
| 1% Sucrose | 44 |
| LSB + 36.5 uM Compound B4 | 1 |
| gTotal | 45 |
| 1% Sucrose selected (p-value) | 0.001 |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An ingestible composition comprising
   a compound having a structure of Formula (IIIa) or (IIIa'),

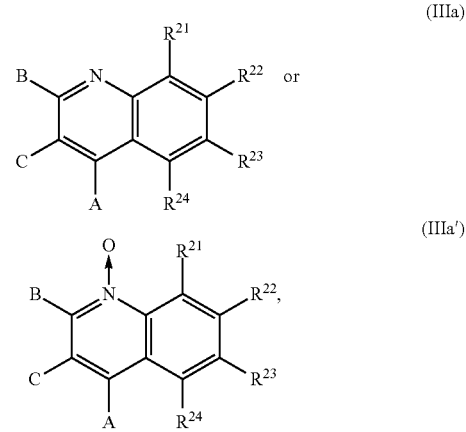

or a tautomer, and/or salt thereof; and
   an ingestibly acceptable excipient,
   wherein:
   A is $-NH_2$;
   B is hydrogen, alkyl, $-CN$, $-OR^4$, $-S(O)_aR^4$, $-NR^4R^5$, $-C(O)NR^4R^5$, $-CO_2R^4$, $-NR^4CO_2R^5$, $-NR^4C(O)NR^5R^6$, $-NR^4C(S)NR^5R^6$, $-NR^4C(=NH)NR^5R^6$, $-SO_2NR^4R^5$, $-NR^4SO_2R^5$, $-NR^4SO_2NR^5R^6$, $-B(OR^4)(OR^5)$, $-P(O)(OR^4)(OR^5)$, or $-P(O)(R^4)(OR^5)$;
   C is $-CO_2R^7$;
   a is 0, 1 or 2;
   $R^4$, $R^5$, $R^6$, and $R^7$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, $R^4$ and $R^5$, or $R^5$ and $R^6$, together with the atoms to which they are bonded, form a cycloheteroalkyl or substituted cycloheteroalkyl ring;
   $R^{21}$ is hydrogen;
   $R^{22}$ is hydrogen, alkyl, substituted alkyl, halo, $-CN$, or $-OR^{27}$;
   $R^{23}$ is hydrogen, alkyl, substituted alkyl, $-CN$, $OR^{29}$, $-S(O)_rR^{29}$, $-OC(O)R^{29}$, $-NR^{29}R^{30}$, $-C(O)NR^{29}R^{30}$, $-C(O)R^{29}$, $-CO_2R^{29}$, $-SO_2NR^{29}R^{30}$, or $-NR^{29}SO_2R^{30}$;
   $R^{24}$ is $-O-L^1-L^2-R^{33}$ or $OR^{33}$;
   $L^1$ is alkylene or substituted alkylene;
   $L^2$ is $-NR^{34}-$, $-O-$, $-S-$, $-NR^{34}-C(O)-$, $-C(O)-NR^{34}-$, $-O-C(O)-$, $-C(O)-O-$, $-NR^{34}-C(O)-O-$, $-O-C(O)-NR^{34}-$, —NR³⁴—C(O)—NR³⁵—, —O—C(O)—O—, -heterocyclylene-C(O)—, or -(substituted heterocyclylene)-C(O)—;

R³³ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and R³⁴ and R³⁵ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl;

f is 0, 1 or 2; and

R²⁷, R²⁹, and R³⁰ are independently hydrogen, or alkyl;

wherein substituted, when used to modify a specified group or radical, means that one or more hydrogen atoms of the specified group or radical are each independently replaced with one or more substituent group(s);

wherein substituent groups on saturated carbon atoms in the substituted group or radical include one or more of —Rᵃ, halo, =O, —ORᵇ, —SRᵇ, =S, —NRᶜRᶜ, =NRᵇ, =N—ORᵇ, trihalomethyl, —CF₃, —CN, —OCN, —SCN, —NO, —NO₂, N₂, —N₃, —S(O)₂Rᵇ, —S(O)₂NRᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ, wherein each Rᵃ is independently selected from the group consisting of alkyl, cycloalkyl, heteroalkyl, cycloheteroalkyl, aryl, arylalkyl, heteroaryl and heteroarylalkyl; each Rᵇ is independently hydrogen or Rᵃ; and each Rᶜ is independently Rᵇ or alternatively, the two Rᶜs may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S;

wherein the one or more substituent groups, taken together with the atoms to which they are bonded, may form a cyclic ring including cycloalkyl and cycloheteroalkyl;

wherein substituent groups on unsaturated carbon atoms in the specified group or radical include —Rᵃ, halo, —ORᵇ, —SRᵇ, —NRᶜRᶜ, trihalomethyl, —CF₃, —CN, —OCN, —SCN, —NO, —NO₂, —N₃, —S(O)₂Rᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)O⁻, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ;

wherein substituent groups on nitrogen atoms in heteroatom-containing groups include —Rᵃ, —ORᵇ, —SRᵇ, trihalomethyl, —CF₃, —CN, —NO, —NO₂, —S(O)₂Rᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ; and wherein substituents used to substitute a specified group can be further substituted with one or more of the same or different substituent groups.

2. The ingestible composition of claim 1, further comprising one or more sweeteners.

3. The ingestible composition of claim 2, wherein the sweetener is selected from the group consisting of sucrose, fructose, glucose, galactose, mannose, lactose, tagatose, maltose, corn syrup, D-tryptophan, glycine, erythritol, isomalt, lactitol, mannitol, sorbitol, xylitol, maltodextrin, maltitol, isomalt, hydrogenated glucose syrup (HGS), hydrogenated starch hydrolyzate (HSH), stevioside, rebaudioside A, other sweet Stevia-based glycosides, carrelame, other guanidine-based sweeteners, saccharin, acesulfame-K, cyclamate, sucralose, alitame, mogroside, neotame, aspartame, other aspartame derivatives, and combinations thereof.

4. The ingestible composition of claim 1, which has an increased sweet taste as compared to the ingestible composition not containing the compound of claim 1, as judged by a majority of a panel of at least eight human taste testers.

5. The ingestible composition of claim 1, which is in form of a food or beverage product, a pharmaceutical composition, a nutritional product, a dietary supplement, over-the-counter medication, or oral care product.

6. The ingestible composition of claim 5, wherein the food or beverage product is for human or animal consumption.

7. The ingestible composition of claim 1, wherein the food or beverage product is selected from the group consisting of the Soup category; the Dried Processed Food category; the Beverage category; the Ready Meal category; the Canned or Preserved Food category; the Frozen Processed Food category; the Chilled Processed Food category; the Snack Food category; the Baked Goods category; the Confectionary category; the Dairy Product category; the Ice Cream category; the Meal Replacement category; the Pasta and Noodle category; the Sauces, Dressings, Condiments category; the Baby Food category; the Spreads category; sweet coatings, frostings, or glazes; and combinations thereof.

8. A method of enhancing the sweet taste of an ingestible composition comprising contacting the ingestible composition thereof with a compound having the structure of Formula (IIIa or (IIIa'),

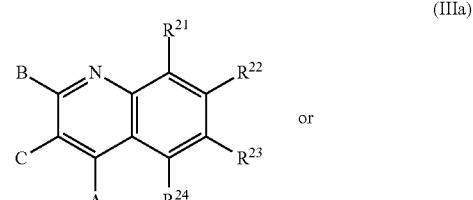

(IIIa)

or

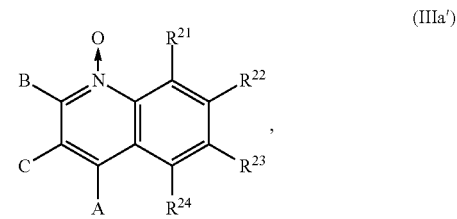

(IIIa')

or a tautomer, and/or salt thereof, to form a modified ingestible composition, wherein:

A is —NH$_2$;

B is hydrogen, alkyl, —CN, —OR$^4$, —S(O)$_a$R$^4$, —NR$^4$R$^5$, —C(O)NR$^4$R$^5$, —CO$_2$R$^4$, —NR$^4$CO$_2$R$^5$, —NR$^4$C(O)NR$^5$R$^6$, —NR$^4$C(S)NR$^5$R$^6$, —NR$^4$C(=NH)NR$^5$R$^6$, —SO$_2$NR$^4$R$^5$, —NR$^4$SO$_2$R$^5$, —NR$^4$SO$_2$NR$^5$R$^6$, —B(OR$^4$)(OR$^5$), —P(O)(OR$^4$)(OR$^5$), or —P(O)(R$^4$)(OR$^5$);

C is —CO$_2$R$^7$;

a is 0, 1 or 2;

R$^4$, R$^5$, R$^6$, and R$^7$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^4$ and R$^5$, or R$^5$ and R$^6$, together with the atoms to which they are bonded, form a cycloheteroalkyl or substituted cycloheteroalkyl ring;

R$^{21}$ is hydrogen;

R$^{22}$ is hydrogen, alkyl, substituted alkyl, halo, —CN, or —OR$^{27}$;

R$^{23}$ is hydrogen, alkyl, substituted alkyl, —CN, OR$^{29}$, —S(O)$_f$R$^{29}$, —OC(O)R$^{29}$, —NR$^{29}$R$^{30}$, —C(O)NR$^{29}$R$^{30}$, —C(O)R$^{29}$, —CO$_2$R$^{29}$, —SO$_2$NR$^{29}$R$^{30}$, or —NR$^{29}$SO$_2$R$^{30}$;

R$^{24}$ is —O-L$^1$-L$^2$-R$^{33}$ or —OR$^{33}$;

L$^1$ is alkylene or substituted alkylene;

L$^2$ is —NR$^{34}$—, —O—, —S—, —NR$^{34}$—C(O)—, —C(O)—NR$^{34}$—, —O—C(O)—, —C(O)—O—, —NR$^{34}$—C(O)—O—, —O—C(O)—NR$^{34}$—, —NR$^{34}$—C(O)—NR$^{35}$—, —O—C(O)—O—, -heterocyclylene-C(O)—, or -(substituted heterocyclylene)-C(O)—;

R$^{33}$ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and R$^{34}$ and R$^{35}$ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl;

f is 0, 1 or 2; and

R$^{27}$, R$^{29}$, and R$^{30}$ are independently hydrogen, or alkyl;

wherein substituted, when used to modify a specified group or radical, means that one or more hydrogen atoms of the specified group or radical are each independently replaced with one or more substituent group(s);

wherein substituent groups on saturated carbon atoms in the substituted group or radical include one or more of —R$^a$, halo, =O, —OR$^b$, —SR$^b$, =S, —NR$^c$R$^c$, =NR$^b$, =N—OR$^b$, trihalomethyl, —CF$_3$, —CN, —OCN, —SCN, —NO, —NO$_2$, N$_2$, —N$_3$, —S(O)$_2$R$^b$, —S(O)$_2$NR$^b$, —S(O)$_2$OR$^b$, —OS(O)$_2$R$^b$, —OS(O)$_2$OR$^b$, —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ or —NR$^b$C(NR$^b$)NR$^c$R$^c$, wherein each R$^a$ is independently selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S;

wherein the one or more substituent groups, taken together with the atoms to which they are bonded, may form a cyclic ring including cycloalkyl and cycloheteroalkyl;

wherein substituent groups on unsaturated carbon atoms in the specified group or radical include —R$^a$, halo, —OR$^b$, —SR$^b$, —NR$^c$R$^c$, trihalomethyl, —CF$_3$, —CN, —OCN, —SCN, —NO, —NO$_2$, —N$_3$, —S(O)$_2$R$^b$, —S(O)$_2$OR$^b$, —OS(O)$_2$R$^b$, —OS(O)$_2$OR$^b$, —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ or —NR$^b$C(NR$^b$)NR$^c$R$^c$;

wherein substituent groups on nitrogen atoms in heteroatom-containing groups include —R$^a$, —OR$^b$, —SR$^b$, trihalomethyl, —CF$_3$, —CN, —NO, —NO$_2$, —S(O)$_2$R$^b$, —S(O)$_2$OR$^b$, —OS(O)$_2$R$^b$, —OS(O)$_2$OR$^b$, —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ or —NR$^b$C(NR$^b$)NR$^c$R$^c$; and wherein substituents used to substitute a specified group can be further substituted with one or more of the same or different substituent groups.

9. A sweet enhancing composition, comprising a compound having the structure of Formula (IIIa or (IIIa'),

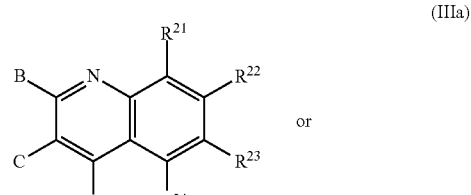

(IIIa)

or

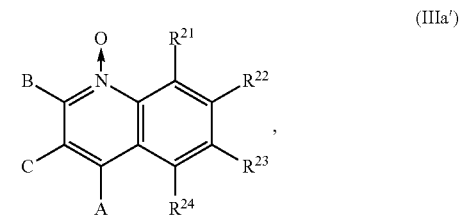

(IIIa')

Or a tautomer, and/or salt thereof, in an amount effective to provide sweetening in combination with a first amount of sweetener, wherein the sweetening is more than the sweetening provided by the first amount of sweetener without the compound, wherein:

A is —NH$_2$;

B is hydrogen, alkyl, —CN, —OR$^4$, —S(O)$_a$R$^4$, —NR$^4$R$^5$, —C(O)NR$^4$R$^5$, —CO$_2$R$^4$, —NR$^4$CO$_2$R$^5$, —NR$^4$C(O)NR$^5$R$^6$, —NR$^4$C(S)NR$^5$R$^6$, —NR$^4$C(=NH)NR$^5$R$^6$, —SO$_2$NR$^4$R$^5$, —NR$^4$SO$_2$R$^5$, —NR⁴SO₂NR⁵R⁶, —B(OR⁴)(OR⁵), —P(O)(OR⁴)(OR⁵), or —P(O)(R⁴)(OR⁵);
C is —CO₂R⁷;
a is 0, 1 or 2;
R⁴, R⁵, R⁶, and R⁷ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R⁴ and R⁵, or R⁵ and R⁶, together with the atoms to which they are bonded, form a cycloheteroalkyl or substituted cycloheteroalkyl ring;
R²¹ is hydrogen;
R²² is hydrogen, alkyl, substituted alkyl, halo, —CN, or —OR²⁷;
R²³ is hydrogen, alkyl, substituted alkyl, —CN, OR²⁹, —S(O)ₓR²⁹, —OC(O)R²⁹, —NR²⁹R³⁰, —C(O)NR²⁹R³⁰, —C(O)R²⁹, —CO₂R²⁹, —SO₂NR²⁹R³⁰, or —NR²⁹SO₂R³⁰;
R²⁴ is —O-L¹-L²-R³³ or OR³³;
L¹ is alkylene or substituted alkylene;
L² is —NR³⁴—, —O—, —S—, —NR³⁴—C(O)—, —C(O)—NR³⁴—, —O—C(O)—, —C(O)—O—, —NR³⁴—C(O)—O—, —O—C(O)—NR³⁴—, —NR³⁴—C(O)—NR³⁵—, —O—C(O)—O—, -heterocyclylene-C(O)—, or -(substituted heterocyclylene)-C(O)—;
R³³ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and
R³⁴ and R³⁵ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl;
f is 0, 1 or 2; and
R²⁷, R²⁹, and R³⁰ are independently hydrogen, or alkyl;
wherein substituted, when used to modify a specified group or radical, means that one or more hydrogen atoms of the specified group or radical are each independently replaced with one or more substituent group(s);
wherein substituent groups on saturated carbon atoms in the substituted group or radical include one or more of —Rᵃ, halo, =O, —ORᵇ, —SRᵇ, =S, —NRᶜRᶜ, =NRᵇ, =N—ORᵇ, trihalomethyl, —CF₃, —CN, —OCN, —SCN, —NO, —NO₂, N₂, —N₃, —S(O)₂Rᵇ, —S(O)₂NRᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ,
wherein each Rᵃ is independently selected from the group consisting of alkyl, cycloalkyl, heteroalkyl, cycloheteroalkyl, aryl, arylalkyl, heteroaryl and heteroarylalkyl; each Rᵇ is independently hydrogen or Rᵃ; and each Rᶜ is independently Rᵇ or alternatively, the two Rᶜs may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S;

wherein the one or more substituent groups, taken together with the atoms to which they are bonded, may form a cyclic ring including cycloalkyl and cycloheteroalkyl;
wherein substituent groups on unsaturated carbon atoms in the specified group or radical include —Rᵃ, halo, —ORᵇ, —SRᵇ, —NRᶜRᶜ, trihalomethyl, —CF₃, —CN, —OCN, —SCN, —NO, —NO₂, —N₃, —S(O)₂Rᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)O⁻, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ;
wherein substituent groups on nitrogen atoms in heteroatom-containing groups include —Rᵃ, —ORᵇ, —SRᵇ, trihalomethyl, —CF₃, —CN, —NO, —NO₂, —S(O)₂Rᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ; and
wherein substituents used to substitute a specified group can be further substituted with one or more of the same or different substituent groups.

10. An ingestible composition comprising the sweet enhancing composition of claim 9.

11. The ingestible composition of claim 10, which is in form of a food or beverage product, a pharmaceutical composition, a nutritional product, a dietary supplement, over-the-counter medication, or oral care product.

12. A flavoring concentrate formulation comprising
i) as flavor modifying ingredient, a compound having the structure of Formula (IIIa or (IIIa'),

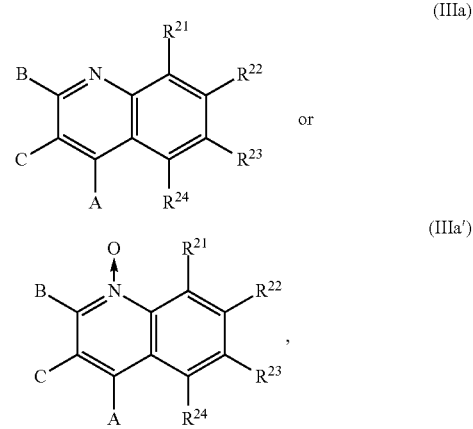

or a tautomer, and/or salt thereof;
ii) a carrier; and
iii) optionally at least one adjuvant,
wherein:
A is —NH₂;
B is hydrogen, alkyl, —CN, —OR⁴, —S(O)ₐR⁴, —NR⁴R⁵, —C(O)NR⁴R⁵, —CO₂R⁴, —NR⁴CO₂R⁵, —NR⁴C(O)NR⁵R⁶, —NR⁴C(S)NR⁵R⁶, —NR⁴C(=NH)NR⁵R⁶, —SO₂NR⁴R⁵, —NR⁴SO₂R⁵, —NR⁴SO₂NR⁵R⁶, —B(OR⁴)(OR⁵), —P(O)(OR⁴)(OR⁵), or —P(O)(R⁴)(OR⁵);

C is —CO₂R⁷;

a is 0, 1 or 2;

R⁴, R⁵, R⁶, and R⁷ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R⁴ and R⁵, or R⁵ and R⁶, together with the atoms to which they are bonded, form a cycloheteroalkyl or substituted cycloheteroalkyl ring;

R²¹ is hydrogen;

R²² is hydrogen, alkyl, substituted alkyl, halo, —CN, or —OR²⁷;

R²³ is hydrogen, alkyl, substituted alkyl, —CN, OR²⁹, —S(O)ᶠR²⁹, —OC(O)R²⁹, —NR²⁹R³⁰, —C(O)NR²⁹R³⁰, —C(O)R²⁹, —CO₂R²⁹, —SO₂NR²⁹R³⁰, or —NR²⁹SO₂R³⁰;

R²⁴ is —O-L¹-L²-R³³ or OR³³;

L¹ is alkylene or substituted alkylene;

L² is —NR³⁴—, —O—, —S—, —NR³⁴—C(O)—, —C(O)—NR³⁴—, —O—C(O)—, —C(O)—O—, —NR³⁴—C(O)—O—, —O—C(O)—NR³⁴—, —NR³⁴—C(O)—NR³⁵—, —O—C(O)—O—, -heterocyclylene-C(O)—, or -(substituted heterocyclylene)-C(O)—;

R³³ is alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl; and R³⁴ and R³⁵ are independently hydrogen, alkyl, substituted alkyl, carbocyclyl, substituted carbocyclyl; aryl, substituted aryl, arylalkyl, substituted arylalkyl, heterocyclyl, substituted heterocyclyl, heteroalkyl, substituted heteroalkyl, heteroaryl, substituted heteroaryl, heteroarylalkyl, or substituted heteroarylalkyl;

f is 0, 1 or 2; and

R²⁷, R²⁹, and R³⁰ are independently hydrogen, or alkyl;

wherein substituted, when used to modify a specified group or radical, means that one or more hydrogen atoms of the specified group or radical are each independently replaced with one or more substituent group(s);

wherein substituent groups on saturated carbon atoms in the substituted group or radical include one or more of —Rᵃ, halo, ═O, —ORᵇ, —SRᵇ, ═S, —NRᶜRᶜ, ═NRᵇ, ═N—ORᵇ, trihalomethyl, —CF₃, —CN, —OCN, —SCN, —NO, —NO₂, ═N₂, —N₃, —S(O)₂Rᵇ, —S(O)₂NRᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ, wherein each Rᵃ is independently selected from the group consisting of alkyl, cycloalkyl, heteroalkyl, cycloheteroalkyl, aryl, arylalkyl, heteroaryl and heteroarylalkyl; each Rᵇ is independently hydrogen or Rᵃ; and each Rᶜ is independently Rᵇ or alternatively, the two Rᶜs may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S;

wherein the one or more substituent groups, taken together with the atoms to which they are bonded, may form a cyclic ring including cycloalkyl and cycloheteroalkyl;

wherein substituent groups on unsaturated carbon atoms in the specified group or radical include —Rᵃ, halo, —ORᵇ, —SRᵇ, —NRᶜRᶜ, trihalomethyl, —CF₃, —CN, —OCN, —SCN, —NO, —NO₂, —N₃, —S(O)₂Rᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)O⁻, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ;

wherein substituent groups on nitrogen atoms in heteroatom-containing groups include —Rᵃ, —ORᵇ, —SRᵇ, trihalomethyl, —CF₃, —CN, —NO, —NO₂, —S(O)₂Rᵇ, —S(O)₂ORᵇ, —OS(O)₂Rᵇ, —OS(O)₂ORᵇ, —P(O)(ORᵇ)(ORᵇ), —C(O)Rᵇ, —C(S)Rᵇ, —C(NRᵇ)Rᵇ, —C(O)ORᵇ, —C(S)ORᵇ, —C(O)NRᶜRᶜ, —C(NRᵇ)NRᶜRᶜ, —OC(O)Rᵇ, —OC(S)Rᵇ, —OC(O)ORᵇ, —OC(S)ORᵇ, —NRᵇC(O)Rᵇ, —NRᵇC(S)Rᵇ, —NRᵇC(O)ORᵇ, —NRᵇC(S)ORᵇ, —NRᵇC(O)NRᶜRᶜ, —NRᵇC(NRᵇ)Rᵇ or —NRᵇC(NRᵇ)NRᶜRᶜ; and wherein substituents used to substitute a specified group can be further substituted with one or more of the same or different substituent groups.

13. The flavoring concentrate formulation of claim 12, wherein the at least one adjuvant comprises one or more flavoring agents.

14. The flavoring concentrate formulation of claim 13, wherein the at least one adjuvant comprises one or more sweeteners.

15. The flavoring concentrate formulation of claim 14, wherein the at least one adjuvant comprises one or more ingredients selected from the group consisting of a emulsifier, a stabilizer, an antimicrobial preservative, an antioxidant, vitamins, minerals, fats, starches, protein concentrates and isolates, salts, a freezing point depressant, nucleating agent, and combinations thereof.

16. The flavoring concentrate formulation of claim 15, which is in a form selected from the group consisting of liquid, solid, semi-solid, foamy material, paste, gel, cream, lotion, and combinations thereof.

17. The flavoring concentrate formulation of claim 16, wherein the compound is in a concentration that is at least 2 times of the concentration in a ready-to-use composition.

18. The ingestible composition of claim 1, wherein R²¹, R²², and R²³ are all hydrogen.

19. The ingestible composition of claim 1, wherein R²¹ and R²² are all hydrogen.

20. The ingestible composition of claim 1, wherein the compound has a structure of Formula (IIIb) or (IIIb'),

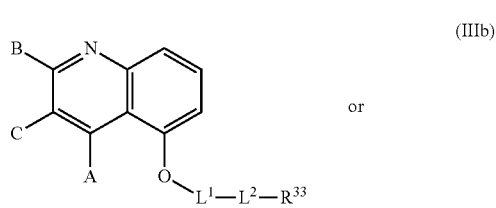

-continued

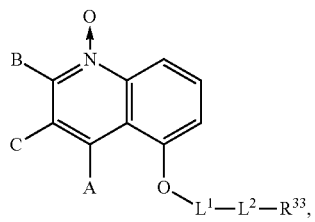
(IIIb')

or a tautomer, and/or salt thereof.

21. The ingestible composition of claim 1, wherein the compound has a structure of Formula (IIIc) or (IIIc'),

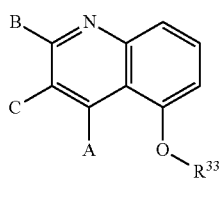
(IIIc)

or

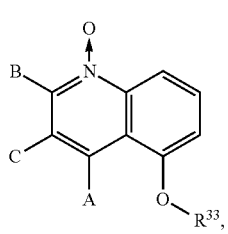
(IIIc')

or a tautomer, and/or salt thereof.

22. The ingestible composition of claim 21, wherein $R^{33}$ is alkyl, substituted alkyl, carbocyclyl, substituted carbocyclyl; heterocyclyl, substituted heterocyclyl, heteroalkyl, or substituted heteroalkyl.

23. The ingestible composition of claim 21, wherein B is hydrogen or alkyl.

24. The ingestible composition of claim 20, wherein
B is hydrogen, or alkyl;
$L^2$ is —$NR^{34}$—, —O—, —$NR^{34}$—C(O)—, —C(O)—$NR^{34}$—, —O—C(O)—, —C(O)—O—, -hetercyclylene-C(O)—, or -(substituted hetercyclylene)-C(O)—; and
$R^{34}$ is hydrogen, alkyl, or substituted alkyl.

25. The ingestible composition of claim 21, wherein
B is hydrogen, or alkyl;
$R^{33}$ is alkyl, substituted alkyl, carbocyclyl, substituted carbocyclyl; heterocyclyl, substituted heterocyclyl, heteroalkyl, or substituted heteroalkyl.

26. The ingestible composition of claim 1, wherein the compound is selected from the groups consisting of

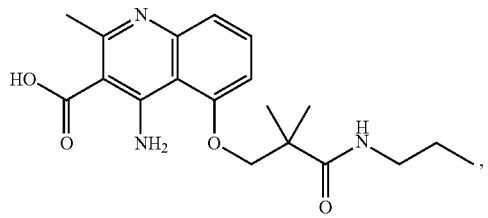

-continued

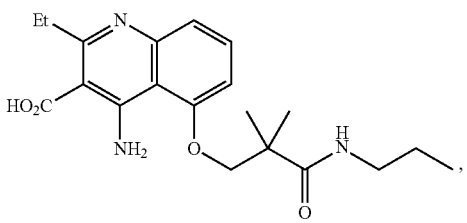

165
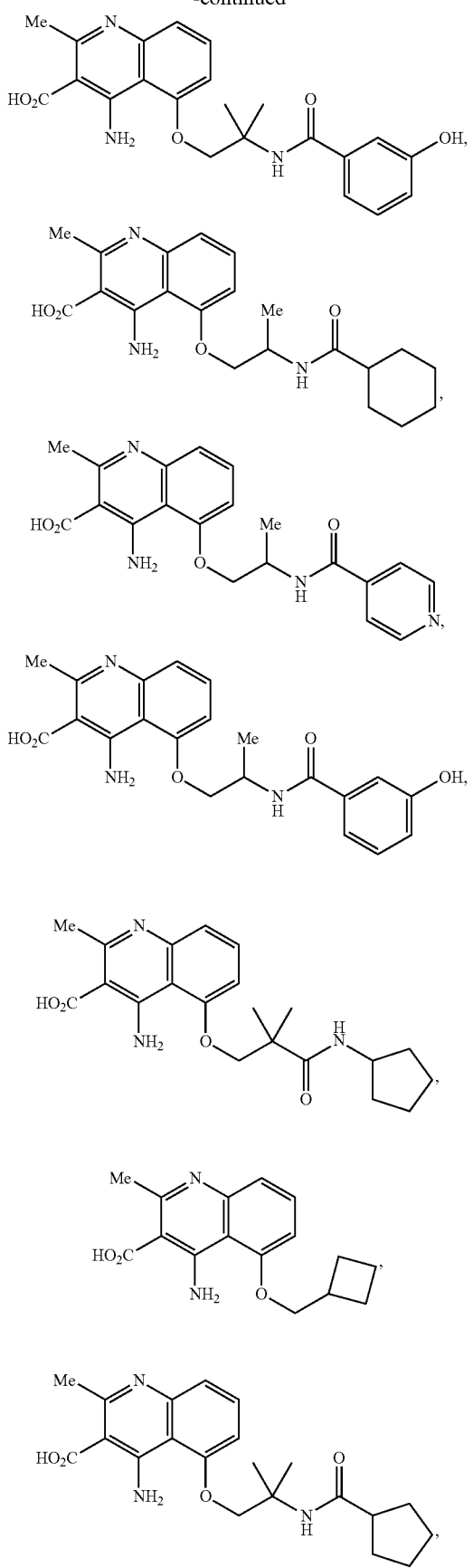
-continued
166
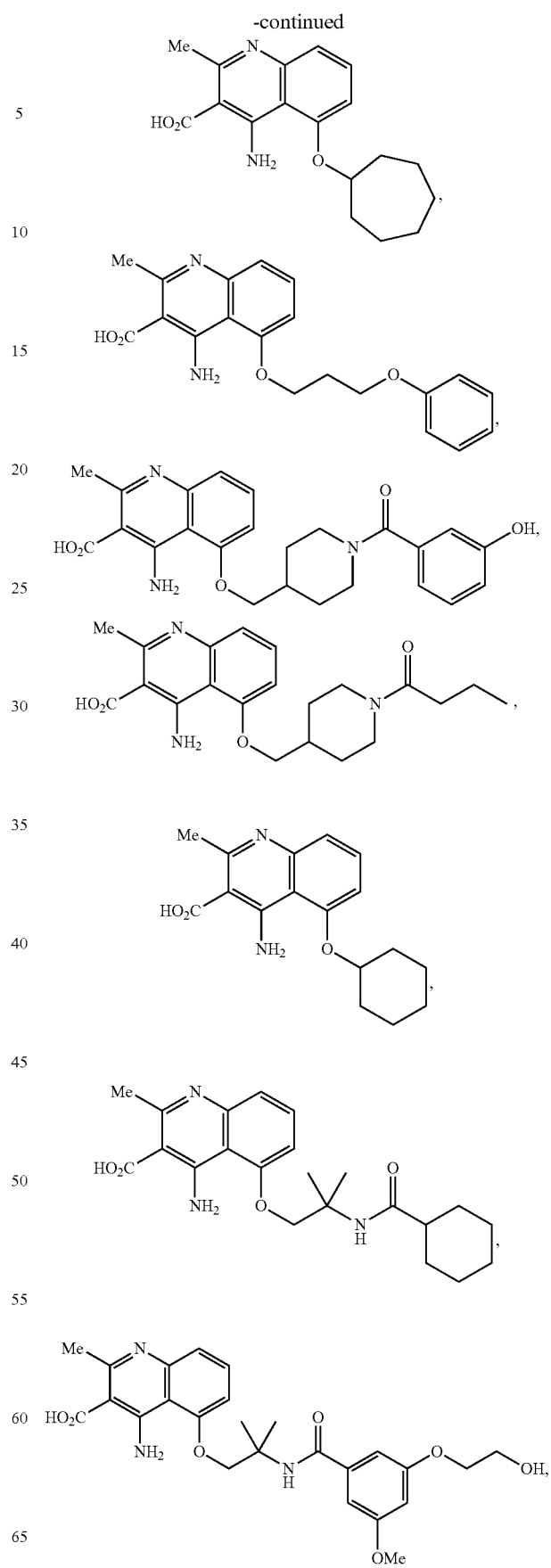
-continued

167
-continued
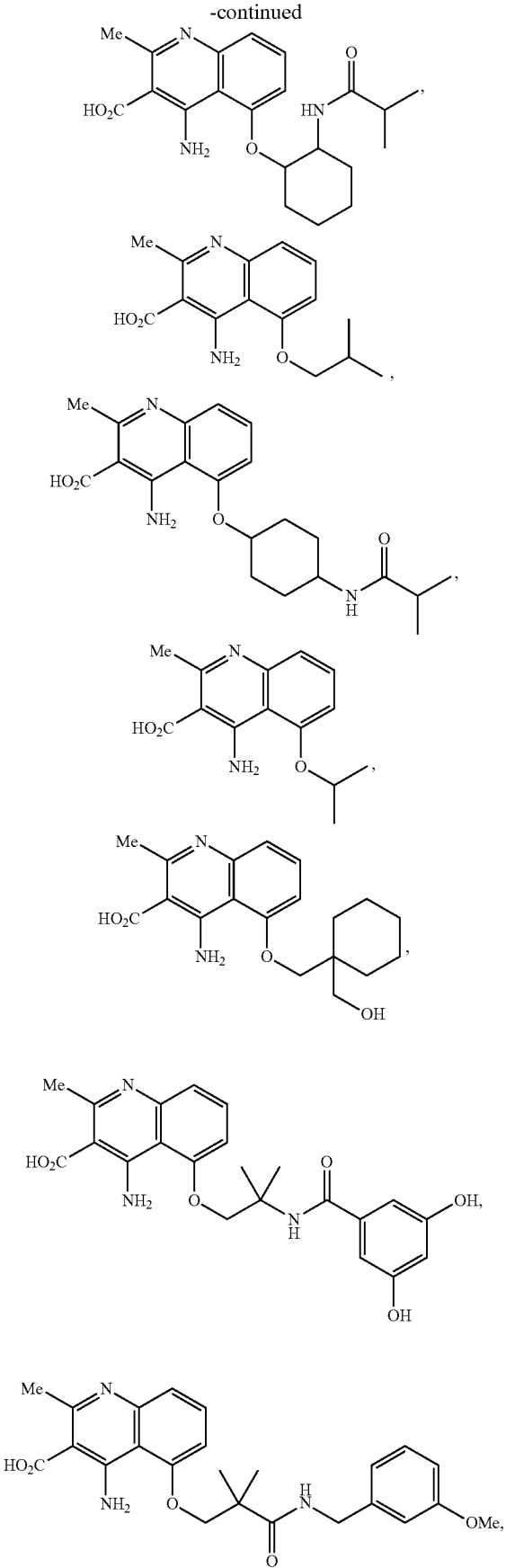
168
-continued
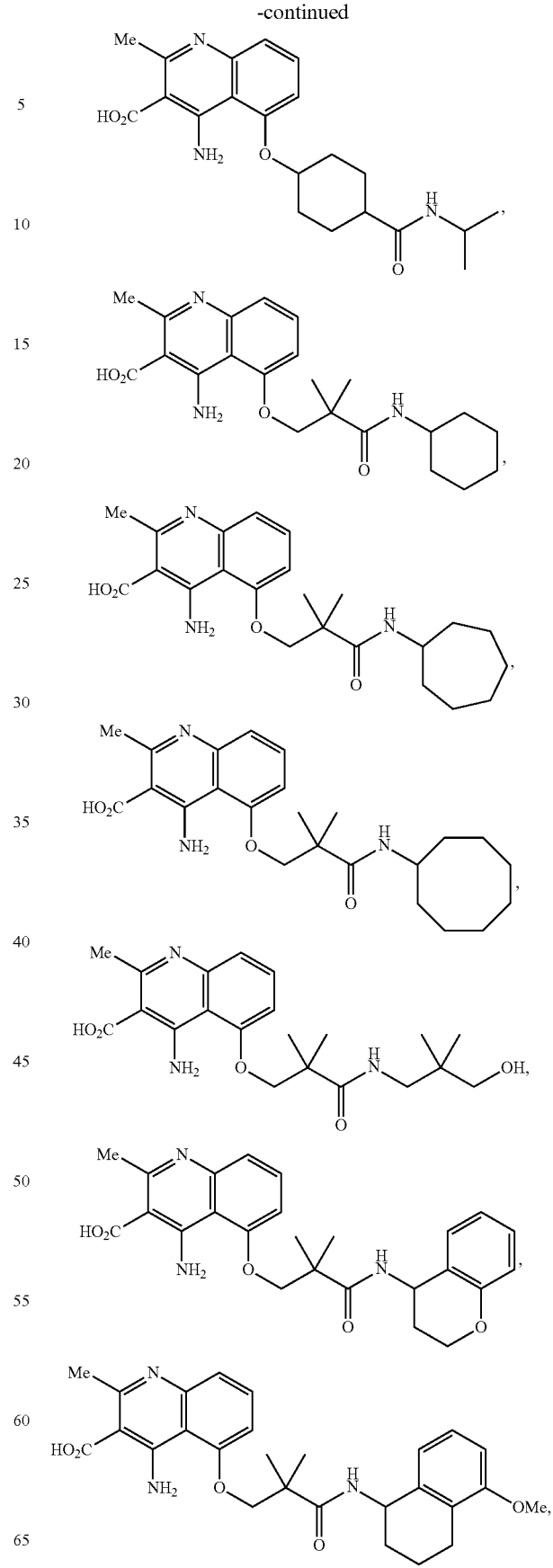

169
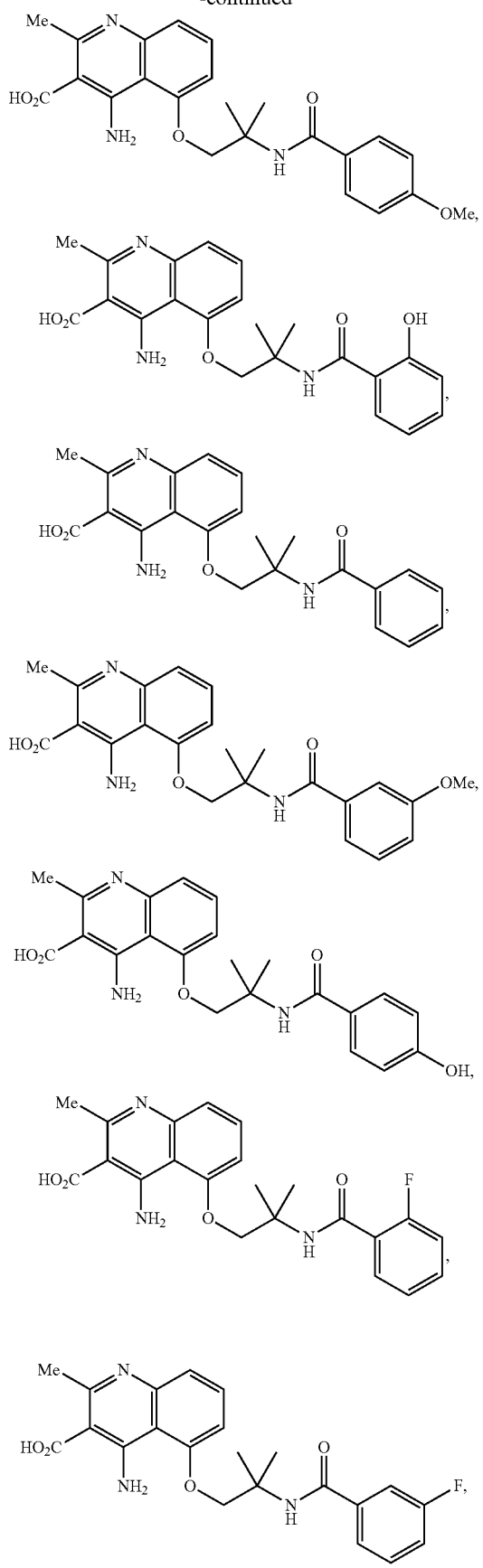
-continued
170
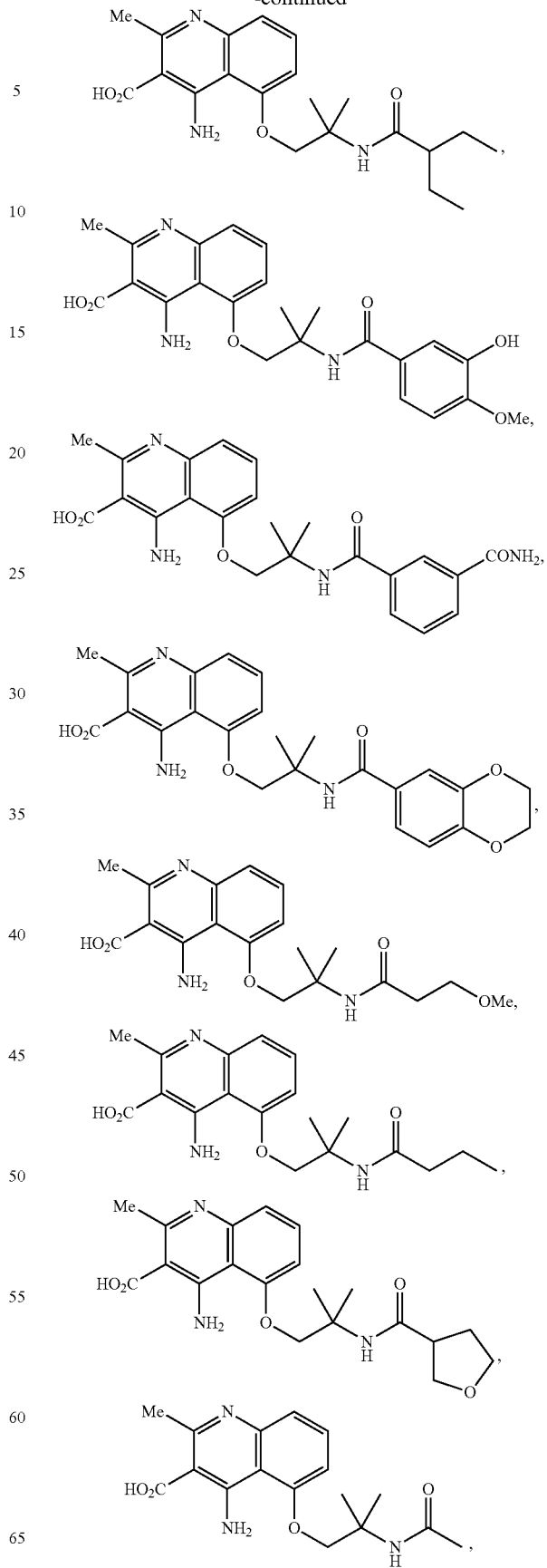
-continued

171
-continued
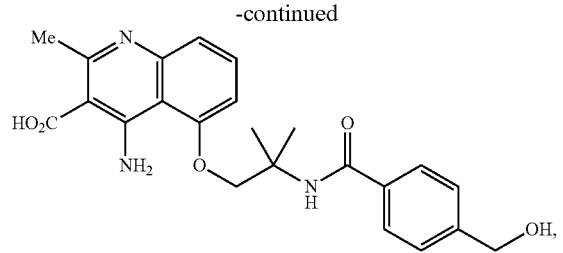
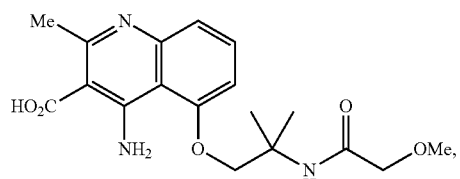
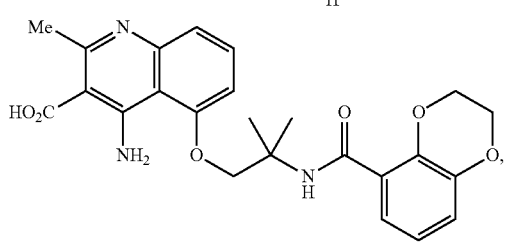
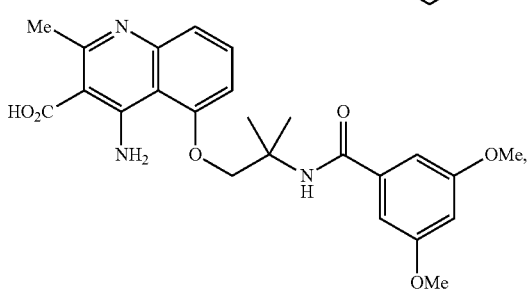
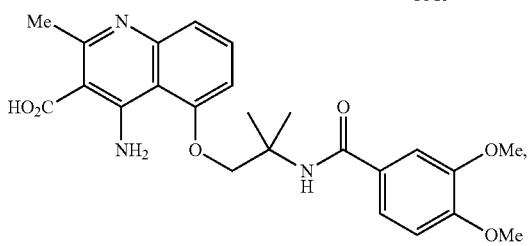
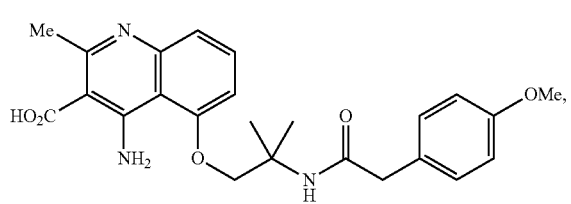
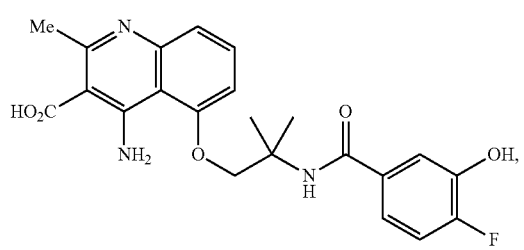
172
-continued
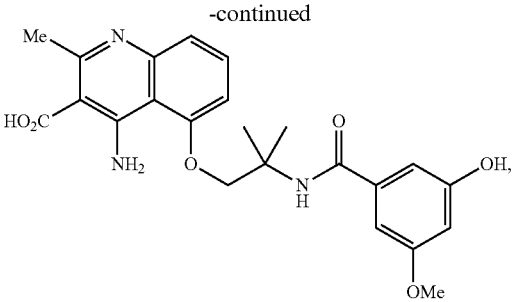
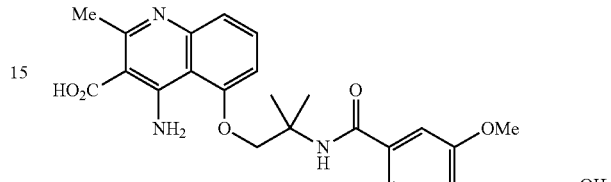
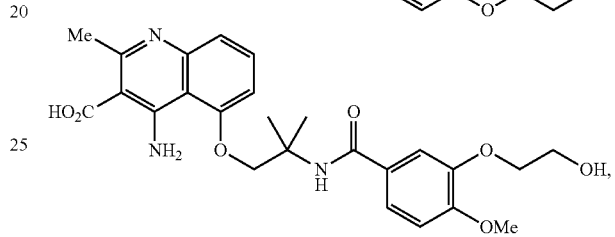
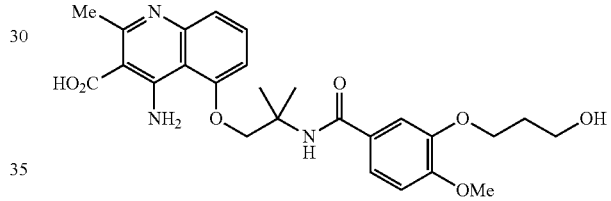
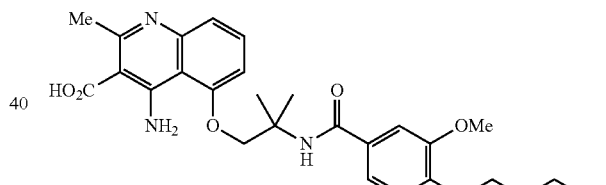
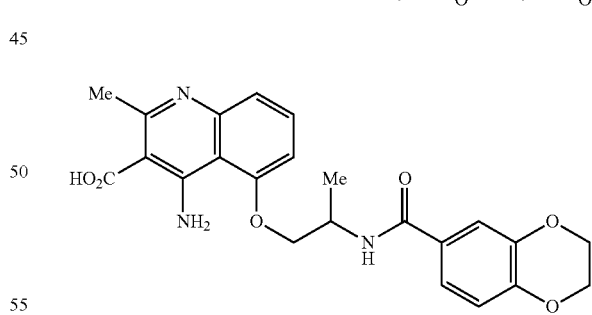
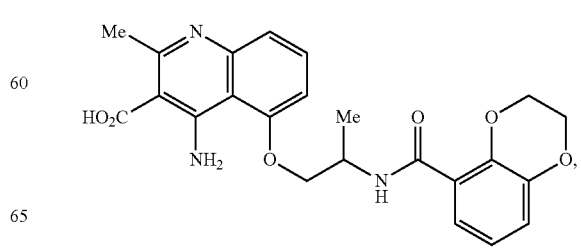

173
-continued
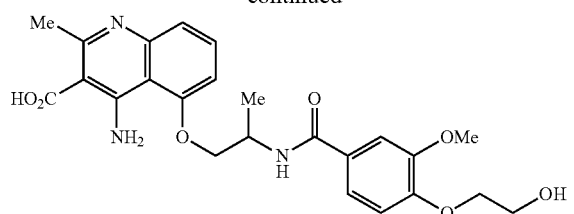
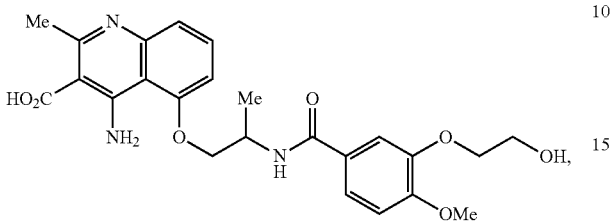
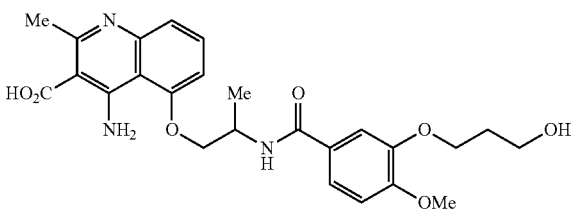
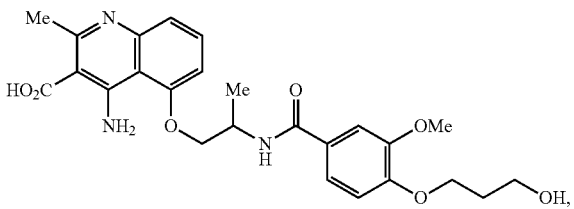
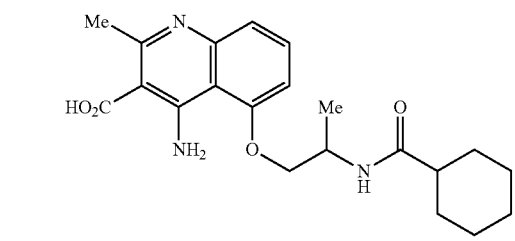
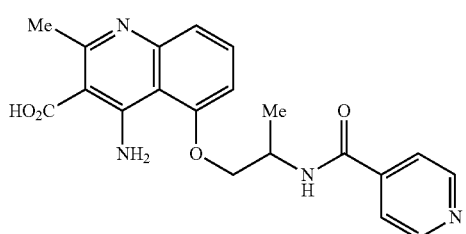
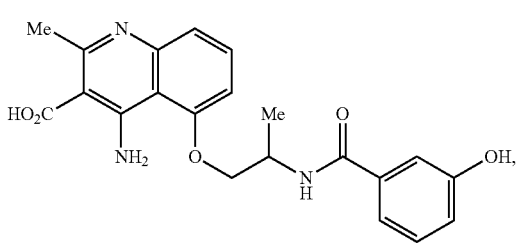
174
-continued
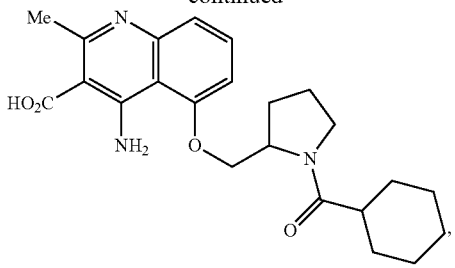
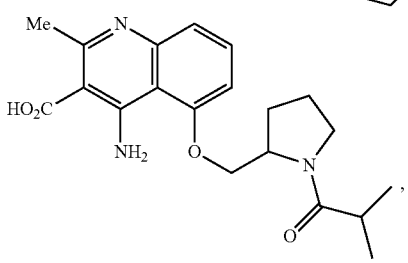
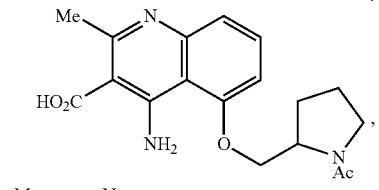
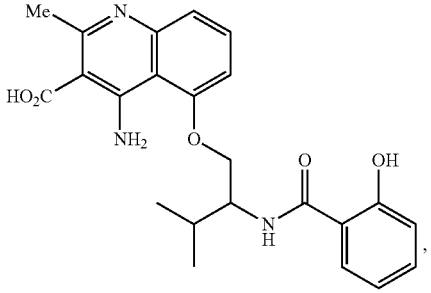
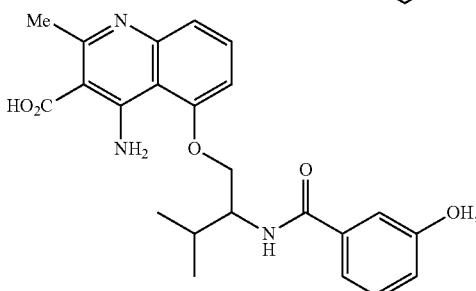
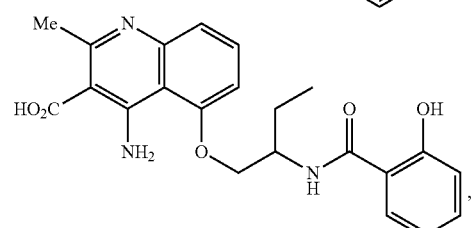
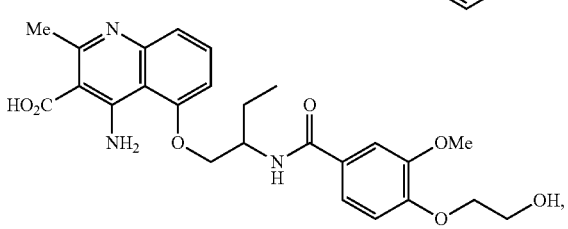

175
-continued
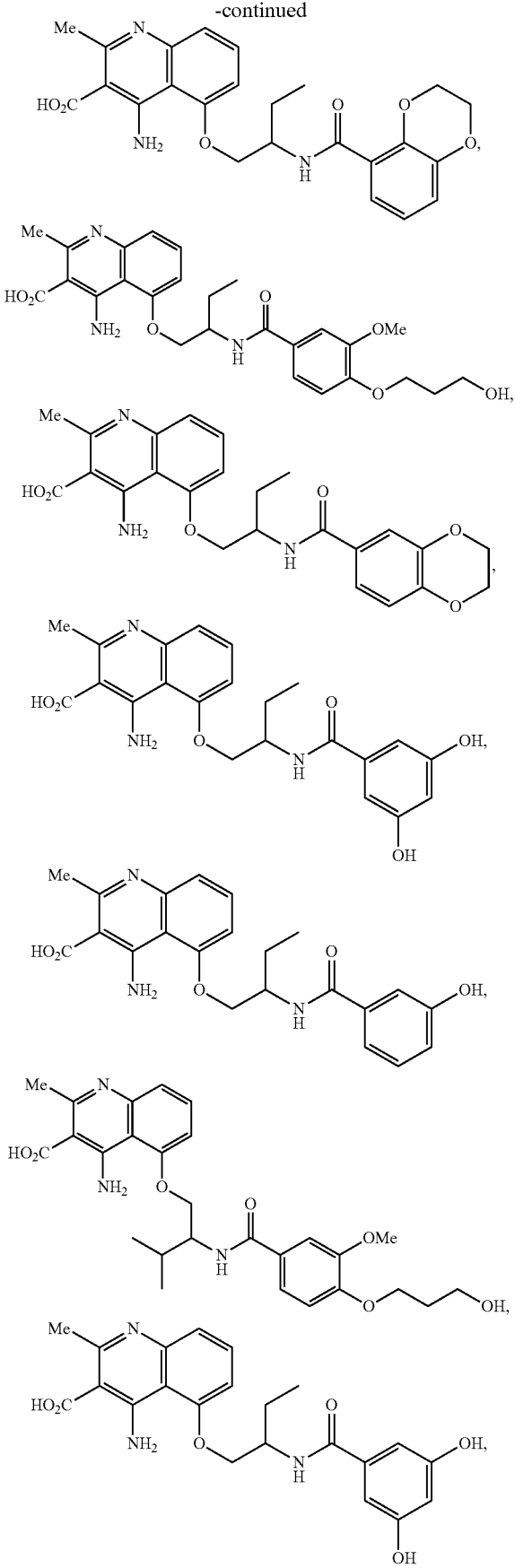
176
-continued
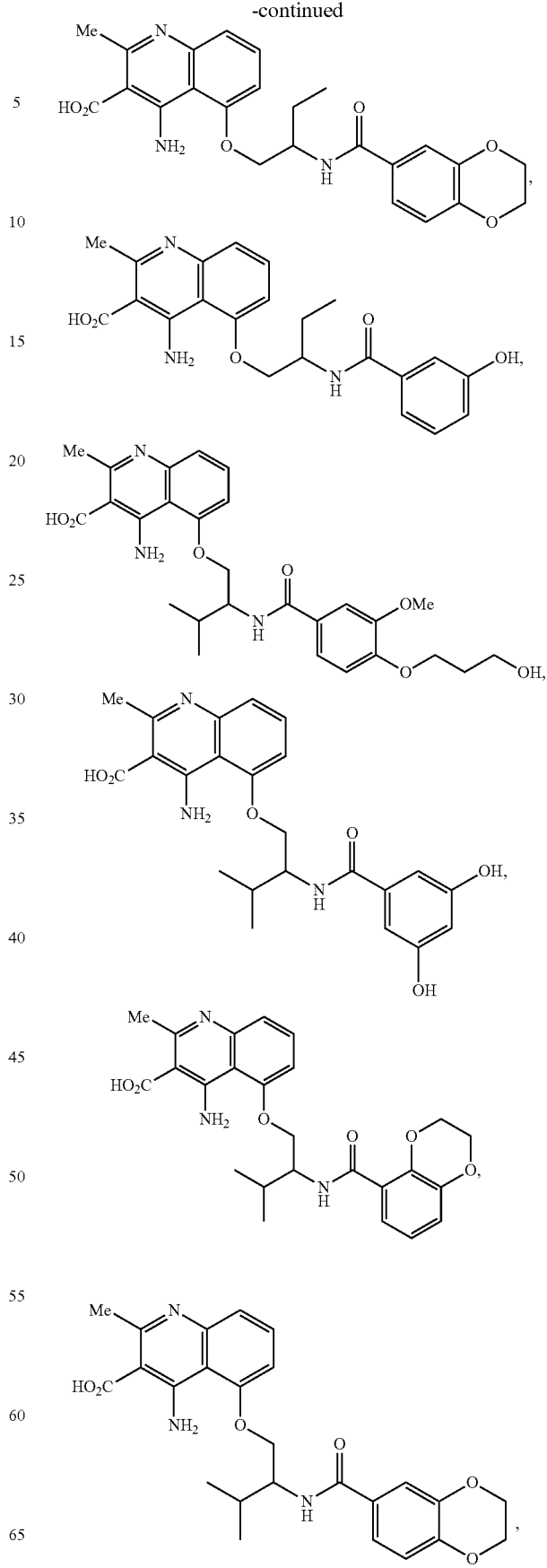

177
-continued
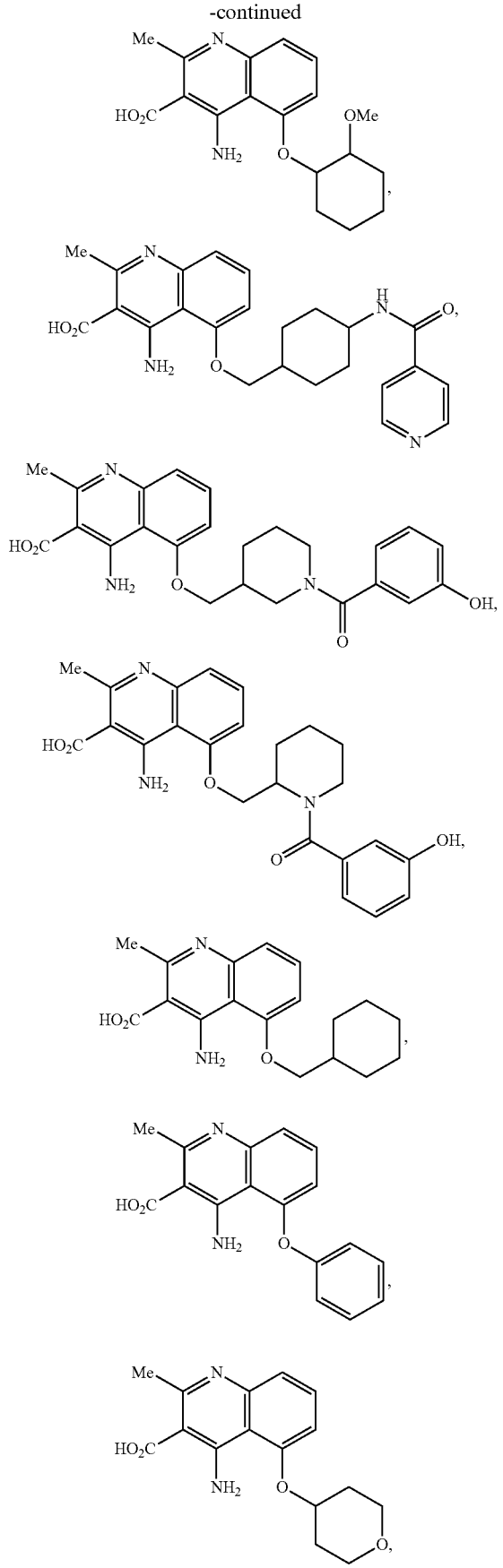
178
-continued
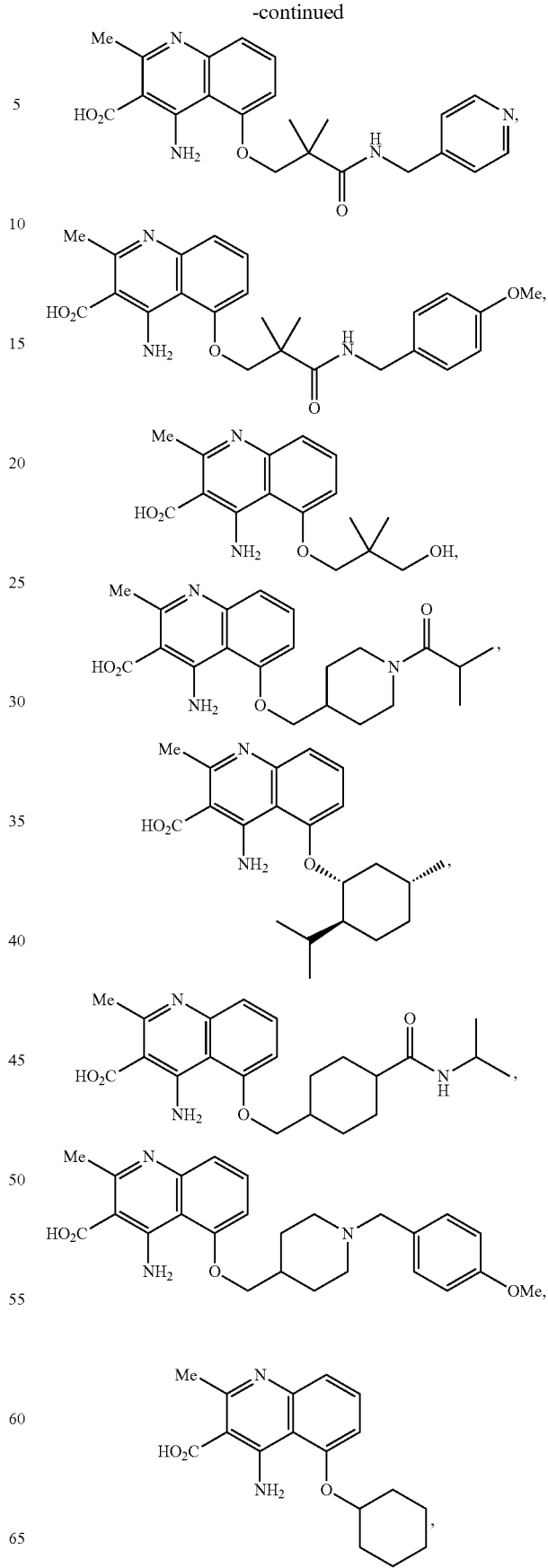

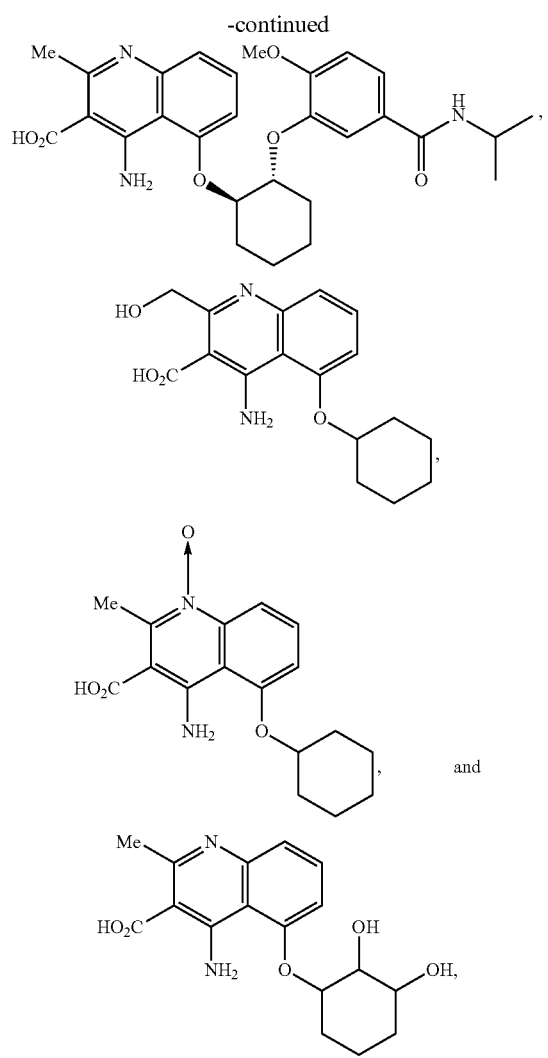
or a tautomer, and/or salt thereof.
27. A ingestible composition comprising a compound is selected from the group consisting of -continued
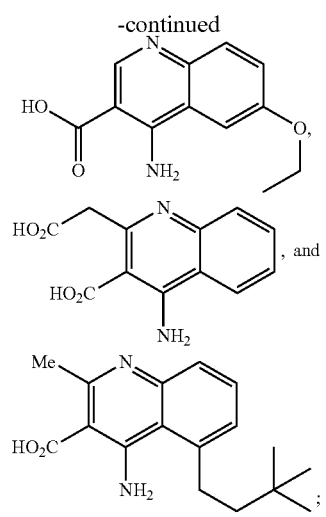
or a tautomer, and/or salt thereof; and an ingestibly acceptable excipient.
* * * * *